United States Patent
Kahn et al.

(10) Patent No.: US 12,201,620 B2
(45) Date of Patent: Jan. 21, 2025

(54) COMPOSITIONS AND METHODS FOR TREATING CHEMOTHERAPY RESISTANT CANCER

(71) Applicant: The Brigham And Women's Hospital, Inc., Boston, MA (US)

(72) Inventors: Josephine Kahn, Boston, MA (US); Siddhartha Jaiswal, Boston, MA (US); Benjamin Ebert, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 358 days.

(21) Appl. No.: 17/688,222

(22) Filed: Mar. 7, 2022

(65) Prior Publication Data
US 2022/0362228 A1    Nov. 17, 2022

Related U.S. Application Data

(62) Division of application No. 16/083,687, filed as application No. PCT/US2017/021830 on Mar. 10, 2017, now Pat. No. 11,304,938.
(Continued)

(51) Int. Cl.
*A61K 31/4436* (2006.01)
*A61K 31/381* (2006.01)
(Continued)

(52) U.S. Cl.
CPC ........ *A61K 31/4436* (2013.01); *A61K 31/381* (2013.01); *A61K 31/675* (2013.01);
(Continued)

(58) Field of Classification Search
CPC .............. A61K 2300/00; A61K 31/381; A61K 31/4436; A61K 31/555; A61K 31/675;
(Continued)

(56) References Cited

U.S. PATENT DOCUMENTS

| 5,399,346 A | 3/1995 | Anderson et al. |
| 11,304,938 B2 | 4/2022 | Kahn et al. |

(Continued)

FOREIGN PATENT DOCUMENTS

WO    2012149102 A1    11/2012

OTHER PUBLICATIONS

Akbari et al., "PPM1D Mutations in Circulating White Blood Cells and the Risk for Ovarian Cancer," JNCI: Journal of the National Cancer Institute, Jan. 1, 2014, vol. 106, No. 1, djt323, pp. 1-4.
(Continued)

*Primary Examiner* — Savitha M Rao
(74) *Attorney, Agent, or Firm* — Greenberg Traurig LLP; Melissa Hunter-Ensor; Leslie Serunian

(57) ABSTRACT

The present invention features methods for increasing sensitivity and/or reversing resistance to chemotherapy, methods for treating or preventing a cancer in a subject, methods for treating clonal hematopoiesis of indeterminate potential in a subject, and methods of identifying resistance or sensitivity to chemotherapy in a subject. In some embodiments, the methods contain the step of administering an agent that inhibits the expression or activity of a Protein phosphatase 1D (PPM1D) polypeptide or polynucleotide. The present invention also features compositions for increasing sensitivity and/or reversing resistance to chemotherapy.

17 Claims, 52 Drawing Sheets

Specification includes a Sequence Listing.

Related U.S. Application Data

(60) Provisional application No. 62/306,952, filed on Mar. 11, 2016.

(51) Int. Cl.
  *A61K 31/675* (2006.01)
  *A61K 31/704* (2006.01)
  *A61K 31/7068* (2006.01)
  *A61K 33/243* (2019.01)
  *A61P 35/00* (2006.01)

(52) U.S. Cl.
  CPC ........ *A61K 31/704* (2013.01); *A61K 31/7068* (2013.01); *A61K 33/243* (2019.01); *A61P 35/00* (2018.01)

(58) Field of Classification Search
  CPC .............. A61K 31/704; A61K 31/7068; A61K 33/243; A61K 45/06
  See application file for complete search history.

(56) References Cited

U.S. PATENT DOCUMENTS

| | | |
|---|---|---|
| 2011/0288050 A1 | 11/2011 | Sakaguchi et al. |
| 2015/0284806 A1 | 10/2015 | Rahman |

OTHER PUBLICATIONS

Belova et al., "Chemical inhibition of Wip1 phosphatase contributes to suppression of tumorigenesis," Cancer Biology & Therapy, Oct. 2005, vol. 4, No. 10, pp. 1154-1158.
Brigham et al., "Rapid Communication: In vivo Transfection of Murine Lungs with a Functioning Prokaryotic Gene Using a Liposome Vehicle," The American Journal of the Medical Sciences, Oct. 1989, vol. 298, No. 4, pp. 278-281.
Candelaria et al., "Therapy-related myelodysplastic syndrome," Expert Opinion on Drug Safety, 2015, vol. 14, No. 5, pp. 655-665.
Esfandiari et al., "Chemical Inhibition of Wild-Type p53-Induced Phosphatase 1 (WIP1/PPM1D) by GSK2830371 Potentiates the Sensitivity to MDM2 Inhibitors in a p53-Dependent Manner," Molecular Cancer Therapeutics, 2016, vol. 15, No. 3, pp. 379-391.
Felgner et al., "Lipofection: A highly efficient, lipid-mediated DNA-transfection procedure," Proceedings of the National Academy of Sciences of the United States of America, Nov. 1987, vol. 84, pp. 7413-7417.
Fiscella et al., "Wip1, a novel human protein phosphatase that is induced in response to ionizing radiation in a p53-dependent manner," Proceedings of the National Academy of Sciences of the United States of America, Jun. 1997, vol. 94, pp. 6048-6053.
Fujimoto et al., "Regulation of the antioncogenic Chk2 kinase by the oncogenic Wip1 phosphatase," Cell Death and Differentiation, 2006, vol. 13, pp. 1170-1180.
Genovese et al., "Clonal Hematopoiesis and Blood-Cancer Risk Inferred from Blood DNA Sequence," The New England Journal of Medicine, Dec. 25, 2014, vol. 371, No. 26, pp. 2477-2487.
Gibson et al., "Clonal Hematopoiesis Associated With Adverse Outcomes After Autologous Stem-Cell Transplantation for Lymphoma," Journal of Clinical Oncology, May 10, 2017, vol. 35, No. 14, pp. 1598-1605.
Gilmartin et al., "Allosteric Wip1 phosphatase inhibition through flap-subdomain interaction," Nature Chemical Biology, Mar. 2014, vol. 10, pp. 181-187.
Hsu et al., "Development and Applications of CRISPR-Cas9 for Genome Engineering," Cell, Jun. 5, 2014, vol. 157, No. 6, pp. 1262-1278.
Jaiswal et al., "Age-Related Clonal Hematopoiesis Associated with Adverse Outcomes," The New England Journal of Medicine, Dec. 25, 2014, vol. 371, No. 26, pp. 2488-2498.
Kahn et al., "PPM1D Truncating Mutations Confer Chemotherapy Resistance in Hematopoietic Stem Cells, Which Is Reversible By PPM1D Inhibition," Blood, American Society of Hematology, US, Dec. 2, 2016, vol. 128, No. 22, p. 740.
Kleiblova et al., "Gain-of-function mutations of PPM1D/Wip1 impair the p53-dependent G1 checkpoint," The Journal of Cell Biology, 2013, vol. 201, No. 4, pp. 511-521.
Lindsley et al., "Prognostic Mutations in Myelodysplastic Syndrome after Stem-Cell Transplantation," The New England Journal of Medicine, Feb. 9, 2017, vol. 376, No. 6, pp. 536-547.
Lu et al., "PPM1D dephosphorylates Chk1 and p53 and abrogates cell cycle checkpoints," Genes & Development, 2005, vol. 19, pp. 1162-1174.
Lu et al., "Reversal of the ATM/ATR-Mediated DNA Damage Response by the Oncogenic Phosphatase PPM1D," Cell Cycle, Aug. 2005, vol. 4, No. 8, pp. 4060-4064.
Lu et al., "The type 2C phosphatase Wip1: An oncogenic regulator of tumor suppressor and DNA damage response pathways," Cancer and Metastasis Reviews, 2008, vol. 27, pp. 123-135.
Malmgren et al., "Therapy-related Myelodysplastic Syndrome Following Primary Breast Cancer," Leukemia Research, Aug. 2016, vol. 47, pp. 178-184.
Morton et al., "Evolving risk of therapy-related acute myeloid leukemia following cancer chemotherapy among adults in the United States, 1975-2008," Blood, Apr. 11, 2013, vol. 121, No. 15, pp. 2996-3004.
Ono et al., "Plasmid DNAs directly injected into mouse brain with lipofectin can be incorporated and expressed by brain cells," Neuroscience Letters, 1990, vol. 117, pp. 259-263.
Peng et al., "PPM1D is a prognostic marker and therapeutic target in colorectal cancer," Experimental and Therapeutic Medicine, 2014, vol. 8, pp. 430-434.
Pharoah et al., "PPM1D Mosaic Truncating Variants in Ovarian Cancer Cases May Be Treatment-Related Somatic Mutations," JNCI: Journal of the National Cancer Institute, 2016, vol. 108, No. 3, djv347, pp. 1-5.
Rayter et al., "A chemical inhibitor of PPM1D that selectively kills cells overexpressing PPM1D," Oncogene, 2008, vol. 27, pp. 1036-1044.
Rayter et al., "Correction: A chemical inhibitor of PPM1D that selectively kills cells overexpressing PPM1D," Oncogene, 2020, vol. 39, p. 4780.
Roboz et al., "Arsenic trioxide and low-dose cytarabine in older patients with untreated acute myeloid leukemia, excluding acute promyelocytic leukemia," Cancer, Nov. 1, 2008, vol. 113, No. 9, pp. 2504-2511.
Rosenberg et al., "Gene Transfer into Humans—Immunotherapy of Patients with Advanced Melanoma, Using Tumor-Infiltrating Lymphocytes Modified by Retroviral Gene Transduction," The New England Journal of Medicine, Aug. 30, 1990, vol. 323, No. 9, pp. 570-578.
Ruark et al., "Mosaic PPM1D mutations are associated with predisposition to breast and ovarian cancer," Nature, Jan. 17, 2013, vol. 493, No. 7432, pp. 406-410.
Sander et al., "CRISPR-Cas systems for genome editing, regulation and targeting," Nature Biotechnology, Apr. 2014, vol. 32, No. 4, pp. 347-355.
Straubinger et al., "Liposomes as Carriers for Intracellular Delivery of Nucleic Acids," Methods in Enzymology, 1983, vol. 101, pp. 512-527.
Swisher et al., "Somatic Mosaic Mutations in PPM1D and TP53 in the Blood of Women With Ovarian Carcinoma," JAMA Oncology, Mar. 2016, vol. 2, No. 3, pp. 370-372.
Takekawa et al., "p53-inducible Wip1 phosphatase mediates a negative feedback regulation of p38 MAPK-p53 signaling in response to UV radiation," The EMBO Journal, 2000, vol. 19, No. 23, pp. 6517-6526.
Wang et al., "Deficient DNA Damage Signaling Leads to Chemoresistance to Cisplatin in Oral Cancer," Molecular Cancer Therapeutics, Nov. 2012, vol. 11, No. 11, pp. 2401-2409.
Wolff et al., "Direct Gene Transfer into Mouse Muscle in Vivo," Science, Mar. 23, 1990, vol. 247, No. 4949, pp. 1465-1468.
Wong et al., "The Role of TP53 Mutations in the Origin and Evolution of Therapy-Related AML," Nature, Feb. 26, 2015, vol. 518, No. 7540, pp. 552-555.

(56) References Cited

OTHER PUBLICATIONS

Wu et al., "Receptor-mediated Gene Delivery and Expression in Vivo," The Journal of Biological Chemistry, Oct. 15, 1988, vol. 263, No. 29, pp. 14621-14624.

Wu et al., "Targeting Genes: Delivery and Persistent Expression of a Foreign Gene Driven by Mammalian Regulatory Elements in Vivo," The Journal of Biological Chemistry, Oct. 15, 1989, vol. 264, No. 29, pp. 16985-16987.

Xie et al., "Age-related cancer mutations associated with clonal hematopoietic expansion," Nature Medicine, Dec. 2014, vol. 20, No. 12, pp. 1472-1478.

Yagi et al., "A small molecule inhibitor of p53-inducible protein phosphatase PPM1D," Bioorganic & Medicinal Chemistry Letters, Jan. 1, 2012, vol. 22, No. 1, pp. 729-732.

Yang et al., "PPM1D overexpression predicts poor prognosis in non-small cell lung cancer," Tumor Biology, 2015, vol. 36, pp. 2179-2184.

Zajkowicz et al., "Truncating mutations of PPM1D are found in blood DNA samples of lung cancer patients," British Journal of Cancer, 2015, vol. 112, pp. 1114-1120.

Zhang et al., "Phosphorylation and Degradation of MdmX Is Inhibited by Wip1 Phosphatase in the DNA Damage Response," Cancer Research, Oct. 15, 2009, vol. 69, No. 20, pp. 7960-7968.

International Search Report and Written Opinion mailed Jul. 26, 2017 in corresponding International PCT Patent Application No. PCT/US2017/021830 (11 pages).

Partial Supplementary European Search Report mailed Oct. 18, 2019 in corresponding European Patent Application No. 17764199.0 (23 pages).

Day 12

Day 20

Day 24

FIG. 12

| | Input | Quota | Target Taxon | Target Gene ID | Target Gene Symbol | Target Transcript | Custom Target Sequence Reference | Target Mode (GENE, TRANSCRIPT, CDS) | PAM Policy | Initial Spacing Requirement | Off-Target Match Ruleset Version | Off-Target Tier Policy | Off-Target Match Bin Policy | Genomic Sequence |
|---|---|---|---|---|---|---|---|---|---|---|---|---|---|---|
| 1 | NM_003620 [CDS] | 5 | 9606 | 8493 | PPM1D | NM_003620.3 | | CDS | NGG | 5 | 1 | 1 | 5,20,100 | NC_000017.11 |
| 2 | NM_003620 [CDS] | 5 | 9606 | 8493 | PPM1D | NM_003620.3 | | CDS | NGG | 5 | 1 | 1 | 5,20,100 | NC_000017.11 |
| 3 | NM_003620 [CDS] | 5 | 9606 | 8493 | PPM1D | NM_003620.3 | | CDS | NGG | 5 | 1 | 1 | 5,20,100 | NC_000017.11 |
| 4 | NM_003620 [CDS] | 5 | 9606 | 8493 | PPM1D | NM_003620.3 | | CDS | NGG | 5 | 1 | 1 | 5,20,100 | NC_000017.11 |
| 5 | NM_003620 [CDS] | 5 | 9606 | 8493 | PPM1D | NM_003620.3 | | CDS | NGG | 5 | 1 | 1 | 5,20,100 | NC_000017.11 |
| 6 | NM_003620 [CDS] | 5 | 9606 | 8493 | PPM1D | NM_003620.3 | | CDS | NGG | 5 | 1 | 1 | 5,20,100 | NC_000017.11 |
| 7 | NM_003620 [CDS] | 5 | 9606 | 8493 | PPM1D | NM_003620.3 | | CDS | NGG | 5 | 1 | 1 | 5,20,100 | NC_000017.11 |
| 8 | NM_003620 [CDS] | 5 | 9606 | 8493 | PPM1D | NM_003620.3 | | CDS | NGG | 5 | 1 | 1 | 5,20,100 | NC_000017.11 |
| 9 | NM_003620 [CDS] | 5 | 9606 | 8493 | PPM1D | NM_003620.3 | | CDS | NGG | 5 | 1 | 1 | 5,20,100 | NC_000017.11 |
| 10 | NM_003620 [CDS] | 5 | 9606 | 8493 | PPM1D | NM_003620.3 | | CDS | NGG | 5 | 1 | 1 | 5,20,100 | NC_000017.11 |
| 11 | NM_003620 [CDS] | 5 | 9606 | 8493 | PPM1D | NM_003620.3 | | CDS | NGG | 5 | 1 | 1 | 5,20,100 | NC_000017.11 |
| 12 | NM_003620 [CDS] | 5 | 9606 | 8493 | PPM1D | NM_003620.3 | | CDS | NGG | 5 | 1 | 1 | 5,20,100 | NC_000017.11 |
| 13 | NM_003620 [CDS] | 5 | 9606 | 8493 | PPM1D | NM_003620.3 | | CDS | NGG | 5 | 1 | 1 | 5,20,100 | NC_000017.11 |
| 14 | NM_003620 [CDS] | 5 | 9606 | 8493 | PPM1D | NM_003620.3 | | CDS | NGG | 5 | 1 | 1 | 5,20,100 | NC_000017.11 |
| 15 | NM_003620 [CDS] | 5 | 9606 | 8493 | PPM1D | NM_003620.3 | | CDS | NGG | 5 | 1 | 1 | 5,20,100 | NC_000017.11 |
| 16 | NM_003620 [CDS] | 5 | 9606 | 8493 | PPM1D | NM_003620.3 | | CDS | NGG | 5 | 1 | 1 | 5,20,100 | NC_000017.11 |
| 17 | NM_003620 [CDS] | 5 | 9606 | 8493 | PPM1D | NM_003620.3 | | CDS | NGG | 5 | 1 | 1 | 5,20,100 | NC_000017.11 |
| 18 | NM_003620 [CDS] | 5 | 9606 | 8493 | PPM1D | NM_003620.3 | | CDS | NGG | 5 | 1 | 1 | 5,20,100 | NC_000017.11 |
| 19 | NM_003620 [CDS] | 5 | 9606 | 8493 | PPM1D | NM_003620.3 | | CDS | NGG | 5 | 1 | 1 | 5,20,100 | NC_000017.11 |
| 20 | NM_003620 [CDS] | 5 | 9606 | 8493 | PPM1D | NM_003620.3 | | CDS | NGG | 5 | 1 | 1 | 5,20,100 | NC_000017.11 |
| 21 | NM_003620 [CDS] | 5 | 9606 | 8493 | PPM1D | NM_003620.3 | | CDS | NGG | 5 | 1 | 1 | 5,20,100 | NC_000017.11 |
| 22 | NM_003620 [CDS] | 5 | 9606 | 8493 | PPM1D | NM_003620.3 | | CDS | NGG | 5 | 1 | 1 | 5,20,100 | NC_000017.11 |
| 23 | NM_003620 [CDS] | 5 | 9606 | 8493 | PPM1D | NM_003620.3 | | CDS | NGG | 5 | 1 | 1 | 5,20,100 | NC_000017.11 |
| 24 | NM_003620 [CDS] | 5 | 9606 | 8493 | PPM1D | NM_003620.3 | | CDS | NGG | 5 | 1 | 1 | 5,20,100 | NC_000017.11 |
| 25 | NM_003620 [CDS] | 5 | 9606 | 8493 | PPM1D | NM_003620.3 | | CDS | NGG | 5 | 1 | 1 | 5,20,100 | NC_000017.11 |
| 26 | NM_003620 [CDS] | 5 | 9606 | 8493 | PPM1D | NM_003620.3 | | CDS | NGG | 5 | 1 | 1 | 5,20,100 | NC_000017.11 |
| 27 | NM_003620 [CDS] | 5 | 9606 | 8493 | PPM1D | NM_003620.3 | | CDS | NGG | 5 | 1 | 1 | 5,20,100 | NC_000017.11 |
| 28 | NM_003620 [CDS] | 5 | 9606 | 8493 | PPM1D | NM_003620.3 | | CDS | NGG | 5 | 1 | 1 | 5,20,100 | NC_000017.11 |
| 29 | NM_003620 [CDS] | 5 | 9606 | 8493 | PPM1D | NM_003620.3 | | CDS | NGG | 5 | 1 | 1 | 5,20,100 | NC_000017.11 |
| 30 | NM_003620 [CDS] | 5 | 9606 | 8493 | PPM1D | NM_003620.3 | | CDS | NGG | 5 | 1 | 1 | 5,20,100 | NC_000017.11 |
| 31 | NM_003620 [CDS] | 5 | 9606 | 8493 | PPM1D | NM_003620.3 | | CDS | NGG | 5 | 1 | 1 | 5,20,100 | NC_000017.11 |
| 32 | NM_003620 [CDS] | 5 | 9606 | 8493 | PPM1D | NM_003620.3 | | CDS | NGG | 5 | 1 | 1 | 5,20,100 | NC_000017.11 |
| 33 | NM_003620 [CDS] | 5 | 9606 | 8493 | PPM1D | NM_003620.3 | | CDS | NGG | 5 | 1 | 1 | 5,20,100 | NC_000017.11 |
| 34 | NM_003620 [CDS] | 5 | 9606 | 8493 | PPM1D | NM_003620.3 | | CDS | NGG | 5 | 1 | 1 | 5,20,100 | NC_000017.11 |

FIG. 12 (cont.)

| | Input | Quota | Target Taxon | Target Gene ID | Target Gene Symbol | Target Transcript | Custom Target Sequence Reference | Target Mode (GENE, TRANSCRIPT, CDS) | PAM Policy | Initial Spacing Requirement | Off-Target Match Ruleset Version | Off-Target Tier Policy | Off-Target Match Bin Policy | Genomic Sequence |
|---|---|---|---|---|---|---|---|---|---|---|---|---|---|---|
| 35 | NM_003620 [CDS] | 5 | 9606 | 8493 | PPM1D | NM_003620.3 | | CDS | NGG | 5 | 1 | 1 | 5,20,100 | NC_000017.11 |
| 36 | NM_003620 [CDS] | 5 | 9606 | 8493 | PPM1D | NM_003620.3 | | CDS | NGG | 5 | 1 | 1 | 5,20,100 | NC_000017.11 |
| 37 | NM_003620 [CDS] | 5 | 9606 | 8493 | PPM1D | NM_003620.3 | | CDS | NGG | 5 | 1 | 1 | 5,20,100 | NC_000017.11 |
| 38 | NM_003620 [CDS] | 5 | 9606 | 8493 | PPM1D | NM_003620.3 | | CDS | NGG | 5 | 1 | 1 | 5,20,100 | NC_000017.11 |
| 39 | NM_003620 [CDS] | 5 | 9606 | 8493 | PPM1D | NM_003620.3 | | CDS | NGG | 5 | 1 | 1 | 5,20,100 | NC_000017.11 |
| 40 | NM_003620 [CDS] | 5 | 9606 | 8493 | PPM1D | NM_003620.3 | | CDS | NGG | 5 | 1 | 1 | 5,20,100 | NC_000017.11 |
| 41 | NM_003620 [CDS] | 5 | 9606 | 8493 | PPM1D | NM_003620.3 | | CDS | NGG | 5 | 1 | 1 | 5,20,100 | NC_000017.11 |
| 42 | NM_003620 [CDS] | 5 | 9606 | 8493 | PPM1D | NM_003620.3 | | CDS | NGG | 5 | 1 | 1 | 5,20,100 | NC_000017.11 |
| 43 | NM_003620 [CDS] | 5 | 9606 | 8493 | PPM1D | NM_003620.3 | | CDS | NGG | 5 | 1 | 1 | 5,20,100 | NC_000017.11 |
| 44 | NM_003620 [CDS] | 5 | 9606 | 8493 | PPM1D | NM_003620.3 | | CDS | NGG | 5 | 1 | 1 | 5,20,100 | NC_000017.11 |
| 45 | NM_003620 [CDS] | 5 | 9606 | 8493 | PPM1D | NM_003620.3 | | CDS | NGG | 5 | 1 | 1 | 5,20,100 | NC_000017.11 |
| 46 | NM_003620 [CDS] | 5 | 9606 | 8493 | PPM1D | NM_003620.3 | | CDS | NGG | 5 | 1 | 1 | 5,20,100 | NC_000017.11 |
| 47 | NM_003620 [CDS] | 5 | 9606 | 8493 | PPM1D | NM_003620.3 | | CDS | NGG | 5 | 1 | 1 | 5,20,100 | NC_000017.11 |
| 48 | NM_003620 [CDS] | 5 | 9606 | 8493 | PPM1D | NM_003620.3 | | CDS | NGG | 5 | 1 | 1 | 5,20,100 | NC_000017.11 |
| 49 | NM_003620 [CDS] | 5 | 9606 | 8493 | PPM1D | NM_003620.3 | | CDS | NGG | 5 | 1 | 1 | 5,20,100 | NC_000017.11 |
| 50 | NM_003620 [CDS] | 5 | 9606 | 8493 | PPM1D | NM_003620.3 | | CDS | NGG | 5 | 1 | 1 | 5,20,100 | NC_000017.11 |
| 51 | NM_003620 [CDS] | 5 | 9606 | 8493 | PPM1D | NM_003620.3 | | CDS | NGG | 5 | 1 | 1 | 5,20,100 | NC_000017.11 |
| 52 | NM_003620 [CDS] | 5 | 9606 | 8493 | PPM1D | NM_003620.3 | | CDS | NGG | 5 | 1 | 1 | 5,20,100 | NC_000017.11 |
| 53 | NM_003620 [CDS] | 5 | 9606 | 8493 | PPM1D | NM_003620.3 | | CDS | NGG | 5 | 1 | 1 | 5,20,100 | NC_000017.11 |
| 54 | NM_003620 [CDS] | 5 | 9606 | 8493 | PPM1D | NM_003620.3 | | CDS | NGG | 5 | 1 | 1 | 5,20,100 | NC_000017.11 |
| 55 | NM_003620 [CDS] | 5 | 9606 | 8493 | PPM1D | NM_003620.3 | | CDS | NGG | 5 | 1 | 1 | 5,20,100 | NC_000017.11 |
| 56 | NM_003620 [CDS] | 5 | 9606 | 8493 | PPM1D | NM_003620.3 | | CDS | NGG | 5 | 1 | 1 | 5,20,100 | NC_000017.11 |
| 57 | NM_003620 [CDS] | 5 | 9606 | 8493 | PPM1D | NM_003620.3 | | CDS | NGG | 5 | 1 | 1 | 5,20,100 | NC_000017.11 |
| 58 | NM_003620 [CDS] | 5 | 9606 | 8493 | PPM1D | NM_003620.3 | | CDS | NGG | 5 | 1 | 1 | 5,20,100 | NC_000017.11 |
| 59 | NM_003620 [CDS] | 5 | 9606 | 8493 | PPM1D | NM_003620.3 | | CDS | NGG | 5 | 1 | 1 | 5,20,100 | NC_000017.11 |
| 60 | NM_003620 [CDS] | 5 | 9606 | 8493 | PPM1D | NM_003620.3 | | CDS | NGG | 5 | 1 | 1 | 5,20,100 | NC_000017.11 |
| 61 | NM_003620 [CDS] | 5 | 9606 | 8493 | PPM1D | NM_003620.3 | | CDS | NGG | 5 | 1 | 1 | 5,20,100 | NC_000017.11 |
| 62 | NM_003620 [CDS] | 5 | 9606 | 8493 | PPM1D | NM_003620.3 | | CDS | NGG | 5 | 1 | 1 | 5,20,100 | NC_000017.11 |
| 63 | NM_003620 [CDS] | 5 | 9606 | 8493 | PPM1D | NM_003620.3 | | CDS | NGG | 5 | 1 | 1 | 5,20,100 | NC_000017.11 |
| 64 | NM_003620 [CDS] | 5 | 9606 | 8493 | PPM1D | NM_003620.3 | | CDS | NGG | 5 | 1 | 1 | 5,20,100 | NC_000017.11 |
| 65 | NM_003620 [CDS] | 5 | 9606 | 8493 | PPM1D | NM_003620.3 | | CDS | NGG | 5 | 1 | 1 | 5,20,100 | NC_000017.11 |
| 66 | NM_003620 [CDS] | 5 | 9606 | 8493 | PPM1D | NM_003620.3 | | CDS | NGG | 5 | 1 | 1 | 5,20,100 | NC_000017.11 |
| 67 | NM_003620 [CDS] | 5 | 9606 | 8493 | PPM1D | NM_003620.3 | | CDS | NGG | 5 | 1 | 1 | 5,20,100 | NC_000017.11 |
| 68 | NM_003620 [CDS] | 5 | 9606 | 8493 | PPM1D | NM_003620.3 | | CDS | NGG | 5 | 1 | 1 | 5,20,100 | NC_000017.11 |

FIG. 12 (cont.)

| | Input | Quota | Target Taxon | Target Gene ID | Target Gene Symbol | Target Transcript | Custom Target Sequence Reference | Target Mode (GENE, TRANSCRIPT, CDS) | PAM Policy | Initial Spacing Requirement | Off-Target Match Ruleset Version | Off-Target Tier Policy | Off-Target Match Bin Policy | Genomic Sequence |
|---|---|---|---|---|---|---|---|---|---|---|---|---|---|---|
| 69 | NM_003620 [CDS] | 5 | 9606 | 8493 | PPM1D | NM_003620.3 | | CDS | NGG | 5 | 1 | 1 | 5,20,100 | NC_000017.11 |
| 70 | NM_003620 [CDS] | 5 | 9606 | 8493 | PPM1D | NM_003620.3 | | CDS | NGG | 5 | 1 | 1 | 5,20,100 | NC_000017.11 |
| 71 | NM_003620 [CDS] | 5 | 9606 | 8493 | PPM1D | NM_003620.3 | | CDS | NGG | 5 | 1 | 1 | 5,20,100 | NC_000017.11 |
| 72 | NM_003620 [CDS] | 5 | 9606 | 8493 | PPM1D | NM_003620.3 | | CDS | NGG | 5 | 1 | 1 | 5,20,100 | NC_000017.11 |
| 73 | NM_003620 [CDS] | 5 | 9606 | 8493 | PPM1D | NM_003620.3 | | CDS | NGG | 5 | 1 | 1 | 5,20,100 | NC_000017.11 |
| 74 | NM_003620 [CDS] | 5 | 9606 | 8493 | PPM1D | NM_003620.3 | | CDS | NGG | 5 | 1 | 1 | 5,20,100 | NC_000017.11 |
| 75 | NM_003620 [CDS] | 5 | 9606 | 8493 | PPM1D | NM_003620.3 | | CDS | NGG | 5 | 1 | 1 | 5,20,100 | NC_000017.11 |
| 76 | NM_003620 [CDS] | 5 | 9606 | 8493 | PPM1D | NM_003620.3 | | CDS | NGG | 5 | 1 | 1 | 5,20,100 | NC_000017.11 |
| 77 | NM_003620 [CDS] | 5 | 9606 | 8493 | PPM1D | NM_003620.3 | | CDS | NGG | 5 | 1 | 1 | 5,20,100 | NC_000017.11 |
| 78 | NM_003620 [CDS] | 5 | 9606 | 8493 | PPM1D | NM_003620.3 | | CDS | NGG | 5 | 1 | 1 | 5,20,100 | NC_000017.11 |
| 79 | NM_003620 [CDS] | 5 | 9606 | 8493 | PPM1D | NM_003620.3 | | CDS | NGG | 5 | 1 | 1 | 5,20,100 | NC_000017.11 |
| 80 | NM_003620 [CDS] | 5 | 9606 | 8493 | PPM1D | NM_003620.3 | | CDS | NGG | 5 | 1 | 1 | 5,20,100 | NC_000017.11 |
| 81 | NM_003620 [CDS] | 5 | 9606 | 8493 | PPM1D | NM_003620.3 | | CDS | NGG | 5 | 1 | 1 | 5,20,100 | NC_000017.11 |
| 82 | NM_003620 [CDS] | 5 | 9606 | 8493 | PPM1D | NM_003620.3 | | CDS | NGG | 5 | 1 | 1 | 5,20,100 | NC_000017.11 |
| 83 | NM_003620 [CDS] | 5 | 9606 | 8493 | PPM1D | NM_003620.3 | | CDS | NGG | 5 | 1 | 1 | 5,20,100 | NC_000017.11 |
| 84 | NM_003620 [CDS] | 5 | 9606 | 8493 | PPM1D | NM_003620.3 | | CDS | NGG | 5 | 1 | 1 | 5,20,100 | NC_000017.11 |
| 85 | NM_003620 [CDS] | 5 | 9606 | 8493 | PPM1D | NM_003620.3 | | CDS | NGG | 5 | 1 | 1 | 5,20,100 | NC_000017.11 |
| 86 | NM_003620 [CDS] | 5 | 9606 | 8493 | PPM1D | NM_003620.3 | | CDS | NGG | 5 | 1 | 1 | 5,20,100 | NC_000017.11 |
| 87 | NM_003620 [CDS] | 5 | 9606 | 8493 | PPM1D | NM_003620.3 | | CDS | NGG | 5 | 1 | 1 | 5,20,100 | NC_000017.11 |
| 88 | NM_003620 [CDS] | 5 | 9606 | 8493 | PPM1D | NM_003620.3 | | CDS | NGG | 5 | 1 | 1 | 5,20,100 | NC_000017.11 |
| 89 | NM_003620 [CDS] | 5 | 9606 | 8493 | PPM1D | NM_003620.3 | | CDS | NGG | 5 | 1 | 1 | 5,20,100 | NC_000017.11 |
| 90 | NM_003620 [CDS] | 5 | 9606 | 8493 | PPM1D | NM_003620.3 | | CDS | NGG | 5 | 1 | 1 | 5,20,100 | NC_000017.11 |
| 91 | NM_003620 [CDS] | 5 | 9606 | 8493 | PPM1D | NM_003620.3 | | CDS | NGG | 5 | 1 | 1 | 5,20,100 | NC_000017.11 |
| 92 | NM_003620 [CDS] | 5 | 9606 | 8493 | PPM1D | NM_003620.3 | | CDS | NGG | 5 | 1 | 1 | 5,20,100 | NC_000017.11 |
| 93 | NM_003620 [CDS] | 5 | 9606 | 8493 | PPM1D | NM_003620.3 | | CDS | NGG | 5 | 1 | 1 | 5,20,100 | NC_000017.11 |
| 94 | NM_003620 [CDS] | 5 | 9606 | 8493 | PPM1D | NM_003620.3 | | CDS | NGG | 5 | 1 | 1 | 5,20,100 | NC_000017.11 |
| 95 | NM_003620 [CDS] | 5 | 9606 | 8493 | PPM1D | NM_003620.3 | | CDS | NGG | 5 | 1 | 1 | 5,20,100 | NC_000017.11 |
| 96 | NM_003620 [CDS] | 5 | 9606 | 8493 | PPM1D | NM_003620.3 | | CDS | NGG | 5 | 1 | 1 | 5,20,100 | NC_000017.11 |
| 97 | NM_003620 [CDS] | 5 | 9606 | 8493 | PPM1D | NM_003620.3 | | CDS | NGG | 5 | 1 | 1 | 5,20,100 | NC_000017.11 |
| 98 | NM_003620 [CDS] | 5 | 9606 | 8493 | PPM1D | NM_003620.3 | | CDS | NGG | 5 | 1 | 1 | 5,20,100 | NC_000017.11 |
| 99 | NM_003620 [CDS] | 5 | 9606 | 8493 | PPM1D | NM_003620.3 | | CDS | NGG | 5 | 1 | 1 | 5,20,100 | NC_000017.11 |
| 100 | NM_003620 [CDS] | 5 | 9606 | 8493 | PPM1D | NM_003620.3 | | CDS | NGG | 5 | 1 | 1 | 5,20,100 | NC_000017.11 |
| 101 | NM_003620 [CDS] | 5 | 9606 | 8493 | PPM1D | NM_003620.3 | | CDS | NGG | 5 | 1 | 1 | 5,20,100 | NC_000017.11 |
| 102 | NM_003620 [CDS] | 5 | 9606 | 8493 | PPM1D | NM_003620.3 | | CDS | NGG | 5 | 1 | 1 | 5,20,100 | NC_000017.11 |

FIG. 12 (cont.)

| | Input | Quota | Target Taxon | Target Gene ID | Target Gene Symbol | Target Transcript | Custom Target Sequence Reference | Target Mode (GENE, TRANSCRIPT, CDS) | PAM Policy | Initial Spacing Requirement | Off-Target Match Ruleset Version | Off-Target Tier Policy | Off-Target Match Bin Policy | Genomic Sequence |
|---|---|---|---|---|---|---|---|---|---|---|---|---|---|---|
| 103 | NM_003620 [CDS] | 5 | 9606 | 8493 | PPM1D | NM_003620.3 | | CDS | NGG | 5 | 1 | 1 | 5,20,100 | NC_000017.11 |
| 104 | NM_003620 [CDS] | 5 | 9606 | 8493 | PPM1D | NM_003620.3 | | CDS | NGG | 5 | 1 | 1 | 5,20,100 | NC_000017.11 |
| 105 | NM_003620 [CDS] | 5 | 9606 | 8493 | PPM1D | NM_003620.3 | | CDS | NGG | 5 | 1 | 1 | 5,20,100 | NC_000017.11 |
| 106 | NM_003620 [CDS] | 5 | 9606 | 8493 | PPM1D | NM_003620.3 | | CDS | NGG | 5 | 1 | 1 | 5,20,100 | NC_000017.11 |
| 107 | NM_003620 [CDS] | 5 | 9606 | 8493 | PPM1D | NM_003620.3 | | CDS | NGG | 5 | 1 | 1 | 5,20,100 | NC_000017.11 |
| 108 | NM_003620 [CDS] | 5 | 9606 | 8493 | PPM1D | NM_003620.3 | | CDS | NGG | 5 | 1 | 1 | 5,20,100 | NC_000017.11 |
| 109 | NM_003620 [CDS] | 5 | 9606 | 8493 | PPM1D | NM_003620.3 | | CDS | NGG | 5 | 1 | 1 | 5,20,100 | NC_000017.11 |
| 110 | NM_003620 [CDS] | 5 | 9606 | 8493 | PPM1D | NM_003620.3 | | CDS | NGG | 5 | 1 | 1 | 5,20,100 | NC_000017.11 |
| 111 | NM_003620 [CDS] | 5 | 9606 | 8493 | PPM1D | NM_003620.3 | | CDS | NGG | 5 | 1 | 1 | 5,20,100 | NC_000017.11 |
| 112 | NM_003620 [CDS] | 5 | 9606 | 8493 | PPM1D | NM_003620.3 | | CDS | NGG | 5 | 1 | 1 | 5,20,100 | NC_000017.11 |
| 113 | NM_003620 [CDS] | 5 | 9606 | 8493 | PPM1D | NM_003620.3 | | CDS | NGG | 5 | 1 | 1 | 5,20,100 | NC_000017.11 |
| 114 | NM_003620 [CDS] | 5 | 9606 | 8493 | PPM1D | NM_003620.3 | | CDS | NGG | 5 | 1 | 1 | 5,20,100 | NC_000017.11 |
| 115 | NM_003620 [CDS] | 5 | 9606 | 8493 | PPM1D | NM_003620.3 | | CDS | NGG | 5 | 1 | 1 | 5,20,100 | NC_000017.11 |
| 116 | NM_003620 [CDS] | 5 | 9606 | 8493 | PPM1D | NM_003620.3 | | CDS | NGG | 5 | 1 | 1 | 5,20,100 | NC_000017.11 |
| 117 | NM_003620 [CDS] | 5 | 9606 | 8493 | PPM1D | NM_003620.3 | | CDS | NGG | 5 | 1 | 1 | 5,20,100 | NC_000017.11 |
| 118 | NM_003620 [CDS] | 5 | 9606 | 8493 | PPM1D | NM_003620.3 | | CDS | NGG | 5 | 1 | 1 | 5,20,100 | NC_000017.11 |
| 119 | NM_003620 [CDS] | 5 | 9606 | 8493 | PPM1D | NM_003620.3 | | CDS | NGG | 5 | 1 | 1 | 5,20,100 | NC_000017.11 |
| 120 | NM_003620 [CDS] | 5 | 9606 | 8493 | PPM1D | NM_003620.3 | | CDS | NGG | 5 | 1 | 1 | 5,20,100 | NC_000017.11 |
| 121 | NM_003620 [CDS] | 5 | 9606 | 8493 | PPM1D | NM_003620.3 | | CDS | NGG | 5 | 1 | 1 | 5,20,100 | NC_000017.11 |
| 122 | NM_003620 [CDS] | 5 | 9606 | 8493 | PPM1D | NM_003620.3 | | CDS | NGG | 5 | 1 | 1 | 5,20,100 | NC_000017.11 |
| 123 | NM_003620 [CDS] | 5 | 9606 | 8493 | PPM1D | NM_003620.3 | | CDS | NGG | 5 | 1 | 1 | 5,20,100 | NC_000017.11 |
| 124 | NM_003620 [CDS] | 5 | 9606 | 8493 | PPM1D | NM_003620.3 | | CDS | NGG | 5 | 1 | 1 | 5,20,100 | NC_000017.11 |
| 125 | NM_003620 [CDS] | 5 | 9606 | 8493 | PPM1D | NM_003620.3 | | CDS | NGG | 5 | 1 | 1 | 5,20,100 | NC_000017.11 |
| 126 | NM_003620 [CDS] | 5 | 9606 | 8493 | PPM1D | NM_003620.3 | | CDS | NGG | 5 | 1 | 1 | 5,20,100 | NC_000017.11 |
| 127 | NM_003620 [CDS] | 5 | 9606 | 8493 | PPM1D | NM_003620.3 | | CDS | NGG | 5 | 1 | 1 | 5,20,100 | NC_000017.11 |
| 128 | NM_003620 [CDS] | 5 | 9606 | 8493 | PPM1D | NM_003620.3 | | CDS | NGG | 5 | 1 | 1 | 5,20,100 | NC_000017.11 |
| 129 | NM_003620 [CDS] | 5 | 9606 | 8493 | PPM1D | NM_003620.3 | | CDS | NGG | 5 | 1 | 1 | 5,20,100 | NC_000017.11 |
| 130 | NM_003620 [CDS] | 5 | 9606 | 8493 | PPM1D | NM_003620.3 | | CDS | NGG | 5 | 1 | 1 | 5,20,100 | NC_000017.11 |
| 131 | NM_003620 [CDS] | 5 | 9606 | 8493 | PPM1D | NM_003620.3 | | CDS | NGG | 5 | 1 | 1 | 5,20,100 | NC_000017.11 |
| 132 | NM_003620 [CDS] | 5 | 9606 | 8493 | PPM1D | NM_003620.3 | | CDS | NGG | 5 | 1 | 1 | 5,20,100 | NC_000017.11 |
| 133 | NM_003620 [CDS] | 5 | 9606 | 8493 | PPM1D | NM_003620.3 | | CDS | NGG | 5 | 1 | 1 | 5,20,100 | NC_000017.11 |
| 134 | NM_003620 [CDS] | 5 | 9606 | 8493 | PPM1D | NM_003620.3 | | CDS | NGG | 5 | 1 | 1 | 5,20,100 | NC_000017.11 |
| 135 | NM_003620 [CDS] | 5 | 9606 | 8493 | PPM1D | NM_003620.3 | | CDS | NGG | 5 | 1 | 1 | 5,20,100 | NC_000017.11 |
| 136 | NM_003620 [CDS] | 5 | 9606 | 8493 | PPM1D | NM_003620.3 | | CDS | NGG | 5 | 1 | 1 | 5,20,100 | NC_000017.11 |

FIG. 12 (cont.)

| | Input | Quota | Target Taxon | Target Gene ID | Target Gene Symbol | Target Transcript | Custom Target Sequence Reference | Target Mode (GENE, TRANSCRIPT, CDS) | PAM Policy | Initial Spacing Requirement | Off-Target Match Ruleset Version | Off-Target Tier Policy | Off-Target Match Bin Policy | Genomic Sequence |
|---|---|---|---|---|---|---|---|---|---|---|---|---|---|---|
| 137 | NM_003620 [CDS] | 5 | 9606 | 8493 | PPM1D | NM_003620.3 | | CDS | NGG | 5 | | | 5,20,100 | NC_000017.11 |
| 138 | NM_003620 [CDS] | 5 | 9606 | 8493 | PPM1D | NM_003620.3 | | CDS | NGG | 5 | 1 | 1 | 5,20,100 | NC_000017.11 |
| 139 | NM_003620 [CDS] | 5 | 9606 | 8493 | PPM1D | NM_003620.3 | | CDS | NGG | 5 | 1 | | 5,20,100 | NC_000017.11 |
| 140 | NM_003620 [CDS] | 5 | 9606 | 8493 | PPM1D | NM_003620.3 | | CDS | NGG | 5 | 1 | | 5,20,100 | NC_000017.11 |
| 141 | NM_003620 [CDS] | 5 | 9606 | 8493 | PPM1D | NM_003620.3 | | CDS | NGG | 5 | 1 | 1 | 5,20,100 | NC_000017.11 |
| 142 | NM_003620 [CDS] | 5 | 9606 | 8493 | PPM1D | NM_003620.3 | | CDS | NGG | 5 | 1 | | 5,20,100 | NC_000017.11 |
| 143 | NM_003620 [CDS] | 5 | 9606 | 8493 | PPM1D | NM_003620.3 | | CDS | NGG | 5 | 1 | 1 | 5,20,100 | NC_000017.11 |
| 144 | NM_003620 [CDS] | 5 | 9606 | 8493 | PPM1D | NM_003620.3 | | CDS | NGG | 5 | 1 | | 5,20,100 | NC_000017.11 |
| 145 | NM_003620 [CDS] | 5 | 9606 | 8493 | PPM1D | NM_003620.3 | | CDS | NGG | 5 | 1 | 1 | 5,20,100 | NC_000017.11 |
| 146 | NM_003620 [CDS] | 5 | 9606 | 8493 | PPM1D | NM_003620.3 | | CDS | NGG | 5 | 1 | | 5,20,100 | NC_000017.11 |
| 147 | NM_003620 [CDS] | 5 | 9606 | 8493 | PPM1D | NM_003620.3 | | CDS | NGG | 5 | 1 | 1 | 5,20,100 | NC_000017.11 |
| 148 | NM_003620 [CDS] | 5 | 9606 | 8493 | PPM1D | NM_003620.3 | | CDS | NGG | 5 | 1 | | 5,20,100 | NC_000017.11 |
| 149 | NM_003620 [CDS] | 5 | 9606 | 8493 | PPM1D | NM_003620.3 | | CDS | NGG | 5 | 1 | 1 | 5,20,100 | NC_000017.11 |
| 150 | NM_003620 [CDS] | 5 | 9606 | 8493 | PPM1D | NM_003620.3 | | CDS | NGG | 5 | 1 | | 5,20,100 | NC_000017.11 |
| 151 | NM_003620 [CDS] | 5 | 9606 | 8493 | PPM1D | NM_003620.3 | | CDS | NGG | 5 | 1 | 1 | 5,20,100 | NC_000017.11 |
| 152 | NM_003620 [CDS] | 5 | 9606 | 8493 | PPM1D | NM_003620.3 | | CDS | NGG | 5 | 1 | 1 | 5,20,100 | NC_000017.11 |
| 153 | NM_003620 [CDS] | 5 | 9606 | 8493 | PPM1D | NM_003620.3 | | CDS | NGG | 5 | 1 | 1 | 5,20,100 | NC_000017.11 |
| 154 | NM_003620 [CDS] | 5 | 9606 | 8493 | PPM1D | NM_003620.3 | | CDS | NGG | 5 | 1 | 1 | 5,20,100 | NC_000017.11 |
| 155 | NM_003620 [CDS] | 5 | 9606 | 8493 | PPM1D | NM_003620.3 | | CDS | NGG | 5 | 1 | 1 | 5,20,100 | NC_000017.11 |
| 156 | NM_003620 [CDS] | 5 | 9606 | 8493 | PPM1D | NM_003620.3 | | CDS | NGG | 5 | 1 | 1 | 5,20,100 | NC_000017.11 |
| 157 | NM_003620 [CDS] | 5 | 9606 | 8493 | PPM1D | NM_003620.3 | | CDS | NGG | 5 | 1 | 1 | 5,20,100 | NC_000017.11 |
| 158 | NM_003620 [CDS] | 5 | 9606 | 8493 | PPM1D | NM_003620.3 | | CDS | NGG | 5 | 1 | 1 | 5,20,100 | NC_000017.11 |
| 159 | NM_003620 [CDS] | 5 | 9606 | 8493 | PPM1D | NM_003620.3 | | CDS | NGG | 5 | 1 | 1 | 5,20,100 | NC_000017.11 |
| 160 | NM_003620 [CDS] | 5 | 9606 | 8493 | PPM1D | NM_003620.3 | | CDS | NGG | 5 | 1 | 1 | 5,20,100 | NC_000017.11 |
| 161 | NM_003620 [CDS] | 5 | 9606 | 8493 | PPM1D | NM_003620.3 | | CDS | NGG | 5 | 1 | 1 | 5,20,100 | NC_000017.11 |
| 162 | NM_003620 [CDS] | 5 | 9606 | 8493 | PPM1D | NM_003620.3 | | CDS | NGG | 5 | 1 | 1 | 5,20,100 | NC_000017.11 |
| 163 | NM_003620 [CDS] | 5 | 9606 | 8493 | PPM1D | NM_003620.3 | | CDS | NGG | 5 | 1 | 1 | 5,20,100 | NC_000017.11 |
| 164 | NM_003620 [CDS] | 5 | 9606 | 8493 | PPM1D | NM_003620.3 | | CDS | NGG | 5 | 1 | 1 | 5,20,100 | NC_000017.11 |
| 165 | NM_003620 [CDS] | 5 | 9606 | 8493 | PPM1D | NM_003620.3 | | CDS | NGG | 5 | 1 | 1 | 5,20,100 | NC_000017.11 |
| 166 | NM_003620 [CDS] | 5 | 9606 | 8493 | PPM1D | NM_003620.3 | | CDS | NGG | 5 | 1 | 1 | 5,20,100 | NC_000017.11 |
| 167 | NM_003620 [CDS] | 5 | 9606 | 8493 | PPM1D | NM_003620.3 | | CDS | NGG | 5 | 1 | 1 | 5,20,100 | NC_000017.11 |
| 168 | NM_003620 [CDS] | 5 | 9606 | 8493 | PPM1D | NM_003620.3 | | CDS | NGG | 5 | 1 | 1 | 5,20,100 | NC_000017.11 |
| 169 | NM_003620 [CDS] | 5 | 9606 | 8493 | PPM1D | NM_003620.3 | | CDS | NGG | 5 | 1 | 1 | 5,20,100 | NC_000017.11 |

FIG. 12 (cont.)

| | Input | Quota | Target Taxon | Target Gene ID | Target Gene Symbol | Target Transcript | Custom Target Sequence Reference | Target Mode (GENE, TRANSCRIPT, CDS) | PAM Policy | Initial Spacing Requirement | Off-Target Match Ruleset Version | Off-Target Tier Policy | Off-Target Match Bin Policy | Genomic Sequence |
|---|---|---|---|---|---|---|---|---|---|---|---|---|---|---|
| 170 | NM_003620 [CDS] | 5 | 9606 | 8493 | PPM1D | NM_003620.3 | | CDS | NGG | 5 | 1 | 1 | 5,20,100 | NC_000017.11 |
| 171 | NM_003620 [CDS] | 5 | 9606 | 8493 | PPM1D | NM_003620.3 | | CDS | NGG | 5 | 1 | 1 | 5,20,100 | NC_000017.11 |
| 172 | NM_003620 [CDS] | 5 | 9606 | 8493 | PPM1D | NM_003620.3 | | CDS | NGG | 5 | 1 | 1 | 5,20,100 | NC_000017.11 |
| 173 | NM_003620 [CDS] | 5 | 9606 | 8493 | PPM1D | NM_003620.3 | | CDS | NGG | 5 | 1 | 1 | 5,20,100 | NC_000017.11 |
| 174 | NM_003620 [CDS] | 5 | 9606 | 8493 | PPM1D | NM_003620.3 | | CDS | NGG | 5 | 1 | 1 | 5,20,100 | NC_000017.11 |
| 175 | NM_003620 [CDS] | 5 | 9606 | 8493 | PPM1D | NM_003620.3 | | CDS | NGG | 5 | 1 | 1 | 5,20,100 | NC_000017.11 |
| 176 | NM_003620 [CDS] | 5 | 9606 | 8493 | PPM1D | NM_003620.3 | | CDS | NGG | 5 | 1 | 1 | 5,20,100 | NC_000017.11 |
| 177 | NM_003620 [CDS] | 5 | 9606 | 8493 | PPM1D | NM_003620.3 | | CDS | NGG | 5 | 1 | 1 | 5,20,100 | NC_000017.11 |
| 178 | NM_003620 [CDS] | 5 | 9606 | 8493 | PPM1D | NM_003620.3 | | CDS | NGG | 5 | 1 | 1 | 5,20,100 | NC_000017.11 |
| 179 | NM_003620 [CDS] | 5 | 9606 | 8493 | PPM1D | NM_003620.3 | | CDS | NGG | 5 | 1 | 1 | 5,20,100 | NC_000017.11 |
| 180 | NM_003620 [CDS] | 5 | 9606 | 8493 | PPM1D | NM_003620.3 | | CDS | NGG | 5 | 1 | 1 | 5,20,100 | NC_000017.11 |
| 181 | NM_003620 [CDS] | 5 | 9606 | 8493 | PPM1D | NM_003620.3 | | CDS | NGG | 5 | 1 | 1 | 5,20,100 | NC_000017.11 |
| 182 | NM_003620 [CDS] | 5 | 9606 | 8493 | PPM1D | NM_003620.3 | | CDS | NGG | 5 | 1 | 1 | 5,20,100 | NC_000017.11 |
| 183 | NM_003620 [CDS] | 5 | 9606 | 8493 | PPM1D | NM_003620.3 | | CDS | NGG | 5 | 1 | 1 | 5,20,100 | NC_000017.11 |
| 184 | NM_003620 [CDS] | 5 | 9606 | 8493 | PPM1D | NM_003620.3 | | CDS | NGG | 5 | 1 | 1 | 5,20,100 | NC_000017.11 |
| 185 | NM_003620 [CDS] | 5 | 9606 | 8493 | PPM1D | NM_003620.3 | | CDS | NGG | 5 | 1 | 1 | 5,20,100 | NC_000017.11 |
| 186 | NM_003620 [CDS] | 5 | 9606 | 8493 | PPM1D | NM_003620.3 | | CDS | NGG | 5 | 1 | 1 | 5,20,100 | NC_000017.11 |
| 187 | NM_003620 [CDS] | 5 | 9606 | 8493 | PPM1D | NM_003620.3 | | CDS | NGG | 5 | 1 | 1 | 5,20,100 | NC_000017.11 |
| 188 | NM_003620 [CDS] | 5 | 9606 | 8493 | PPM1D | NM_003620.3 | | CDS | NGG | 5 | 1 | 1 | 5,20,100 | NC_000017.11 |
| 189 | NM_003620 [CDS] | 5 | 9606 | 8493 | PPM1D | NM_003620.3 | | CDS | NGG | 5 | 1 | 1 | 5,20,100 | NC_000017.11 |
| 190 | NM_003620 [CDS] | 5 | 9606 | 8493 | PPM1D | NM_003620.3 | | CDS | NGG | 5 | 1 | 1 | 5,20,100 | NC_000017.11 |
| 191 | NM_003620 [CDS] | 5 | 9606 | 8493 | PPM1D | NM_003620.3 | | CDS | NGG | 5 | 1 | 1 | 5,20,100 | NC_000017.11 |
| 192 | NM_003620 [CDS] | 5 | 9606 | 8493 | PPM1D | NM_003620.3 | | CDS | NGG | 5 | 1 | 1 | 5,20,100 | NC_000017.11 |
| 193 | NM_003620 [CDS] | 5 | 9606 | 8493 | PPM1D | NM_003620.3 | | CDS | NGG | 5 | 1 | 1 | 5,20,100 | NC_000017.11 |
| 194 | NM_003620 [CDS] | 5 | 9606 | 8493 | PPM1D | NM_003620.3 | | CDS | NGG | 5 | 1 | 1 | 5,20,100 | NC_000017.11 |
| 195 | NM_003620 [CDS] | 5 | 9606 | 8493 | PPM1D | NM_003620.3 | | CDS | NGG | 5 | 1 | 1 | 5,20,100 | NC_000017.11 |
| 196 | NM_003620 [CDS] | 5 | 9606 | 8493 | PPM1D | NM_003620.3 | | CDS | NGG | 5 | 1 | 1 | 5,20,100 | NC_000017.11 |
| 197 | NM_003620 [CDS] | 5 | 9606 | 8493 | PPM1D | NM_003620.3 | | CDS | NGG | 5 | 1 | 1 | 5,20,100 | NC_000017.11 |
| 198 | NM_003620 [CDS] | 5 | 9606 | 8493 | PPM1D | NM_003620.3 | | CDS | NGG | 5 | 1 | 1 | 5,20,100 | NC_000017.11 |
| 199 | NM_003620 [CDS] | 5 | 9606 | 8493 | PPM1D | NM_003620.3 | | CDS | NGG | 5 | 1 | 1 | 5,20,100 | NC_000017.11 |
| 200 | NM_003620 [CDS] | 5 | 9606 | 8493 | PPM1D | NM_003620.3 | | CDS | NGG | 5 | 1 | 1 | 5,20,100 | NC_000017.11 |
| 201 | NM_003620 [CDS] | 5 | 9606 | 8493 | PPM1D | NM_003620.3 | | CDS | NGG | 5 | 1 | 1 | 5,20,100 | NC_000017.11 |
| 202 | NM_003620 [CDS] | 5 | 9606 | 8493 | PPM1D | NM_003620.3 | | CDS | NGG | 5 | 1 | 1 | 5,20,100 | NC_000017.11 |
| 203 | NM_003620 [CDS] | 5 | 9606 | 8493 | PPM1D | NM_003620.3 | | CDS | NGG | 5 | 1 | 1 | 5,20,100 | NC_000017.11 |

FIG. 12 (cont.)

| | Input | Quota | Target Taxon | Target Gene ID | Target Gene Symbol | Target Transcript | Custom Target Sequence Reference | Target Mode (GENE, TRANSCRIPT, CDS) | PAM Policy | Initial Spacing Requirement | Off-Target Match Ruleset Version | Off-Target Tier Policy | Off-Target Match Bin Policy | Genomic Sequence |
|---|---|---|---|---|---|---|---|---|---|---|---|---|---|---|
| 204 | NM_003620 [CDS] | 5 | 9606 | 8493 | PPM1D | NM_003620.3 | | CDS | NGG | 5 | 1 | 1 | 5,20,100 | NC_000017.11 |
| 205 | NM_003620 [CDS] | 5 | 9606 | 8493 | PPM1D | NM_003620.3 | | CDS | NGG | 5 | 1 | 1 | 5,20,100 | NC_000017.11 |
| 206 | NM_003620 [CDS] | 5 | 9606 | 8493 | PPM1D | NM_003620.3 | | CDS | NGG | 5 | 1 | 1 | 5,20,100 | NC_000017.11 |
| 207 | NM_003620 [CDS] | 5 | 9606 | 8493 | PPM1D | NM_003620.3 | | CDS | NGG | 5 | 1 | 1 | 5,20,100 | NC_000017.11 |
| 208 | NM_003620 [CDS] | 5 | 9606 | 8493 | PPM1D | NM_003620.3 | | CDS | NGG | 5 | 1 | 1 | 5,20,100 | NC_000017.11 |
| 209 | NM_003620 [CDS] | 5 | 9606 | 8493 | PPM1D | NM_003620.3 | | CDS | NGG | 5 | 1 | 1 | 5,20,100 | NC_000017.11 |
| 210 | NM_003620 [CDS] | 5 | 9606 | 8493 | PPM1D | NM_003620.3 | | CDS | NGG | 5 | 1 | 1 | 5,20,100 | NC_000017.11 |
| 211 | NM_003620 [CDS] | 5 | 9606 | 8493 | PPM1D | NM_003620.3 | | CDS | NGG | 5 | 1 | 1 | 5,20,100 | NC_000017.11 |
| 212 | NM_003620 [CDS] | 5 | 9606 | 8493 | PPM1D | NM_003620.3 | | CDS | NGG | 5 | 1 | 1 | 5,20,100 | NC_000017.11 |
| 213 | NM_003620 [CDS] | 5 | 9606 | 8493 | PPM1D | NM_003620.3 | | CDS | NGG | 5 | 1 | 1 | 5,20,100 | NC_000017.11 |
| 214 | NM_003620 [CDS] | 5 | 9606 | 8493 | PPM1D | NM_003620.3 | | CDS | NGG | 5 | 1 | 1 | 5,20,100 | NC_000017.11 |
| 215 | NM_003620 [CDS] | 5 | 9606 | 8493 | PPM1D | NM_003620.3 | | CDS | NGG | 5 | 1 | 1 | 5,20,100 | NC_000017.11 |
| 216 | NM_003620 [CDS] | 5 | 9606 | 8493 | PPM1D | NM_003620.3 | | CDS | NGG | 5 | 1 | 1 | 5,20,100 | NC_000017.11 |
| 217 | NM_003620 [CDS] | 5 | 9606 | 8493 | PPM1D | NM_003620.3 | | CDS | NGG | 5 | 1 | 1 | 5,20,100 | NC_000017.11 |
| 218 | NM_003620 [CDS] | 5 | 9606 | 8493 | PPM1D | NM_003620.3 | | CDS | NGG | 5 | 1 | 1 | 5,20,100 | NC_000017.11 |
| 219 | NM_003620 [CDS] | 5 | 9606 | 8493 | PPM1D | NM_003620.3 | | CDS | NGG | 5 | 1 | 1 | 5,20,100 | NC_000017.11 |
| 220 | NM_003620 [CDS] | 5 | 9606 | 8493 | PPM1D | NM_003620.3 | | CDS | NGG | 5 | 1 | 1 | 5,20,100 | NC_000017.11 |
| 221 | NM_003620 [CDS] | 5 | 9606 | 8493 | PPM1D | NM_003620.3 | | CDS | NGG | 5 | 1 | 1 | 5,20,100 | NC_000017.11 |
| 222 | NM_003620 [CDS] | 5 | 9606 | 8493 | PPM1D | NM_003620.3 | | CDS | NGG | 5 | 1 | 1 | 5,20,100 | NC_000017.11 |
| 223 | NM_003620 [CDS] | 5 | 9606 | 8493 | PPM1D | NM_003620.3 | | CDS | NGG | 5 | 1 | 1 | 5,20,100 | NC_000017.11 |
| 224 | NM_003620 [CDS] | 5 | 9606 | 8493 | PPM1D | NM_003620.3 | | CDS | NGG | 5 | 1 | 1 | 5,20,100 | NC_000017.11 |
| 225 | NM_003620 [CDS] | 5 | 9606 | 8493 | PPM1D | NM_003620.3 | | CDS | NGG | 5 | 1 | 1 | 5,20,100 | NC_000017.11 |
| 226 | NM_003620 [CDS] | 5 | 9606 | 8493 | PPM1D | NM_003620.3 | | CDS | NGG | 5 | 1 | 1 | 5,20,100 | NC_000017.11 |
| 227 | NM_003620 [CDS] | 5 | 9606 | 8493 | PPM1D | NM_003620.3 | | CDS | NGG | 5 | 1 | 1 | 5,20,100 | NC_000017.11 |
| 228 | NM_003620 [CDS] | 5 | 9606 | 8493 | PPM1D | NM_003620.3 | | CDS | NGG | 5 | 1 | 1 | 5,20,100 | NC_000017.11 |
| 229 | NM_003620 [CDS] | 5 | 9606 | 8493 | PPM1D | NM_003620.3 | | CDS | NGG | 5 | 1 | 1 | 5,20,100 | NC_000017.11 |
| 230 | NM_003620 [CDS] | 5 | 9606 | 8493 | PPM1D | NM_003620.3 | | CDS | NGG | 5 | 1 | 1 | 5,20,100 | NC_000017.11 |
| 231 | NM_003620 [CDS] | 5 | 9606 | 8493 | PPM1D | NM_003620.3 | | CDS | NGG | 5 | 1 | 1 | 5,20,100 | NC_000017.11 |
| 232 | NM_003620 [CDS] | 5 | 9606 | 8493 | PPM1D | NM_003620.3 | | CDS | NGG | 5 | 1 | 1 | 5,20,100 | NC_000017.11 |
| 233 | NM_003620 [CDS] | 5 | 9606 | 8493 | PPM1D | NM_003620.3 | | CDS | NGG | 5 | 1 | 1 | 5,20,100 | NC_000017.11 |
| 234 | NM_003620 [CDS] | 5 | 9606 | 8493 | PPM1D | NM_003620.3 | | CDS | NGG | 5 | 1 | 1 | 5,20,100 | NC_000017.11 |
| 235 | NM_003620 [CDS] | 5 | 9606 | 8493 | PPM1D | NM_003620.3 | | CDS | NGG | 5 | 1 | 1 | 5,20,100 | NC_000017.11 |
| 236 | NM_003620 [CDS] | 5 | 9606 | 8493 | PPM1D | NM_003620.3 | | CDS | NGG | 5 | 1 | 1 | 5,20,100 | NC_000017.11 |
| 237 | NM_003620 [CDS] | 5 | 9606 | 8493 | PPM1D | NM_003620.3 | | CDS | NGG | 5 | 1 | 1 | 5,20,100 | NC_000017.11 |

FIG. 12 (cont.)

| | Input | Quota | Target Taxon | Target Gene ID | Target Gene Symbol | Target Transcript | Custom Target Sequence Reference | Target Mode (GENE, TRANSCRIPT, CDS) | PAM Policy | Initial Spacing Requirement | Off-Target Match Ruleset Version | Off-Target Tier Policy | Off-Target Match Bin Policy | Genomic Sequence |
|---|---|---|---|---|---|---|---|---|---|---|---|---|---|---|
| 238 | NM_003620 [CDS] | 5 | 9606 | 8493 | PPM1D | NM_003620.3 | | CDS | NGG | 5 | 1 | 1 | 5.20.100 | NC_000017.11 |
| 239 | NM_003620 [CDS] | 5 | 9606 | 8493 | PPM1D | NM_003620.3 | | CDS | NGG | 5 | 1 | 1 | 5.20.100 | NC_000017.11 |
| 240 | NM_003620 [CDS] | 5 | 9606 | 8493 | PPM1D | NM_003620.3 | | CDS | NGG | 5 | 1 | 1 | 5.20.100 | NC_000017.11 |
| 241 | NM_003620 [CDS] | 5 | 9606 | 8493 | PPM1D | NM_003620.3 | | CDS | NGG | 5 | 1 | 1 | 5.20.100 | NC_000017.11 |
| 242 | NM_003620 [CDS] | 5 | 9606 | 8493 | PPM1D | NM_003620.3 | | CDS | NGG | 5 | 1 | 1 | 5.20.100 | NC_000017.11 |
| 243 | NM_003620 [CDS] | 5 | 9606 | 8493 | PPM1D | NM_003620.3 | | CDS | NGG | 5 | 1 | 1 | 5.20.100 | NC_000017.11 |
| 244 | NM_003620 [CDS] | 5 | 9606 | 8493 | PPM1D | NM_003620.3 | | CDS | NGG | 5 | 1 | 1 | 5.20.100 | NC_000017.11 |
| 245 | NM_003620 [CDS] | 5 | 9606 | 8493 | PPM1D | NM_003620.3 | | CDS | NGG | 5 | 1 | 1 | 5.20.100 | NC_000017.11 |
| 246 | NM_003620 [CDS] | 5 | 9606 | 8493 | PPM1D | NM_003620.3 | | CDS | NGG | 5 | 1 | 1 | 5.20.100 | NC_000017.11 |
| 247 | NM_003620 [CDS] | 5 | 9606 | 8493 | PPM1D | NM_003620.3 | | CDS | NGG | 5 | 1 | 1 | 5.20.100 | NC_000017.11 |
| 248 | NM_003620 [CDS] | 5 | 9606 | 8493 | PPM1D | NM_003620.3 | | CDS | NGG | 5 | 1 | 1 | 5.20.100 | NC_000017.11 |
| 249 | NM_003620 [CDS] | 5 | 9606 | 8493 | PPM1D | NM_003620.3 | | CDS | NGG | 5 | 1 | 1 | 5.20.100 | NC_000017.11 |
| 250 | NM_003620 [CDS] | 5 | 9606 | 8493 | PPM1D | NM_003620.3 | | CDS | NGG | 5 | 1 | 1 | 5.20.100 | NC_000017.11 |
| 251 | NM_003620 [CDS] | 5 | 9606 | 8493 | PPM1D | NM_003620.3 | | CDS | NGG | 5 | 1 | 1 | 5.20.100 | NC_000017.11 |
| 252 | NM_003620 [CDS] | 5 | 9606 | 8493 | PPM1D | NM_003620.3 | | CDS | NGG | 5 | 1 | 1 | 5.20.100 | NC_000017.11 |
| 253 | NM_003620 [CDS] | 5 | 9606 | 8493 | PPM1D | NM_003620.3 | | CDS | NGG | 5 | 1 | 1 | 5.20.100 | NC_000017.11 |
| 254 | NM_003620 [CDS] | 5 | 9606 | 8493 | PPM1D | NM_003620.3 | | CDS | NGG | 5 | 1 | 1 | 5.20.100 | NC_000017.11 |
| 255 | NM_003620 [CDS] | 5 | 9606 | 8493 | PPM1D | NM_003620.3 | | CDS | NGG | 5 | 1 | 1 | 5.20.100 | NC_000017.11 |
| 256 | NM_003620 [CDS] | 5 | 9606 | 8493 | PPM1D | NM_003620.3 | | CDS | NGG | 5 | 1 | 1 | 5.20.100 | NC_000017.11 |
| 257 | NM_003620 [CDS] | 5 | 9606 | 8493 | PPM1D | NM_003620.3 | | CDS | NGG | 5 | 1 | 1 | 5.20.100 | NC_000017.11 |
| 258 | NM_003620 [CDS] | 5 | 9606 | 8493 | PPM1D | NM_003620.3 | | CDS | NGG | 5 | 1 | 1 | 5.20.100 | NC_000017.11 |
| 259 | NM_003620 [CDS] | 5 | 9606 | 8493 | PPM1D | NM_003620.3 | | CDS | NGG | 5 | 1 | 1 | 5.20.100 | NC_000017.11 |
| 260 | NM_003620 [CDS] | 5 | 9606 | 8493 | PPM1D | NM_003620.3 | | CDS | NGG | 5 | 1 | 1 | 5.20.100 | NC_000017.11 |
| 261 | NM_003620 [CDS] | 5 | 9606 | 8493 | PPM1D | NM_003620.3 | | CDS | NGG | 5 | 1 | 1 | 5.20.100 | NC_000017.11 |
| 262 | NM_003620 [CDS] | 5 | 9606 | 8493 | PPM1D | NM_003620.3 | | CDS | NGG | 5 | 1 | 1 | 5.20.100 | NC_000017.11 |
| 263 | NM_003620 [CDS] | 5 | 9606 | 8493 | PPM1D | NM_003620.3 | | CDS | NGG | 5 | 1 | 1 | 5.20.100 | NC_000017.11 |
| 264 | NM_003620 [CDS] | 5 | 9606 | 8493 | PPM1D | NM_003620.3 | | CDS | NGG | 5 | 1 | 1 | 5.20.100 | NC_000017.11 |
| 265 | NM_003620 [CDS] | 5 | 9606 | 8493 | PPM1D | NM_003620.3 | | CDS | NGG | 5 | 1 | 1 | 5.20.100 | NC_000017.11 |

FIG. 12 (cont.)

| Position of Base After Cut (1-based) | Strand | sgRNA Target Sequence | Target Context Sequence | PAM Sequence | Exon Number | Target Concat Cut Length | Target Concat Total Length | Target Concat Cut % | # Off-Target Tier I Match Bin I Matches | # Off-Target Tier II Match Bin I Matches |
|---|---|---|---|---|---|---|---|---|---|---|
| 1 | 60600415 | antisense | GAGTACAGCCCCGCCATGGC | CAGCGAGTACAGCCCCGCCATGGCCGGCTG | CGG | 1 | 1 | 1818 | 0.1 | 0 | 0 |
| 2 | 60600416 | sense | TCCCGGCCAGCCGGCCATGG | GGGATCCCGGCCAGCCGGCCATGGCGGGGC | CGG | 1 | 2 | 1818 | 0.1 | 0 | 0 |
| 3 | 60600417 | sense | CCCGGCCAGCCGGCCATGGC | GGATCCCGGCCAGCCGGCCATGGCGGGGCT | GGG | 1 | 3 | 1818 | 0.2 | 0 | 0 |
| 4 | 60600418 | sense | CCGGCCAGCCGGCCATGGCG | GATCCCGGCCAGCCGGCCATGGCGGGGCTG | GGG | 1 | 4 | 1818 | 0.2 | 0 | 0 |
| 5 | 60600419 | antisense | CAGCGAGTACAGCCCCGCCA | CTCCCAGCGAGTACAGCCCCGCCATGGCCA | TGG | 1 | 5 | 1818 | 0.3 | 0 | 0 |
| 6 | 60600431 | sense | CATGGCGGGGCTGTACTCGC | CGGCCATGGCGGGGCTGTACTCGCTGGGAG | TGG | 1 | 17 | 1818 | 0.9 | 0 | 0 |
| 7 | 60600432 | sense | ATGGCGGGGCTGTACTCGCT | GGCCATGGCGGGGCTGTACTCGCTGGGAGT | GGG | 1 | 18 | 1818 | 1 | 0 | 0 |
| 8 | 60600455 | sense | AGTGAGCGTCTTCTCCGACC | TGGGAGTGAGCGTCTTCTCCGACCAGGGCG | AGG | 1 | 41 | 1818 | 2.3 | 0 | 0 |
| 9 | 60600456 | sense | GTGAGCGTCTTCTCCGACCA | GGGAGTGAGCGTCTTCTCCGACCAGGGCGG | GGG | 1 | 42 | 1818 | 2.3 | 0 | 0 |
| 10 | 60600458 | antisense | GTACTTCCTCCCGCCCTGGT | CCATGTACTTCCTCCCGCCCTGGTCGGAGA | CGG | 1 | 44 | 1818 | 2.4 | 0 | 0 |
| 11 | 60600459 | sense | AGCGTCTTCTCCGACCAGGG | AGTGAGCGTCTTCTCCGACCAGGGCGGGAG | CGG | 1 | 45 | 1818 | 2.5 | 0 | 0 |
| 12 | 60600460 | sense | GCGTCTTCTCCGACCAGGGC | GTGAGCGTCTTCTCCGACCAGGGCGGGAGG | GGG | 1 | 46 | 1818 | 2.5 | 0 | 0 |
| 13 | 60600462 | antisense | CCATGTACTTCCTCCCGCCC | TCCTCCATGTACTTCCTCCCGCCCTGGTCG | TGG | 1 | 48 | 1818 | 2.6 | 0 | 0 |
| 14 | 60600463 | sense | TCTTCTCCGACCAGGGCGGG | AGCGTCTTCTCCGACCAGGGCGGGAGGAAG | AGG | 1 | 49 | 1818 | 2.7 | 0 | 0 |
| 15 | 60600473 | sense | CCAGGGCGGGAGGAAGTACA | CCGACCAGGGCGGGAGGAAGTACATGGAGG | TGG | 1 | 59 | 1818 | 3.2 | 0 | 0 |
| 16 | 60600476 | sense | GGGCGGGAGGAAGTACATGG | ACCAGGGCGGGAGGAAGTACATGGAGGACG | AGG | 1 | 62 | 1818 | 3.4 | 0 | 0 |
| 17 | 60600497 | sense | GGACGTTACTCAAATCGTTG | TGGAGGACGTTACTCAAATCGTTGTGGAGC | TGG | 1 | 83 | 1818 | 4.6 | 0 | 0 |
| 18 | 60600511 | antisense | TTTTCTTCAGCCGTCGGTTC | GGGCTTTTCTTCAGCCGTCGGTTCGGGCTC | GGG | 1 | 97 | 1818 | 5.3 | 0 | 0 |
| 19 | 60600512 | sense | CGTTGTGGAGCCCGAACCGA | AAATCGTTGTGGAGCCCGAACCGACGGCTG | GGG | 1 | 98 | 1818 | 5.4 | 0 | 0 |
| 20 | 60600512 | antisense | CTTTTCTTCAGCCGTCGGTT | AGGGCTTTTCTTCAGCCGTCGGTTCGGGCT | CGG | 1 | 98 | 1818 | 5.4 | 0 | 0 |
| 21 | 60600517 | sense | GAGGGCTTTTCTTCAGCCGT | CGGGGAGGGCTTTTCTTCAGCCGTCGGTTC | AGG | 1 | 103 | 1818 | 5.7 | 0 | 0 |
| 22 | 60600535 | sense | CTGAAGAAAAGCCCTCGCCG | ACGGCTGAAGAAAAGCCCTCGCCGGCGGCG | CGG | 1 | 121 | 1818 | 6.7 | 0 | 0 |
| 23 | 60600535 | antisense | GACAGCGACCGCGCGGCGCA | CTGAGACAGCGACCGCGCGGCGCAGAGGCTT | GGG | 1 | 121 | 1818 | 6.7 | 0 | 0 |
| 24 | 60600536 | antisense | AGACAGCGACCGCGCGGCGC | GCTGAGACAGCGACCGCGCGGCGCGAGGGCT | AGG | 1 | 122 | 1818 | 6.7 | 0 | 0 |
| 25 | 60600538 | sense | AAGAAAAGCCCTCGCCGGCG | GCTGAAGAAAAGCCCTCGCCGCGCGTCG | CGG | 1 | 124 | 1818 | 6.8 | 0 | 0 |
| 26 | 60600541 | antisense | GGCTGAGACAGCGACCGCGC | CAACGGCTGAGACAGCGACCGCGCGGCGCA | CGG | 1 | 127 | 1818 | 7 | 0 | 0 |
| 27 | 60600562 | antisense | GGCGACGGCGCGGAGGCAA | GGCCGGCGACGGCCGTTGCCTCCGCGGCTG | CGG | 1 | 148 | 1818 | 8.1 | 0 | 0 |
| 28 | 60600565 | sense | TGTCTCAGCCGTTGCCTCCG | TCGGTGTCTCAGCCGTTGCCTCCGCGGCCG | CGG | 1 | 151 | 1818 | 8.3 | 0 | 0 |
| 29 | 60600568 | sense | GCGCCGGCGACGGCCTGGCAA | AAGGGCGCCGGCGACGGCCGGAGGCAA | AGG | 1 | 154 | 1818 | 8.5 | 0 | 0 |
| 30 | 60600571 | sense | AGGGGCGCCGGCGACGGCCG | GGGAAGGGCGCCGGCGACGGCCGCGAGG | CGG | 1 | 157 | 1818 | 8.6 | 0 | 0 |
| 31 | 60600575 | sense | GTTGCCTCCGCGGCCGTGC | AGCCGTTGCCTCCGCGGCCGTGCGCCGGCCG | CGG | 1 | 161 | 1818 | 8.9 | 0 | 0 |
| 32 | 60600577 | antisense | CCGGAAGGGCGCCGGCGACG | GCCCGGGAAGGGCGCCGGCGACGGCCGA | CGG | 1 | 163 | 1818 | 9 | 0 | 0 |
| 33 | 60600583 | antisense | TCGCGCCGGAAGGGCGCCGG | GACTTCGCCGGAAGGGCGCCGGCGACGGA | CGG | 1 | 169 | 1818 | 9.3 | 0 | 1 |
| 34 | 60600587 | antisense | GACTTCGCCCGGGAAGGG | CCGAGACTTCGCCGCGCGGGAAGGGGCCG | CGG | 1 | 173 | 1818 | 9.5 | 0 | 0 |

FIG. 12 (cont.)

| | Position of Base After Cut (1-based) | Strand | sgRNA Target Sequence | Target Context Sequence | PAM Sequence | Exon Number | Target Concat Cut Length | Target Concat Total Length | Target Concat Cut % | # Off-Target Tier I Match Bin I Matches | # Off-Target Tier II Match Bin I Matches |
|---|---|---|---|---|---|---|---|---|---|---|---|
| 35 | 60600588 | sense | CCGTCGCGCGGCGCCCTTCC | GCGGCCGTCGCGCGGCGCCCTTCCCGGCGG | CGG | 1 | 174 | 1818 | 9.6 | 0 | 0 |
| 36 | 60600590 | antisense | CGAGACTTCGCCGCCGCGGGAA | TCCCCGAGACTTCGCCGCCGCGGGAAGGGCGG | GGG | 1 | 176 | 1818 | 9.7 | 0 | 0 |
| 37 | 60600591 | antisense | CCGAGACTTCGCCGCCGGGGA | TTCCCCGAGACTTCGCCGCCGGGGAAGGGCG | AGG | 1 | 177 | 1818 | 9.7 | 0 | 0 |
| 38 | 60600591 | sense | TCGCGGCCGCGCCCTTCCCGG | GCCGTCGCGGCCGCGCCCTTCCCGGCGGCGA | CGG | 1 | 177 | 1818 | 9.7 | 0 | 0 |
| 39 | 60600595 | antisense | TTCCCCGAGACTTCGCGCGC | GCCTTTCCCCGAGACTTCGCGCGCGGGAAG | GGG | 1 | 181 | 1818 | 10 | 0 | 0 |
| 40 | 60600596 | antisense | TTTCCCCGAGACTTCGCGCGC | GGCCTTTCCCCGAGACTTCGCGCGCGGGAA | CGG | 1 | 182 | 1818 | 10 | 0 | 0 |
| 41 | 60600602 | sense | CCTTCCCGGCGGCGAAGTCT | CCGCCCTTCCCGGCGGCGAAGTCTCGGGGA | CGG | 1 | 188 | 1818 | 10.3 | 0 | 0 |
| 42 | 60600603 | sense | CTTCCCGGCGGCGAAGTCTC | CGCCCTTCCCGGCGGCGAAGTCTCGGGGAA | CGG | 1 | 189 | 1818 | 10.4 | 0 | 0 |
| 43 | 60600604 | sense | TTCCCGGCGGCGAAGTCTCG | GCCCTTCCCGGCGGCGAAGTCTCGGGGAAA | GGG | 1 | 190 | 1818 | 10.5 | 0 | 0 |
| 44 | 60600609 | sense | GGCGGCGAAGTCTCGGGGAA | TCCCGGCGGCGAAGTCTCGGGGAAAGGCCC | AGG | 1 | 195 | 1818 | 10.7 | 0 | 0 |
| 45 | 60600617 | sense | AGTCTCGGGGAAAGGCCCAG | GCGAAGTCTCGGGGAAAGGCCCAGCGGTGG | CGG | 1 | 203 | 1818 | 11.2 | 0 | 3 |
| 46 | 60600620 | sense | CTCGGGGAAAGGCCCAGCGG | AAGTCTCGGGGAAAGGCCCAGCGGTGCAG | TGG | 1 | 206 | 1818 | 11.3 | 0 | 0 |
| 47 | 60600621 | antisense | CCTCTCGGGCTGCCACCGCT | CGAGCCTCTCGGGCTGCCACCGCTGGGCT | GGG | 1 | 207 | 1818 | 11.4 | 0 | 1 |
| 48 | 60600622 | antisense | GCCTCTCGGGCTGCCACCGC | GCGAGCCTCTCGGGCTGCCACCGCTGGGCC | TGG | 1 | 208 | 1818 | 11.4 | 0 | 0 |
| 49 | 60600632 | sense | CCAGCGGTGGCAGCCCGAG | AAGGCCCAGCGGTGGCAGCCCGAGAGGCTC | AGG | 1 | 218 | 1818 | 12 | 0 | 0 |
| 50 | 60600635 | antisense | GAGAGGGTCGCGAGCCTCTC | CCGGAGAGGGTCGCGAGCCTCTCGGGCTG | GGG | 1 | 221 | 1818 | 12.2 | 0 | 0 |
| 51 | 60600636 | antisense | GGAGAGGGTCGCGAGCCTCT | TCCGGAGAGGGTCGCGAGCCTCTCGGGCT | CGG | 1 | 222 | 1818 | 12.2 | 0 | 0 |
| 52 | 60600650 | sense | AGAGGCTCGCGACCCTCTCC | CCCGAGAGGCTCGCGACCCTCTCCGGACG | CGG | 1 | 236 | 1818 | 13 | 0 | 0 |
| 53 | 60600651 | antisense | AGGCCCCGGCGTCCGGAGA | GGGAGGCCCCGGCGTCCGGAGAGGGTCG | GGG | 1 | 237 | 1818 | 13 | 0 | 0 |
| 54 | 60600652 | antisense | GAGGCCCCGGCGTCCGGAGAG | CGGGAGGCCCCGGCGTCCGGAGAGGGTC | AGG | 1 | 238 | 1818 | 13.1 | 0 | 0 |
| 55 | 60600657 | sense | CGGCGACCCTCTCCGGACGC | GGGTCGCGACCCTCTCCGGACGCGGGGCC | CGG | 1 | 243 | 1818 | 13.4 | 0 | 0 |
| 56 | 60600657 | antisense | CCGCGAGGCCCGGCGTCC | GGTGCCGGCGAGGCCCGGCGTCCGGAGA | GGG | 1 | 243 | 1818 | 13.4 | 0 | 0 |
| 57 | 60600658 | sense | GCGACCCTCTCCGGACGCC | GCTCGCGACCCTCTCCGGACGCCGGCC | CGG | 1 | 244 | 1818 | 13.4 | 0 | 0 |
| 58 | 60600658 | antisense | GCCGCGAGGCCCGGCGTC | AGGTGCCGCGAGGCCCGGCGTCCGGGAG | CGG | 1 | 244 | 1818 | 13.4 | 0 | 0 |
| 59 | 60600659 | sense | CGACCCTCTCCGGACGCCG | CTCGCGACCCTCTCCGGACGCCGGGGCCT | CGG | 1 | 245 | 1818 | 13.5 | 0 | 0 |
| 60 | 60600665 | antisense | GCTAGGTGCCGCGAGGCCC | AGCGGCTAGGTGCCGCGAGGCCCGGCGT | CGG | 1 | 251 | 1818 | 13.8 | 0 | 0 |
| 61 | 60600668 | sense | CCCGGACGCGGGGCCTCGC | CTCGCGGACGCGGGGCCTCGCCGGCAC | CGG | 1 | 254 | 1818 | 14 | 0 | 0 |
| 62 | 60600671 | antisense | GCAGCGGCTAGGTGCCGTGC | GGCAGCGGCTAGGTGCCGCGAGGCCC | AGG | 1 | 257 | 1818 | 14.1 | 0 | 1 |
| 63 | 60600676 | antisense | CGGCAGCGGCTAGGTGC | GCGGCAGCGGCTAGGTGCCGCGA | CGG | 1 | 262 | 1818 | 14.4 | 0 | 0 |
| 64 | 60600682 | antisense | CGGCGGCAGCGGCT | CGGGCGGCAGCGGCTAGGTGC | AGG | 1 | 268 | 1818 | 14.4 | 0 | 1 |
| 65 | 60600687 | sense | AGGAACGCGGCGGCAG | GGAACGCGGCGGCAGCGGCTA | CGG | 1 | 273 | 1818 | 14.7 | 0 | 1 |
| 66 | 60600696 | antisense | AGGCCACGGAGAACGGCGG | AAAAGGCCACGGAGAACGGCGGCAG | CGG | 1 | 282 | 1818 | 15 | 0 | 0 |
| 67 | 60600699 | antisense | AAAAGGCCACGGAGAACGG | GCGAAAAGGCCACGGAGAACGGCGG | CGG | 1 | 285 | 1818 | 15.5 | 0 | 0 |
| 68 | 60600702 | antisense | CGAAAAGGCCACGGAGGAA | ACGCGAAAAGGCCACGGAGGAACGG | CGG | 1 | 288 | 1818 | 15.7 | 0 | 0 |

FIG. 12 (cont.)

| | Position of Base After Cut (1-based) | Strand | sgRNA Target Sequence | Target Context Sequence | PAM Sequence | Exon Number | Target Concat Cut Length | Target Concat Total Length | Target Concat Cut % | # Off-Target Tier I Match Bin I Matches | # Off-Target Tier II Match Bin I Matches |
|---|---|---|---|---|---|---|---|---|---|---|---|
| 69 | 50600704 | sense | CTGCGCGCCGCCGTTCCTCCG | GCTGCTGCCGCCGCCGTTCCTCCGTGGCCT | TGG | 1 | 290 | 1818 | 16 | 0 | 0 |
| 70 | 50600707 | antisense | CACGGCGAAAAAGGCCACGG | CGGACACGGCGAAAAAGGCCACGGAGGAAC | AGG | 1 | 293 | 1818 | 16.1 | 0 | 0 |
| 71 | 50600710 | antisense | GCACACGGCGAAAAAGGCCA | CGTCGCACACGGCGAAAAAGGCCACGGAGG | CGG | 1 | 296 | 1818 | 16.3 | 0 | 0 |
| 72 | 50600716 | antisense | CCCGTCGCACACGGCGAAAA | CGTGCCCGTCGCACACGGCGAAAAAGGCCA | AGG | 1 | 302 | 1818 | 16.6 | 0 | 0 |
| 73 | 50600725 | antisense | CCCCGCCGTGCCCGTCGCACA | CCCCGCCGTGCCCGTCGCACACGGCGGGA | CGG | 1 | 311 | 1818 | 17.1 | 0 | 0 |
| 74 | 50600726 | sense | GCCTTTTTCGCCGTGTGCGA | CGTGGCCTTTTTCGCCGTGTGCGACGGGCA | CGG | 1 | 312 | 1818 | 17.2 | 0 | 0 |
| 75 | 50600727 | sense | CCTTTTTCGCCGTGTGCGAC | GTGGCCTTTTTCGCCGTGTGCGACGGGCAC | CGG | 1 | 313 | 1818 | 17.2 | 0 | 0 |
| 76 | 50600732 | sense | TTCGCCGTGTGCGACGGGCA | CTTTTCGCCGTGTGCGACGGGCACGGCGG | CGG | 1 | 318 | 1818 | 17.5 | 0 | 0 |
| 77 | 50600735 | sense | GCCGTGTGCGACGGGCACGG | TTTCGCCGTGTGCGACGGGCACGGCGGGCG | CGG | 1 | 321 | 1818 | 17.7 | 0 | 0 |
| 78 | 50600736 | sense | CCGTGTGCGACGGGCACGGC | TTCGCCGTGTGCGACGGGCACGGCGGGCGG | GGG | 1 | 322 | 1818 | 17.7 | 0 | 0 |
| 79 | 50600739 | sense | TGTGCGACGGGCACGGCGGG | GCCGTGTGCGACGGGCACGGCGGGCGGGAG | CGG | 1 | 325 | 1818 | 17.9 | 0 | 0 |
| 80 | 50600740 | sense | GTGCGACGGGCACGGCGGGC | CCGTGTGCGACGGGCACGGCGGGCGGGAGG | CGG | 1 | 326 | 1818 | 17.9 | 0 | 0 |
| 81 | 50600743 | sense | CGACGGGCACGGCGGGCGGG | TGTGCGACGGGCACGGCGGGCGGGAGGCGG | AGG | 1 | 329 | 1818 | 18.1 | 0 | 0 |
| 82 | 50600746 | sense | CGGGCACGGCGGGCGGGAGG | GCGACGGGCACGGCGGGCGGGAGGCGCAC | CGG | 1 | 332 | 1818 | 18.3 | 0 | 0 |
| 83 | 50600760 | sense | GGGAGGCGGCACAGTTTGCC | GGGCGGGAGGCGGCACAGTTTGCCCGGGAG | CGG | 1 | 346 | 1818 | 19 | 0 | 0 |
| 84 | 50600761 | sense | GGAGGCGGCACAGTTTGCCC | GGAGGCGGCACAGTTTGCCCGGGAGC | GGG | 1 | 347 | 1818 | 19.1 | 0 | 0 |
| 85 | 50600767 | antisense | GAAAACCCACAAGTGCTCCC | TGATGAAACCCCACAAGTGCTCCCGGGCAA | GGG | 1 | 353 | 1818 | 19.4 | 0 | 0 |
| 86 | 50600768 | antisense | TGAAACCCCACAAGTGCTCC | TTGATGAAACCCCACAAGTGCTCCCGGGCA | CGG | 1 | 354 | 1818 | 19.5 | 0 | 0 |
| 87 | 50600772 | sense | AGTTTGCCCGGGAGCACTTG | GCACAGTTTGCCCGGGAGCACTTGTGGGGT | TGG | 1 | 358 | 1818 | 19.7 | 0 | 0 |
| 88 | 50600773 | sense | GTTTGCCCGGGAGCACTTGT | CACAGTTTGCCCGGGAGCACTTGTGGGGTT | GGG | 1 | 359 | 1818 | 19.7 | 0 | 0 |
| 89 | 50600774 | sense | TTTGCCCGGGAGCACTTGTG | ACAGTTTGCCCGGGAGCACTTGTGGGGTTT | GGG | 1 | 360 | 1818 | 19.8 | 0 | 0 |
| 90 | 50600794 | sense | GGGTTTCATCAAGAAGCAGA | TGTGGGGTTTCATCAAGAAGCAGAAGGGTT | AGG | 1 | 380 | 1818 | 20.9 | 0 | 0 |
| 91 | 50600795 | sense | GGTTTCATCAAGAAGCAGAA | GTGGGGTTTCATCAAGAAGCAGAAGGGTTT | GGG | 1 | 381 | 1818 | 21 | 0 | 0 |
| 92 | 50600812 | antisense | AACCTTAGCCGGCTCGGACG | CCGAAACCTTAGCCGGCTCGGACGAGGTGA | AGG | 1 | 398 | 1818 | 21.9 | 0 | 0 |
| 93 | 50600815 | sense | GGGTTTCACCTCGTCCGAGC | AGAAGGGTTTCACCTCGTCCGAGCCGGCTA | CGG | 1 | 401 | 1818 | 22.1 | 0 | 0 |
| 94 | 50600818 | antisense | AGCGCCAAACCTTAGCCGGCT | TGGCAGCGCAAACCTTAGCCGGCTCGACG | CGG | 1 | 404 | 1818 | 22.2 | 0 | 0 |
| 95 | 50600821 | sense | CACCTCGTCCGAGCCGGCTA | GTTTCACCTCGTCCGAGCCGGCTAAGGTTT | AGG | 1 | 407 | 1818 | 22.4 | 0 | 0 |
| 96 | 50600823 | antisense | ATGGCAGCGCAAACCTTAGC | GCGGATGGCAGCGCAAACCTTAGCCGGCTC | TGG | 1 | 409 | 1818 | 22.5 | 0 | 0 |
| 97 | 50600842 | antisense | AGCGAGAAAGCCCTTTGCGGA | GACAAGCGAGAAAGCCCTTTGCGGATGGCAG | CGG | 1 | 428 | 1818 | 23.5 | 0 | 0 |
| 98 | 50600843 | sense | GTTTGCGCTGCCATCCGCAA | TAAGGTTTGCGCTGCCATCCGCAAAGGCTT | AGG | 1 | 429 | 1818 | 23.6 | 0 | 0 |
| 99 | 50600846 | sense | GACAAGCGAGAAAGCCCTTT | AGGTGACAAGCGAGAAAGCCCTTTGCGGATG | CGG | 1 | 432 | 1818 | 23.8 | 0 | 0 |
| 100 | 50600870 | antisense | CCAGTTTCTTCCACATGGCA | TTACCCAGTTTCTTCCACATGGCAAGGTGA | AGG | 1 | 456 | 1818 | 25.1 | 0 | 1 |
| 101 | 50600871 | sense | TCGCTTGTCACCTTGCCATG | TTTCTGCCTTGTCACCTTGCCATGTGGAAG | TGG | 1 | 457 | 1818 | 25.1 | 0 | 0 |
| 102 | 50600875 | antisense | CTTACCCAGTTTCTTCCACA | GGAACTTACCCAGTTTCTTCCACATGGCAA | TGG | 1 | 461 | 1818 | 25.4 | 0 | 0 |

FIG. 12 (cont.)

| | Position of Base After Cut (1-based) | Strand | sgRNA Target Sequence | Target Context Sequence | PAM Sequence | Exon Number | Target Concat Cut Length | Target Concat Total Length | Target Concat Cut % | # Off-Target Tier I Match Bin I Matches | # Off-Target Tier II Match Bin I Matches |
|---|---|---|---|---|---|---|---|---|---|---|---|
| 103 | 60600881 | sense | CCTTGCCATGTGGAAGAAAC | GTCACCTTGCCATGTGGAAGAAACTGGGTA | TGG | 1 | 467 | 1818 | 25.7 | 0 | 0 |
| 104 | 60600882 | sense | CTTGCCATGTGGAAGAAACT | TCACCTTGCCATGTGGAAGAAACTGGGTAA | GGG | 1 | 468 | 1818 | 25.7 | 0 | 0 |
| 105 | 60623523 | sense | TATTTCTTATTACAGCGGAA | ATTTTATTTCTTATTACAGCGGAATGGCCA | TGG | 2 | 475 | 1818 | 26.1 | 0 | 0 |
| 106 | 60623535 | antisense | GGAAGACCCGTCATAGTCTT | GCTAGGAAGACCCGTCATAGTCTTTGGCCA | TGG | 2 | 487 | 1818 | 26.8 | 0 | 0 |
| 107 | 60623539 | sense | GGAATGGCCAAAGACTATGA | CAGGCGGAATGGCCAAAGACTATGACGGGTC | CGG | 2 | 491 | 1818 | 27 | 0 | 0 |
| 108 | 60623540 | sense | GAATGGCCAAAGACTATGAC | AGCGGAATGGCCAAAGACTATGACGGGTCT | GGG | 2 | 492 | 1818 | 27.1 | 0 | 0 |
| 109 | 60623556 | antisense | GCAGTTGTCCCTGATGTGCT | ACTGGCAGTTGTCCCTGATGTGCTAGGAAG | AGG | 2 | 508 | 1818 | 27.9 | 0 | 0 |
| 110 | 60623558 | sense | ACGGGTCTTCCTAGCACATC | TATGACGGGTCTTCCTAGCACATCAGGGAC | AGG | 2 | 510 | 1818 | 28.1 | 0 | 0 |
| 111 | 60623559 | sense | CGGGTCTTCCTAGCACATCA | ATGACGGGTCTTCCTAGCACATCAGGGACA | GGG | 2 | 511 | 1818 | 28.1 | 0 | 0 |
| 112 | 60623575 | sense | ATCAGGGACAACTGCCAGTG | GGCACATCAGGGACAACTGCCAGTGTGGTCA | TGG | 2 | 527 | 1818 | 29 | 0 | 0 |
| 113 | 60623578 | antisense | GCCCCGAATGATGACCACAC | TCATGCCCCGAATGATGACCACACTGGCAG | CGG | 2 | 530 | 1818 | 29.2 | 0 | 1 |
| 114 | 60623586 | sense | CTGCCAGTGTGGTCATCATT | ACAACTGCCAGTGTGGTCATCATTCGGGGC | CGG | 2 | 538 | 1818 | 29.6 | 0 | 0 |
| 115 | 60623587 | sense | TGCCAGTGTGGTCATCATTC | CAACTGCCAGTGTGGTCATCATTCGGGGCA | GGG | 2 | 539 | 1818 | 29.6 | 0 | 0 |
| 116 | 60623588 | sense | GCCAGTGTGGTCATCATTCG | AACTGCCAGTGTGGTCATCATTCGGGGCAT | GGG | 2 | 540 | 1818 | 29.7 | 0 | 0 |
| 117 | 60623615 | sense | AAGATGTATGTAGCTCACGT | CATGAAGATGTATGTAGCTCACGTAGGTGA | AGG | 2 | 567 | 1818 | 31.2 | 0 | 0 |
| 118 | 60623624 | sense | GTAGCTCACGTAGGTGACTC | GTATGTAGCTCACGTAGGTGACTCAGGGGT | AGG | 2 | 576 | 1818 | 31.7 | 0 | 0 |
| 119 | 60623625 | sense | TAGCTCACGTAGGTGACTCA | TATGTAGCTCACGTAGGTGACTCAGGGGTG | GGG | 2 | 577 | 1818 | 31.7 | 0 | 0 |
| 120 | 60623626 | sense | AGCTCACGTAGGTGACTCAG | ATGTAGCTCACGTAGGTGACTCAGGGGTGG | GGG | 2 | 578 | 1818 | 31.8 | 0 | 0 |
| 121 | 60623629 | sense | TCACGTAGGTGACTCAGGGG | TAGCTCACGTAGGTGACTCAGGGGTGGTTC | TGG | 2 | 581 | 1818 | 32 | 0 | 0 |
| 122 | 60623636 | sense | GGTGACTCAGGGGTGGTTCT | CGTAGGTGACTCAGGGGTGGTTCTTGGAAT | TGG | 2 | 586 | 1818 | 32.3 | 0 | 0 |
| 123 | 60623644 | sense | AGGGGTGGTTCTTGGAATTC | ACTCAGGGGTGGTTCTTGGAATTCAGGATG | AGG | 2 | 596 | 1818 | 32.8 | 0 | 0 |
| 124 | 60623656 | sense | TGGAATTCAGGATGACCCGA | TTCTTGGAATTCAGGATGACCCGAAGGATG | AGG | 2 | 608 | 1818 | 33.4 | 0 | 0 |
| 125 | 60623660 | antisense | CTCTGACAAAGTCATCCTTC | ACAGCTCTGACAAAGTCATCCTTCGGGTCA | GGG | 2 | 612 | 1818 | 33.7 | 0 | 0 |
| 126 | 60623661 | antisense | GCTCTGACAAAGTCATCCTT | CACAGCTCTGACAAAGTCATCCTTCGGGTC | CGG | 2 | 613 | 1818 | 33.7 | 0 | 0 |
| 127 | 60623677 | sense | GGATGACTTTGTCAGAGCTG | CGAAGGATGACTTTGTCAGAGCTGTGGAGG | TGG | 2 | 629 | 1818 | 34.6 | 0 | 0 |
| 128 | 60623680 | sense | TGACTTTGTCAGAGCTGTGG | AGGATGACTTTGTCAGAGCTGTGGAGGTGA | AGG | 2 | 632 | 1818 | 34.8 | 0 | 0 |
| 129 | 60623689 | sense | CAGAGCTGTGGAGGTGACAC | TTGTCAGAGCTGTGGAGGTGACACAGGACC | AGG | 2 | 641 | 1818 | 35.3 | 0 | 0 |
| 130 | 60623702 | antisense | CCTTGGGAAGTTCTGGCTTA | CTTTCCTTGGGAAGTTCTGGCTTATGGTCC | TGG | 2 | 654 | 1818 | 36 | 0 | 0 |
| 131 | 60623709 | sense | TCTCTTCCTTGGGAAGTTC | TCGTTCTCTTCCTTGGGAAGTTCTGGCTT | TGG | 2 | 661 | 1818 | 36.4 | 0 | 0 |
| 132 | 60623713 | antisense | CCATAAGCCAGAACTTCCCA | AGGACCATAAGCCAGAACTTCCCAAGGAAA | AGG | 2 | 665 | 1818 | 36.6 | 0 | 0 |
| 133 | 60623718 | antisense | TCGATTCGTTCTCTTCTT | TCCTTCGATTCGTTCTCTTCCTTGGGAAG | GGG | 2 | 670 | 1818 | 36.8 | 0 | 0 |
| 134 | 60623719 | antisense | TTCGATTCGTTCTCTTCCT | GTCCTTCGATTCGTTCTCTTCCTTGGGAA | TGG | 2 | 671 | 1818 | 36.9 | 0 | 0 |
| 135 | 60623732 | sense | AAGGAAAGAGAACGAATCGA | TCCCAAGGAAAGAGAACGAATCGAAGGACT | AGG | 2 | 684 | 1818 | 37.6 | 0 | 0 |
| 136 | 60623738 | sense | AGAGAACGAATCGAAGGACT | GGAAAGAGAACGAATCGAAGGACTTGGTGG | TGG | 2 | 690 | 1818 | 38 | 0 | 0 |

FIG. 12 (cont.)

| | Position of Base After Cut (1-based) | Strand | sgRNA Target Sequence | Target Context Sequence | PAM Sequence | Exon Number | Target Concat Cut Length | Target Concat Total Length | Target Concat Cut % | # Off-Target Tier I Match Bin I Matches | # Off-Target Tier II Match Bin I Matches |
|---|---|---|---|---|---|---|---|---|---|---|---|
| 137 | 60623741 | sense | GAACGAATCGAAGGACTTGG | AAGAGAACGAATCGAAGGACTTGGTGGGAG | TGG | 2 | 693 | 1818 | 38.1 | 0 | 0 |
| 138 | 60623742 | sense | AACGAATCGAAGGACTTGGT | AGAGAACGAATCGAAGGACTTGGTGGGAGG | GGG | 2 | 694 | 1818 | 38.2 | 0 | 0 |
| 139 | 60623745 | sense | GAATCGAAGGACTTGGTGGG | GAACGAATCGAAGGACTTGGTGGGAGGTAA | AGG | 2 | 697 | 1818 | 38.3 | 0 | 0 |
| 140 | 60633865 | sense | TTTAGTGTAATGAACAAGTC | TATTTTAGTGTAATGAACAAGTCTGGGGT | TGG | 3 | 714 | 1818 | 39.3 | 0 | 0 |
| 141 | 60633866 | sense | TTAGTGTAATGAACAAGTCT | ATTTTTAGTGTAATGAACAAGTCTGGGGTG | GGG | 3 | 715 | 1818 | 39.3 | 0 | 1 |
| 142 | 60633867 | sense | TAGTGTAATGAACAAGTCTG | TTTTTAGTGTAATGAACAAGTCTGGGGTGA | GGG | 3 | 716 | 1818 | 39.4 | 0 | 0 |
| 143 | 60633884 | sense | CTGGGGTGAATCGTGTAGTT | AAGTCTGGGGTGAATCGTGTAGTTTGGAAA | TGG | 3 | 733 | 1818 | 40.3 | 0 | 0 |
| 144 | 60633902 | antisense | GGTCCATTGTGAGTGAGTCG | AACAGGTCCATTGTGAGTGAGTCGAGGTCG | AGG | 3 | 751 | 1818 | 41.3 | 0 | 0 |
| 145 | 60633910 | sense | CGACCTCGACTCACTCACAA | GAAACGACCTCGACTCACTCACAATGGACC | TGG | 3 | 759 | 1818 | 41.7 | 0 | 0 |
| 146 | 60633923 | antisense | ATAACTGTGTCCTTCTAAC | GTCAATAACTGTGTCCTTCTAACAGGTCC | AGG | 3 | 772 | 1818 | 42.5 | 0 | 1 |
| 147 | 60633923 | sense | CTCACAATGGACCTGTTAGA | CTCACTCACAATGGACCTGTTAGAAGGAGC | AGG | 3 | 772 | 1818 | 42.5 | 0 | 0 |
| 148 | 60633949 | antisense | CTACTGCCAGAAAAGGAATC | CTTGCTACTGCCAGAAAAGGAATCTGGTCA | TGG | 3 | 798 | 1818 | 43.9 | 0 | 0 |
| 149 | 60633954 | sense | TATTGACCAGATTCCTTTTC | CAGTTATTGACCAGATTCCTTTTCTGGCAG | TGG | 3 | 803 | 1818 | 44.2 | 0 | 0 |
| 150 | 60633956 | antisense | GCTCTTGCTACTGCCAGAAA | AAGTGCTCTTGCTACTGCCAGAAAAGGAAT | AGG | 3 | 805 | 1818 | 44.3 | 0 | 0 |
| 151 | 60633973 | sense | CTGGCAGTAGCAAGAGCACT | TTTTCTGGCAGTAGCAAGAGCACTTGGTAA | TGG | 3 | 822 | 1818 | 45.2 | 0 | 0 |
| 152 | 60647892 | antisense | ATAGCTCCACAAATCACCTG | AATCATAGCTCCACAAATCACCTGGGGGAA | GGG | 4 | 827 | 1818 | 45.5 | 0 | 0 |
| 153 | 60647893 | antisense | CATAGCTCCACAAATCACCT | AAATCATAGCTCCACAAATCACCTGGGGA | TGG | 4 | 828 | 1818 | 45.5 | 0 | 0 |
| 154 | 60647894 | antisense | TCATAGCTCCACAAATCACC | GAAATCATAGCTCCACAAATCACCTGGGGG | GGG | 4 | 829 | 1818 | 45.6 | 0 | 0 |
| 155 | 60647897 | sense | CCCTTCCCCCAGGTGATTTG | TGCTCCCTTCCCCCAGGTGATTTGTGGAGC | AGG | 4 | 832 | 1818 | 45.8 | 0 | 0 |
| 156 | 60647917 | sense | TGGAGCTATGATTCTTCAG | TTTGTGGAGCTATGATTCTTCAGTGGTGA | TGG | 4 | 852 | 1818 | 46.9 | 0 | 0 |
| 157 | 60647928 | sense | TTTCTTCAGTGGTGAATTTG | ATGATTTCTTCAGTGGTGAATTTGTGGTGT | TGG | 4 | 863 | 1818 | 47.5 | 0 | 0 |
| 158 | 60647945 | antisense | TGGACACTTGTGTCTGGTTC | AGTGTGGACACTTGTGTCTGGTTCAGGTGA | AGG | 4 | 880 | 1818 | 48.4 | 0 | 0 |
| 159 | 60647951 | antisense | AGAGTGTGGACACTTGTGTC | GTCAAGAGTGTGGACACTTGTGTCTGGTTC | TGG | 4 | 886 | 1818 | 48.7 | 0 | 0 |
| 160 | 60647965 | antisense | GCTTCTGAGGGTCAAGAGTG | TTGTGCTTCTGAGGGTCAAGAGTGTGGACA | TGG | 4 | 900 | 1818 | 49.5 | 0 | 0 |
| 161 | 60647977 | sense | TAATATACTTGTGCTTCTGA | AATATAATATACTTGTGCTTCTGAGGGTCA | GGG | 4 | 912 | 1818 | 50.2 | 0 | 0 |
| 162 | 60647978 | antisense | ATAATATACTTGTGCTTCTG | CAATATAATATACTTGTGCTTCTGAGGGTC | AGG | 4 | 913 | 1818 | 50.2 | 0 | 0 |
| 163 | 60647994 | sense | GAAGCACAAGTATATATAT | CTCAGAAGCACAAGTATATATATATTGGGAG | TGG | 4 | 929 | 1818 | 51.1 | 0 | 0 |
| 164 | 60647995 | sense | AAGCACAAGTATATATATT | TCAGAAGCACAAGTATATATATTGGGGAG | AGG | 4 | 930 | 1818 | 51.2 | 0 | 0 |
| 165 | 60647996 | sense | AGCACAAGTATATATATTG | CAGAAGCACAAGTATATATATTGGGGAGT | GGG | 4 | 931 | 1818 | 51.2 | 0 | 0 |
| 166 | 60648004 | sense | TATATATTGGGGAGTGA | CAAGTATATATTGGGGAGTGACT | TGG | 4 | 939 | 1818 | 51.7 | 0 | 0 |
| 167 | 60648011 | sense | TATTATATTGGGGAGTGACT | ATTATATTGGGGAGTGACTTGGAAT | TGG | 4 | 946 | 1818 | 52 | 0 | 0 |
| 168 | 60648032 | antisense | ATTGAGATGGCATCTTGTGG | GCACATTGAGATGGCATCTTGTGGTGGTGG | TGG | 4 | 967 | 1818 | 53.2 | 0 | 0 |
| 169 | 60648035 | antisense | CACATTGAGATGGCATCTTG | CTGGCACATTGAGATGGCATCTTGTGTGG | TGG | 4 | 970 | 1818 | 53.4 | 0 | 0 |

FIG. 12 (cont.)

| | Position of Base After Cut (1-based) | Strand | sgRNA Target Sequence | Target Context Sequence | PAM Sequence | Exon Number | Target Concat Cut Length | Target Concat Total Length | Target Concat Cut % | # Off-Target Tier I Match Bin I Matches | # Off-Target Tier II Match Bin I Matches |
|---|---|---|---|---|---|---|---|---|---|---|---|
| 170 | 60648045 | antisense | TTGGTCCTGGCACATTGAGA | CCTCTTGGTCCTGGCACATTGAGATGGCAT | TGG | 4 | 980 | 1818 | 53.9 | 0 | 0 |
| 171 | 60648051 | sense | AGATGCCATCTCAATGTGCC | CACAAGATGCCATCTCAATGTGCCAGGACC | AGG | 4 | 986 | 1818 | 54.2 | 0 | 0 |
| 172 | 60648058 | antisense | ATTTTTTCTCCTCTTGGTCC | AGGTATTTTTTCTCCTCTTGGTCCAGGCAC | TGG | 4 | 993 | 1818 | 54.6 | 0 | 0 |
| 173 | 60648060 | sense | CTCAATGTGCCAGGACCAAG | CCATCTCAATGTGCCAGGACCAAGAGGAGA | AGG | 4 | 995 | 1818 | 54.7 | 0 | 0 |
| 174 | 60648064 | antisense | TCAGGTATTTTTTCTCCTCT | ACCATCAGGTATTTTTTCTCCTCTTGGTCC | TGG | 4 | 999 | 1818 | 55 | 0 | 0 |
| 175 | 60648078 | sense | AGAGGAGAAAAAATACCTGA | ACCAAGAGGAGAAAAAATACCTGATGGTGA | TGG | 4 | 1013 | 1818 | 55.7 | 0 | 0 |
| 176 | 60656604 | sense | TTTTGAATACAGGGTGAGCA | GTTCTTTTGAATACAGGGTGAGCATGGACA | AGG | 5 | 1023 | 1818 | 56.3 | 0 | 0 |
| 177 | 60656627 | antisense | TGCTCGATTCACAAGCATTT | CCAATGCTCGATTCACAAGCATTTTGGCAC | TGG | 5 | 1046 | 1818 | 57.5 | 0 | 0 |
| 178 | 60656642 | sense | AATGCTTGTGAATCGAGCAT | CCAAAATGCTTGTGAATCGAGCATTGGGCC | TGG | 5 | 1061 | 1818 | 58.4 | 0 | 0 |
| 179 | 60656643 | sense | ATGCTTGTGAATCGAGCATT | CAAAAATGCTTGTGAATCGAGCATTGGGCCG | GGG | 5 | 1062 | 1818 | 58.4 | 0 | 0 |
| 180 | 60656650 | sense | TGAATCGAGCATTGGGCCGC | CTTGTGAATCGAGCATTGGGCCGCTGGAGG | TGG | 5 | 1069 | 1818 | 58.8 | 0 | 0 |
| 181 | 60656653 | sense | ATCGAGCATTGGGCCGCTGG | GTGAATCGAGCATTGGGCCGCTGGAGGCAG | AGG | 5 | 1072 | 1818 | 59 | 0 | 0 |
| 182 | 60656655 | antisense | GGAGCATACGCTGCCTCCAG | GCTCGGAGCATACGCTGCCTCCAGCGGCCC | CGG | 5 | 1074 | 1818 | 59.1 | 0 | 1 |
| 183 | 60656676 | antisense | TGGCACTAGTGTTATCTGCT | ACTATGGCACTAGTGTTATCTGCTCGGAGC | CGG | 5 | 1095 | 1818 | 60.2 | 0 | 0 |
| 184 | 60656696 | antisense | TGGAGAGATGCAGATTACTA | CTTCTGGAGAGATGCAGATTACTATGGCAC | TGG | 5 | 1115 | 1818 | 61.3 | 0 | 0 |
| 185 | 60656714 | sense | AATCTGCATCTCTCCAGAAG | TAGTAATCTGCATCTCTCCAGAAGTGGACA | TGG | 5 | 1133 | 1818 | 62.3 | 0 | 0 |
| 186 | 60656716 | antisense | TTTCCCTGATTGTCCACTTC | AAAGTTTCCCTGATTGTCCACTTCTGGAGA | AGG | 5 | 1135 | 1818 | 62.4 | 0 | 0 |
| 187 | 60656723 | sense | CTCTCCAGAAGTGGACAATC | GCATCTCTCCAGAAGTGGACAATCAGGGAA | TGG | 5 | 1142 | 1818 | 62.8 | 0 | 0 |
| 188 | 60656724 | sense | TCTCCAGAAGTGGACAATCA | CATCTCTCCAGAAGTGGACAATCAGGGAAA | GGG | 5 | 1143 | 1818 | 62.9 | 0 | 0 |
| 189 | 60656744 | antisense | CAGGTATAACTCATCTTCAT | GGTTCAGGTATAACTCATCTTCATTGGTAA | TGG | 5 | 1163 | 1818 | 64 | 0 | 0 |
| 190 | 60656763 | antisense | AAGGGCTGTCAGTCAGGTTC | TAGGAAGGGCTGTCAGTCAGGTTCAGGTAT | AGG | 5 | 1182 | 1818 | 65 | 0 | 0 |
| 191 | 60656769 | antisense | TATAGGAAGGGCTGTCAGTC | CTATTATAGGAAGGGCTGTCAGTCAGGTTC | AGG | 5 | 1188 | 1818 | 65.3 | 0 | 0 |
| 192 | 60656781 | sense | TTTCTTGACTATTATAGGAA | CAGGTTTCTTGACTATTATAGGAAGGGCTG | TGG | 5 | 1200 | 1818 | 66 | 0 | 0 |
| 193 | 60656782 | antisense | GTTTCTTGACTATTATAGGA | ACAGGTTTCTTGACTATTATAGGAAGGGCT | AGG | 5 | 1201 | 1818 | 66.1 | 0 | 0 |
| 194 | 60656786 | antisense | ACAGGTTTCTTGACTATTAT | TCACACAGGTTTCTTGACTATTATAGGAAG | AGG | 5 | 1205 | 1818 | 66.3 | 0 | 0 |
| 195 | 60656804 | antisense | TGGGGAAGGAGTCATCACAC | AACATGGGGAAGGAGTCATCACACAGGTTT | AGG | 5 | 1223 | 1818 | 67.3 | 0 | 0 |
| 196 | 60656818 | antisense | GGTGGTGTAGAACATGGGGA | GACTGGTGGTGTAGAACATGGGGAAGGAGT | GGG | 5 | 1237 | 1818 | 68 | 0 | 0 |
| 197 | 60656822 | antisense | GACTGGTGGTGTAGAACATG | CCTTGACTGGTGGTGTAGAACATGGGGAAG | GGG | 5 | 1241 | 1818 | 68.3 | 0 | 0 |
| 198 | 60656823 | antisense | TGACTGGTGGTGTAGAACAT | ACCTTGACTGGTGGTGTAGAACATGGGGAA | AGG | 5 | 1242 | 1818 | 68.3 | 0 | 0 |
| 199 | 60656824 | antisense | TTGACTGGTGGTGTAGAACA | TACCTTGACTGGTGGTGTAGAACATGGGGA | AGG | 5 | 1243 | 1818 | 68.4 | 0 | 0 |
| 200 | 60656836 | antisense | GAACTATATACCTTGACTGG | TATGGAACTATATACCTTGACTGGTGGTGT | TGG | 5 | 1255 | 1818 | 69 | 0 | 0 |
| 201 | 60656837 | sense | ATGTTCTACACCACCAGTCA | CCCCATGTTCTACACCACCAGTCAAGGTAT | AGG | 5 | 1256 | 1818 | 69.1 | 0 | 0 |
| 202 | 60656839 | antisense | ATGGAACTATATACCTTGAC | AACTATGGAACTATATACCTTGACTGGTGG | TGG | 5 | 1258 | 1818 | 69.2 | 0 | 0 |
| 203 | 60662996 | sense | CCTTCTTATTTTTCAGTCAC | TTTACCTTCTTATTTTTCAGTCACTGGAGG | TGG | 6 | 1262 | 1818 | 69.4 | 0 | 0 |

FIG. 12 (cont.)

| | Position of Base After Cut (1-based) | Strand | sgRNA Target Sequence | Target Context Sequence | PAM Sequence | Exon Number | Target Concat Cut Length | Target Concat Total Length | Target Concat Cut % | # Off-Target Tier I Match Bin I Matches | # Off-Target Tier II Match Bin I Matches |
|---|---|---|---|---|---|---|---|---|---|---|---|
| 204 | 60662999 | sense | TCTTATTTTCAGTCACTGG | ACCTTCTATTTTCAGTCACTGGAGGAGG | AGG | 6 | 1265 | 1818 | 69.6 | 0 | 0 |
| 205 | 60663002 | sense | TATTTTCAGTCACTGGAGG | TTCTTATTTTCAGTCACTGGAGGAGGATC | AGG | 6 | 1268 | 1818 | 69.7 | 0 | 0 |
| 206 | 60663010 | sense | AGTCACTGGAGGAGGATCCA | AGTCACTGGAGGAGGATCCATGGCCA | TGG | 6 | 1276 | 1818 | 70.2 | 0 | 0 |
| 207 | 60663016 | sense | TGGAGGAGGATCCATGGCCA | TCACTGGAGGAGGATCCATGGCCAAGGGTG | AGG | 6 | 1282 | 1818 | 70.5 | 0 | 0 |
| 208 | 60663016 | antisense | TTAGAATTCACCCTTGGCCA | GTCCTTAGAATTCACCCTTGGCCATGGATC | TGG | 6 | 1282 | 1818 | 70.5 | 0 | 0 |
| 209 | 60663017 | sense | GGAGGAGGATCCATGGCCAA | CACTGGAGGAGGATCCATGGCCAAGGGTGA | GGG | 6 | 1283 | 1818 | 70.6 | 0 | 0 |
| 210 | 60663022 | antisense | TGGTCCTTAGAATTCACCCT | TATATGGTCCTTAGAATTCACCCTTGGCCA | TGG | 6 | 1288 | 1818 | 70.8 | 0 | 0 |
| 211 | 60663029 | sense | ATGGCCAAGGGTGAATTCTA | ATCCATGGCCAAGGGTGAATTCTAAGGACC | AGG | 6 | 1295 | 1818 | 71.2 | 0 | 0 |
| 212 | 60663042 | antisense | TACGAACCAGGGCAGGTATA | TTGCTACGAACCAGGGCAGGTATATGGTCC | TGG | 6 | 1308 | 1818 | 71.9 | 0 | 0 |
| 213 | 60663047 | sense | TAAGGACCATATACCTGCCC | ATTCTAAGGACCATATACCTGCCCTGGTTC | TGG | 6 | 1313 | 1818 | 72.2 | 0 | 0 |
| 214 | 60663049 | antisense | GCATTGCTACGAACCAGGGC | GAAGGCATTGCTACGAACCAGGGCAGGTAT | AGG | 6 | 1315 | 1818 | 72.3 | 0 | 0 |
| 215 | 60663053 | antisense | GAAGGCATTGCTACGAACCA | CTGAGAAGGCATTGCTACGAACCAGGGCAG | AGG | 6 | 1319 | 1818 | 72.6 | 0 | 0 |
| 216 | 60663054 | antisense | AGAAGGCATTGCTACGAACC | TCTGAGAAGGCATTGCTACGAACCAGGGCA | AGG | 6 | 1320 | 1818 | 72.6 | 0 | 0 |
| 217 | 60663071 | antisense | CTCTAAAAATTCTGAGA | AAACCTCTAAAAATTCTGAGAAGGCAT | AGG | 6 | 1337 | 1818 | 73.5 | 0 | 0 |
| 218 | 60663083 | sense | CTTCTCAGAGAATTTTTAG | ATGCCTTCTCAGAGAATTTTTAGAGGTTT | AGG | 6 | 1349 | 1818 | 74.2 | 0 | 0 |
| 219 | 60663117 | sense | ATAGCTCGAGAGAATGTCCA | TGAGATAGCTCGAGAGAATGTCCAAGGTGT | AGG | 6 | 1383 | 1818 | 76.1 | 0 | 0 |
| 220 | 60663123 | antisense | TTGAGGGTATGACTACACCT | TCTTTTGAGGGTATGACTACACCTTGGACA | TGG | 6 | 1389 | 1818 | 76.4 | 0 | 0 |
| 221 | 60663139 | antisense | AGTGGTTCTCGGATCTTTTGA | TTCAAGTGGTTCTCGGATCTTTTGAGGGTAT | GGG | 6 | 1405 | 1818 | 77.3 | 0 | 0 |
| 222 | 60663140 | antisense | AAGTGGTTCTCGGATCTTTTG | CTTCAAGTGGTTCTCGGATCTTTTGAGGGTA | AGG | 6 | 1406 | 1818 | 77.3 | 0 | 0 |
| 223 | 60663151 | antisense | CAATTTCTTCAAGTGGTTC | AGGGCAATTTCTTCAAGTGGTTCTCGGATC | TGG | 6 | 1417 | 1818 | 77.9 | 0 | 0 |
| 224 | 60663157 | antisense | TTAGCGCCAATTTCTTCAAG | GGCTTTAGCGCCAATTTCTTCAAGTGGTTC | AGG | 6 | 1423 | 1818 | 78.3 | 0 | 0 |
| 225 | 60663182 | antisense | ATCATGTATCCTTAAAGTCA | AAGAATCATGTATCCTTAAAGTCAGGGCTT | GGG | 6 | 1448 | 1818 | 79.6 | 0 | 0 |
| 226 | 60663183 | antisense | AATCATGTATCCTTAAAGTC | AAAGAATCATGTATCCTTAAAGTCAGGGCT | AGG | 6 | 1449 | 1818 | 79.7 | 0 | 0 |
| 227 | 60663184 | sense | GCGCTAAAGCCCTGACTTTA | AATTGCGCTAAAGCCCTGACTTTAAGGATA | AGG | 6 | 1450 | 1818 | 79.8 | 0 | 0 |
| 228 | 60663219 | antisense | TAGGCACAAGGCCAATTGGA | TTAGTAGGCACAAGGCCAATTGGAAGGCTA | AGG | 6 | 1485 | 1818 | 81.7 | 0 | 1 |
| 229 | 60663219 | sense | TTGAATATAGCCTTCCAAT | TTCTTTGAATATAGCCTTCCAATTGGCCT | AGG | 6 | 1485 | 1818 | 81.7 | 0 | 0 |
| 230 | 60663223 | antisense | TTAGTAGGCACAAGGCCAAT | TGAATTAGTAGGCACAAGGCCAATTGGAAG | AGG | 6 | 1489 | 1818 | 81.9 | 0 | 0 |
| 231 | 60663231 | sense | TTGTTGAATTAGTAGGCACA | GTGTTTGTTGAATTAGTAGGCACAAGGCCA | AGG | 6 | 1497 | 1818 | 82.3 | 0 | 0 |
| 232 | 60663238 | antisense | ACAGTGTTTGTTGAATTAGT | CATGACAGTGTTTGTTGAATTAGTAGGCAC | AGG | 6 | 1504 | 1818 | 82.7 | 0 | 0 |
| 233 | 60663254 | sense | TAATTCAACAAACACTGTCA | CTACTAATTCAACAAACACTGTCATGGACC | TGG | 6 | 1520 | 1818 | 83.6 | 0 | 0 |
| 234 | 60663267 | antisense | TTGACATCTTCAAATTTT | AAAAAATTTGACATCTTCAAATTTTTGGTCC | AGG | 6 | 1533 | 1818 | 84.3 | 0 | 0 |
| 235 | 60663285 | sense | AATTTGAAGATGTCAACTCC | AATTTTGAAGATGTCAACTCCTGGCCA | TGG | 6 | 1551 | 1818 | 85.3 | 0 | 0 |
| 236 | 60663292 | antisense | TCTTGGGCTTTCATTTGGCC | AATTTCTTGGGCTTTCATTTGGCCAGGAGT | AGG | 6 | 1558 | 1818 | 85.7 | 0 | 0 |
| 237 | 60663297 | antisense | CAATTTCTTGGGCTTTCATT | CTTTCAATTTCTTGGGCTTTCATTTGGCCA | TGG | 6 | 1563 | 1818 | 86 | 0 | 0 |

FIG. 12 (cont.)

| | Position of Base After Cut (1-based) | Strand | sgRNA Target Sequence | Target Context Sequence | PAM Sequence | Exon Number | Target Concat Cut Length | Target Concat Total Length | Target Concat Cut % | # Off-Target Tier I Match Bin I Matches | # Off-Target Tier II Match Bin I Matches |
|---|---|---|---|---|---|---|---|---|---|---|---|
| 238 | 50663308 | antisense | AGGGGTTCTTTCAATTCTT | TTGGAGGGGTTCTTTCAATTCTTGGGCTT | GGG | 6 | 1574 | 1818 | 86.6 | 0 | 0 |
| 239 | 50663309 | antisense | GAGGGGTTCTTTCAATTCT | GTTGGAGGGGTTCTTTCAATTCTTGGGCT | TGG | 6 | 1575 | 1818 | 86.6 | 0 | 0 |
| 240 | 50663326 | antisense | CCTTTAAAGTTTGTTGGAG | ATGTCCTTTAAAGTTTGTTGGAGGGGTTC | GGG | 6 | 1592 | 1818 | 87.6 | 0 | 0 |
| 241 | 50663327 | antisense | TCCTTTAAAGTTTGTTGGA | AATGTCCTTTAAAGTTTGTTGGAGGGGTT | GGG | 6 | 1593 | 1818 | 87.6 | 0 | 1 |
| 242 | 50663328 | antisense | GTCCTTTAAAGTTTGTTGG | TAATGTCCTTTAAAGTTTGTTGGAGGGGT | AGG | 6 | 1594 | 1818 | 87.7 | 0 | 0 |
| 243 | 50663331 | antisense | AATGTCCTTTAAAGTTTGT | TTCTAATGTCCTTTAAAGTTTGTTGGAGG | TGG | 6 | 1597 | 1818 | 87.8 | 0 | 0 |
| 244 | 50663337 | sense | CCCCTCCAACAAACTTTAAA | AGAACCCTCCAACAAACTTTAAAAGGACA | AGG | 6 | 1603 | 1818 | 88.2 | 0 | 0 |
| 245 | 50663360 | sense | ACATTAGAAGAGTCCAATTC | AAGGACATTAGAAGAGTCCAATTCTGGCCC | TGG | 6 | 1626 | 1818 | 89.4 | 0 | 0 |
| 246 | 50663362 | antisense | CTTCATCAGGGGCCAGAAT | GCTTCTTCATCAGGGGCCAGAATTGGACT | GGG | 6 | 1628 | 1818 | 89.5 | 0 | 0 |
| 247 | 50663372 | antisense | GTCTATGCTTCTTCATCAGG | TTTCGTCTATGCTTCTTCATCAGGGGGCCA | GGG | 6 | 1638 | 1818 | 90.1 | 0 | 0 |
| 248 | 50663373 | antisense | CGTCTATGCTTCTTCATCAG | ATTTCGTCTATGCTTCTTCATCAGGGGCC | AGG | 6 | 1639 | 1818 | 90.2 | 0 | 0 |
| 249 | 50663374 | antisense | TCGTCTATGCTTCTTCATCA | CATTTCGTCTATGCTTCTTCATCAGGGGC | GGG | 6 | 1640 | 1818 | 90.2 | 0 | 0 |
| 250 | 50663375 | antisense | TTCGTCTATGCTTCTTCATC | CCATTTCGTCTATGCTTCTTCATCAGGGG | AGG | 6 | 1641 | 1818 | 90.3 | 0 | 0 |
| 251 | 50663390 | sense | ATGAAGAAGCATAGACGAAA | CCTGATGAAGAAGCATAGACGAAATGGCTT | TGG | 6 | 1656 | 1818 | 91.1 | 0 | 1 |
| 252 | 50663408 | sense | AATGGCTTAAGTCGAAGTAG | ACGAAATGGCTTAAGTCGAAGTAGTGGTGC | AGG | 6 | 1674 | 1818 | 92.1 | 0 | 0 |
| 253 | 50663427 | antisense | GAGGTTGTGGGGAGACTTGC | CTGTGAGGTTGTGGGGAGACTTGCAGGCTG | AGG | 6 | 1693 | 1818 | 93.1 | 0 | 1 |
| 254 | 50663438 | antisense | TCTTTCGCTGTGAGGTTGTG | GAGTTCTTTCGCTGTGAGGTTGTGGGGAGA | GGG | 6 | 1704 | 1818 | 93.7 | 0 | 0 |
| 255 | 50663439 | antisense | TTCTTTCGCTGTGAGGTTGT | AGAGTTCTTTCGCTGTGAGGTTGTGGGGAG | GGG | 6 | 1705 | 1818 | 93.8 | 0 | 0 |
| 256 | 50663440 | antisense | GTTCTTTCGCTGTGAGGTTG | CAGAGTTCTTTCGCTGTGAGGTTGTGGGGA | TGG | 6 | 1706 | 1818 | 93.8 | 0 | 0 |
| 257 | 50663446 | antisense | AACAGAGTTCTTTCGCTGTG | GTTTAACAGAGTTCTTTCGCTGTGAGGTTG | AGG | 6 | 1712 | 1818 | 94.2 | 0 | 0 |
| 258 | 50663476 | antisense | GCCCCTAAGTCTGCGTCGCA | TCTGGCCCCTAAGTCTGCGTCGCATGGTGA | TGG | 6 | 1742 | 1818 | 95.8 | 0 | 0 |
| 259 | 50663484 | sense | TCACCATGCGACGCAGACTT | AAACTCACCATGCGACGCAGACTTAGGGGC | AGG | 6 | 1750 | 1818 | 96.3 | 0 | 0 |
| 260 | 50663485 | sense | CACCATGCGACGCAGACTTA | AACTCACCATGCGACGCAGACTTAGGGGCC | GGG | 6 | 1751 | 1818 | 96.3 | 0 | 0 |
| 261 | 50663486 | sense | ACCATGCGACGCAGACTTAG | ACTCACCATGCGACGCAGACTTAGGGGCCA | GGG | 6 | 1752 | 1818 | 96.4 | 0 | 0 |
| 262 | 50663498 | antisense | AAGGATTCCAATTTCTTC | AGTAAAGGATTCCAATTTCTTCTGGCCC | TGG | 6 | 1764 | 1818 | 97 | 0 | 0 |
| 263 | 50663501 | sense | CTTAGGGGCCAGAAGAAAAT | CAGACTTAGGGGCCAGAAGAAAATTGGAAA | TGG | 6 | 1767 | 1818 | 97.2 | 0 | 0 |
| 264 | 50663517 | antisense | TTCCTGTGTTGATGAAGTAA | AGTTTTCCTGTGTTGATGAAGTAAAGGATT | AGG | 6 | 1783 | 1818 | 98.1 | 0 | 0 |
| 265 | 50663526 | sense | ATCCTTTACTTCATCAACAC | GGAAATCCTTTACTTCATCAACACAGGAAA | AGG | 6 | 1792 | 1818 | 98.6 | 0 | 0 |

FIG. 12 (cont.)

| | # Off-Target Tier III Match Bin I Matches | # Off-Target Tier IV Match Bin I Matches | # Off-Target Tier I Match Bin II Matches | # Off-Target Tier II Match Bin II Matches | # Off-Target Tier III Match Bin II Matches | # Off-Target Tier IV Match Bin II Matches | # Off-Target Tier I Match Bin III Matches | # Off-Target Tier II Match Bin III Matches | # Off-Target Tier III Match Bin III Matches | # Off-Target Tier IV Match Bin III Matches | # Off-Target Tier I Match Bin IV Matches | # Off-Target Tier II Match Bin IV Matches | # Off-Target Tier III Match Bin IV Matches | # Off-Target Tier IV Match Bin IV Matches | On-Target Ruleset |
|---|---|---|---|---|---|---|---|---|---|---|---|---|---|---|---|
| 1 | 0 | 0 | 6 | 29 | 6 | 25 | 16 | 50 | 13 | 17 | 16 | 97 | 22 | 66 | 2 |
| 2 | 0 | 0 | 9 | 58 | 13 | 48 | 24 | 120 | 26 | 85 | 31 | 261 | 69 | 194 | 2 |
| 3 | 0 | 0 | 11 | 37 | 14 | 35 | 18 | 129 | 22 | 60 | 31 | 231 | 57 | 128 | 2 |
| 4 | 0 | 0 | 11 | 58 | 11 | 36 | 20 | 92 | 19 | 47 | 18 | 79 | 16 | 35 | 2 |
| 5 | 0 | 0 | 4 | 40 | 10 | 12 | 6 | 26 | 20 | 64 | 10 | 22 | 16 | 18 | 2 |
| 6 | 0 | 0 | 5 | 19 | 7 | 9 | 12 | 30 | 13 | 17 | 8 | 62 | 9 | 35 | 2 |
| 7 | 0 | 0 | 5 | 13 | 8 | 12 | 4 | 20 | 8 | 15 | 6 | 25 | 17 | 21 | 2 |
| 8 | 0 | 0 | 8 | 24 | 10 | 10 | 9 | 17 | 6 | 13 | 5 | 92 | 12 | 7 | 2 |
| 9 | 0 | 0 | 3 | 18 | 5 | 9 | 1 | 32 | 10 | 40 | 7 | 59 | 32 | 99 | 2 |
| 10 | 0 | 0 | 12 | 80 | 24 | 66 | 8 | 158 | 42 | 97 | 22 | 199 | 53 | 130 | 2 |
| 11 | 0 | 0 | 4 | 32 | 8 | 50 | 4 | 122 | 66 | 186 | 9 | 52 | 19 | 50 | 2 |
| 12 | 0 | 0 | 7 | 48 | 19 | 51 | 14 | 87 | 33 | 89 | 8 | 95 | 33 | 81 | 2 |
| 13 | 0 | 0 | 6 | 67 | 18 | 31 | 8 | 76 | 31 | 55 | 12 | 93 | 21 | 81 | 2 |
| 14 | 0 | 0 | 4 | 39 | 13 | 23 | 10 | 66 | 13 | 30 | 6 | 33 | 22 | 20 | 2 |
| 15 | 0 | 0 | 16 | 106 | 36 | 104 | 4 | 144 | 52 | 107 | 16 | 174 | 61 | 199 | 2 |
| 16 | 0 | 0 | 70 | 78 | 117 | 74 | 12 | 76 | 21 | 71 | 23 | 127 | 69 | 103 | 2 |
| 17 | 0 | 0 | 0 | 7 | 1 | 9 | 1 | 23 | 1 | 17 | 1 | 15 | 8 | 4 | 2 |
| 18 | 0 | 0 | 2 | 1 | 2 | 3 | 5 | 10 | 9 | 8 | 6 | 46 | 13 | 18 | 2 |
| 19 | 0 | 0 | 0 | 10 | 3 | 8 | 2 | 15 | 13 | 15 | 5 | 23 | 4 | 21 | 2 |
| 20 | 0 | 0 | 0 | 12 | 4 | 12 | 4 | 24 | 10 | 20 | 0 | 21 | 8 | 19 | 2 |
| 21 | 0 | 0 | 2 | 52 | 12 | 41 | 5 | 73 | 16 | 63 | 3 | 60 | 39 | 63 | 2 |
| 22 | 0 | 0 | 0 | 24 | 4 | 27 | 4 | 52 | 18 | 35 | 3 | 47 | 18 | 42 | 2 |
| 23 | 0 | 0 | 6 | 14 | 6 | 9 | 16 | 52 | 9 | 15 | 22 | 54 | 12 | 11 | 2 |
| 24 | 0 | 0 | 18 | 21 | 6 | 16 | 22 | 73 | 16 | 24 | 32 | 120 | 20 | 50 | 2 |
| 25 | 0 | 0 | 1 | 12 | 5 | 9 | 2 | 26 | 6 | 23 | 0 | 35 | 14 | 68 | 2 |
| 26 | 0 | 0 | 1 | 11 | 34 | 12 | 8 | 25 | 20 | 12 | 3 | 26 | 6 | 6 | 2 |
| 27 | 0 | 0 | 9 | 40 | 4 | 23 | 14 | 70 | 16 | 23 | 5 | 34 | 5 | 17 | 2 |
| 28 | 0 | 0 | 6 | 85 | 29 | 54 | 12 | 77 | 22 | 61 | 5 | 54 | 12 | 30 | 2 |
| 29 | 0 | 0 | 101 | 179 | 42 | 61 | 442 | 1393 | 232 | 568 | 116 | 229 | 52 | 98 | 2 |
| 30 | 0 | 0 | 36 | 43 | 16 | 21 | 56 | 122 | 21 | 48 | 96 | 235 | 33 | 99 | 2 |
| 31 | 0 | 0 | 53 | 113 | 25 | 48 | 16 | 63 | 13 | 28 | 86 | 206 | 44 | 77 | 2 |
| 32 | 0 | 0 | 16 | 47 | 4 | 41 | 15 | 80 | 19 | 51 | 18 | 194 | 34 | 100 | 2 |
| 33 | 0 | 0 | 17 | 114 | 28 | 51 | 18 | 135 | 37 | 75 | 23 | 174 | 38 | 44 | 2 |
| 34 | 0 | 0 | 0 | 31 | 7 | 21 | 3 | 48 | 8 | 12 | 1 | 44 | 8 | 11 | 2 |

FIG. 12 (cont.)

| | # Off-Target Tier III Match Bin I Matches | # Off-Target Tier IV Match Bin I Matches | # Off-Target Tier I Match Bin II Matches | # Off-Target Tier II Match Bin II Matches | # Off-Target Tier III Match Bin II Matches | # Off-Target Tier IV Match Bin II Matches | # Off-Target Tier I Match Bin III Matches | # Off-Target Tier II Match Bin III Matches | # Off-Target Tier III Match Bin III Matches | # Off-Target Tier IV Match Bin III Matches | # Off-Target Tier I Match Bin IV Matches | # Off-Target Tier II Match Bin IV Matches | # Off-Target Tier III Match Bin IV Matches | # Off-Target Tier IV Match Bin IV Matches | On-Target Ruleset |
|---|---|---|---|---|---|---|---|---|---|---|---|---|---|---|---|
| 35 | 0 | 0 | 5 | 49 | 19 | 35 | 10 | 82 | 25 | 37 | 9 | 57 | 19 | 44 | 2 |
| 36 | 0 | 0 | 3 | 13 | 5 | 3 | 3 | 16 | 0 | 5 | 4 | 13 | 12 | 23 | 2 |
| 37 | 0 | 0 | 1 | 14 | 7 | 10 | 3 | 24 | 5 | 11 | 2 | 10 | 6 | 11 | 2 |
| 38 | 0 | 0 | 12 | 87 | 23 | 31 | 17 | 118 | 22 | 47 | 18 | 172 | 66 | 87 | 2 |
| 39 | 0 | 0 | 2 | 22 | 7 | 7 | 4 | 25 | 11 | 15 | 11 | 33 | 8 | 15 | 2 |
| 40 | 0 | 0 | 1 | 8 | 0 | 6 | 2 | 10 | 7 | 5 | 7 | 38 | 6 | 20 | 2 |
| 41 | 0 | 0 | 2 | 6 | 4 | 3 | 1 | 23 | 6 | 22 | 5 | 22 | 14 | 7 | 2 |
| 42 | 0 | 0 | 1 | 20 | 9 | 11 | 7 | 30 | 10 | 18 | 6 | 25 | 5 | 14 | 2 |
| 43 | 0 | 0 | 1 | 3 | 4 | 8 | 5 | 23 | 11 | 8 | 1 | 7 | 4 | 5 | 2 |
| 44 | 0 | 0 | 6 | 71 | 13 | 44 | 2 | 39 | 9 | 31 | 6 | 52 | 11 | 31 | 2 |
| 45 | 0 | 1 | 7 | 147 | 42 | 112 | 7 | 158 | 35 | 102 | 9 | 109 | 37 | 87 | 2 |
| 46 | 0 | 0 | 7 | 113 | 47 | 94 | 11 | 198 | 52 | 160 | 11 | 281 | 73 | 172 | 2 |
| 47 | 0 | 0 | 5 | 34 | 11 | 31 | 7 | 68 | 16 | 36 | 5 | 86 | 8 | 33 | 2 |
| 48 | 0 | 0 | 3 | 39 | 17 | 16 | 6 | 39 | 7 | 29 | 10 | 101 | 9 | 88 | 2 |
| 49 | 0 | 0 | 8 | 76 | 15 | 49 | 6 | 77 | 26 | 52 | 12 | 82 | 11 | 38 | 2 |
| 50 | 0 | 0 | 3 | 16 | 6 | 17 | 6 | 41 | 12 | 31 | 1 | 33 | 29 | 21 | 2 |
| 51 | 0 | 0 | 2 | 17 | 5 | 13 | 4 | 36 | 8 | 26 | 1 | 20 | 5 | 10 | 2 |
| 52 | 0 | 0 | 2 | 20 | 7 | 23 | 9 | 68 | 8 | 36 | 4 | 50 | 21 | 28 | 2 |
| 53 | 0 | 0 | 11 | 63 | 17 | 36 | 11 | 71 | 21 | 32 | 15 | 68 | 10 | 28 | 2 |
| 54 | 0 | 0 | 6 | 45 | 16 | 21 | 17 | 125 | 30 | 72 | 28 | 171 | 48 | 97 | 2 |
| 55 | 0 | 0 | 8 | 23 | 1 | 22 | 5 | 41 | 15 | 34 | 20 | 79 | 11 | 40 | 2 |
| 56 | 0 | 0 | 6 | 58 | 16 | 22 | 27 | 134 | 26 | 66 | 15 | 116 | 30 | 74 | 2 |
| 57 | 0 | 0 | 5 | 42 | 12 | 19 | 8 | 60 | 47 | 42 | 19 | 127 | 32 | 50 | 2 |
| 58 | 0 | 0 | 7 | 48 | 21 | 20 | 13 | 90 | 18 | 38 | 42 | 168 | 28 | 44 | 2 |
| 59 | 0 | 0 | 12 | 60 | 21 | 33 | 14 | 120 | 26 | 73 | 18 | 134 | 25 | 84 | 2 |
| 60 | 0 | 0 | 41 | 126 | 35 | 66 | 14 | 161 | 25 | 66 | 22 | 169 | 43 | 66 | 2 |
| 61 | 0 | 0 | 11 | 86 | 20 | 44 | 15 | 85 | 39 | 68 | 25 | 131 | 25 | 52 | 2 |
| 62 | 0 | 0 | 5 | 31 | 7 | 13 | 6 | 50 | 8 | 20 | 8 | 42 | 14 | 13 | 2 |
| 63 | 0 | 1 | 3 | 51 | 12 | 36 | 15 | 88 | 38 | 109 | 32 | 147 | 56 | 111 | 2 |
| 64 | 0 | 0 | 50 | 177 | 54 | 67 | 144 | 361 | 75 | 171 | 281 | 564 | 132 | 193 | 2 |
| 65 | 0 | 0 | 114 | 249 | 56 | 102 | 228 | 571 | 95 | 148 | 108 | 279 | 72 | 95 | 2 |
| 66 | 0 | 0 | 3 | 18 | 2 | 6 | 6 | 36 | 4 | 14 | 11 | 66 | 25 | 55 | 2 |
| 67 | 0 | 0 | 2 | 64 | 28 | 35 | 6 | 109 | 29 | 85 | 15 | 140 | 21 | 101 | 2 |
| 68 | 0 | 0 | 2 | 79 | 36 | 91 | 6 | 213 | 70 | 147 | 10 | 233 | 76 | 179 | 2 |

FIG. 12 (cont.)

| | # Off-Target Tier III Match Bin I Matches | # Off-Target Tier IV Match Bin I Matches | # Off-Target Tier I Match Bin II Matches | # Off-Target Tier II Match Bin II Matches | # Off-Target Tier III Match Bin II Matches | # Off-Target Tier IV Match Bin II Matches | # Off-Target Tier I Match Bin III Matches | # Off-Target Tier II Match Bin III Matches | # Off-Target Tier III Match Bin III Matches | # Off-Target Tier IV Match Bin III Matches | # Off-Target Tier I Match Bin IV Matches | # Off-Target Tier II Match Bin IV Matches | # Off-Target Tier III Match Bin IV Matches | # Off-Target Tier IV Match Bin IV Matches | On-Target Ruleset |
|---|---|---|---|---|---|---|---|---|---|---|---|---|---|---|---|
| 69 | 0 | 0 | 7 | 25 | 9 | 18 | 11 | 43 | 18 | 17 | 19 | 55 | 8 | 25 | 2 |
| 70 | 0 | 0 | 10 | 30 | 14 | 54 | 7 | 49 | 32 | 123 | 8 | 49 | 9 | 21 | 2 |
| 71 | 0 | 0 | 7 | 64 | 25 | 56 | 6 | 32 | 22 | 35 | 5 | 32 | 15 | 18 | 2 |
| 72 | 0 | 0 | 0 | 7 | 0 | 9 | 1 | 4 | 1 | 3 | 3 | 10 | 4 | 112 | 2 |
| 73 | 0 | 0 | 1 | 1 | 2 | 2 | 12 | 13 | 4 | 9 | 8 | 47 | 11 | 28 | 2 |
| 74 | 0 | 0 | 3 | 21 | 2 | 23 | 0 | 14 | 3 | 15 | 1 | 103 | 12 | 59 | 2 |
| 75 | 0 | 0 | 2 | 1 | 0 | 4 | 1 | 15 | 9 | 8 | 0 | 50 | 12 | 46 | 2 |
| 76 | 0 | 0 | 4 | 22 | 3 | 5 | 2 | 37 | 7 | 22 | 11 | 34 | 13 | 26 | 2 |
| 77 | 0 | 0 | 4 | 178 | 28 | 109 | 7 | 215 | 53 | 142 | 3 | 66 | 18 | 33 | 2 |
| 78 | 0 | 0 | 2 | 13 | 1 | 7 | 3 | 30 | 7 | 13 | 10 | 51 | 24 | 24 | 2 |
| 79 | 0 | 0 | 10 | 57 | 11 | 24 | 24 | 98 | 29 | 43 | 16 | 153 | 39 | 85 | 2 |
| 80 | 0 | 0 | 9 | 44 | 14 | 21 | 27 | 95 | 13 | 29 | 18 | 70 | 11 | 26 | 2 |
| 81 | 0 | 0 | 46 | 249 | 57 | 172 | 41 | 263 | 66 | 152 | 43 | 268 | 48 | 126 | 2 |
| 82 | 0 | 0 | 26 | 229 | 56 | 132 | 50 | 383 | 65 | 199 | 28 | 224 | 37 | 128 | 2 |
| 83 | 0 | 0 | 2 | 42 | 14 | 31 | 4 | 65 | 16 | 47 | 5 | 92 | 35 | 75 | 2 |
| 84 | 0 | 0 | 3 | 28 | 8 | 23 | 9 | 63 | 18 | 37 | 14 | 68 | 10 | 38 | 2 |
| 85 | 0 | 0 | 1 | 39 | 14 | 35 | 5 | 97 | 46 | 95 | 6 | 128 | 47 | 88 | 2 |
| 86 | 0 | 0 | 0 | 41 | 13 | 34 | 6 | 95 | 17 | 58 | 4 | 134 | 38 | 94 | 2 |
| 87 | 0 | 0 | 5 | 34 | 11 | 21 | 3 | 37 | 14 | 30 | 4 | 51 | 18 | 40 | 2 |
| 88 | 0 | 0 | 0 | 17 | 11 | 19 | 5 | 35 | 13 | 37 | 6 | 65 | 20 | 56 | 2 |
| 89 | 0 | 1 | 2 | 50 | 11 | 27 | 5 | 65 | 21 | 50 | 2 | 65 | 11 | 58 | 2 |
| 90 | 1 | 0 | 6 | 168 | 71 | 149 | 27 | 189 | 73 | 179 | 12 | 262 | 109 | 222 | 2 |
| 91 | 0 | 0 | 10 | 173 | 75 | 204 | 19 | 260 | 111 | 335 | 23 | 235 | 110 | 281 | 2 |
| 92 | 0 | 0 | 2 | 3 | 1 | 3 | 3 | 7 | 4 | 3 | 4 | 12 | 6 | 10 | 2 |
| 93 | 0 | 0 | 0 | 13 | 5 | 9 | 5 | 25 | 6 | 21 | 2 | 20 | 6 | 14 | 2 |
| 94 | 0 | 0 | 1 | 29 | 4 | 21 | 0 | 36 | 7 | 33 | 0 | 37 | 12 | 33 | 2 |
| 95 | 0 | 0 | 1 | 7 | 0 | 7 | 6 | 11 | 1 | 5 | 5 | 8 | 4 | 8 | 2 |
| 96 | 0 | 0 | 0 | 11 | 3 | 14 | 0 | 33 | 14 | 19 | 12 | 27 | 11 | 26 | 2 |
| 97 | 0 | 0 | 4 | 47 | 17 | 52 | 9 | 55 | 28 | 61 | 3 | 118 | 42 | 99 | 2 |
| 98 | 0 | 0 | 4 | 14 | 6 | 9 | 1 | 30 | 16 | 18 | 3 | 26 | 15 | 21 | 2 |
| 99 | 0 | 0 | 3 | 104 | 25 | 70 | 3 | 82 | 40 | 96 | 10 | 84 | 35 | 74 | 2 |
| 100 | 0 | 0 | 3 | 97 | 25 | 95 | 5 | 216 | 94 | 315 | 2 | 195 | 68 | 283 | 2 |
| 101 | 0 | 0 | 5 | 71 | 19 | 57 | 1 | 104 | 47 | 80 | 4 | 129 | 43 | 123 | 2 |
| 102 | 0 | 0 | 11 | 77 | 34 | 78 | 8 | 185 | 56 | 164 | 8 | 261 | 81 | 206 | 2 |

FIG. 12 (cont.)

| | # Off-Target Tier III Match Bin I Matches | # Off-Target Tier IV Match Bin I Matches | # Off-Target Tier I Match Bin II Matches | # Off-Target Tier II Match Bin II Matches | # Off-Target Tier III Match Bin II Matches | # Off-Target Tier IV Match Bin II Matches | # Off-Target Tier I Match Bin III Matches | # Off-Target Tier II Match Bin III Matches | # Off-Target Tier III Match Bin III Matches | # Off-Target Tier IV Match Bin III Matches | # Off-Target Tier I Match Bin IV Matches | # Off-Target Tier II Match Bin IV Matches | # Off-Target Tier III Match Bin IV Matches | # Off-Target Tier IV Match Bin IV Matches | On-Target Ruleset |
|---|---|---|---|---|---|---|---|---|---|---|---|---|---|---|---|
| 103 | 0 | 0 | 4 | 132 | 63 | 173 | 10 | 228 | 76 | 194 | 9 | 300 | 98 | 250 | 2 |
| 104 | 0 | 0 | 4 | 85 | 33 | 94 | 7 | 139 | 48 | 144 | 13 | 263 | 93 | 287 | 2 |
| 105 | 0 | 1 | 3 | 48 | 21 | 52 | 1 | 66 | 26 | 55 | 3 | 56 | 24 | 68 | 2 |
| 106 | 0 | 0 | 1 | 19 | 5 | 15 | 1 | 18 | 10 | 16 | 3 | 37 | 21 | 22 | 2 |
| 107 | 0 | 0 | 1 | 57 | 20 | 52 | 2 | 71 | 21 | 73 | 7 | 112 | 59 | 141 | 2 |
| 108 | 0 | 0 | 0 | 20 | 3 | 22 | 4 | 55 | 29 | 62 | 4 | 93 | 25 | 107 | 2 |
| 109 | 0 | 0 | 4 | 73 | 33 | 59 | 4 | 61 | 22 | 48 | 12 | 122 | 36 | 110 | 2 |
| 110 | 0 | 0 | 0 | 35 | 17 | 38 | 2 | 71 | 24 | 75 | 8 | 121 | 50 | 118 | 2 |
| 111 | 0 | 0 | 2 | 54 | 17 | 50 | 5 | 92 | 29 | 71 | 8 | 131 | 46 | 108 | 2 |
| 112 | 0 | 0 | 2 | 64 | 26 | 62 | 2 | 120 | 42 | 117 | 3 | 149 | 42 | 194 | 2 |
| 113 | 0 | 0 | 1 | 24 | 6 | 18 | 1 | 33 | 14 | 25 | 7 | 54 | 28 | 58 | 2 |
| 114 | 0 | 0 | 1 | 38 | 12 | 32 | 11 | 122 | 51 | 76 | 4 | 145 | 60 | 132 | 2 |
| 115 | 0 | 0 | 1 | 51 | 15 | 36 | 14 | 72 | 48 | 66 | 13 | 169 | 61 | 181 | 2 |
| 116 | 0 | 0 | 0 | 15 | 10 | 16 | 1 | 35 | 7 | 29 | 4 | 46 | 25 | 62 | 2 |
| 117 | 0 | 0 | 1 | 19 | 7 | 29 | 0 | 39 | 45 | 108 | 1 | 48 | 25 | 78 | 2 |
| 118 | 0 | 0 | 1 | 20 | 15 | 26 | 3 | 25 | 12 | 21 | 7 | 53 | 14 | 32 | 2 |
| 119 | 0 | 0 | 1 | 24 | 11 | 38 | 15 | 40 | 20 | 29 | 3 | 45 | 15 | 25 | 2 |
| 120 | 0 | 0 | 1 | 34 | 14 | 26 | 10 | 47 | 12 | 37 | 1 | 30 | 16 | 18 | 2 |
| 121 | 0 | 0 | 2 | 46 | 15 | 33 | 4 | 61 | 18 | 45 | 7 | 68 | 18 | 27 | 2 |
| 122 | 0 | 0 | 4 | 83 | 25 | 83 | 3 | 98 | 33 | 90 | 7 | 150 | 40 | 142 | 2 |
| 123 | 0 | 1 | 2 | 48 | 20 | 57 | 5 | 104 | 28 | 88 | 9 | 168 | 47 | 131 | 2 |
| 124 | 0 | 0 | 4 | 25 | 13 | 39 | 1 | 49 | 26 | 56 | 4 | 33 | 13 | 39 | 2 |
| 125 | 0 | 0 | 2 | 51 | 19 | 62 | 15 | 117 | 34 | 137 | 16 | 135 | 56 | 188 | 2 |
| 126 | 0 | 0 | 4 | 50 | 9 | 59 | 10 | 179 | 54 | 185 | 6 | 129 | 45 | 121 | 2 |
| 127 | 0 | 2 | 6 | 121 | 36 | 103 | 8 | 127 | 52 | 137 | 11 | 171 | 65 | 186 | 2 |
| 128 | 0 | 0 | 3 | 165 | 38 | 121 | 7 | 125 | 52 | 138 | 5 | 162 | 56 | 157 | 2 |
| 129 | 0 | 0 | 5 | 91 | 25 | 85 | 8 | 144 | 37 | 117 | 23 | 349 | 142 | 288 | 2 |
| 130 | 0 | 0 | 0 | 135 | 47 | 122 | 7 | 197 | 88 | 210 | 8 | 258 | 75 | 222 | 2 |
| 131 | 0 | 1 | 5 | 117 | 43 | 308 | 12 | 159 | 66 | 153 | 23 | 223 | 82 | 195 | 2 |
| 132 | 0 | 0 | 1 | 109 | 36 | 91 | 1 | 109 | 48 | 149 | 3 | 152 | 63 | 126 | 2 |
| 133 | 0 | 1 | 16 | 187 | 81 | 244 | 7 | 182 | 83 | 218 | 12 | 416 | 208 | 556 | 2 |
| 134 | 0 | 0 | 5 | 103 | 39 | 155 | 5 | 122 | 48 | 119 | 5 | 153 | 68 | 209 | 2 |
| 135 | 0 | 0 | 2 | 28 | 5 | 34 | 1 | 76 | 33 | 81 | 1 | 163 | 67 | 242 | 2 |
| 136 | 0 | 0 | 1 | 13 | 6 | 25 | 1 | 29 | 8 | 18 | 2 | 16 | 7 | 16 | 2 |

FIG. 12 (cont.)

| | # Off-Target Tier III Match Bin I Matches | # Off-Target Tier IV Match Bin I Matches | # Off-Target Tier I Match Bin II Matches | # Off-Target Tier II Match Bin II Matches | # Off-Target Tier III Match Bin II Matches | # Off-Target Tier IV Match Bin II Matches | # Off-Target Tier I Match Bin III Matches | # Off-Target Tier II Match Bin III Matches | # Off-Target Tier III Match Bin III Matches | # Off-Target Tier IV Match Bin III Matches | # Off-Target Tier I Match Bin IV Matches | # Off-Target Tier II Match Bin IV Matches | # Off-Target Tier III Match Bin IV Matches | # Off-Target Tier IV Match Bin IV Matches | On-Target Ruleset |
|---|---|---|---|---|---|---|---|---|---|---|---|---|---|---|---|
| 137 | 0 | 0 | 1 | 20 | 5 | 12 | 5 | 21 | 5 | 9 | 2 | 6 | 3 | 4 | 2 |
| 138 | 0 | 0 | 2 | 33 | 8 | 45 | 2 | 40 | 14 | 32 | 3 | 45 | 13 | 42 | 2 |
| 139 | 0 | 0 | 5 | 232 | 104 | 377 | 3 | 145 | 48 | 136 | 5 | 73 | 25 | 59 | 2 |
| 140 | 0 | 0 | 1 | 587 | 217 | 650 | 0 | 197 | 68 | 232 | 1 | 193 | 78 | 295 | 2 |
| 141 | 0 | 1 | 0 | 91 | 45 | 132 | 0 | 585 | 254 | 713 | 2 | 244 | 86 | 328 | 2 |
| 142 | 0 | 0 | 2 | 78 | 23 | 88 | 7 | 120 | 57 | 149 | 3 | 286 | 118 | 372 | 2 |
| 143 | 0 | 0 | 1 | 17 | 4 | 16 | 1 | 33 | 7 | 35 | 0 | 30 | 8 | 30 | 2 |
| 144 | 0 | 0 | 1 | 27 | 6 | 23 | 4 | 61 | 17 | 50 | 5 | 61 | 10 | 43 | 2 |
| 145 | 0 | 0 | 1 | 29 | 6 | 26 | 0 | 32 | 11 | 31 | 4 | 43 | 7 | 37 | 2 |
| 146 | 0 | 0 | 4 | 34 | 13 | 40 | 7 | 103 | 35 | 115 | 7 | 131 | 53 | 107 | 2 |
| 147 | 0 | 0 | 2 | 54 | 22 | 105 | 2 | 55 | 31 | 60 | 2 | 56 | 35 | 70 | 2 |
| 148 | 0 | 0 | 2 | 96 | 31 | 86 | 4 | 180 | 65 | 176 | 11 | 230 | 88 | 206 | 2 |
| 149 | 0 | 0 | 2 | 69 | 26 | 67 | 5 | 103 | 39 | 118 | 7 | 166 | 67 | 159 | 2 |
| 150 | 0 | 0 | 1 | 54 | 38 | 63 | 5 | 113 | 35 | 95 | 4 | 167 | 62 | 180 | 2 |
| 151 | 0 | 0 | 8 | 80 | 38 | 85 | 7 | 116 | 33 | 130 | 9 | 175 | 63 | 165 | 2 |
| 152 | 0 | 0 | 0 | 51 | 13 | 42 | 2 | 75 | 35 | 77 | 7 | 157 | 52 | 148 | 2 |
| 153 | 0 | 0 | 1 | 34 | 14 | 48 | 3 | 127 | 66 | 284 | 10 | 176 | 54 | 166 | 2 |
| 154 | 0 | 0 | 0 | 35 | 16 | 54 | 3 | 115 | 50 | 118 | 1 | 85 | 23 | 76 | 2 |
| 155 | 0 | 0 | 3 | 64 | 17 | 62 | 5 | 94 | 26 | 75 | 10 | 178 | 54 | 167 | 2 |
| 156 | 0 | 0 | 3 | 131 | 64 | 135 | 10 | 150 | 60 | 167 | 5 | 245 | 85 | 253 | 2 |
| 157 | 0 | 0 | 1 | 70 | 40 | 83 | 4 | 139 | 52 | 137 | 5 | 170 | 64 | 169 | 2 |
| 158 | 0 | 0 | 0 | 60 | 21 | 66 | 3 | 95 | 36 | 98 | 2 | 141 | 59 | 149 | 2 |
| 159 | 0 | 0 | 0 | 66 | 12 | 68 | 2 | 123 | 35 | 99 | 4 | 351 | 119 | 184 | 2 |
| 160 | 0 | 0 | 4 | 128 | 40 | 141 | 6 | 230 | 100 | 219 | 12 | 202 | 67 | 184 | 2 |
| 161 | 0 | 0 | 4 | 109 | 46 | 97 | 4 | 108 | 49 | 113 | 5 | 140 | 57 | 145 | 2 |
| 162 | 0 | 0 | 3 | 114 | 56 | 141 | 3 | 138 | 53 | 147 | 5 | 190 | 65 | 183 | 2 |
| 163 | 0 | 0 | 0 | 58 | 23 | 63 | 1 | 112 | 43 | 182 | 0 | 134 | 48 | 150 | 2 |
| 164 | 0 | 1 | 0 | 91 | 24 | 94 | 0 | 168 | 60 | 160 | 1 | 277 | 118 | 312 | 2 |
| 165 | 0 | 0 | 0 | 92 | 31 | 114 | 1 | 164 | 58 | 181 | 4 | 198 | 73 | 249 | 2 |
| 166 | 0 | 0 | 0 | 103 | 38 | 92 | 3 | 127 | 57 | 158 | 0 | 94 | 42 | 105 | 2 |
| 167 | 0 | 0 | 1 | 62 | 14 | 69 | 11 | 126 | 50 | 126 | 14 | 263 | 99 | 327 | 2 |
| 168 | 0 | 0 | 0 | 248 | 124 | 445 | 19 | 419 | 191 | 690 | 4 | 177 | 51 | 201 | 2 |
| 169 | 0 | 0 | 3 | 78 | 28 | 74 | 2 | 121 | 39 | 113 | 3 | 329 | 97 | 241 | 2 |

FIG. 12 (cont.)

| | # Off-Target Tier III Match Bin I Matches | # Off-Target Tier IV Match Bin I Matches | # Off-Target Tier I Match Bin II Matches | # Off-Target Tier II Match Bin II Matches | # Off-Target Tier III Match Bin II Matches | # Off-Target Tier IV Match Bin II Matches | # Off-Target Tier I Match Bin III Matches | # Off-Target Tier II Match Bin III Matches | # Off-Target Tier III Match Bin III Matches | # Off-Target Tier IV Match Bin III Matches | # Off-Target Tier I Match Bin IV Matches | # Off-Target Tier II Match Bin IV Matches | # Off-Target Tier III Match Bin IV Matches | # Off-Target Tier IV Match Bin IV Matches | On-Target Ruleset |
|---|---|---|---|---|---|---|---|---|---|---|---|---|---|---|---|
| 170 | 0 | 0 | 1 | 57 | 20 | 46 | 4 | 123 | 34 | 88 | 4 | 224 | 57 | 216 | 2 |
| 171 | 0 | 0 | 2 | 56 | 20 | 69 | 6 | 226 | 79 | 224 | 3 | 135 | 53 | 99 | 2 |
| 172 | 0 | 1 | 22 | 128 | 58 | 112 | 13 | 136 | 62 | 169 | 45 | 347 | 147 | 356 | 2 |
| 173 | 0 | 0 | 7 | 81 | 22 | 74 | 8 | 151 | 46 | 148 | 4 | 141 | 45 | 117 | 2 |
| 174 | 0 | 0 | 8 | 173 | 65 | 202 | 13 | 212 | 101 | 267 | 20 | 360 | 126 | 366 | 2 |
| 175 | 0 | 1 | 5 | 183 | 72 | 220 | 12 | 218 | 105 | 280 | 17 | 327 | 107 | 357 | 2 |
| 176 | 1 | 0 | 3 | 90 | 37 | 84 | 2 | 140 | 54 | 142 | 6 | 169 | 56 | 147 | 2 |
| 177 | 0 | 0 | 0 | 71 | 13 | 34 | 1 | 115 | 43 | 94 | 2 | 56 | 21 | 51 | 2 |
| 178 | 0 | 0 | 0 | 8 | 1 | 12 | 4 | 11 | 1 | 16 | 2 | 36 | 11 | 34 | 2 |
| 179 | 0 | 0 | 0 | 12 | 4 | 20 | 0 | 43 | 9 | 23 | 2 | 44 | 12 | 57 | 2 |
| 180 | 0 | 0 | 0 | 9 | 6 | 15 | 1 | 6 | 10 | 8 | 0 | 10 | 1 | 7 | 2 |
| 181 | 0 | 0 | 4 | 46 | 4 | 13 | 13 | 38 | 14 | 25 | 15 | 84 | 26 | 66 | 2 |
| 182 | 0 | 0 | 1 | 58 | 15 | 39 | 8 | 61 | 22 | 39 | 18 | 90 | 25 | 89 | 2 |
| 183 | 0 | 0 | 0 | 46 | 15 | 54 | 0 | 61 | 29 | 61 | 2 | 65 | 17 | 82 | 2 |
| 184 | 0 | 0 | 1 | 59 | 17 | 51 | 4 | 120 | 34 | 124 | 6 | 158 | 61 | 129 | 2 |
| 185 | 0 | 0 | 9 | 116 | 60 | 106 | 8 | 166 | 46 | 158 | 13 | 227 | 97 | 219 | 2 |
| 186 | 0 | 0 | 5 | 38 | 16 | 54 | 6 | 48 | 16 | 66 | 10 | 154 | 41 | 142 | 2 |
| 187 | 0 | 0 | 4 | 51 | 18 | 45 | 3 | 112 | 38 | 137 | 8 | 111 | 35 | 121 | 2 |
| 188 | 0 | 0 | 1 | 37 | 12 | 40 | 1 | 108 | 39 | 134 | 20 | 279 | 101 | 332 | 2 |
| 189 | 0 | 0 | 3 | 41 | 12 | 39 | 2 | 66 | 28 | 55 | 4 | 111 | 44 | 115 | 2 |
| 190 | 0 | 0 | 6 | 46 | 16 | 49 | 7 | 111 | 29 | 62 | 10 | 110 | 35 | 93 | 2 |
| 191 | 0 | 0 | 3 | 47 | 20 | 37 | 7 | 147 | 35 | 124 | 11 | 277 | 104 | 201 | 2 |
| 192 | 0 | 0 | 1 | 66 | 21 | 77 | 1 | 85 | 30 | 89 | 0 | 121 | 39 | 111 | 2 |
| 193 | 0 | 0 | 2 | 55 | 24 | 84 | 1 | 72 | 30 | 99 | 1 | 89 | 26 | 94 | 2 |
| 194 | 0 | 0 | 1 | 31 | 15 | 41 | 2 | 59 | 22 | 91 | 3 | 143 | 44 | 152 | 2 |
| 195 | 0 | 0 | 2 | 53 | 18 | 49 | 13 | 93 | 32 | 89 | 11 | 189 | 74 | 257 | 2 |
| 196 | 0 | 0 | 5 | 134 | 50 | 131 | 6 | 115 | 38 | 110 | 13 | 115 | 52 | 90 | 2 |
| 197 | 0 | 1 | 7 | 45 | 15 | 48 | 4 | 96 | 42 | 100 | 20 | 158 | 60 | 135 | 2 |
| 198 | 0 | 0 | 4 | 43 | 12 | 29 | 3 | 74 | 36 | 84 | 10 | 108 | 27 | 89 | 2 |
| 199 | 0 | 0 | 1 | 51 | 32 | 50 | 2 | 82 | 37 | 54 | 15 | 109 | 35 | 126 | 2 |
| 200 | 0 | 0 | 0 | 46 | 14 | 31 | 1 | 36 | 14 | 44 | 2 | 52 | 24 | 43 | 2 |
| 201 | 0 | 0 | 0 | 27 | 11 | 26 | 0 | 38 | 18 | 64 | 9 | 108 | 43 | 135 | 2 |
| 202 | 0 | 0 | 1 | 27 | 13 | 31 | 0 | 54 | 24 | 63 | 3 | 66 | 24 | 68 | 2 |
| 203 | 0 | 0 | 6 | 118 | 40 | 122 | 9 | 190 | 65 | 164 | 17 | 418 | 146 | 408 | 2 |

FIG. 12 (cont.)

| | # Off-Target Tier III Match Bin I Matches | # Off-Target Tier IV Match Bin I Matches | # Off-Target Tier I Match Bin II Matches | # Off-Target Tier II Match Bin II Matches | # Off-Target Tier III Match Bin II Matches | # Off-Target Tier IV Match Bin II Matches | # Off-Target Tier I Match Bin III Matches | # Off-Target Tier II Match Bin III Matches | # Off-Target Tier III Match Bin III Matches | # Off-Target Tier IV Match Bin III Matches | # Off-Target Tier I Match Bin IV Matches | # Off-Target Tier II Match Bin IV Matches | # Off-Target Tier III Match Bin IV Matches | # Off-Target Tier IV Match Bin IV Matches | On-Target Ruleset |
|---|---|---|---|---|---|---|---|---|---|---|---|---|---|---|---|
| 204 | 0 | 0 | 3 | 74 | 37 | 67 | 2 | 123 | 30 | 148 | 17 | 319 | 129 | 310 | 2 |
| 205 | 0 | 0 | 12 | 120 | 62 | 137 | 4 | 134 | 41 | 123 | 12 | 169 | 64 | 166 | 2 |
| 206 | 0 | 0 | 5 | 70 | 23 | 62 | 11 | 121 | 43 | 90 | 15 | 204 | 98 | 180 | 2 |
| 207 | 0 | 0 | 0 | 71 | 30 | 56 | 7 | 130 | 52 | 118 | 15 | 172 | 60 | 168 | 2 |
| 208 | 0 | 0 | 0 | 55 | 16 | 61 | 6 | 74 | 27 | 79 | 8 | 105 | 45 | 110 | 2 |
| 209 | 0 | 0 | 2 | 55 | 15 | 52 | 10 | 83 | 19 | 74 | 10 | 131 | 50 | 133 | 2 |
| 210 | 0 | 0 | 1 | 72 | 19 | 56 | 3 | 76 | 20 | 60 | 5 | 160 | 61 | 162 | 2 |
| 211 | 0 | 0 | 1 | 70 | 19 | 60 | 1 | 104 | 26 | 83 | 1 | 86 | 24 | 91 | 2 |
| 212 | 0 | 0 | 3 | 55 | 19 | 46 | 8 | 95 | 31 | 108 | 4 | 124 | 26 | 105 | 2 |
| 213 | 0 | 0 | 3 | 29 | 6 | 26 | 1 | 57 | 14 | 50 | 2 | 64 | 10 | 53 | 2 |
| 214 | 0 | 0 | 6 | 40 | 12 | 24 | 3 | 30 | 12 | 24 | 1 | 31 | 2 | 30 | 2 |
| 215 | 0 | 0 | 1 | 14 | 4 | 6 | 0 | 23 | 3 | 13 | 2 | 52 | 14 | 42 | 2 |
| 216 | 0 | 0 | 0 | 4 | 3 | 10 | 1 | 15 | 7 | 10 | 1 | 66 | 13 | 34 | 2 |
| 217 | 0 | 0 | 6 | 174 | 69 | 207 | 5 | 273 | 104 | 297 | 5 | 569 | 198 | 677 | 2 |
| 218 | 0 | 0 | 2 | 198 | 68 | 214 | 1 | 192 | 58 | 182 | 4 | 211 | 80 | 257 | 2 |
| 219 | 0 | 0 | 2 | 40 | 13 | 24 | 2 | 42 | 17 | 46 | 2 | 43 | 19 | 47 | 2 |
| 220 | 0 | 1 | 0 | 21 | 13 | 18 | 8 | 43 | 19 | 65 | 1 | 35 | 17 | 50 | 2 |
| 221 | 0 | 0 | 9 | 98 | 33 | 109 | 7 | 120 | 38 | 85 | 6 | 143 | 49 | 187 | 2 |
| 222 | 1 | 0 | 8 | 89 | 37 | 127 | 7 | 204 | 77 | 255 | 10 | 288 | 123 | 382 | 2 |
| 223 | 1 | 0 | 3 | 117 | 55 | 123 | 19 | 214 | 77 | 202 | 25 | 309 | 122 | 395 | 2 |
| 224 | 0 | 0 | 3 | 41 | 12 | 31 | 2 | 38 | 9 | 40 | 1 | 34 | 16 | 40 | 2 |
| 225 | 0 | 0 | 1 | 68 | 31 | 63 | 1 | 130 | 62 | 166 | 4 | 164 | 80 | 184 | 2 |
| 226 | 0 | 0 | 2 | 40 | 18 | 45 | 3 | 67 | 21 | 66 | 2 | 156 | 60 | 92 | 2 |
| 227 | 0 | 0 | 0 | 61 | 18 | 63 | 1 | 147 | 55 | 125 | 4 | 100 | 35 | 110 | 2 |
| 228 | 0 | 0 | 0 | 37 | 26 | 46 | 2 | 101 | 40 | 88 | 2 | 61 | 32 | 54 | 2 |
| 229 | 0 | 0 | 0 | 64 | 24 | 68 | 3 | 157 | 61 | 186 | 2 | 164 | 51 | 183 | 2 |
| 230 | 0 | 0 | 0 | 26 | 28 | 39 | 0 | 52 | 38 | 67 | 2 | 73 | 22 | 65 | 2 |
| 231 | 0 | 0 | 1 | 50 | 21 | 62 | 1 | 73 | 28 | 89 | 3 | 158 | 49 | 135 | 2 |
| 232 | 0 | 0 | 0 | 107 | 45 | 106 | 2 | 187 | 64 | 209 | 3 | 266 | 91 | 244 | 2 |
| 233 | 0 | 0 | 10 | 87 | 20 | 77 | 3 | 170 | 50 | 174 | 4 | 225 | 86 | 250 | 2 |
| 234 | 0 | 0 | 3 | 191 | 62 | 249 | 6 | 393 | 149 | 423 | 20 | 518 | 241 | 675 | 2 |
| 235 | 1 | 0 | 1 | 38 | 14 | 46 | 14 | 76 | 31 | 106 | 16 | 157 | 66 | 153 | 2 |
| 236 | 0 | 0 | 0 | 67 | 22 | 48 | 6 | 110 | 31 | 121 | 3 | 165 | 56 | 135 | 2 |
| 237 | 0 | 0 | 4 | 119 | 58 | 143 | 3 | 175 | 95 | 205 | 6 | 327 | 143 | 418 | 2 |

FIG. 12 (cont.)

| | # Off-Target Tier III Match Bin I Matches | # Off-Target Tier IV Match Bin I Matches | # Off-Target Tier I Match Bin II Matches | # Off-Target Tier II Match Bin II Matches | # Off-Target Tier III Match Bin III Matches | # Off-Target Tier IV Match Bin IV Matches | # Off-Target Tier I Match Bin III Matches | # Off-Target Tier II Match Bin III Matches | # Off-Target Tier III Match Bin III Matches | # Off-Target Tier IV Match Bin IV Matches | # Off-Target Tier I Match Bin IV Matches | # Off-Target Tier II Match Bin IV Matches | # Off-Target Tier III Match Bin IV Matches | # Off-Target Tier IV Match Bin IV Matches | On-Target Ruleset |
|---|---|---|---|---|---|---|---|---|---|---|---|---|---|---|---|
| 238 | 0 | 0 | 4 | 122 | 54 | 146 | 14 | 229 | 107 | 298 | 16 | 324 | 125 | 369 | 2 |
| 239 | 0 | 0 | 4 | 136 | 48 | 166 | 5 | 321 | 87 | 300 | 9 | 225 | 95 | 246 | 2 |
| 240 | 0 | 0 | 3 | 158 | 38 | 139 | 3 | 289 | 84 | 248 | 2 | 270 | 95 | 268 | 2 |
| 241 | 0 | 1 | 0 | 241 | 78 | 251 | 5 | 309 | 99 | 348 | 4 | 490 | 154 | 442 | 2 |
| 242 | 0 | 0 | 2 | 231 | 76 | 284 | 1 | 107 | 36 | 147 | 3 | 386 | 142 | 433 | 2 |
| 243 | 0 | 0 | 0 | 146 | 43 | 148 | 6 | 150 | 71 | 202 | 4 | 365 | 163 | 616 | 2 |
| 244 | 0 | 0 | 1 | 108 | 36 | 119 | 2 | 145 | 49 | 147 | 2 | 211 | 70 | 192 | 2 |
| 245 | 0 | 0 | 1 | 30 | 9 | 32 | 1 | 63 | 24 | 69 | 0 | 171 | 69 | 143 | 2 |
| 246 | 0 | 0 | 1 | 43 | 18 | 35 | 5 | 85 | 31 | 73 | 6 | 114 | 47 | 117 | 2 |
| 247 | 0 | 0 | 8 | 60 | 24 | 69 | 2 | 80 | 31 | 111 | 15 | 85 | 29 | 99 | 2 |
| 248 | 0 | 0 | 7 | 60 | 29 | 57 | 5 | 60 | 51 | 70 | 12 | 170 | 42 | 171 | 2 |
| 249 | 0 | 0 | 4 | 77 | 38 | 75 | 8 | 107 | 48 | 130 | 10 | 178 | 67 | 174 | 2 |
| 250 | 0 | 0 | 2 | 48 | 25 | 53 | 4 | 101 | 35 | 130 | 10 | 136 | 54 | 153 | 2 |
| 251 | 0 | 1 | 4 | 95 | 27 | 112 | 3 | 138 | 55 | 158 | 3 | 115 | 56 | 145 | 2 |
| 252 | 0 | 0 | 1 | 14 | 8 | 10 | 2 | 24 | 13 | 24 | 3 | 25 | 8 | 13 | 2 |
| 253 | 0 | 0 | 5 | 88 | 33 | 66 | 8 | 105 | 36 | 93 | 3 | 111 | 36 | 84 | 2 |
| 254 | 0 | 0 | 4 | 82 | 25 | 82 | 6 | 81 | 37 | 64 | 1 | 59 | 22 | 36 | 2 |
| 255 | 0 | 0 | 2 | 74 | 23 | 53 | 1 | 43 | 16 | 50 | 6 | 65 | 24 | 60 | 2 |
| 256 | 0 | 0 | 5 | 68 | 25 | 52 | 4 | 102 | 29 | 66 | 1 | 52 | 32 | 52 | 2 |
| 257 | 0 | 0 | 4 | 42 | 18 | 52 | 0 | 77 | 22 | 70 | 2 | 93 | 36 | 89 | 2 |
| 258 | 0 | 0 | 0 | 9 | 2 | 15 | 2 | 14 | 2 | 11 | 1 | 40 | 7 | 12 | 2 |
| 259 | 0 | 0 | 1 | 31 | 7 | 11 | 1 | 15 | 3 | 16 | 1 | 12 | 6 | 18 | 2 |
| 260 | 0 | 0 | 0 | 5 | 1 | 7 | 1 | 11 | 1 | 13 | 2 | 6 | 3 | 5 | 2 |
| 261 | 0 | 0 | 0 | 14 | 4 | 8 | 1 | 15 | 6 | 25 | 0 | 5 | 2 | 4 | 2 |
| 262 | 0 | 0 | 3 | 136 | 35 | 159 | 13 | 213 | 87 | 279 | 10 | 472 | 217 | 731 | 2 |
| 263 | 0 | 1 | 2 | 261 | 98 | 366 | 93 | 258 | 133 | 243 | 14 | 345 | 140 | 375 | 2 |
| 264 | 0 | 0 | 1 | 89 | 32 | 114 | 4 | 138 | 69 | 130 | 9 | 136 | 57 | 140 | 2 |
| 265 | 0 | 0 | 1 | 44 | 11 | 23 | 3 | 74 | 32 | 80 | 16 | 183 | 69 | 202 | 2 |

FIG. 12 (cont.)

| | On-Target Efficacy Score | On-Target Rank | Off-Target Rank | On-Target Rank Weight | Off-Target Rank Weight | Combined Rank | Pick Order | Picking Round | Picking Notes |
|---|---|---|---|---|---|---|---|---|---|
| 1 | 0.4761 | 146 | 181 | 1 | 1 | 187 | | | Outside Target Window: 5-65% |
| 2 | 0.4343 | 177 | 207 | 1 | 1 | 214 | | | Outside Target Window: 5-65% |
| 3 | 0.265 | 252 | 213 | 1 | 1 | 257 | | | Outside Target Window: 5-65% |
| 4 | 0.4887 | 137 | 214 | 1 | 1 | 201 | | | Outside Target Window: 5-65% |
| 5 | 0.6042 | 53 | 148 | 1 | 1 | 78 | | | Outside Target Window: 5-65% |
| 6 | 0.2899 | 246 | 167 | 1 | 1 | 233 | | | Outside Target Window: 5-65% |
| 7 | 0.4387 | 172 | 166 | 1 | 1 | 193 | | | Outside Target Window: 5-65% |
| 8 | 0.5512 | 98 | 200 | 1 | 1 | 162 | | | Outside Target Window: 5-65%; Spacing Violation: Too close to earlier pick at position 121 |
| 9 | 0.5394 | 105 | 121 | 1 | 1 | 101 | | | Outside Target Window: 5-65%; Spacing Violation: Too close to earlier pick at position 121 |
| 10 | 0.5203 | 118 | 218 | 1 | 1 | 192 | | | Outside Target Window: 5-65%; Spacing Violation: Too close to earlier pick at position 121 |
| 11 | 0.6706 | 13 | 146 | 1 | 1 | 51 | | | Outside Target Window: 5-65%; Spacing Violation: Too close to earlier pick at position 121 |
| 12 | 0.51 | 124 | 193 | 1 | 1 | 179 | | | Outside Target Window: 5-65%; Spacing Violation: Too close to earlier pick at position 121 |
| 13 | 0.4706 | 153 | 186 | 1 | 1 | 194 | | | Outside Target Window: 5-65%; Spacing Violation: Too close to earlier pick at position 121 |
| 14 | 0.5896 | 63 | 147 | 1 | 1 | 85 | | | Outside Target Window: 5-65%; Spacing Violation: Too close to earlier pick at position 121 |
| 15 | 0.4854 | 140 | 221 | 1 | 1 | 206 | | | Outside Target Window: 5-65%; Spacing Violation: Too close to earlier pick at position 121 |
| 16 | 0.719 | 4 | 230 | 1 | 1 | 110 | | | Outside Target Window: 5-65%; Spacing Violation: Too close to earlier pick at position 121 |
| 17 | 0.6348 | 34 | 4 | 1 | 1 | 3 | | | Outside Target Window: 5-65%; Spacing Violation: Too close to earlier pick at position 121 |
| 18 | 0.3351 | 233 | 88 | 1 | 1 | 181 | | | Spacing Violation: Too close to earlier pick at position 121; Transcriptional Incompatibility ("TTTT") |
| 19 | 0.5569 | 94 | 8 | 1 | 1 | 19 | | | Spacing Violation: Too close to earlier pick at position 121 |
| 20 | 0.3413 | 231 | 10 | 1 | 1 | 117 | | | Spacing Violation: Too close to earlier pick at position 121; Transcriptional Incompatibility ("TTTT") |
| 21 | 0.5629 | 89 | 104 | 1 | 1 | 67 | | | Spacing Violation: Too close to earlier pick at position 121; Transcriptional Incompatibility ("TTTT") |
| 22 | 0.6918 | 8 | 18 | 1 | 1 | 1 | 1 | | |
| 23 | 0.5036 | 127 | 180 | 1 | 1 | 176 | | | Spacing Violation: Too close to earlier pick at position 121 |
| 24 | 0.4899 | 132 | 224 | 1 | 1 | 204 | | | Spacing Violation: Too close to earlier pick at position 121 |
| 25 | 0.6287 | 37 | 43 | 1 | 1 | 15 | | | Spacing Violation: Too close to earlier pick at position 121 |
| 26 | 0.6548 | 23 | 42 | 1 | 1 | 7 | | | Spacing Violation: Too close to earlier pick at position 121 |
| 27 | 0.377 | 210 | 205 | 1 | 1 | 235 | | | Spacing Violation: Too close to earlier pick at position 121 |
| 28 | 0.6629 | 18 | 188 | 1 | 1 | 83 | | | Spacing Violation: Too close to earlier pick at position 121 |
| 29 | 0.4359 | 175 | 231 | 1 | 1 | 225 | | | Spacing Violation: Too close to earlier pick at position 121 |
| 30 | 0.2564 | 254 | 226 | 1 | 1 | 261 | | | Spacing Violation: Too close to earlier pick at position 121 |
| 31 | 0.3914 | 206 | 229 | 1 | 1 | 248 | | | Spacing Violation: Too close to earlier pick at position 121 |
| 32 | 0.2476 | 255 | 260 | 1 | 1 | 265 | | | Spacing Violation: Too close to earlier pick at position 121 |
| 33 | 0.4145 | 187 | 223 | 1 | 1 | 229 | | | Spacing Violation: Too close to earlier pick at position 121 |
| 34 | 0.5121 | 123 | 21 | 1 | 1 | 44 | | | Spacing Violation: Too close to earlier pick at position 121 |

FIG. 12 (cont.)

| | On-Target Efficacy Score | On-Target Rank | Off-Target Rank | On-Target Rank Weight | Off-Target Rank Weight | Combined Rank | Pick Order | Picking Round | Picking Notes |
|---|---|---|---|---|---|---|---|---|---|
| 35 | 0.1506 | 263 | 172 | 1 | 1 | 247 | | | On-Target Efficacy Score < 0.2; Spacing Violation: Too close to earlier pick at position 121 |
| 36 | 0.4562 | 163 | 118 | 1 | 1 | 148 | | | Spacing Violation: Too close to earlier pick at position 121 |
| 37 | 0.4616 | 158 | 46 | 1 | 1 | 81 | | | Spacing Violation: Too close to earlier pick at position 121 |
| 38 | 0.5665 | 85 | 219 | 1 | 1 | 171 | | | Spacing Violation: Too close to earlier pick at position 121 |
| 39 | 0.5129 | 122 | 94 | 1 | 1 | 91 | | | Spacing Violation: Too close to earlier pick at position 121 |
| 40 | 0.4621 | 157 | 41 | 1 | 1 | 73 | | | Spacing Violation: Too close to earlier pick at position 121 |
| 41 | 0.3642 | 221 | 90 | 1 | 1 | 178 | | | Spacing Violation: Too close to earlier pick at position 121 |
| 42 | 0.3998 | 201 | 51 | 1 | 1 | 127 | | | Spacing Violation: Too close to earlier pick at position 121 |
| 43 | 0.5306 | 112 | 39 | 1 | 1 | 49 | | | Spacing Violation: Too close to earlier pick at position 121 |
| 44 | 0.5253 | 116 | 187 | 1 | 1 | 169 | | | Spacing Violation: Too close to earlier pick at position 121 |
| 45 | 0.7291 | 2 | 265 | 1 | 1 | 140 | | | Spacing Violation: Too close to earlier pick at position 121 |
| 46 | 0.5984 | 56 | 198 | 1 | 1 | 128 | | | Spacing Violation: Too close to earlier pick at position 121 |
| 47 | 0.4478 | 167 | 257 | 1 | 1 | 240 | | | Spacing Violation: Too close to earlier pick at position 121 |
| 48 | 0.1534 | 262 | 125 | 1 | 1 | 219 | | | On-Target Efficacy Score < 0.2; Spacing Violation: Too close to earlier pick at position 121 |
| 49 | 0.5557 | 97 | 202 | 1 | 1 | 164 | | | Quota Met |
| 50 | 0.4189 | 184 | 119 | 1 | 1 | 170 | | | Quota Met |
| 51 | 0.4317 | 180 | 92 | 1 | 1 | 142 | | | Quota Met |
| 52 | 0.472 | 151 | 93 | 1 | 1 | 120 | | | Quota Met |
| 53 | 0.3936 | 203 | 215 | 1 | 1 | 237 | | | Quota Met |
| 54 | 0.3434 | 229 | 183 | 1 | 1 | 231 | | | Quota Met |
| 55 | 0.4179 | 185 | 199 | 1 | 1 | 216 | | | Quota Met |
| 56 | 0.3757 | 212 | 185 | 1 | 1 | 222 | | | Quota Met |
| 57 | 0.388 | 208 | 171 | 1 | 1 | 212 | | | Quota Met |
| 58 | 0.2323 | 256 | 194 | 1 | 1 | 254 | | | Quota Met |
| 59 | 0.6359 | 33 | 217 | 1 | 1 | 125 | | | Quota Met |
| 60 | 0.3708 | 216 | 227 | 1 | 1 | 252 | | | Quota Met |
| 61 | 0.4252 | 182 | 259 | 1 | 1 | 250 | | | Quota Met |
| 62 | 0.5956 | 59 | 168 | 1 | 1 | 102 | | | Quota Met |
| 63 | 0.475 | 148 | 264 | 1 | 1 | 232 | | | Quota Met |
| 64 | 0.4404 | 169 | 261 | 1 | 1 | 244 | | | Quota Met |
| 65 | 0.4895 | 134 | 232 | 1 | 1 | 208 | | | Quota Met |
| 66 | 0.5173 | 120 | 120 | 1 | 1 | 115 | | | Quota Met |
| 67 | 0.597 | 58 | 110 | 1 | 1 | 56 | | | Quota Met |
| 68 | 0.5275 | 115 | 114 | 1 | 1 | 105 | | | Quota Met |

FIG. 12 (cont.)

| | On-Target Efficacy Score | On-Target Rank | Off-Target Rank | On-Target Rank Weight | Off-Target Rank Weight | Combined Rank | Pick Order | Picking Round | Picking Notes |
|---|---|---|---|---|---|---|---|---|---|
| 69 | 0.569 | 83 | 191 | 1 | 1 | 143 | | | Quota Met |
| 70 | 0.6491 | 24 | 209 | 1 | 1 | 106 | | | Quota Met |
| 71 | 0.6632 | 16 | 196 | 1 | 1 | 88 | | | Quota Met |
| 72 | 0.3399 | 232 | 3 | 1 | 1 | 111 | | | Quota Met |
| 73 | 0.4074 | 196 | 38 | 1 | 1 | 108 | | | Quota Met |
| 74 | 0.372 | 213 | 122 | 1 | 1 | 191 | | | Transcriptional Incompatibility ('TTTT') |
| 75 | 0.4005 | 200 | 87 | 1 | 1 | 153 | | | Transcriptional Incompatibility ('TTTT') |
| 76 | 0.4675 | 154 | 144 | 1 | 1 | 163 | | | Quota Met |
| 77 | 0.5722 | 76 | 165 | 1 | 1 | 118 | | | Quota Met |
| 78 | 0.4114 | 192 | 91 | 1 | 1 | 149 | | | Quota Met |
| 79 | 0.3766 | 211 | 210 | 1 | 1 | 238 | | | Quota Met |
| 80 | 0.3598 | 222 | 206 | 1 | 1 | 243 | | | Quota Met |
| 81 | 0.392 | 205 | 228 | 1 | 1 | 246 | | | Quota Met |
| 82 | 0.2151 | 257 | 225 | 1 | 1 | 262 | | | Quota Met |
| 83 | 0.4641 | 156 | 99 | 1 | 1 | 131 | | | Quota Met |
| 84 | 0.5565 | 95 | 123 | 1 | 1 | 96 | | | Quota Met |
| 85 | 0.5861 | 64 | 65 | 1 | 1 | 31 | | | Quota Met |
| 86 | 0.4743 | 149 | 24 | 1 | 1 | 57 | | | Quota Met |
| 87 | 0.4302 | 181 | 169 | 1 | 1 | 199 | | | Quota Met |
| 88 | 0.4327 | 178 | 16 | 1 | 1 | 68 | | | Quota Met |
| 89 | 0.5706 | 80 | 102 | 1 | 1 | 61 | | | Quota Met |
| 90 | 0.5724 | 75 | 249 | 1 | 1 | 184 | | | Quota Met |
| 91 | 0.6278 | 39 | 212 | 1 | 1 | 126 | | | Quota Met |
| 92 | 0.5059 | 126 | 89 | 1 | 1 | 90 | | | Quota Met |
| 93 | 0.5321 | 110 | 12 | 1 | 1 | 30 | | | Quota Met |
| 94 | 0.4787 | 145 | 56 | 1 | 1 | 77 | | | Quota Met |
| 95 | 0.4402 | 170 | 40 | 1 | 1 | 86 | | | Quota Met |
| 96 | 0.432 | 179 | 9 | 1 | 1 | 65 | | | Quota Met |
| 97 | 0.5777 | 71 | 151 | 1 | 1 | 99 | | | Quota Met |
| 98 | 0.5821 | 67 | 143 | 1 | 1 | 87 | | | Quota Met |
| 99 | 0.4974 | 129 | 254 | 1 | 1 | 213 | | | Quota Met |
| 100 | 0.5456 | 103 | 135 | 1 | 1 | 114 | | | Spacing Violation: Too close to earlier pick at position 540 |
| 101 | 0.6244 | 44 | 174 | 1 | 1 | 94 | | | Spacing Violation: Too close to earlier pick at position 540 |
| 102 | 0.5685 | 84 | 216 | 1 | 1 | 166 | | | Spacing Violation: Too close to earlier pick at position 540 |

FIG. 12 (cont.)

| | On-Target Efficacy Score | On-Target Rank | Off-Target Rank | On-Target Rank Weight | Off-Target Rank Weight | Combined Rank | Pick Order | Picking Round | Picking Notes |
|---|---|---|---|---|---|---|---|---|---|
| 103 | 0.3045 | 240 | 163 | 1 | 1 | 224 | | | Spacing Violation: Too close to earlier pick at position 540 |
| 104 | 0.5942 | 60 | 158 | 1 | 1 | 95 | | | Spacing Violation: Too close to earlier pick at position 540 |
| 105 | 0.5479 | 101 | 239 | 1 | 1 | 195 | | | Spacing Violation: Too close to earlier pick at position 540 |
| 106 | 0.3968 | 202 | 48 | 1 | 1 | 124 | | | Spacing Violation: Too close to earlier pick at position 540 |
| 107 | 0.6722 | 12 | 73 | 1 | 1 | 17 | | | Spacing Violation: Too close to earlier pick at position 540 |
| 108 | 0.5458 | 102 | 17 | 1 | 1 | 28 | | | Spacing Violation: Too close to earlier pick at position 540 |
| 109 | 0.5714 | 79 | 154 | 1 | 1 | 107 | | | Spacing Violation: Too close to earlier pick at position 540 |
| 110 | 0.439 | 171 | 23 | 1 | 1 | 70 | | | Spacing Violation: Too close to earlier pick at position 540 |
| 111 | 0.6404 | 28 | 106 | 1 | 1 | 37 | | | Spacing Violation: Too close to earlier pick at position 540 |
| 112 | 0.6415 | 27 | 109 | 1 | 1 | 38 | | | Spacing Violation: Too close to earlier pick at position 540 |
| 113 | 0.703 | 6 | 253 | 1 | 1 | 136 | | | Spacing Violation: Too close to earlier pick at position 540 |
| 114 | 0.3651 | 220 | 64 | 1 | 1 | 152 | | | Spacing Violation: Too close to earlier pick at position 540 |
| 115 | 0.3469 | 227 | 69 | 1 | 1 | 160 | | | Spacing Violation: Too close to earlier pick at position 540 |
| 116 | 0.638 | 30 | 14 | 1 | 1 | 5 | 3 | 1 | |
| 117 | 0.7198 | 3 | 49 | 1 | 1 | 6 | | | Spacing Violation: Too close to earlier pick at position 540 |
| 118 | 0.4736 | 150 | 52 | 1 | 1 | 79 | | | Spacing Violation: Too close to earlier pick at position 540 |
| 119 | 0.5603 | 91 | 53 | 1 | 1 | 43 | | | Spacing Violation: Too close to earlier pick at position 540 |
| 120 | 0.717 | 5 | 61 | 1 | 1 | 8 | | | Spacing Violation: Too close to earlier pick at position 540 |
| 121 | 0.6575 | 21 | 100 | 1 | 1 | 29 | | | Spacing Violation: Too close to earlier pick at position 540 |
| 122 | 0.3436 | 228 | 157 | 1 | 1 | 218 | | | Spacing Violation: Too close to earlier pick at position 540 |
| 123 | 0.3565 | 224 | 236 | 1 | 1 | 255 | | | Spacing Violation: Too close to earlier pick at position 540 |
| 124 | 0.63 | 36 | 145 | 1 | 1 | 60 | | | Spacing Violation: Too close to earlier pick at position 540 |
| 125 | 0.4876 | 139 | 103 | 1 | 1 | 119 | | | Spacing Violation: Too close to earlier pick at position 540 |
| 126 | 0.4362 | 173 | 152 | 1 | 1 | 185 | | | Spacing Violation: Too close to earlier pick at position 540 |
| 127 | 0.6186 | 46 | 245 | 1 | 1 | 155 | | | Spacing Violation: Too close to earlier pick at position 540 |
| 128 | 0.7019 | 7 | 141 | 1 | 1 | 46 | | | Quota Met |
| 129 | 0.6046 | 52 | 175 | 1 | 1 | 103 | | | Quota Met |
| 130 | 0.1887 | 260 | 251 | 1 | 1 | 264 | | | On-Target Efficacy Score < 0.2 |
| 131 | 0.3018 | 241 | 177 | 1 | 1 | 236 | | | Cloning Incompatibility ('CGTCTC') |
| 132 | 0.6376 | 31 | 235 | 1 | 1 | 139 | | | Quota Met |
| 133 | 0.4103 | 193 | 222 | 1 | 1 | 234 | | | Quota Met |
| 134 | 0.2652 | 251 | 176 | 1 | 1 | 242 | | | Quota Met |
| 135 | 0.6265 | 42 | 95 | 1 | 1 | 41 | | | Quota Met |
| 136 | 0.5641 | 87 | 44 | 1 | 1 | 34 | | | Quota Met |

FIG. 12 (cont.)

| | On-Target Efficacy Score | On-Target Rank | Off-Target Rank | On-Target Rank Weight | Off-Target Rank Weight | Combined Rank | Pick Order | Picking Round | Picking Notes |
|---|---|---|---|---|---|---|---|---|---|
| 137 | 0.5642 | 86 | 50 | 1 | 1 | 40 | | | Quota Met |
| 138 | 0.6284 | 38 | 96 | 1 | 1 | 36 | | | Quota Met |
| 139 | 0.657 | 22 | 179 | 1 | 1 | 76 | | | Quota Met |
| 140 | 0.3147 | 237 | 86 | 1 | 1 | 183 | | | Quota Met |
| 141 | 0.491 | 131 | 262 | 1 | 1 | 220 | | | Quota Met |
| 142 | 0.6348 | 35 | 113 | 1 | 1 | 48 | | | Quota Met |
| 143 | 0.4116 | 191 | 15 | 1 | 1 | 82 | | | Quota Met |
| 144 | 0.6629 | 17 | 54 | 1 | 1 | 11 | | | Spacing Violation: Too close to earlier pick at position 827 |
| 145 | 0.6002 | 55 | 252 | 1 | 1 | 175 | | | Spacing Violation: Too close to earlier pick at position 827 |
| 146 | 0.4047 | 197 | 60 | 1 | 1 | 134 | | | Spacing Violation: Too close to earlier pick at position 827 |
| 147 | 0.4143 | 188 | 153 | 1 | 1 | 197 | | | Spacing Violation: Too close to earlier pick at position 827 |
| 148 | 0.4501 | 166 | 115 | 1 | 1 | 147 | | | Spacing Violation: Too close to earlier pick at position 827 |
| 149 | 0.1356 | 264 | 111 | 1 | 1 | 210 | | | On-Target Efficacy Score < 0.2; Spacing Violation: Too close to earlier pick at position 827; Transcriptional Incompatibility (TTTT) |
| 150 | 0.4787 | 144 | 71 | 1 | 1 | 89 | | | Spacing Violation: Too close to earlier pick at position 827 |
| 151 | 0.492 | 130 | 203 | 1 | 1 | 190 | | | Spacing Violation: Too close to earlier pick at position 827 |
| 152 | 0.6822 | 10 | 28 | 1 | 1 | 2 | 2 | 1 | |
| 153 | 0.5971 | 57 | 62 | 1 | 1 | 27 | | | Spacing Violation: Too close to earlier pick at position 827 |
| 154 | 0.5332 | 109 | 22 | 1 | 1 | 35 | | | Spacing Violation: Too close to earlier pick at position 827 |
| 155 | 0.3479 | 226 | 130 | 1 | 1 | 203 | | | Spacing Violation: Too close to earlier pick at position 827 |
| 156 | 0.549 | 99 | 138 | 1 | 1 | 112 | | | Spacing Violation: Too close to earlier picks at positions 827, 931 |
| 157 | 0.4603 | 159 | 132 | 1 | 1 | 156 | | | Spacing Violation: Too close to earlier picks at positions 827, 931 |
| 158 | 0.3707 | 217 | 76 | 1 | 1 | 158 | | | Spacing Violation: Too close to earlier picks at positions 827, 931 |
| 159 | 0.4827 | 143 | 32 | 1 | 1 | 58 | | | Spacing Violation: Too close to earlier picks at positions 827, 931 |
| 160 | 0.6469 | 25 | 162 | 1 | 1 | 64 | | | Spacing Violation: Too close to earlier picks at positions 827, 931 |
| 161 | 0.5915 | 62 | 159 | 1 | 1 | 98 | | | Spacing Violation: Too close to earlier picks at positions 827, 931 |
| 162 | 0.4893 | 135 | 136 | 1 | 1 | 141 | | | Spacing Violation: Too close to earlier picks at positions 827, 931 |
| 163 | 0.2943 | 244 | 30 | 1 | 1 | 144 | | | Spacing Violation: Too close to earlier picks at positions 827, 931 |
| 164 | 0.317 | 236 | 233 | 1 | 1 | 258 | | | Spacing Violation: Too close to earlier picks at positions 827, 931 |
| 165 | 0.6263 | 43 | 36 | 1 | 1 | 14 | 4 | 1 | |
| 166 | 0.5238 | 117 | 82 | 1 | 1 | 74 | | | Spacing Violation: Too close to earlier pick at position 931 |
| 167 | 0.3579 | 223 | 31 | 1 | 1 | 129 | | | Spacing Violation: Too close to earlier pick at position 931 |
| 168 | 0.6458 | 26 | 85 | 1 | 1 | 22 | | | Spacing Violation: Too close to earlier pick at position 931 |
| 169 | 0.5749 | 72 | 134 | 1 | 1 | 84 | | | Spacing Violation: Too close to earlier pick at position 931 |

FIG. 12 (cont.)

| | On-Target Efficacy Score | On-Target Rank | Off-Target Rank | On-Target Rank Weight | Off-Target Rank Weight | Combined Rank | Pick Order | Picking Round | Picking Notes |
|---|---|---|---|---|---|---|---|---|---|
| 170 | 0.5079 | 125 | 72 | 1 | 1 | 72 | | | Spacing Violation: Too close to earlier pick at position 931 |
| 171 | 0.5304 | 113 | 237 | 1 | 1 | 200 | | | Spacing Violation: Too close to earlier pick at position 931 |
| 172 | 0.4024 | 198 | 244 | 1 | 1 | 251 | | | Spacing Violation: Too close to earlier pick at position 931; Transcriptional Incompatibility ("TTTT") |
| 173 | 0.6115 | 48 | 197 | 1 | 1 | 121 | | | Spacing Violation: Too close to earlier pick at position 931 |
| 174 | 0.3175 | 235 | 204 | 1 | 1 | 249 | | | Spacing Violation: Too close to earlier pick at position 931; Transcriptional Incompatibility ("TTTT") |
| 175 | 0.6265 | 41 | 242 | 1 | 1 | 151 | | | Spacing Violation: Too close to earlier picks at positions 931, 1095 |
| 176 | 0.5341 | 107 | 247 | 1 | 1 | 202 | | | Spacing Violation: Too close to earlier pick at position 1095; Transcriptional Incompatibility ("TTTT") |
| 177 | 0.2086 | 258 | 34 | 1 | 1 | 157 | | | Spacing Violation: Too close to earlier pick at position 1095 |
| 178 | 0.5348 | 106 | 5 | 1 | 1 | 23 | | | Spacing Violation: Too close to earlier pick at position 1095 |
| 179 | 0.4759 | 147 | 11 | 1 | 1 | 50 | | | Spacing Violation: Too close to earlier pick at position 1095 |
| 180 | 0.4581 | 160 | 7 | 1 | 1 | 55 | | | Spacing Violation: Too close to earlier pick at position 1095 |
| 181 | 0.5738 | 73 | 150 | 1 | 1 | 100 | | | Spacing Violation: Too close to earlier pick at position 1095 |
| 182 | 0.5636 | 88 | 74 | 1 | 1 | 52 | | | Spacing Violation: Too close to earlier pick at position 1095 |
| 183 | 0.5838 | 66 | 26 | 1 | 1 | 18 | 5 | 1 | |
| 184 | 0.4212 | 183 | 75 | 1 | 1 | 135 | | | Spacing Violation: Too close to earlier pick at position 1095 |
| 185 | 0.5692 | 81 | 208 | 1 | 1 | 154 | | | Spacing Violation: Too close to earlier pick at position 1095 |
| 186 | 0.2584 | 253 | 170 | 1 | 1 | 239 | | | Spacing Violation: Too close to earlier pick at position 1095 |
| 187 | 0.3484 | 225 | 255 | 1 | 1 | 259 | | | Spacing Violation: Too close to earlier pick at position 1095 |
| 188 | 0.6112 | 49 | 63 | 1 | 1 | 24 | | | Cloning Incompatibility ("CGTCTC"); Spacing Violation: Too close to earlier pick at position 1095 |
| 189 | 0.3923 | 204 | 127 | 1 | 1 | 189 | | | Spacing Violation: Too close to earlier pick at position 1095 |
| 190 | 0.4163 | 186 | 184 | 1 | 1 | 209 | | | Outside Target Window: 5-65%; Spacing Violation: Too close to earlier pick at position 1095 |
| 191 | 0.4362 | 174 | 128 | 1 | 1 | 168 | | | Outside Target Window: 5-65% |
| 192 | 0.5333 | 108 | 78 | 1 | 1 | 62 | | | Outside Target Window: 5-65% |
| 193 | 0.52 | 119 | 108 | 1 | 1 | 104 | | | Outside Target Window: 5-65% |
| 194 | 0.2738 | 250 | 59 | 1 | 1 | 177 | | | Outside Target Window: 5-65% |
| 195 | 0.7581 | 1 | 105 | 1 | 1 | 20 | | | Outside Target Window: 5-65% |
| 196 | 0.6902 | 9 | 178 | 1 | 1 | 63 | | | Outside Target Window: 5-65% |
| 197 | 0.6813 | 11 | 192 | 1 | 1 | 80 | | | Outside Target Window: 5-65% |
| 198 | 0.6685 | 15 | 240 | 1 | 1 | 130 | | | Outside Target Window: 5-65% |
| 199 | 0.6274 | 40 | 70 | 1 | 1 | 21 | | | Outside Target Window: 5-65% |
| 200 | 0.6703 | 14 | 25 | 1 | 1 | 4 | | | Outside Target Window: 5-65% |
| 201 | 0.6127 | 47 | 20 | 1 | 1 | 9 | | | Outside Target Window: 5-65% |
| 202 | 0.5311 | 111 | 55 | 1 | 1 | 53 | | | Outside Target Window: 5-65% |
| 203 | 0.3698 | 218 | 189 | 1 | 1 | 227 | | | Outside Target Window: 5-65%; Transcriptional Incompatibility ("TTTT") |

FIG. 12 (cont.)

| | On-Target Efficacy Score | On-Target Rank | Off-Target Rank | On-Target Rank Weight | Off-Target Rank Weight | Combined Rank | Pick Order | Picking Round | Picking Notes |
|---|---|---|---|---|---|---|---|---|---|
| 204 | 0.5929 | 61 | 133 | 1 | 1 | 69 | | | Outside Target Window: 5-65%, Transcriptional Incompatibility ("TTTT") |
| 205 | 0.4854 | 141 | 220 | 1 | 1 | 207 | | | Outside Target Window: 5-65%, Transcriptional Incompatibility ("TTTT") |
| 206 | 0.5725 | 74 | 173 | 1 | 1 | 122 | | | Outside Target Window: 5-65% |
| 207 | 0.5721 | 77 | 35 | 1 | 1 | 25 | | | Outside Target Window: 5-65% |
| 208 | 0.4881 | 138 | 29 | 1 | 1 | 54 | | | Outside Target Window: 5-65% |
| 209 | 0.6399 | 29 | 107 | 1 | 1 | 39 | | | Outside Target Window: 5-65% |
| 210 | 0.609 | 50 | 80 | 1 | 1 | 33 | | | Outside Target Window: 5-65% |
| 211 | 0.4421 | 168 | 79 | 1 | 1 | 123 | | | Outside Target Window: 5-65% |
| 212 | 0.4095 | 194 | 129 | 1 | 1 | 182 | | | Outside Target Window: 5-65% |
| 213 | 0.5563 | 96 | 124 | 1 | 1 | 97 | | | Outside Target Window: 5-65% |
| 214 | 0.56 | 92 | 182 | 1 | 1 | 145 | | | Outside Target Window: 5-65% |
| 215 | 0.636 | 32 | 45 | 1 | 1 | 13 | | | Outside Target Window: 5-65% |
| 216 | 0.4976 | 128 | 1 | 1 | 1 | 32 | | | Outside Target Window: 5-65% |
| 217 | 0.5586 | 93 | 190 | 1 | 1 | 150 | | | Outside Target Window: 5-65% |
| 218 | 0.291 | 245 | 116 | 1 | 1 | 205 | | | Outside Target Window: 5-65%, Transcriptional Incompatibility ("TTTT") |
| 219 | 0.6585 | 19 | 98 | 1 | 1 | 26 | | | Outside Target Window: 5-65% |
| 220 | 0.6041 | 54 | 246 | 1 | 1 | 165 | | | Outside Target Window: 5-65% |
| 221 | 0.4135 | 189 | 243 | 1 | 1 | 245 | | | Outside Target Window: 5-65%, Transcriptional Incompatibility ("TTTT") |
| 222 | 0.3711 | 215 | 248 | 1 | 1 | 256 | | | Outside Target Window: 5-65%, Transcriptional Incompatibility ("TTTT") |
| 223 | 0.276 | 248 | 137 | 1 | 1 | 217 | | | Outside Target Window: 5-65%, Transcriptional Incompatibility ("TTTT") |
| 224 | 0.5293 | 114 | 126 | 1 | 1 | 116 | | | Outside Target Window: 5-65%, Transcriptional Incompatibility ("TTTT") |
| 225 | 0.5841 | 65 | 131 | 1 | 1 | 71 | | | Outside Target Window: 5-65% |
| 226 | 0.4135 | 190 | 66 | 1 | 1 | 132 | | | Outside Target Window: 5-65% |
| 227 | 0.1156 | 265 | 77 | 1 | 1 | 198 | | | On-Target Efficacy Score < 0.2; Outside Target Window: 5-65% |
| 228 | 0.6055 | 51 | 97 | 1 | 1 | 47 | | | Outside Target Window: 5-65% |
| 229 | 0.4581 | 161 | 250 | 1 | 1 | 230 | | | Outside Target Window: 5-65% |
| 230 | 0.4579 | 162 | 19 | 1 | 1 | 59 | | | Outside Target Window: 5-65% |
| 231 | 0.6187 | 45 | 27 | 1 | 1 | 12 | | | Outside Target Window: 5-65% |
| 232 | 0.4082 | 195 | 83 | 1 | 1 | 146 | | | Outside Target Window: 5-65% |
| 233 | 0.5604 | 90 | 211 | 1 | 1 | 167 | | | Outside Target Window: 5-65% |
| 234 | 0.1941 | 259 | 142 | 1 | 1 | 223 | | | On-Target Efficacy Score < 0.2; Outside Target Window: 5-65%, Transcriptional Incompatibility ("TTTT") |
| 235 | 0.5792 | 70 | 234 | 1 | 1 | 172 | | | Outside Target Window: 5-65% |
| 236 | 0.4654 | 155 | 33 | 1 | 1 | 66 | | | Outside Target Window: 5-65% |
| 237 | 0.2853 | 247 | 160 | 1 | 1 | 226 | | | Outside Target Window: 5-65% |

FIG. 12 (cont.)

| | On-Target Efficacy Score | On-Target Rank | Off-Target Rank | On-Target Rank Weight | Off-Target Rank Weight | Combined Rank | Pick Order | Picking Round | Picking Notes |
|---|---|---|---|---|---|---|---|---|---|
| 238 | 0.3275 | 234 | 161 | 1 | 1 | 221 | | | Outside Target Window: 5-65% |
| 239 | 0.1679 | 261 | 164 | 1 | 1 | 241 | | | On-Target Efficacy Score < 0.2; Outside Target Window: 5-65% |
| 240 | 0.4502 | 165 | 140 | 1 | 1 | 173 | | | Outside Target Window: 5-65%; Transcriptional Incompatibility ('TTTT') |
| 241 | 0.5148 | 121 | 263 | 1 | 1 | 215 | | | Outside Target Window: 5-65%; Transcriptional Incompatibility ('TTTT') |
| 242 | 0.4844 | 142 | 117 | 1 | 1 | 137 | | | Outside Target Window: 5-65%; Transcriptional Incompatibility ('TTTT') |
| 243 | 0.3657 | 219 | 37 | 1 | 1 | 133 | | | Outside Target Window: 5-65% |
| 244 | 0.2961 | 243 | 84 | 1 | 1 | 188 | | | Outside Target Window: 5-65% |
| 245 | 0.3821 | 209 | 57 | 1 | 1 | 138 | | | Outside Target Window: 5-65% |
| 246 | 0.3427 | 230 | 67 | 1 | 1 | 161 | | | Outside Target Window: 5-65% |
| 247 | 0.5444 | 104 | 201 | 1 | 1 | 174 | | | Outside Target Window: 5-65% |
| 248 | 0.5488 | 100 | 195 | 1 | 1 | 159 | | | Outside Target Window: 5-65% |
| 249 | 0.4537 | 164 | 155 | 1 | 1 | 180 | | | Outside Target Window: 5-65% |
| 250 | 0.3068 | 239 | 101 | 1 | 1 | 196 | | | Outside Target Window: 5-65% |
| 251 | 0.471 | 152 | 256 | 1 | 1 | 228 | | | Outside Target Window: 5-65% |
| 252 | 0.6576 | 20 | 47 | 1 | 1 | 10 | | | Outside Target Window: 5-65% |
| 253 | 0.2745 | 249 | 258 | 1 | 1 | 263 | | | Outside Target Window: 5-65% |
| 254 | 0.5692 | 82 | 156 | 1 | 1 | 113 | | | Outside Target Window: 5-65% |
| 255 | 0.3719 | 214 | 112 | 1 | 1 | 186 | | | Outside Target Window: 5-65% |
| 256 | 0.3881 | 207 | 241 | 1 | 1 | 253 | | | Outside Target Window: 5-65% |
| 257 | 0.5798 | 69 | 149 | 1 | 1 | 93 | | | Outside Target Window: 5-65% |
| 258 | 0.4897 | 133 | 6 | 1 | 1 | 42 | | | Outside Target Window: 5-65% |
| 259 | 0.4346 | 176 | 58 | 1 | 1 | 109 | | | Outside Target Window: 5-65% |
| 260 | 0.4022 | 199 | 2 | 1 | 1 | 75 | | | Outside Target Window: 5-65% |
| 261 | 0.5816 | 68 | 13 | 1 | 1 | 16 | | | Outside Target Window: 5-65% |
| 262 | 0.3143 | 238 | 139 | 1 | 1 | 211 | | | Outside Target Window: 5-65%; Transcriptional Incompatibility ('TTTT') |
| 263 | 0.3014 | 242 | 238 | 1 | 1 | 260 | | | Outside Target Window: 5-65% |
| 264 | 0.489 | 136 | 81 | 1 | 1 | 92 | | | Outside Target Window: 5-65% |
| 265 | 0.5716 | 78 | 68 | 1 | 1 | 45 | | | Outside Target Window: 5-65% |

SEQUENCE LISTING

```
<160> NUMBER OF SEQ ID NOS: 565

<210> SEQ ID NO 1
<211> LENGTH: 605
<212> TYPE: PRT
<213> ORGANISM: Homo sapiens

<400> SEQUENCE: 1

Met Ala Gly Leu Tyr Ser Leu Gly Val Ser Val Phe Ser Asp Gln Gly
1               5                   10                  15

Gly Arg Lys Tyr Met Glu Asp Val Thr Gln Ile Val Val Glu Pro Glu
                20                  25                  30

Pro Thr Ala Glu Glu Lys Pro Ser Pro Arg Arg Ser Leu Ser Gln Pro
            35                  40                  45

Leu Pro Pro Arg Pro Ser Pro Ala Ala Leu Pro Gly Gly Glu Val Ser
        50                  55                  60

Gly Lys Gly Pro Ala Val Ala Ala Arg Glu Ala Arg Asp Pro Leu Pro
65                  70                  75                  80

Asp Ala Gly Ala Ser Pro Ala Pro Ser Arg Cys Cys Arg Arg Arg Ser
                85                  90                  95

Ser Val Ala Phe Phe Ala Val Cys Asp Gly His Gly Gly Arg Glu Ala
                100                 105                 110

Ala Gln Phe Ala Arg Glu His Leu Trp Gly Phe Ile Lys Lys Gln Lys
            115                 120                 125

Gly Phe Thr Ser Ser Glu Pro Ala Lys Val Cys Ala Ala Ile Arg Lys
130                 135                 140

Gly Phe Leu Ala Cys His Leu Ala Met Trp Lys Lys Leu Ala Glu Trp
145                 150                 155                 160

Pro Lys Thr Met Thr Gly Leu Pro Ser Thr Ser Gly Thr Thr Ala Ser
                165                 170                 175

Val Val Ile Ile Arg Gly Met Lys Met Tyr Val Ala His Val Gly Asp
                180                 185                 190

Ser Gly Val Val Leu Gly Ile Gln Asp Asp Pro Lys Asp Asp Phe Val
            195                 200                 205

Arg Ala Val Glu Val Thr Gln Asp His Lys Pro Glu Leu Pro Lys Glu
210                 215                 220

Arg Glu Arg Ile Glu Gly Leu Gly Gly Ser Val Met Asn Lys Ser Gly
225                 230                 235                 240

Val Asn Arg Val Val Trp Lys Arg Pro Arg Leu Thr His Asn Gly Pro
                245                 250                 255

Val Arg Arg Ser Thr Val Ile Asp Gln Ile Pro Phe Leu Ala Val Ala
                260                 265                 270

Arg Ala Leu Gly Asp Leu Trp Ser Tyr Asp Phe Phe Ser Gly Glu Phe
            275                 280                 285

Val Val Ser Pro Glu Pro Asp Thr Ser Val His Thr Leu Asp Pro Gln
```

| | | | | | | | | | 290 | | | | | 295 | | | | | 300 | | | | |

Lys His Lys Tyr Ile Ile Leu Gly Ser Asp Gly Leu Trp Asn Met Ile
305                 310                 315                 320

Pro Pro Gln Asp Ala Ile Ser Met Cys Gln Asp Gln Glu Glu Lys Lys
            325                 330                 335

Tyr Leu Met Gly Glu His Gly Gln Ser Cys Ala Lys Met Leu Val Asn
            340                 345                 350

Arg Ala Leu Gly Arg Trp Arg Gln Arg Met Leu Arg Ala Asp Asn Thr
            355                 360                 365

Ser Ala Ile Val Ile Cys Ile Ser Pro Glu Val Asp Asn Gln Gly Asn
            370                 375                 380

Phe Thr Asn Glu Asp Glu Leu Tyr Leu Asn Leu Thr Asp Ser Pro Ser
385                 390                 395                 400

Tyr Asn Ser Gln Glu Thr Cys Val Met Thr Pro Ser Pro Cys Ser Thr
            405                 410                 415

Pro Pro Val Lys Ser Leu Glu Glu Asp Pro Trp Pro Arg Val Asn Ser
            420                 425                 430

Lys Asp His Ile Pro Ala Leu Val Arg Ser Asn Ala Phe Ser Glu Asn
            435                 440                 445

Phe Leu Glu Val Ser Ala Glu Ile Ala Arg Glu Asn Val Gln Gly Val
    450                 455                 460

Val Ile Pro Ser Lys Asp Pro Glu Pro Leu Glu Glu Asn Cys Ala Lys
465                 470                 475                 480

Ala Leu Thr Leu Arg Ile His Asp Ser Leu Asn Asn Ser Leu Pro Ile
            485                 490                 495

Gly Leu Val Pro Thr Asn Ser Thr Asn Thr Val Met Asp Gln Lys Asn
            500                 505                 510

Leu Lys Met Ser Thr Pro Gly Gln Met Lys Ala Gln Glu Ile Glu Arg
            515                 520                 525

Thr Pro Pro Thr Asn Phe Lys Arg Thr Leu Glu Glu Ser Asn Ser Gly
            530                 535                 540

Pro Leu Met Lys Lys His Arg Arg Asn Gly Leu Ser Arg Ser Ser Gly
545                 550                 555                 560

Ala Gln Pro Ala Ser Leu Pro Thr Thr Ser Gln Arg Lys Asn Ser Val
            565                 570                 575

Lys Leu Thr Met Arg Arg Arg Leu Arg Gly Gln Lys Lys Ile Gly Asn
            580                 585                 590

Pro Leu Leu His Gln His Arg Lys Thr Val Cys Val Cys
            595                 600                 605

<210> SEQ ID NO 2
<211> LENGTH: 4790
<212> TYPE: DNA
<213> ORGANISM: Homo sapiens

<400> SEQUENCE: 2
ggggaagcgc agtgcgcagg cgcaactgcc tggctctgct cgctccggcg ctccggccca    60
gctctcgcgg acaagtccag acatcgcgcg ccccccttc tccgggtccg ccccctcccc    120
cttctcggcg tcgtcgaaga taaacaatag ttggccggcg agcgcctagt gtgtctcccg    180
ccgccggatt cggcgggctg cgtgggaccg gcgggatccc ggccagccgg ccatggcggg    240
gctgtactcg ctgggagtga gcgtcttctc cgaccagggc gggaggaagt acatggagga    300
cgttactcaa atcgttgtgg agcccgaacc gacggctgaa gaaaagccct cgccgcggcg    360

```
gtcgctgtct cagccgttgc ctccgcggcc gtcgccggcc gcccttcccg gcggcgaagt    420
ctcggggaaa ggcccagcgg tggcagcccg agaggctcgc gaccctctcc cggacgccgg    480
ggcctcgccg gcacctagcc gctgctgccg ccgccgttcc tccgtggcct ttttcgccgt    540
gtgcgacggg cacggcggc gggaggcggc acagtttgcc cgggagcact tgtggggttt      600
catcaagaag cagaagggtt tcacctcgtc cgagccggct aaggtttgcg ctgccatccg    660
caaaggcttt ctcgcttgtc accttgccat gtggaagaaa ctggcggaat ggccaaagac    720
tatgacgggt cttcctagca catcagggac aactgccagt gtggtcatca ttcggggcat    780
gaagatgtat gtagctcacg taggtgactc agggggtggtt cttggaattc aggatgaccc   840
gaaggatgac tttgtcagag ctgtggaggt gacacaggac cataagccag aacttcccaa    900
ggaaagagaa cgaatcgaag gacttggtgg gagtgtaatg aacaagtctg gggtgaatcg    960
tgtagtttgg aaacgacctc gactcactca caatggacct gttagaagga gcacagttat   1020
tgaccagatt ccttttctgg cagtagcaag agcacttggt gatttgtgga gctatgattt    1080
cttcagtggt gaatttgtgg tgtcacctga accagacaca agtgtccaca ctcttgaccc    1140
tcagaagcac aagtatatta tattggggag tgatggactt tggaatatga ttccaccaca    1200
agatgccatc tcaatgtgcc aggaccaaga ggagaaaaaa tacctgatgg gtgagcatgg    1260
acaatcttgt gccaaaatgc ttgtgaatcg agcattgggc cgctggaggc agcgtatgct    1320
ccgagcagat aacactagtg ccatagtaat ctgcatctct ccagaagtgg acaatcaggg    1380
aaactttacc aatgaagatg agttatacct gaacctgact gacagccctt cctataatag    1440
tcaagaaacc tgtgtgatga ctccttcccc atgttctaca ccaccagtca agtcactgga    1500
ggaggatcca tggccaaggg tgaattctaa ggaccatata cctgccctgg ttcgtagcaa    1560
tgccttctca gagaattttt tagaggtttc agctgagata gctcgagaga atgtccaagg    1620
tgtagtcata ccctcaaaag atccagaacc acttgaagaa aattgcgcta aagccctgac    1680
tttaaggata catgattctt tgaataatag ccttccaatt ggccttgtgc ctactaattc    1740
aacaaacact gtcatggacc aaaaaaattt gaagatgtca actcctggcc aaatgaaagc    1800
ccaagaaatt gaaagaaccc ctccaacaaa ctttaaaagg acattagaag agtccaattc    1860 tggcccctg atgaagaagc atagacgaaa tggcttaagt cgaagtagtg gtgctcagcc    1920
tgcaagtctc cccacaacct cacagcgaaa gaactctgtt aaactcacca tgcgacgcag    1980
acttaggggc cagaagaaaa ttggaaatcc tttacttcat caacacagga aaactgtttg    2040
tgtttgctga aatgcatctg ggaaatgagg tttttccaaa cttaggatat aagagggctt    2100
tttaaatttg gtgccgatgt tgaacttttt ttaaggggag aaaattaaaa gaaatataca    2160
gtttgacttt ttggaattca gcagttttat cctggccttg tacttgcttg tattgtaaat    2220
gtggattttg tagatgttag ggtataagtt gctgtaaaat ttgtgtaaat ttgtatccac    2280
acaaattcag tctctgaata cacagtattc agagtctctg atacacagta attgtgacaa    2340
tagggctaaa tgtttaaaga aatcaaaaga atctattaga ttttagaaaa acatttaaac    2400 ttttttaaaat acttattaaa aaatttgtat aagccacttg tcttgaaaac tgtgcaactt    2460
tttaaagtaa attattaagc agactggaaa agtgatgtat tttcatagtg acctgtgttt    2520
cacttaatgt ttcttagagc caagtgtctt ttaaacatta ttttttattt ctgatttcat    2580
aattcagaac taaattttc atagaagtgt tgagccatgc tacagttagt cttgtcccaa    2640
ttaaaatact atgcagtatc tcttacatca gtagcatttt tctaaaacct tagtcatcag    2700
atatgcttac taaatcttca gcatagaagg aagtgtgttt gcctaaaaca atctaaaaca    2760
```

```
attcccttct ttttcatccc agaccaatgg cattattagg tcttaaagta gttactccct    2820
tctcgtgttt gcttaaaata tgtgaagttt tccttgctat ttcaataaca gatggtgctg    2880
ctaattccca acatttctta aattatttta tatcatacag ttttcattga ttatatgggt    2940
atatattcat ctaataaatc agtgaactgt tcctcatgtt gctgaatttg tagttgttgg    3000
tttattttaa tggtatgtac aagttgagta tcccttatcc aaaatgcttg ggaccagaag    3060
tgtttcagat ttttttaaaat tttggaatat ttgcttata ctgagctttt gagtgttccc    3120
aatctgaaat tcaaaatgct ctaatgagca tttcctttga gcatcatgcc tgctctgaaa    3180
aagtttctga ttctggagca ttttggattt tggattttca gattagggat gcttaacctg    3240
gattaacatt ctgttgtgcc atgatcatgc tttacagtga gtgtatttta tttatttatt    3300 atttgtttg tttgtttgag atggagtctc actctgtcat ccaggctaga gtgcagtggc    3360
gtgatctcgg ctgactgcaa cctctgcctc ccgggttcaa gtgattctcc tgcctcaatc    3420
tctctcccca gaagctggga ttacaggtgt gtgccaccac acccggctaa tttttttttt    3480 ttttttttgag atggagtcta gctctgtcat ccaggctgga gtgcagtggt gtgatctcgg    3540
ctccctgcaa cctctgcctt ctgggttcct gcgattctcc tgcctcagcc tcctgagtag    3600
ctgagattac aggcacgcgc cactgtgccc agccaatttt tgtattttta gtagagatgg    3660
ggtttcacat gtcagtcatg ctggtcttga tctcctgacc tcgtgatcca cccgcctcga    3720
cctcccaaag tactgggatt acaggcgtga gccaccgcat ccggcctgag ttttatgctt    3780
tcaatgtatt tcttacattt cagttcaagt gattttcatg tctcagcctc ctgagtagct    3840
ggaactacag gtgcgtgcca ccatgcctgg ctaagttttg tattttagt agagatgggt    3900 tttcatcatg ttggccaaga tggtcttgat ctcttgacct catgatccac cagcctaggc    3960
ctcccaaagt gctgggatta caggtgtgag ccaccgtgcc cagccaacta tgccattatt    4020
taaccatgtc cacacattct ggttattttc aatattttgc agaagataat tcttgatcgg    4080
tgtgtcttat gccacaagga ttaaaatatg tattcattgc tacaaaacaa tatctcgaaa    4140
tttagcagtt taaaacaaca aatattatct ccagtttctg agcctcagaa atctgagagt    4200
ggtttagctg ggtgatagtc tcgtggtttt ggtcaagcta ccaaccaggg ctacaatctt    4260
tcgaaggtgt cattgggggct agaagatctg cttcccgcaa gactcacagc tgttggcagg    4320
agacctcagt ttgttgccac atgttcccct ccagagggcc tctcacaaca tggcagttat    4380
ttgtccccag agcaagcaac accggagggc aaggaagaag ccatgatgtt ttttgtaacc    4440
tagcctctga aagtgtcata ccaattctgt attttgttgg tcacacagac caagtcaact    4500
acaacgtggg agactcctac acaaggcatg aattctagga ggtgggcatt tttaagtgtc    4560
atctggaagg aggctgtcac aacctggaag ttaaaagcat tgatattctg aaatacagcg    4620
tgtataacat tgttttagta gggtgtgcaa tagttatgtt ttggtaatag cattaatgaa    4680
caatgttatt ttcatcttcc agacatctgg aagattgctc tagtggagta aaacatctta    4740
atgtattttg tccctaaata aactatctca ctaacaaaaa aaaaaaaaa               4790
```

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Generic Formula for PPM1D substrate

```
                                     candidates
<220> FEATURE:
<221> NAME/KEY: MOD_RES
<222> LOCATION: (1)..(1)
<223> OTHER INFORMATION: Ser, Tyr, Leu, Lys, Gly, Glu, Gln, Asp, Ala,
      Trp, Val, Thr, Asn, Met, Phe, or Cys
<220> FEATURE:
<221> NAME/KEY: MOD_RES
<222> LOCATION: (2)..(2)
<223> OTHER INFORMATION: Arg, Asp, Lys, Glu, Ala, Ser, Gln, Leu, Val,
      Thr, Pro, Gly, Tyr, Trp, or Phe
<220> FEATURE:
<221> NAME/KEY: MOD_RES
<222> LOCATION: (3)..(3)
<223> OTHER INFORMATION: Glu, Leu, Lys, Arg, Gly, Asp, Ala, Val, Cys,
      Tyr, Thr, Gln, Asn, or Phe
<220> FEATURE:
<221> NAME/KEY: MOD_RES
<222> LOCATION: (4)..(4)
<223> OTHER INFORMATION: Glu, Gly, Ser, Asp, Ala, Tyr, Pro, Leu, Arg,
      His, Val, Thr, Asn, Met, or Cys
<220> FEATURE:
<221> NAME/KEY: MOD_RES
<222> LOCATION: (5)..(5)
<223> OTHER INFORMATION: Glu, Ser, Arg, Gly, Thr, Gln, Asp, Ala, Tyr,
      Val, Pro, Asn, Met, Leu, Lys, or Phe
<220> FEATURE:
<221> NAME/KEY: MOD_RES
<222> LOCATION: (6)..(6)
<223> OTHER INFORMATION: Glu, Ala, Gln, Pro, Asp, Val, Thr, Asn, Leu,
      Lys, Gly, Tyr, Ser, Arg, His, or Cys
<220> FEATURE:
<221> NAME/KEY: MOD_RES
<222> LOCATION: (7)..(7)
<223> OTHER INFORMATION: Asp, Leu, Glu, Ser, Asn, Ala, Tyr, Arg, Pro,
      Lys, Thr, Gln, His, Gly, or Cys
<220> FEATURE:
<221> NAME/KEY: MOD_RES
<222> LOCATION: (8)..(8)
<223> OTHER INFORMATION: Ser, Thr, or Tyr
<220> FEATURE:
<221> NAME/KEY: MOD_RES
<222> LOCATION: (9)..(9)
<223> OTHER INFORMATION: Gln, Glu, Leu, Lys, Asp, Pro, Asn, Gly, Lys,
      His, Cys, or Ala
<220> FEATURE:
<221> NAME/KEY: MOD_RES
<222> LOCATION: (10)..(10)
<223> OTHER INFORMATION: Asp, Glu, Leu, Asn, Ala, Thr, Arg, Gln, Pro,
      Lys, Gly, or Cys
<220> FEATURE:
<221> NAME/KEY: MOD_RES
<222> LOCATION: (11)..(11)
<223> OTHER INFORMATION: Glu, Ser, Asp, Thr, Leu, Lys, Gly, Tyr, Val,
      Arg, Gln, Pro, Asn, His, Phe, or Ala
<220> FEATURE:
<221> NAME/KEY: MOD_RES
<222> LOCATION: (12)..(12)
<223> OTHER INFORMATION: Glu, Asp, Ser, Leu, Gln, Gly, Phe, Trp, Thr,
      Arg, Pro, Asn, Met, or Cys
<220> FEATURE:
<221> NAME/KEY: MOD_RES
<222> LOCATION: (13)..(13)
<223> OTHER INFORMATION: Glu, Asp, Ala, Thr, Arg, Gln, Leu, Pro, Gly,
      Val, Ser, Asn, Lys, His, Phe, or Cys
<220> FEATURE:
<221> NAME/KEY: MOD_RES
<222> LOCATION: (14)..(14)
<223> OTHER INFORMATION: Asp, Lys, Glu, Ala, Pro, Thr, Ser, Gln, Leu,
      Tyr, Val, Asn, or Phe
<220> FEATURE:
<221> NAME/KEY: MOD_RES
<222> LOCATION: (15)..(15)
<223> OTHER INFORMATION: Ala, Ser, Leu, Glu, Asp, Lys, Val, Thr, Arg,
      Pro, Phe, Tyr, Gln, Asn, or Gly

<400> SEQUENCE: 3

Xaa Xaa Xaa Xaa Xaa Xaa Xaa Xaa Xaa Xaa Xaa Xaa Xaa Xaa Xaa
```

```
1               5                   10                  15
```

<210> SEQ ID NO 4
<211> LENGTH: 15
<212> TYPE: PRT
<213> ORGANISM: Homo sapiens

<400> SEQUENCE: 4

```
Cys Val Thr Arg Glu Pro Leu Thr Ala Asp Glu Glu Glu Ala Leu
1               5                   10                  15
```

<210> SEQ ID NO 5
<211> LENGTH: 15
<212> TYPE: PRT
<213> ORGANISM: Homo sapiens

<400> SEQUENCE: 5

```
Ser Thr Glu Asp Thr Ala Ser Ser Leu Cys Gly Glu Glu Asp Thr
1               5                   10                  15
```

<210> SEQ ID NO 6
<211> LENGTH: 15
<212> TYPE: PRT
<213> ORGANISM: Homo sapiens

<400> SEQUENCE: 6

```
Ser Leu Cys Gly Glu Glu Asp Thr Glu Asp Glu Glu Leu Glu Ala
1               5                   10                  15
```

<210> SEQ ID NO 7
<211> LENGTH: 15
<212> TYPE: PRT
<213> ORGANISM: Homo sapiens

<400> SEQUENCE: 7

```
Ser Ala Val Gly Ala Arg Gly Ser Pro Glu Thr Asn His Leu Ile
1               5                   10                  15
```

<210> SEQ ID NO 8
<211> LENGTH: 15
<212> TYPE: PRT
<213> ORGANISM: Homo sapiens

<400> SEQUENCE: 8

```
Leu Asp Lys Thr Ala Glu Ser Ser Leu Leu Glu Asp Glu Ile Ala
1               5                   10                  15
```

<210> SEQ ID NO 9
<211> LENGTH: 15
<212> TYPE: PRT
<213> ORGANISM: Homo sapiens

<400> SEQUENCE: 9

```
Tyr Trp Phe Gly Arg Asp Lys Ser Cys Glu Tyr Cys Phe Asp Glu
1               5                   10                  15
```

<210> SEQ ID NO 10
<211> LENGTH: 15
<212> TYPE: PRT
<213> ORGANISM: Homo sapiens

<400> SEQUENCE: 10

```
Thr Asp Lys Tyr Arg Thr Tyr Ser Lys Lys His Phe Arg Ile Phe
1               5                   10                  15
```

```
<210> SEQ ID NO 11
<211> LENGTH: 11
<212> TYPE: PRT
<213> ORGANISM: Homo sapiens

<400> SEQUENCE: 11

Gln Pro Leu Glu Ser Thr Gln Ser Gln Asp Phe
1               5                   10

<210> SEQ ID NO 12
<211> LENGTH: 15
<212> TYPE: PRT
<213> ORGANISM: Homo sapiens

<400> SEQUENCE: 12

Gln Gly Glu Ala Glu Glu Asp Ser Gln Gly Lys Glu Gly Pro Ser
1               5                   10                  15

<210> SEQ ID NO 13
<211> LENGTH: 15
<212> TYPE: PRT
<213> ORGANISM: Homo sapiens

<400> SEQUENCE: 13

Lys Glu Glu Glu Glu Gly Ile Ser Gln Glu Ser Ser Glu Glu Glu
1               5                   10                  15

<210> SEQ ID NO 14
<211> LENGTH: 15
<212> TYPE: PRT
<213> ORGANISM: Homo sapiens

<400> SEQUENCE: 14

Tyr Asp Leu Leu Arg Ala Ala Ser Glu Asn Ser Gln Asp Ala Leu
1               5                   10                  15

<210> SEQ ID NO 15
<211> LENGTH: 15
<212> TYPE: PRT
<213> ORGANISM: Homo sapiens

<400> SEQUENCE: 15

Phe Pro Arg Val Met Pro Leu Ser Lys Pro Val Pro Ala Thr Lys
1               5                   10                  15

<210> SEQ ID NO 16
<211> LENGTH: 15
<212> TYPE: PRT
<213> ORGANISM: Homo sapiens

<400> SEQUENCE: 16

Ser Tyr Lys His Arg Ser Lys Ser Arg Asp Arg Glu Gln Asp Arg
1               5                   10                  15

<210> SEQ ID NO 17
<211> LENGTH: 15
<212> TYPE: PRT
<213> ORGANISM: Homo sapiens

<400> SEQUENCE: 17

Val Lys Gln Glu Lys Ala Asp Thr Gln Asp Glu Trp Thr Pro Gly
1               5                   10                  15

<210> SEQ ID NO 18
```

```
<211> LENGTH: 15
<212> TYPE: PRT
<213> ORGANISM: Homo sapiens

<400> SEQUENCE: 18

Ala Val Glu Gly Pro Cys Pro Ser Gln Glu Ser Leu Ser Gln Glu
1               5                   10                  15

<210> SEQ ID NO 19
<211> LENGTH: 15
<212> TYPE: PRT
<213> ORGANISM: Homo sapiens

<400> SEQUENCE: 19

Gly Ala Glu Ala Phe Gly Asp Ser Glu Glu Asp Gly Glu Asp Val
1               5                   10                  15

<210> SEQ ID NO 20
<211> LENGTH: 15
<212> TYPE: PRT
<213> ORGANISM: Homo sapiens

<400> SEQUENCE: 20

Lys Arg Arg Ser Gly Lys Asn Ser Gln Glu Asp Ser Glu Asp Ser
1               5                   10                  15

<210> SEQ ID NO 21
<211> LENGTH: 15
<212> TYPE: PRT
<213> ORGANISM: Homo sapiens

<400> SEQUENCE: 21

Ser Gln Leu Glu Glu His Leu Ser Gln Leu Gln Asp Asn Pro Pro
1               5                   10                  15

<210> SEQ ID NO 22
<211> LENGTH: 15
<212> TYPE: PRT
<213> ORGANISM: Homo sapiens

<400> SEQUENCE: 22

Trp Arg Glu Arg Tyr Glu Asp Ser Gln Gln Glu Glu Ala Gln Tyr
1               5                   10                  15

<210> SEQ ID NO 23
<211> LENGTH: 15
<212> TYPE: PRT
<213> ORGANISM: Homo sapiens

<400> SEQUENCE: 23

Ser Ala Asp Asp Glu Glu Leu Thr Asn Asp Ser Leu Thr Leu Ser
1               5                   10                  15

<210> SEQ ID NO 24
<211> LENGTH: 15
<212> TYPE: PRT
<213> ORGANISM: Homo sapiens

<400> SEQUENCE: 24

Asp Ala Glu Tyr Ile Tyr Pro Ser Leu Glu Ser Asp Asp Asp Asp
1               5                   10                  15

<210> SEQ ID NO 25
<211> LENGTH: 15
<212> TYPE: PRT
```

-continued

```
<213> ORGANISM: Homo sapiens

<400> SEQUENCE: 25

Gly Ser Leu Asp Arg Ala Thr Ser Pro Arg Pro Arg Ala Phe Asp
1               5                   10                  15

<210> SEQ ID NO 26
<211> LENGTH: 15
<212> TYPE: PRT
<213> ORGANISM: Homo sapiens

<400> SEQUENCE: 26

Ser Glu Glu Glu Leu Glu His Ser Gln Asp Thr Asp Ala Asp Asp
1               5                   10                  15

<210> SEQ ID NO 27
<211> LENGTH: 15
<212> TYPE: PRT
<213> ORGANISM: Homo sapiens

<400> SEQUENCE: 27

Gly Phe Gly Pro Gly Asp Arg Ser His Leu Asp Ser Pro Glu Ala
1               5                   10                  15

<210> SEQ ID NO 28
<211> LENGTH: 15
<212> TYPE: PRT
<213> ORGANISM: Homo sapiens

<400> SEQUENCE: 28

Glu Asp Val Leu Gly Asp Glu Thr Glu Glu Glu Glu Thr Lys Pro
1               5                   10                  15

<210> SEQ ID NO 29
<211> LENGTH: 15
<212> TYPE: PRT
<213> ORGANISM: Homo sapiens

<400> SEQUENCE: 29

Met Arg Ala Met Asn Val Leu Thr Glu Ala Glu Glu Arg Tyr Asn
1               5                   10                  15

<210> SEQ ID NO 30
<211> LENGTH: 15
<212> TYPE: PRT
<213> ORGANISM: Homo sapiens

<400> SEQUENCE: 30

Ser Lys Asp Tyr Asp Val Tyr Ser Asp Asn Asp Ile Cys Ser Gln
1               5                   10                  15

<210> SEQ ID NO 31
<211> LENGTH: 15
<212> TYPE: PRT
<213> ORGANISM: Homo sapiens

<400> SEQUENCE: 31

Lys Lys Ala Glu Glu Asn Ala Ser Gln Glu Glu Glu Glu Ala Ala
1               5                   10                  15

<210> SEQ ID NO 32
<211> LENGTH: 1818
<212> TYPE: DNA
<213> ORGANISM: Homo sapiens
```

<400> SEQUENCE: 32

```
atggcgggc tgtactcgct gggagtgagc gtcttctccg accagggcgg gaggaagtac      60
atggaggacg ttactcaaat cgttgtggag cccgaaccga cggctgaaga aaagccctcg    120
ccgcggcggt cgctgtctca gccgttgcct ccgcggccgt cgccgccgc ccttcccggc     180
ggcgaagtct cggggaaagg cccagcggtg gcagcccgag aggctcgcga ccctctcccg    240
gacgccgggg cctcgccggc acctagccgc tgctgccgcc gccgttcctc cgtggccttt    300
ttcgccgtgt gcgacgggca cggcgggcgg gaggcggcac agtttgcccg ggagcacttg    360
tggggtttca tcaagaagca gaagggtttc acctcgtccg agccggctaa ggtttgcgct    420
gccatccgca aaggctttct cgcttgtcac cttgccatgt ggaagaaact ggcggaatgg    480
ccaaagacta tgacgggtct tcctagcaca tcagggacaa ctgccagtgt ggtcatcatt    540
cggggcatga agatgtatgt agctcacgta ggtgactcag gggtggttct tggaattcag    600
gatgacccga aggatgactt tgtcagagct gtggaggtga cacaggacca taagccagaa    660
cttcccaagg aaagagaacg aatcgaagga cttggtggga gtgtaatgaa caagtctggg    720
gtgaatcgtg tagtttggaa acgacctcga ctcactcaca atggacctgt tagaaggagc    780
acagttattg accagattcc ttttctggca gtagcaagag cacttggtga tttgtggagc    840
tatgatttct tcagtggtga atttgtggtg tcacctgaac cagacacaag tgtccacact    900
cttgaccctc agaagcacaa gtatattata ttggggagtg atggactttg gaatatgatt    960
ccaccacaag atgccatctc aatgtgccag gaccaagagg agaaaaaata cctgatgggt   1020
gagcatggac aatcttgtgc caaaatgctt gtgaatcgag cattgggccg ctggaggcag   1080
cgtatgctcc gagcagataa cactagtgcc atagtaatct gcatctctcc agaagtggac   1140
aatcaggaa actttaccaa tgaagatgag ttatacctga actgactga cagcccttcc    1200
tataatagtc aagaaacctg tgtgatgact ccttccccat gttctacacc accagtcaag   1260
tcactggagg aggatccatg gccaagggtg aattctaagg accatatacc tgccctggtt   1320
cgtagcaatg ccttctcaga gaattttta gaggtttcag ctgagatagc tcgagagaat   1380
gtccaaggtg tagtcatacc ctcaaaagat ccagaaccac ttgaagaaaa ttgcgctaaa   1440
gccctgactt aaggataca tgattctttg aataatagcc ttccaattgg ccttgtgcct   1500
actaattcaa caaacactgt catggaccaa aaaaatttga agatgtcaac tcctggccaa   1560
atgaaagccc aagaaattga agaaccccct ccaacaaact ttaaaaggac attagaagag   1620
tccaattctg gccccctgat gaagaagcat agacgaaatg gcttaagtcg aagtagtggt   1680
gctcagcctg caagtctccc cacaacctca cagcgaaaga actctgttaa actcaccatg   1740
cgacgcagac ttaggggcca gaagaaaatt ggaaatcctt tacttcatca acacaggaaa   1800
actgtttgtg tttgctga                                                1818
```

<210> SEQ ID NO 33
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
atggcgggc tgtactcgct gggagtgagc gtcttctccg accagggcgg gaggaagtac      60
atggaggacg ttactcaaat cgttgtggag cccgaaccga cggctgaaga aaagccctcg    120
```

```
ccgcggcggt cgctgtctca gccgttgcct ccgcggccgt cgccggccgc ccttcccggc    180
ggcgaagtct cggggaaagg cccagcggtg gcagcccgag aggctcgcga ccctctcccg    240
gacgccgggg cctcgccggc acctagccgc tgctgccgcc gccgttcctc cgtggccttt    300
ttcgccgtgt gcgacgggca cggcgggcgg gaggcggcac agtttgcccg ggagcacttg    360
tggggtttca tcaagaagca gaagggtttc acctcgtccg agccggctaa ggtttgcgct    420
gccatccgca aaggctttct cgcttgtcac cttgccatgt ggaagaaact ggcggaatgg    480
ccaaagacta tgacgggtct tcctagcaca tcagggacaa ctgccagtgt ggtcatcatt    540
cggggcatga gatgtatgt agctcacgta ggtgactcag gggtggttct tggaattcag    600
gatgacccga aggatgactt tgtcagagct gtggaggtga cacaggacca taagccagaa    660
cttcccaagg aaagagaacg aatcgaagga cttggtggga gtgtaatgaa caagtctggg    720
gtgaatcgtg tagtttggaa acgacctcga ctcactcaca atggacctgt tagaaggagc    780
acagttattg accagattcc ttttctggca gtagcaagag cacttggtga tttgtggagc    840
tatgatttct tcagtggtga atttgtggtg tcacctgaac cagacacaag tgtccacact    900
cttgaccctc agaagcacaa gtatattata ttggggagtg atggactttg gaatatgatt    960
ccaccacaag atgccatctc aatgtgccag gaccaagaga gaaaaaata cctgatgggt    1020 gagcatggac aatcttgtgc caaaatgctt gtgaatcgag cattgggccg ctggaggcag    1080
cgtatgctcc gagcagataa cactagtgcc atagtaatct gcatctctcc agaagtggac    1140
aatcagggaa actttaccaa tgaagatgag ttatacctga acctgactga cagcccttcc    1200
tataatagtc aagaaacctg tgtgatgact ccttccccat gttctacacc accagtcaag    1260
tcactggagg aggatccatg gccaaggggtg aattctaagg accatatacc tgccctggtt    1320
cgtagcaatg cctctctcaga gaattttta gaggtttcag ctgagatagc tcgagagaat    1380
gtccaaggtg tagtcatacc ctcaaaagat ccagaaccac ttgaagaaaa ttgctaa       1437
```

<210> SEQ ID NO 34
<211> LENGTH: 1428
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
atggcgggc tgtactcgct gggagtgagc gtcttctccg accagggcgg gaggaagtac    60
atggaggacg ttactcaaat cgttgtggag cccgaaccga cggctgaaga aaagccctcg    120
ccgcggcggt cgctgtctca gccgttgcct ccgcggccgt cgccggccgc ccttcccggc    180
ggcgaagtct cggggaaagg cccagcggtg gcagcccgag aggctcgcga ccctctcccg    240
gacgccgggg cctcgccggc acctagccgc tgctgccgcc gccgttcctc cgtggccttt    300
ttcgccgtgt gcgacgggca cggcgggcgg gaggcggcac agtttgcccg ggagcacttg    360
tggggtttca tcaagaagca gaagggtttc acctcgtccg agccggctaa ggtttgcgct    420
gccatccgca aaggctttct cgcttgtcac cttgccatgt ggaagaaact ggcggaatgg    480
ccaaagacta tgacgggtct tcctagcaca tcagggacaa ctgccagtgt ggtcatcatt    540
cggggcatga gatgtatgt agctcacgta ggtgactcag gggtggttct tggaattcag    600
gatgacccga aggatgactt tgtcagagct gtggaggtga cacaggacca taagccagaa    660
cttcccaagg aaagagaacg aatcgaagga cttggtggga gtgtaatgaa caagtctggg    720
```

```
gtgaatcgtg tagtttggaa acgacctcga ctcactcaca atggacctgt tagaaggagc    780
acagttattg accagattcc ttttctggca gtagcaagag cacttggtga tttgtggagc    840
tatgatttct tcagtggtga atttgtggtg tcacctgaac cagacacaag tgtccacact    900
cttgacccct agaagcacaa gtatattata ttggggagtg atggactttg aatatgatt    960 ccaccacaag atgccatctc aatgtgccag gaccaagagg agaaaaaata cctgatgggt   1020
gagcatggac aatcttgtgc caaaatgctt gtgaatcgag cattgggccg ctggaggcag   1080
cgtatgctcc gagcagataa cactagtgcc atagtaatct gcatctctcc agaagtggac   1140
aatcagggaa actttaccaa tgaagatgag ttatacctga acctgactga cagcccttcc   1200
tataatagtc aagaaacctg tgtgatgact ccttccccat gttctacacc accagtcaag   1260
tcactggagg aggatccatg gccaagggtg aattctaagg accatatacc tgccctggtt   1320
cgtagcaatg ccttctcaga gaattttta gaggtttcag ctgagatagc tcgagagaat   1380
gtccaaggtg tagtcatacc ctcaaaagat ccagaaccac ttgaatga                1428
```

```
<210> SEQ ID NO 35
<211> LENGTH: 165
<212> TYPE: DNA
<213> ORGANISM: Homo sapiens

<400> SEQUENCE: 35
cgaaatggct taagtcgaag tagtggtgct cagcctgcaa gtctccccac aacctcacag    60
cgaaagaact ctgttaaact caccatgcga cgcagactta ggggccagaa gaaaattgga   120
aatcctttac ttcatcaaca caggaaaact gtttgtgttt gctga                   165
```

```
<210> SEQ ID NO 36
<211> LENGTH: 20
<212> TYPE: DNA
<213> ORGANISM: Homo sapiens

<400> SEQUENCE: 36
gagtacagcc ccgccatggc                                                20
```

```
<210> SEQ ID NO 37
<211> LENGTH: 20
<212> TYPE: DNA
<213> ORGANISM: Homo sapiens

<400> SEQUENCE: 37
tcccggccag ccggccatgg                                                20
```

```
<210> SEQ ID NO 38
<211> LENGTH: 20
<212> TYPE: DNA
<213> ORGANISM: Homo sapiens

<400> SEQUENCE: 38
cccggccagc cggccatggc                                                20
```

```
<210> SEQ ID NO 39
<211> LENGTH: 20
<212> TYPE: DNA
<213> ORGANISM: Homo sapiens

<400> SEQUENCE: 39
ccggccagcc ggccatggcg                                                20
```

```
<210> SEQ ID NO 40
<211> LENGTH: 20
<212> TYPE: DNA
<213> ORGANISM: Homo sapiens

<400> SEQUENCE: 40
cagcgagtac agccccgcca                                              20

<210> SEQ ID NO 41
<211> LENGTH: 20
<212> TYPE: DNA
<213> ORGANISM: Homo sapiens

<400> SEQUENCE: 41
catggcgggg ctgtactcgc                                              20

<210> SEQ ID NO 42
<211> LENGTH: 20
<212> TYPE: DNA
<213> ORGANISM: Homo sapiens

<400> SEQUENCE: 42 atggcgggc tgtactcgct                                               20

<210> SEQ ID NO 43
<211> LENGTH: 20
<212> TYPE: DNA
<213> ORGANISM: Homo sapiens

<400> SEQUENCE: 43
agtgagcgtc ttctccgacc                                              20

<210> SEQ ID NO 44
<211> LENGTH: 20
<212> TYPE: DNA
<213> ORGANISM: Homo sapiens

<400> SEQUENCE: 44
gtgagcgtct tctccgacca                                              20

<210> SEQ ID NO 45
<211> LENGTH: 20
<212> TYPE: DNA
<213> ORGANISM: Homo sapiens

<400> SEQUENCE: 45
gtacttcctc ccgccctggt                                              20

<210> SEQ ID NO 46
<211> LENGTH: 20
<212> TYPE: DNA
<213> ORGANISM: Homo sapiens

<400> SEQUENCE: 46
agcgtcttct ccgaccaggg                                              20

<210> SEQ ID NO 47
<211> LENGTH: 20
<212> TYPE: DNA
<213> ORGANISM: Homo sapiens

<400> SEQUENCE: 47
gcgtcttctc cgaccagggc                                              20
```

<210> SEQ ID NO 48
<211> LENGTH: 20
<212> TYPE: DNA
<213> ORGANISM: Homo sapiens

<400> SEQUENCE: 48
ccatgtactt cctcccgccc                                                    20

<210> SEQ ID NO 49
<211> LENGTH: 20
<212> TYPE: DNA
<213> ORGANISM: Homo sapiens

<400> SEQUENCE: 49
tcttctccga ccagggcggg                                                    20

<210> SEQ ID NO 50
<211> LENGTH: 20
<212> TYPE: DNA
<213> ORGANISM: Homo sapiens

<400> SEQUENCE: 50
ccagggcggg aggaagtaca                                                    20

<210> SEQ ID NO 51
<211> LENGTH: 20
<212> TYPE: DNA
<213> ORGANISM: Homo sapiens

<400> SEQUENCE: 51
gggcgggagg aagtacatgg                                                    20

<210> SEQ ID NO 52
<211> LENGTH: 20
<212> TYPE: DNA
<213> ORGANISM: Homo sapiens

<400> SEQUENCE: 52
ggacgttact caaatcgttg                                                    20

<210> SEQ ID NO 53
<211> LENGTH: 20
<212> TYPE: DNA
<213> ORGANISM: Homo sapiens

<400> SEQUENCE: 53
ttttcttcag ccgtcggttc                                                    20

<210> SEQ ID NO 54
<211> LENGTH: 20
<212> TYPE: DNA
<213> ORGANISM: Homo sapiens

<400> SEQUENCE: 54
cgttgtggag cccgaaccga                                                    20

<210> SEQ ID NO 55
<211> LENGTH: 20
<212> TYPE: DNA
<213> ORGANISM: Homo sapiens

<400> SEQUENCE: 55
cttttcttca gccgtcggtt                                                    20

<210> SEQ ID NO 56
<211> LENGTH: 20
<212> TYPE: DNA
<213> ORGANISM: Homo sapiens

<400> SEQUENCE: 56
gagggctttt cttcagccgt                                               20

<210> SEQ ID NO 57
<211> LENGTH: 20
<212> TYPE: DNA
<213> ORGANISM: Homo sapiens

<400> SEQUENCE: 57
ctgaagaaaa gccctcgccg                                               20

<210> SEQ ID NO 58
<211> LENGTH: 20
<212> TYPE: DNA
<213> ORGANISM: Homo sapiens

<400> SEQUENCE: 58
gacagcgacc gccgcggcga                                               20

<210> SEQ ID NO 59
<211> LENGTH: 20
<212> TYPE: DNA
<213> ORGANISM: Homo sapiens

<400> SEQUENCE: 59
agacagcgac cgccgcggcg                                               20

<210> SEQ ID NO 60
<211> LENGTH: 20
<212> TYPE: DNA
<213> ORGANISM: Homo sapiens

<400> SEQUENCE: 60
aagaaaagcc ctcgccgcgg                                               20

<210> SEQ ID NO 61
<211> LENGTH: 20
<212> TYPE: DNA
<213> ORGANISM: Homo sapiens

<400> SEQUENCE: 61
ggctgagaca gcgaccgccg                                               20

<210> SEQ ID NO 62
<211> LENGTH: 20
<212> TYPE: DNA
<213> ORGANISM: Homo sapiens

<400> SEQUENCE: 62
ggcgacggcc gcggaggcaa                                               20

<210> SEQ ID NO 63
<211> LENGTH: 20
<212> TYPE: DNA
<213> ORGANISM: Homo sapiens

<400> SEQUENCE: 63
tgtctcagcc gttgcctccg                                              20

<210> SEQ ID NO 64
<211> LENGTH: 20
<212> TYPE: DNA
<213> ORGANISM: Homo sapiens

<400> SEQUENCE: 64
gcggccggcg acggccgcgg                                              20

<210> SEQ ID NO 65
<211> LENGTH: 20
<212> TYPE: DNA
<213> ORGANISM: Homo sapiens

<400> SEQUENCE: 65
agggcggccg gcgacggccg                                              20

<210> SEQ ID NO 66
<211> LENGTH: 20
<212> TYPE: DNA
<213> ORGANISM: Homo sapiens

<400> SEQUENCE: 66
gttgcctccg cggccgtcgc                                              20

<210> SEQ ID NO 67
<211> LENGTH: 20
<212> TYPE: DNA
<213> ORGANISM: Homo sapiens

<400> SEQUENCE: 67
ccgggaaggg cggccggcga                                              20

<210> SEQ ID NO 68
<211> LENGTH: 20
<212> TYPE: DNA
<213> ORGANISM: Homo sapiens

<400> SEQUENCE: 68
tcgccgccgg gaagggcggc                                              20

<210> SEQ ID NO 69
<211> LENGTH: 20
<212> TYPE: DNA
<213> ORGANISM: Homo sapiens

<400> SEQUENCE: 69
gacttcgccg ccgggaaggg                                              20

<210> SEQ ID NO 70
<211> LENGTH: 20
<212> TYPE: DNA
<213> ORGANISM: Homo sapiens

<400> SEQUENCE: 70
ccgtcgccgg ccgcccttcc                                              20

<210> SEQ ID NO 71
<211> LENGTH: 20
<212> TYPE: DNA
<213> ORGANISM: Homo sapiens

<400> SEQUENCE: 71
cgagacttcg ccgccgggaa                                                    20

<210> SEQ ID NO 72
<211> LENGTH: 20
<212> TYPE: DNA
<213> ORGANISM: Homo sapiens

<400> SEQUENCE: 72
ccgagacttc gccgccggga                                                    20

<210> SEQ ID NO 73
<211> LENGTH: 20
<212> TYPE: DNA
<213> ORGANISM: Homo sapiens

<400> SEQUENCE: 73
tcgccggccg cccttcccgg                                                    20

<210> SEQ ID NO 74
<211> LENGTH: 20
<212> TYPE: DNA
<213> ORGANISM: Homo sapiens

<400> SEQUENCE: 74
ttccccgaga cttcgccgcc                                                    20

<210> SEQ ID NO 75
<211> LENGTH: 20
<212> TYPE: DNA
<213> ORGANISM: Homo sapiens

<400> SEQUENCE: 75
tttccccgag acttcgccgc                                                    20

<210> SEQ ID NO 76
<211> LENGTH: 20
<212> TYPE: DNA
<213> ORGANISM: Homo sapiens

<400> SEQUENCE: 76
ccttcccggc ggcgaagtct                                                    20

<210> SEQ ID NO 77
<211> LENGTH: 20
<212> TYPE: DNA
<213> ORGANISM: Homo sapiens

<400> SEQUENCE: 77
cttcccggcg gcgaagtctc                                                    20

<210> SEQ ID NO 78
<211> LENGTH: 20
<212> TYPE: DNA
<213> ORGANISM: Homo sapiens

<400> SEQUENCE: 78
ttcccggcgg cgaagtctcg                                                    20

<210> SEQ ID NO 79
<211> LENGTH: 20
<212> TYPE: DNA
<213> ORGANISM: Homo sapiens

```
<400> SEQUENCE: 79
ggcggcgaag tctcggggaa                                        20

<210> SEQ ID NO 80
<211> LENGTH: 20
<212> TYPE: DNA
<213> ORGANISM: Homo sapiens

<400> SEQUENCE: 80
agtctcgggg aaaggcccag                                        20

<210> SEQ ID NO 81
<211> LENGTH: 20
<212> TYPE: DNA
<213> ORGANISM: Homo sapiens

<400> SEQUENCE: 81
ctcggggaaa ggcccagcgg                                        20

<210> SEQ ID NO 82
<211> LENGTH: 20
<212> TYPE: DNA
<213> ORGANISM: Homo sapiens

<400> SEQUENCE: 82
cctctcgggc tgccaccgct                                        20

<210> SEQ ID NO 83
<211> LENGTH: 20
<212> TYPE: DNA
<213> ORGANISM: Homo sapiens

<400> SEQUENCE: 83
gcctctcggg ctgccaccgc                                        20

<210> SEQ ID NO 84
<211> LENGTH: 20
<212> TYPE: DNA
<213> ORGANISM: Homo sapiens

<400> SEQUENCE: 84
cccagcggtg gcagcccgag                                        20

<210> SEQ ID NO 85
<211> LENGTH: 20
<212> TYPE: DNA
<213> ORGANISM: Homo sapiens

<400> SEQUENCE: 85
gagagggtcg cgagcctctc                                        20

<210> SEQ ID NO 86
<211> LENGTH: 20
<212> TYPE: DNA
<213> ORGANISM: Homo sapiens

<400> SEQUENCE: 86
ggagagggtc gcgagcctct                                        20

<210> SEQ ID NO 87
<211> LENGTH: 20
<212> TYPE: DNA
<213> ORGANISM: Homo sapiens
```

-continued

```
<400> SEQUENCE: 87
agaggctcgc gaccctctcc                                              20

<210> SEQ ID NO 88
<211> LENGTH: 20
<212> TYPE: DNA
<213> ORGANISM: Homo sapiens

<400> SEQUENCE: 88
aggccccggc gtccgggaga                                              20

<210> SEQ ID NO 89
<211> LENGTH: 20
<212> TYPE: DNA
<213> ORGANISM: Homo sapiens

<400> SEQUENCE: 89
gaggccccgg cgtccgggag                                              20

<210> SEQ ID NO 90
<211> LENGTH: 20
<212> TYPE: DNA
<213> ORGANISM: Homo sapiens

<400> SEQUENCE: 90
cgcgaccctc tcccggacgc                                              20

<210> SEQ ID NO 91
<211> LENGTH: 20
<212> TYPE: DNA
<213> ORGANISM: Homo sapiens

<400> SEQUENCE: 91
ccggcgaggc cccggcgtcc                                              20

<210> SEQ ID NO 92
<211> LENGTH: 20
<212> TYPE: DNA
<213> ORGANISM: Homo sapiens

<400> SEQUENCE: 92
gcgaccctct cccggacgcc                                              20

<210> SEQ ID NO 93
<211> LENGTH: 20
<212> TYPE: DNA
<213> ORGANISM: Homo sapiens

<400> SEQUENCE: 93
gccggcgagg ccccggcgtc                                              20

<210> SEQ ID NO 94
<211> LENGTH: 20
<212> TYPE: DNA
<213> ORGANISM: Homo sapiens

<400> SEQUENCE: 94
cgaccctctc ccggacgccg                                              20

<210> SEQ ID NO 95
<211> LENGTH: 20
<212> TYPE: DNA
```

```
<213> ORGANISM: Homo sapiens

<400> SEQUENCE: 95
gctaggtgcc ggcgaggccc                                               20

<210> SEQ ID NO 96
<211> LENGTH: 20
<212> TYPE: DNA
<213> ORGANISM: Homo sapiens

<400> SEQUENCE: 96
cccggacgcc ggggcctcgc                                               20

<210> SEQ ID NO 97
<211> LENGTH: 20
<212> TYPE: DNA
<213> ORGANISM: Homo sapiens

<400> SEQUENCE: 97
gcagcggcta ggtgccggcg                                               20

<210> SEQ ID NO 98
<211> LENGTH: 20
<212> TYPE: DNA
<213> ORGANISM: Homo sapiens

<400> SEQUENCE: 98
cggcagcagc ggctaggtgc                                               20

<210> SEQ ID NO 99
<211> LENGTH: 20
<212> TYPE: DNA
<213> ORGANISM: Homo sapiens

<400> SEQUENCE: 99
cggcggcggc agcagcggct                                               20

<210> SEQ ID NO 100
<211> LENGTH: 20
<212> TYPE: DNA
<213> ORGANISM: Homo sapiens

<400> SEQUENCE: 100
aggaacggcg gcggcagcag                                               20

<210> SEQ ID NO 101
<211> LENGTH: 20
<212> TYPE: DNA
<213> ORGANISM: Homo sapiens

<400> SEQUENCE: 101
aggccacgga ggaacggcgg                                               20

<210> SEQ ID NO 102
<211> LENGTH: 20
<212> TYPE: DNA
<213> ORGANISM: Homo sapiens

<400> SEQUENCE: 102
aaaaggccac ggaggaacgg                                               20

<210> SEQ ID NO 103
<211> LENGTH: 20
```

<212> TYPE: DNA
<213> ORGANISM: Homo sapiens

<400> SEQUENCE: 103
cgaaaaaggc cacggaggaa                                                     20

<210> SEQ ID NO 104
<211> LENGTH: 20
<212> TYPE: DNA
<213> ORGANISM: Homo sapiens

<400> SEQUENCE: 104
ctgccgccgc cgttcctccg                                                     20

<210> SEQ ID NO 105
<211> LENGTH: 20
<212> TYPE: DNA
<213> ORGANISM: Homo sapiens

<400> SEQUENCE: 105
cacggcgaaa aaggccacgg                                                     20

<210> SEQ ID NO 106
<211> LENGTH: 20
<212> TYPE: DNA
<213> ORGANISM: Homo sapiens

<400> SEQUENCE: 106
gcacacggcg aaaaaggcca                                                     20

<210> SEQ ID NO 107
<211> LENGTH: 20
<212> TYPE: DNA
<213> ORGANISM: Homo sapiens

<400> SEQUENCE: 107
cccgtcgcac acggcgaaaa                                                     20

<210> SEQ ID NO 108
<211> LENGTH: 20
<212> TYPE: DNA
<213> ORGANISM: Homo sapiens

<400> SEQUENCE: 108
cccgccgtgc ccgtcgcaca                                                     20

<210> SEQ ID NO 109
<211> LENGTH: 20
<212> TYPE: DNA
<213> ORGANISM: Homo sapiens

<400> SEQUENCE: 109
gcctttttcg ccgtgtgcga                                                     20

<210> SEQ ID NO 110
<211> LENGTH: 20
<212> TYPE: DNA
<213> ORGANISM: Homo sapiens

<400> SEQUENCE: 110 ccttttcgc cgtgtgcgac                                                      20

<210> SEQ ID NO 111

```
<211> LENGTH: 20
<212> TYPE: DNA
<213> ORGANISM: Homo sapiens

<400> SEQUENCE: 111
ttcgccgtgt gcgacgggca                                                  20

<210> SEQ ID NO 112
<211> LENGTH: 20
<212> TYPE: DNA
<213> ORGANISM: Homo sapiens

<400> SEQUENCE: 112
gccgtgtgcg acgggcacgg                                                  20

<210> SEQ ID NO 113
<211> LENGTH: 20
<212> TYPE: DNA
<213> ORGANISM: Homo sapiens

<400> SEQUENCE: 113
ccgtgtgcga cgggcacggc                                                  20

<210> SEQ ID NO 114
<211> LENGTH: 20
<212> TYPE: DNA
<213> ORGANISM: Homo sapiens

<400> SEQUENCE: 114
tgtgcgacgg gcacggcggg                                                  20

<210> SEQ ID NO 115
<211> LENGTH: 20
<212> TYPE: DNA
<213> ORGANISM: Homo sapiens

<400> SEQUENCE: 115
gtgcgacggg cacggcgggc                                                  20

<210> SEQ ID NO 116
<211> LENGTH: 20
<212> TYPE: DNA
<213> ORGANISM: Homo sapiens

<400> SEQUENCE: 116
cgacgggcac ggcgggcggg                                                  20

<210> SEQ ID NO 117
<211> LENGTH: 20
<212> TYPE: DNA
<213> ORGANISM: Homo sapiens

<400> SEQUENCE: 117
cgggcacggc gggcgggagg                                                  20

<210> SEQ ID NO 118
<211> LENGTH: 20
<212> TYPE: DNA
<213> ORGANISM: Homo sapiens

<400> SEQUENCE: 118
gggaggcggc acagtttgcc                                                  20
```

```
<210> SEQ ID NO 119
<211> LENGTH: 20
<212> TYPE: DNA
<213> ORGANISM: Homo sapiens

<400> SEQUENCE: 119
ggaggcggca cagtttgccc                                               20

<210> SEQ ID NO 120
<211> LENGTH: 20
<212> TYPE: DNA
<213> ORGANISM: Homo sapiens

<400> SEQUENCE: 120
gaaaccccac aagtgctccc                                               20

<210> SEQ ID NO 121
<211> LENGTH: 20
<212> TYPE: DNA
<213> ORGANISM: Homo sapiens

<400> SEQUENCE: 121
tgaaacccca caagtgctcc                                               20

<210> SEQ ID NO 122
<211> LENGTH: 20
<212> TYPE: DNA
<213> ORGANISM: Homo sapiens

<400> SEQUENCE: 122
agtttgcccg ggagcacttg                                               20

<210> SEQ ID NO 123
<211> LENGTH: 20
<212> TYPE: DNA
<213> ORGANISM: Homo sapiens

<400> SEQUENCE: 123
gtttgcccgg gagcacttgt                                               20

<210> SEQ ID NO 124
<211> LENGTH: 20
<212> TYPE: DNA
<213> ORGANISM: Homo sapiens

<400> SEQUENCE: 124
tttgcccggg agcacttgtg                                               20

<210> SEQ ID NO 125
<211> LENGTH: 20
<212> TYPE: DNA
<213> ORGANISM: Homo sapiens

<400> SEQUENCE: 125
gggtttcatc aagaagcaga                                               20

<210> SEQ ID NO 126
<211> LENGTH: 20
<212> TYPE: DNA
<213> ORGANISM: Homo sapiens

<400> SEQUENCE: 126
ggtttcatca agaagcagaa                                               20
```

```
<210> SEQ ID NO 127
<211> LENGTH: 20
<212> TYPE: DNA
<213> ORGANISM: Homo sapiens

<400> SEQUENCE: 127
aaccttagcc ggctcggacg                                              20

<210> SEQ ID NO 128
<211> LENGTH: 20
<212> TYPE: DNA
<213> ORGANISM: Homo sapiens

<400> SEQUENCE: 128
gggtttcacc tcgtccgagc                                              20

<210> SEQ ID NO 129
<211> LENGTH: 20
<212> TYPE: DNA
<213> ORGANISM: Homo sapiens

<400> SEQUENCE: 129
agcgcaaacc ttagccggct                                              20

<210> SEQ ID NO 130
<211> LENGTH: 20
<212> TYPE: DNA
<213> ORGANISM: Homo sapiens

<400> SEQUENCE: 130
cacctcgtcc gagccggcta                                              20

<210> SEQ ID NO 131
<211> LENGTH: 20
<212> TYPE: DNA
<213> ORGANISM: Homo sapiens

<400> SEQUENCE: 131
atggcagcgc aaaccttagc                                              20

<210> SEQ ID NO 132
<211> LENGTH: 20
<212> TYPE: DNA
<213> ORGANISM: Homo sapiens

<400> SEQUENCE: 132
agcgagaaag cctttgcgga                                              20

<210> SEQ ID NO 133
<211> LENGTH: 20
<212> TYPE: DNA
<213> ORGANISM: Homo sapiens

<400> SEQUENCE: 133
gtttgcgctg ccatccgcaa                                              20

<210> SEQ ID NO 134
<211> LENGTH: 20
<212> TYPE: DNA
<213> ORGANISM: Homo sapiens

<400> SEQUENCE: 134
gacaagcgag aaagcctttg                                              20
```

```
<210> SEQ ID NO 135
<211> LENGTH: 20
<212> TYPE: DNA
<213> ORGANISM: Homo sapiens

<400> SEQUENCE: 135
ccagtttctt ccacatggca                                              20

<210> SEQ ID NO 136
<211> LENGTH: 20
<212> TYPE: DNA
<213> ORGANISM: Homo sapiens

<400> SEQUENCE: 136
tcgcttgtca ccttgccatg                                              20

<210> SEQ ID NO 137
<211> LENGTH: 20
<212> TYPE: DNA
<213> ORGANISM: Homo sapiens

<400> SEQUENCE: 137
cttacccagt ttcttccaca                                              20

<210> SEQ ID NO 138
<211> LENGTH: 20
<212> TYPE: DNA
<213> ORGANISM: Homo sapiens

<400> SEQUENCE: 138
ccttgccatg tggaagaaac                                              20

<210> SEQ ID NO 139
<211> LENGTH: 20
<212> TYPE: DNA
<213> ORGANISM: Homo sapiens

<400> SEQUENCE: 139
cttgccatgt ggaagaaact                                              20

<210> SEQ ID NO 140
<211> LENGTH: 20
<212> TYPE: DNA
<213> ORGANISM: Homo sapiens

<400> SEQUENCE: 140
tatttcttat tacagcggaa                                              20

<210> SEQ ID NO 141
<211> LENGTH: 20
<212> TYPE: DNA
<213> ORGANISM: Homo sapiens

<400> SEQUENCE: 141
ggaagacccg tcatagtctt                                              20

<210> SEQ ID NO 142
<211> LENGTH: 20
<212> TYPE: DNA
<213> ORGANISM: Homo sapiens

<400> SEQUENCE: 142
```

-continued ggaatggcca aagactatga                                                                        20

<210> SEQ ID NO 143
<211> LENGTH: 20
<212> TYPE: DNA
<213> ORGANISM: Homo sapiens

<400> SEQUENCE: 143
gaatggccaa agactatgac                                                                        20

<210> SEQ ID NO 144
<211> LENGTH: 20
<212> TYPE: DNA
<213> ORGANISM: Homo sapiens

<400> SEQUENCE: 144
gcagttgtcc ctgatgtgct                                                                        20

<210> SEQ ID NO 145
<211> LENGTH: 20
<212> TYPE: DNA
<213> ORGANISM: Homo sapiens

<400> SEQUENCE: 145
acgggtcttc ctagcacatc                                                                        20

<210> SEQ ID NO 146
<211> LENGTH: 20
<212> TYPE: DNA
<213> ORGANISM: Homo sapiens

<400> SEQUENCE: 146
cgggtcttcc tagcacatca                                                                        20

<210> SEQ ID NO 147
<211> LENGTH: 20
<212> TYPE: DNA
<213> ORGANISM: Homo sapiens

<400> SEQUENCE: 147
atcagggaca actgccagtg                                                                        20

<210> SEQ ID NO 148
<211> LENGTH: 20
<212> TYPE: DNA
<213> ORGANISM: Homo sapiens

<400> SEQUENCE: 148
gccccgaatg atgaccacac                                                                        20

<210> SEQ ID NO 149
<211> LENGTH: 20
<212> TYPE: DNA
<213> ORGANISM: Homo sapiens

<400> SEQUENCE: 149
ctgccagtgt ggtcatcatt                                                                        20

<210> SEQ ID NO 150
<211> LENGTH: 20
<212> TYPE: DNA
<213> ORGANISM: Homo sapiens

<400> SEQUENCE: 150
tgccagtgtg gtcatcattc                    20

<210> SEQ ID NO 151
<211> LENGTH: 20
<212> TYPE: DNA
<213> ORGANISM: Homo sapiens

<400> SEQUENCE: 151
gccagtgtgg tcatcattcg                    20

<210> SEQ ID NO 152
<211> LENGTH: 20
<212> TYPE: DNA
<213> ORGANISM: Homo sapiens

<400> SEQUENCE: 152
aagatgtatg tagctcacgt                    20

<210> SEQ ID NO 153
<211> LENGTH: 20
<212> TYPE: DNA
<213> ORGANISM: Homo sapiens

<400> SEQUENCE: 153
gtagctcacg taggtgactc                    20

<210> SEQ ID NO 154
<211> LENGTH: 20
<212> TYPE: DNA
<213> ORGANISM: Homo sapiens

<400> SEQUENCE: 154
tagctcacgt aggtgactca                    20

<210> SEQ ID NO 155
<211> LENGTH: 20
<212> TYPE: DNA
<213> ORGANISM: Homo sapiens

<400> SEQUENCE: 155
agctcacgta ggtgactcag                    20

<210> SEQ ID NO 156
<211> LENGTH: 20
<212> TYPE: DNA
<213> ORGANISM: Homo sapiens

<400> SEQUENCE: 156
tcacgtaggt gactcagggg                    20

<210> SEQ ID NO 157
<211> LENGTH: 20
<212> TYPE: DNA
<213> ORGANISM: Homo sapiens

<400> SEQUENCE: 157
ggtgactcag gggtggttct                    20

<210> SEQ ID NO 158
<211> LENGTH: 20
<212> TYPE: DNA
<213> ORGANISM: Homo sapiens

<400> SEQUENCE: 158
aggggtggtt cttggaattc                                               20

<210> SEQ ID NO 159
<211> LENGTH: 20
<212> TYPE: DNA
<213> ORGANISM: Homo sapiens

<400> SEQUENCE: 159
tggaattcag gatgacccga                                               20

<210> SEQ ID NO 160
<211> LENGTH: 20
<212> TYPE: DNA
<213> ORGANISM: Homo sapiens

<400> SEQUENCE: 160
ctctgacaaa gtcatccttc                                               20

<210> SEQ ID NO 161
<211> LENGTH: 20
<212> TYPE: DNA
<213> ORGANISM: Homo sapiens

<400> SEQUENCE: 161
gctctgacaa agtcatcctt                                               20

<210> SEQ ID NO 162
<211> LENGTH: 20
<212> TYPE: DNA
<213> ORGANISM: Homo sapiens

<400> SEQUENCE: 162
ggatgacttt gtcagagctg                                               20

<210> SEQ ID NO 163
<211> LENGTH: 20
<212> TYPE: DNA
<213> ORGANISM: Homo sapiens

<400> SEQUENCE: 163
tgactttgtc agagctgtgg                                               20

<210> SEQ ID NO 164
<211> LENGTH: 20
<212> TYPE: DNA
<213> ORGANISM: Homo sapiens

<400> SEQUENCE: 164
cagagctgtg gaggtgacac                                               20

<210> SEQ ID NO 165
<211> LENGTH: 20
<212> TYPE: DNA
<213> ORGANISM: Homo sapiens

<400> SEQUENCE: 165
ccttgggaag ttctggctta                                               20

<210> SEQ ID NO 166
<211> LENGTH: 20
<212> TYPE: DNA
<213> ORGANISM: Homo sapiens

```
<400> SEQUENCE: 166
tctctttcct tgggaagttc                                           20

<210> SEQ ID NO 167
<211> LENGTH: 20
<212> TYPE: DNA
<213> ORGANISM: Homo sapiens

<400> SEQUENCE: 167
ccataagcca gaacttccca                                           20

<210> SEQ ID NO 168
<211> LENGTH: 20
<212> TYPE: DNA
<213> ORGANISM: Homo sapiens

<400> SEQUENCE: 168
tcgattcgtt ctctttcctt                                           20

<210> SEQ ID NO 169
<211> LENGTH: 20
<212> TYPE: DNA
<213> ORGANISM: Homo sapiens

<400> SEQUENCE: 169
ttcgattcgt tctctttcct                                           20

<210> SEQ ID NO 170
<211> LENGTH: 20
<212> TYPE: DNA
<213> ORGANISM: Homo sapiens

<400> SEQUENCE: 170
aaggaaagag aacgaatcga                                           20

<210> SEQ ID NO 171
<211> LENGTH: 20
<212> TYPE: DNA
<213> ORGANISM: Homo sapiens

<400> SEQUENCE: 171
agagaacgaa tcgaaggact                                           20

<210> SEQ ID NO 172
<211> LENGTH: 20
<212> TYPE: DNA
<213> ORGANISM: Homo sapiens

<400> SEQUENCE: 172
gaacgaatcg aaggacttgg                                           20

<210> SEQ ID NO 173
<211> LENGTH: 20
<212> TYPE: DNA
<213> ORGANISM: Homo sapiens

<400> SEQUENCE: 173
aacgaatcga aggacttggt                                           20

<210> SEQ ID NO 174
<211> LENGTH: 20
<212> TYPE: DNA
```

```
<213> ORGANISM: Homo sapiens

<400> SEQUENCE: 174
gaatcgaagg acttggtggg                                               20

<210> SEQ ID NO 175
<211> LENGTH: 20
<212> TYPE: DNA
<213> ORGANISM: Homo sapiens

<400> SEQUENCE: 175
tttagtgtaa tgaacaagtc                                               20

<210> SEQ ID NO 176
<211> LENGTH: 20
<212> TYPE: DNA
<213> ORGANISM: Homo sapiens

<400> SEQUENCE: 176
ttagtgtaat gaacaagtct                                               20

<210> SEQ ID NO 177
<211> LENGTH: 20
<212> TYPE: DNA
<213> ORGANISM: Homo sapiens

<400> SEQUENCE: 177
tagtgtaatg aacaagtctg                                               20

<210> SEQ ID NO 178
<211> LENGTH: 20
<212> TYPE: DNA
<213> ORGANISM: Homo sapiens

<400> SEQUENCE: 178
ctggggtgaa tcgtgtagtt                                               20

<210> SEQ ID NO 179
<211> LENGTH: 20
<212> TYPE: DNA
<213> ORGANISM: Homo sapiens

<400> SEQUENCE: 179
ggtccattgt gagtgagtcg                                               20

<210> SEQ ID NO 180
<211> LENGTH: 20
<212> TYPE: DNA
<213> ORGANISM: Homo sapiens

<400> SEQUENCE: 180
cgacctcgac tcactcacaa                                               20

<210> SEQ ID NO 181
<211> LENGTH: 20
<212> TYPE: DNA
<213> ORGANISM: Homo sapiens

<400> SEQUENCE: 181
ataactgtgc tccttctaac                                               20

<210> SEQ ID NO 182
<211> LENGTH: 20
```

<212> TYPE: DNA
<213> ORGANISM: Homo sapiens

<400> SEQUENCE: 182
ctcacaatgg acctgttaga                                            20

<210> SEQ ID NO 183
<211> LENGTH: 20
<212> TYPE: DNA
<213> ORGANISM: Homo sapiens

<400> SEQUENCE: 183
ctactgccag aaaaggaatc                                            20

<210> SEQ ID NO 184
<211> LENGTH: 20
<212> TYPE: DNA
<213> ORGANISM: Homo sapiens

<400> SEQUENCE: 184
tattgaccag attccttttc                                            20

<210> SEQ ID NO 185
<211> LENGTH: 20
<212> TYPE: DNA
<213> ORGANISM: Homo sapiens

<400> SEQUENCE: 185
gctcttgcta ctgccagaaa                                            20

<210> SEQ ID NO 186
<211> LENGTH: 20
<212> TYPE: DNA
<213> ORGANISM: Homo sapiens

<400> SEQUENCE: 186
ctggcagtag caagagcact                                            20

<210> SEQ ID NO 187
<211> LENGTH: 20
<212> TYPE: DNA
<213> ORGANISM: Homo sapiens

<400> SEQUENCE: 187
atagctccac aaatcacctg                                            20

<210> SEQ ID NO 188
<211> LENGTH: 20
<212> TYPE: DNA
<213> ORGANISM: Homo sapiens

<400> SEQUENCE: 188
catagctcca caaatcacct                                            20

<210> SEQ ID NO 189
<211> LENGTH: 20
<212> TYPE: DNA
<213> ORGANISM: Homo sapiens

<400> SEQUENCE: 189
tcatagctcc acaaatcacc                                            20

<210> SEQ ID NO 190

```
<211> LENGTH: 20
<212> TYPE: DNA
<213> ORGANISM: Homo sapiens

<400> SEQUENCE: 190
cccttccccc aggtgatttg                                              20

<210> SEQ ID NO 191
<211> LENGTH: 20
<212> TYPE: DNA
<213> ORGANISM: Homo sapiens

<400> SEQUENCE: 191
tggagctatg atttcttcag                                              20

<210> SEQ ID NO 192
<211> LENGTH: 20
<212> TYPE: DNA
<213> ORGANISM: Homo sapiens

<400> SEQUENCE: 192
tttcttcagt ggtgaatttg                                              20

<210> SEQ ID NO 193
<211> LENGTH: 20
<212> TYPE: DNA
<213> ORGANISM: Homo sapiens

<400> SEQUENCE: 193
tggacacttg tgtctggttc                                              20

<210> SEQ ID NO 194
<211> LENGTH: 20
<212> TYPE: DNA
<213> ORGANISM: Homo sapiens

<400> SEQUENCE: 194
agagtgtgga cacttgtgtc                                              20

<210> SEQ ID NO 195
<211> LENGTH: 20
<212> TYPE: DNA
<213> ORGANISM: Homo sapiens

<400> SEQUENCE: 195
gcttctgagg gtcaagagtg                                              20

<210> SEQ ID NO 196
<211> LENGTH: 20
<212> TYPE: DNA
<213> ORGANISM: Homo sapiens

<400> SEQUENCE: 196
taatatactt gtgcttctga                                              20

<210> SEQ ID NO 197
<211> LENGTH: 20
<212> TYPE: DNA
<213> ORGANISM: Homo sapiens

<400> SEQUENCE: 197
ataatatact tgtgcttctg                                              20
```

```
<210> SEQ ID NO 198
<211> LENGTH: 20
<212> TYPE: DNA
<213> ORGANISM: Homo sapiens

<400> SEQUENCE: 198
gaagcacaag tatattatat                                               20

<210> SEQ ID NO 199
<211> LENGTH: 20
<212> TYPE: DNA
<213> ORGANISM: Homo sapiens

<400> SEQUENCE: 199
aagcacaagt atattatatt                                               20

<210> SEQ ID NO 200
<211> LENGTH: 20
<212> TYPE: DNA
<213> ORGANISM: Homo sapiens

<400> SEQUENCE: 200
agcacaagta tattatattg                                               20

<210> SEQ ID NO 201
<211> LENGTH: 20
<212> TYPE: DNA
<213> ORGANISM: Homo sapiens

<400> SEQUENCE: 201
tatattatat tggggagtga                                               20

<210> SEQ ID NO 202
<211> LENGTH: 20
<212> TYPE: DNA
<213> ORGANISM: Homo sapiens

<400> SEQUENCE: 202
tattggggag tgatggactt                                               20

<210> SEQ ID NO 203
<211> LENGTH: 20
<212> TYPE: DNA
<213> ORGANISM: Homo sapiens

<400> SEQUENCE: 203
attgagatgg catcttgtgg                                               20

<210> SEQ ID NO 204
<211> LENGTH: 20
<212> TYPE: DNA
<213> ORGANISM: Homo sapiens

<400> SEQUENCE: 204
cacattgaga tggcatcttg                                               20

<210> SEQ ID NO 205
<211> LENGTH: 20
<212> TYPE: DNA
<213> ORGANISM: Homo sapiens

<400> SEQUENCE: 205
ttggtcctgg cacattgaga                                               20
```

```
<210> SEQ ID NO 206
<211> LENGTH: 20
<212> TYPE: DNA
<213> ORGANISM: Homo sapiens

<400> SEQUENCE: 206
agatgccatc tcaatgtgcc                                               20

<210> SEQ ID NO 207
<211> LENGTH: 20
<212> TYPE: DNA
<213> ORGANISM: Homo sapiens

<400> SEQUENCE: 207 atttttctc ctcttggtcc                                                20

<210> SEQ ID NO 208
<211> LENGTH: 20
<212> TYPE: DNA
<213> ORGANISM: Homo sapiens

<400> SEQUENCE: 208
ctcaatgtgc caggaccaag                                               20

<210> SEQ ID NO 209
<211> LENGTH: 20
<212> TYPE: DNA
<213> ORGANISM: Homo sapiens

<400> SEQUENCE: 209
tcaggtattt tttctcctct                                               20

<210> SEQ ID NO 210
<211> LENGTH: 20
<212> TYPE: DNA
<213> ORGANISM: Homo sapiens

<400> SEQUENCE: 210
agaggagaaa aaatacctga                                               20

<210> SEQ ID NO 211
<211> LENGTH: 20
<212> TYPE: DNA
<213> ORGANISM: Homo sapiens

<400> SEQUENCE: 211
ttttgaatac agggtgagca                                               20

<210> SEQ ID NO 212
<211> LENGTH: 20
<212> TYPE: DNA
<213> ORGANISM: Homo sapiens

<400> SEQUENCE: 212
tgctcgattc acaagcattt                                               20

<210> SEQ ID NO 213
<211> LENGTH: 20
<212> TYPE: DNA
<213> ORGANISM: Homo sapiens

<400> SEQUENCE: 213
aatgcttgtg aatcgagcat                                               20
```

```
<210> SEQ ID NO 214
<211> LENGTH: 20
<212> TYPE: DNA
<213> ORGANISM: Homo sapiens

<400> SEQUENCE: 214
atgcttgtga atcgagcatt                                              20

<210> SEQ ID NO 215
<211> LENGTH: 20
<212> TYPE: DNA
<213> ORGANISM: Homo sapiens

<400> SEQUENCE: 215
tgaatcgagc attgggccgc                                              20

<210> SEQ ID NO 216
<211> LENGTH: 20
<212> TYPE: DNA
<213> ORGANISM: Homo sapiens

<400> SEQUENCE: 216
atcgagcatt gggccgctgg                                              20

<210> SEQ ID NO 217
<211> LENGTH: 20
<212> TYPE: DNA
<213> ORGANISM: Homo sapiens

<400> SEQUENCE: 217
ggagcatacg ctgcctccag                                              20

<210> SEQ ID NO 218
<211> LENGTH: 20
<212> TYPE: DNA
<213> ORGANISM: Homo sapiens

<400> SEQUENCE: 218
tggcactagt gttatctgct                                              20

<210> SEQ ID NO 219
<211> LENGTH: 20
<212> TYPE: DNA
<213> ORGANISM: Homo sapiens

<400> SEQUENCE: 219
tggagagatg cagattacta                                              20

<210> SEQ ID NO 220
<211> LENGTH: 20
<212> TYPE: DNA
<213> ORGANISM: Homo sapiens

<400> SEQUENCE: 220
aatctgcatc tctccagaag                                              20

<210> SEQ ID NO 221
<211> LENGTH: 20
<212> TYPE: DNA
<213> ORGANISM: Homo sapiens

<400> SEQUENCE: 221
```

| | |
|---|---|
| tttccctgat tgtccacttc | 20 |

<210> SEQ ID NO 222
<211> LENGTH: 20
<212> TYPE: DNA
<213> ORGANISM: Homo sapiens

<400> SEQUENCE: 222

| | |
|---|---|
| ctctccagaa gtggacaatc | 20 |

<210> SEQ ID NO 223
<211> LENGTH: 20
<212> TYPE: DNA
<213> ORGANISM: Homo sapiens

<400> SEQUENCE: 223

| | |
|---|---|
| tctccagaag tggacaatca | 20 |

<210> SEQ ID NO 224
<211> LENGTH: 20
<212> TYPE: DNA
<213> ORGANISM: Homo sapiens

<400> SEQUENCE: 224

| | |
|---|---|
| caggtataac tcatcttcat | 20 |

<210> SEQ ID NO 225
<211> LENGTH: 20
<212> TYPE: DNA
<213> ORGANISM: Homo sapiens

<400> SEQUENCE: 225

| | |
|---|---|
| aagggctgtc agtcaggttc | 20 |

<210> SEQ ID NO 226
<211> LENGTH: 20
<212> TYPE: DNA
<213> ORGANISM: Homo sapiens

<400> SEQUENCE: 226

| | |
|---|---|
| tataggaagg gctgtcagtc | 20 |

<210> SEQ ID NO 227
<211> LENGTH: 20
<212> TYPE: DNA
<213> ORGANISM: Homo sapiens

<400> SEQUENCE: 227

| | |
|---|---|
| tttcttgact attataggaa | 20 |

<210> SEQ ID NO 228
<211> LENGTH: 20
<212> TYPE: DNA
<213> ORGANISM: Homo sapiens

<400> SEQUENCE: 228

| | |
|---|---|
| gtttcttgac tattatagga | 20 |

<210> SEQ ID NO 229
<211> LENGTH: 20
<212> TYPE: DNA
<213> ORGANISM: Homo sapiens

<400> SEQUENCE: 229
acaggtttct tgactattat                                                         20

<210> SEQ ID NO 230
<211> LENGTH: 20
<212> TYPE: DNA
<213> ORGANISM: Homo sapiens

<400> SEQUENCE: 230
tggggaagga gtcatcacac                                                         20

<210> SEQ ID NO 231
<211> LENGTH: 20
<212> TYPE: DNA
<213> ORGANISM: Homo sapiens

<400> SEQUENCE: 231
ggtggtgtag aacatgggga                                                         20

<210> SEQ ID NO 232
<211> LENGTH: 20
<212> TYPE: DNA
<213> ORGANISM: Homo sapiens

<400> SEQUENCE: 232
gactggtggt gtagaacatg                                                         20

<210> SEQ ID NO 233
<211> LENGTH: 20
<212> TYPE: DNA
<213> ORGANISM: Homo sapiens

<400> SEQUENCE: 233
tgactggtgg tgtagaacat                                                         20

<210> SEQ ID NO 234
<211> LENGTH: 20
<212> TYPE: DNA
<213> ORGANISM: Homo sapiens

<400> SEQUENCE: 234
ttgactggtg gtgtagaaca                                                         20

<210> SEQ ID NO 235
<211> LENGTH: 20
<212> TYPE: DNA
<213> ORGANISM: Homo sapiens

<400> SEQUENCE: 235
gaactatata ccttgactgg                                                         20

<210> SEQ ID NO 236
<211> LENGTH: 20
<212> TYPE: DNA
<213> ORGANISM: Homo sapiens

<400> SEQUENCE: 236
atgttctaca ccaccagtca                                                         20

<210> SEQ ID NO 237
<211> LENGTH: 20
<212> TYPE: DNA
<213> ORGANISM: Homo sapiens

```
<400> SEQUENCE: 237
atggaactat ataccttgac                                              20

<210> SEQ ID NO 238
<211> LENGTH: 20
<212> TYPE: DNA
<213> ORGANISM: Homo sapiens

<400> SEQUENCE: 238
ccttcttatt tttcagtcac                                              20

<210> SEQ ID NO 239
<211> LENGTH: 20
<212> TYPE: DNA
<213> ORGANISM: Homo sapiens

<400> SEQUENCE: 239
tcttattttt cagtcactgg                                              20

<210> SEQ ID NO 240
<211> LENGTH: 20
<212> TYPE: DNA
<213> ORGANISM: Homo sapiens

<400> SEQUENCE: 240 tattttcag tcactggagg                                               20

<210> SEQ ID NO 241
<211> LENGTH: 20
<212> TYPE: DNA
<213> ORGANISM: Homo sapiens

<400> SEQUENCE: 241
agtcactgga ggaggatcca                                              20

<210> SEQ ID NO 242
<211> LENGTH: 20
<212> TYPE: DNA
<213> ORGANISM: Homo sapiens

<400> SEQUENCE: 242
tggaggagga tccatggcca                                              20

<210> SEQ ID NO 243
<211> LENGTH: 20
<212> TYPE: DNA
<213> ORGANISM: Homo sapiens

<400> SEQUENCE: 243
ttagaattca cccttggcca                                              20

<210> SEQ ID NO 244
<211> LENGTH: 20
<212> TYPE: DNA
<213> ORGANISM: Homo sapiens

<400> SEQUENCE: 244
ggaggaggat ccatggccaa                                              20

<210> SEQ ID NO 245
<211> LENGTH: 20
<212> TYPE: DNA
<213> ORGANISM: Homo sapiens
```

```
<400> SEQUENCE: 245
tggtccttag aattcaccct                                          20

<210> SEQ ID NO 246
<211> LENGTH: 20
<212> TYPE: DNA
<213> ORGANISM: Homo sapiens

<400> SEQUENCE: 246
atggccaagg gtgaattcta                                          20

<210> SEQ ID NO 247
<211> LENGTH: 20
<212> TYPE: DNA
<213> ORGANISM: Homo sapiens

<400> SEQUENCE: 247
tacgaaccag ggcaggtata                                          20

<210> SEQ ID NO 248
<211> LENGTH: 20
<212> TYPE: DNA
<213> ORGANISM: Homo sapiens

<400> SEQUENCE: 248
taaggaccat atacctgccc                                          20

<210> SEQ ID NO 249
<211> LENGTH: 20
<212> TYPE: DNA
<213> ORGANISM: Homo sapiens

<400> SEQUENCE: 249
gcattgctac gaaccagggc                                          20

<210> SEQ ID NO 250
<211> LENGTH: 20
<212> TYPE: DNA
<213> ORGANISM: Homo sapiens

<400> SEQUENCE: 250
gaaggcattg ctacgaacca                                          20

<210> SEQ ID NO 251
<211> LENGTH: 20
<212> TYPE: DNA
<213> ORGANISM: Homo sapiens

<400> SEQUENCE: 251
agaaggcatt gctacgaacc                                          20

<210> SEQ ID NO 252
<211> LENGTH: 20
<212> TYPE: DNA
<213> ORGANISM: Homo sapiens

<400> SEQUENCE: 252
ctctaaaaaa ttctctgaga                                          20

<210> SEQ ID NO 253
<211> LENGTH: 20
<212> TYPE: DNA
```

```
<213> ORGANISM: Homo sapiens

<400> SEQUENCE: 253
cttctcagag aatttttag                                           20

<210> SEQ ID NO 254
<211> LENGTH: 20
<212> TYPE: DNA
<213> ORGANISM: Homo sapiens

<400> SEQUENCE: 254
atagctcgag agaatgtcca                                          20

<210> SEQ ID NO 255
<211> LENGTH: 20
<212> TYPE: DNA
<213> ORGANISM: Homo sapiens

<400> SEQUENCE: 255
ttgagggtat gactacacct                                          20

<210> SEQ ID NO 256
<211> LENGTH: 20
<212> TYPE: DNA
<213> ORGANISM: Homo sapiens

<400> SEQUENCE: 256
agtggttctg gatcttttga                                          20

<210> SEQ ID NO 257
<211> LENGTH: 20
<212> TYPE: DNA
<213> ORGANISM: Homo sapiens

<400> SEQUENCE: 257
aagtggttct ggatctttg                                           20

<210> SEQ ID NO 258
<211> LENGTH: 20
<212> TYPE: DNA
<213> ORGANISM: Homo sapiens

<400> SEQUENCE: 258
caattttctt caagtggttc                                          20

<210> SEQ ID NO 259
<211> LENGTH: 20
<212> TYPE: DNA
<213> ORGANISM: Homo sapiens

<400> SEQUENCE: 259
ttagcgcaat tttcttcaag                                          20

<210> SEQ ID NO 260
<211> LENGTH: 20
<212> TYPE: DNA
<213> ORGANISM: Homo sapiens

<400> SEQUENCE: 260
atcatgtatc cttaaagtca                                          20

<210> SEQ ID NO 261
<211> LENGTH: 20
```

```
<212> TYPE: DNA
<213> ORGANISM: Homo sapiens

<400> SEQUENCE: 261
aatcatgtat ccttaaagtc                                          20

<210> SEQ ID NO 262
<211> LENGTH: 20
<212> TYPE: DNA
<213> ORGANISM: Homo sapiens

<400> SEQUENCE: 262
gcgctaaagc cctgacttta                                          20

<210> SEQ ID NO 263
<211> LENGTH: 20
<212> TYPE: DNA
<213> ORGANISM: Homo sapiens

<400> SEQUENCE: 263
taggcacaag gccaattgga                                          20

<210> SEQ ID NO 264
<211> LENGTH: 20
<212> TYPE: DNA
<213> ORGANISM: Homo sapiens

<400> SEQUENCE: 264
ttgaataata gccttccaat                                          20

<210> SEQ ID NO 265
<211> LENGTH: 20
<212> TYPE: DNA
<213> ORGANISM: Homo sapiens

<400> SEQUENCE: 265
ttagtaggca caaggccaat                                          20

<210> SEQ ID NO 266
<211> LENGTH: 20
<212> TYPE: DNA
<213> ORGANISM: Homo sapiens

<400> SEQUENCE: 266
ttgttgaatt agtaggcaca                                          20

<210> SEQ ID NO 267
<211> LENGTH: 20
<212> TYPE: DNA
<213> ORGANISM: Homo sapiens

<400> SEQUENCE: 267
acagtgtttg ttgaattagt                                          20

<210> SEQ ID NO 268
<211> LENGTH: 20
<212> TYPE: DNA
<213> ORGANISM: Homo sapiens

<400> SEQUENCE: 268
taattcaaca aacactgtca                                          20

<210> SEQ ID NO 269
```

```
<211> LENGTH: 20
<212> TYPE: DNA
<213> ORGANISM: Homo sapiens

<400> SEQUENCE: 269
ttgacatctt caaattttt                                                    20

<210> SEQ ID NO 270
<211> LENGTH: 20
<212> TYPE: DNA
<213> ORGANISM: Homo sapiens

<400> SEQUENCE: 270
aatttgaaga tgtcaactcc                                                   20

<210> SEQ ID NO 271
<211> LENGTH: 20
<212> TYPE: DNA
<213> ORGANISM: Homo sapiens

<400> SEQUENCE: 271
tcttgggctt tcatttggcc                                                   20

<210> SEQ ID NO 272
<211> LENGTH: 20
<212> TYPE: DNA
<213> ORGANISM: Homo sapiens

<400> SEQUENCE: 272
caatttcttg ggctttcatt                                                   20

<210> SEQ ID NO 273
<211> LENGTH: 20
<212> TYPE: DNA
<213> ORGANISM: Homo sapiens

<400> SEQUENCE: 273
aggggttctt tcaatttctt                                                   20

<210> SEQ ID NO 274
<211> LENGTH: 20
<212> TYPE: DNA
<213> ORGANISM: Homo sapiens

<400> SEQUENCE: 274
gaggggttct ttcaatttct                                                   20

<210> SEQ ID NO 275
<211> LENGTH: 20
<212> TYPE: DNA
<213> ORGANISM: Homo sapiens

<400> SEQUENCE: 275
ccttttaaag tttgttggag                                                   20

<210> SEQ ID NO 276
<211> LENGTH: 20
<212> TYPE: DNA
<213> ORGANISM: Homo sapiens

<400> SEQUENCE: 276 tcctttaaa gtttgttgga                                                    20
```

```
<210> SEQ ID NO 277
<211> LENGTH: 20
<212> TYPE: DNA
<213> ORGANISM: Homo sapiens

<400> SEQUENCE: 277
gtccttttaa agtttgttgg                                               20

<210> SEQ ID NO 278
<211> LENGTH: 20
<212> TYPE: DNA
<213> ORGANISM: Homo sapiens

<400> SEQUENCE: 278
aatgtccttt taaagtttgt                                               20

<210> SEQ ID NO 279
<211> LENGTH: 20
<212> TYPE: DNA
<213> ORGANISM: Homo sapiens

<400> SEQUENCE: 279
cccctccaac aaactttaaa                                               20

<210> SEQ ID NO 280
<211> LENGTH: 20
<212> TYPE: DNA
<213> ORGANISM: Homo sapiens

<400> SEQUENCE: 280
acattagaag agtccaattc                                               20

<210> SEQ ID NO 281
<211> LENGTH: 20
<212> TYPE: DNA
<213> ORGANISM: Homo sapiens

<400> SEQUENCE: 281
cttcatcagg gggccagaat                                               20

<210> SEQ ID NO 282
<211> LENGTH: 20
<212> TYPE: DNA
<213> ORGANISM: Homo sapiens

<400> SEQUENCE: 282
gtctatgctt cttcatcagg                                               20

<210> SEQ ID NO 283
<211> LENGTH: 20
<212> TYPE: DNA
<213> ORGANISM: Homo sapiens

<400> SEQUENCE: 283
cgtctatgct tcttcatcag                                               20

<210> SEQ ID NO 284
<211> LENGTH: 20
<212> TYPE: DNA
<213> ORGANISM: Homo sapiens

<400> SEQUENCE: 284
tcgtctatgc ttcttcatca                                               20
```

```
<210> SEQ ID NO 285
<211> LENGTH: 20
<212> TYPE: DNA
<213> ORGANISM: Homo sapiens

<400> SEQUENCE: 285
ttcgtctatg cttcttcatc                                               20

<210> SEQ ID NO 286
<211> LENGTH: 20
<212> TYPE: DNA
<213> ORGANISM: Homo sapiens

<400> SEQUENCE: 286
atgaagaagc atagacgaaa                                               20

<210> SEQ ID NO 287
<211> LENGTH: 20
<212> TYPE: DNA
<213> ORGANISM: Homo sapiens

<400> SEQUENCE: 287
aatggcttaa gtcgaagtag                                               20

<210> SEQ ID NO 288
<211> LENGTH: 20
<212> TYPE: DNA
<213> ORGANISM: Homo sapiens

<400> SEQUENCE: 288
gaggttgtgg ggagacttgc                                               20

<210> SEQ ID NO 289
<211> LENGTH: 20
<212> TYPE: DNA
<213> ORGANISM: Homo sapiens

<400> SEQUENCE: 289
tctttcgctg tgaggttgtg                                               20

<210> SEQ ID NO 290
<211> LENGTH: 20
<212> TYPE: DNA
<213> ORGANISM: Homo sapiens

<400> SEQUENCE: 290
ttctttcgct gtgaggttgt                                               20

<210> SEQ ID NO 291
<211> LENGTH: 20
<212> TYPE: DNA
<213> ORGANISM: Homo sapiens

<400> SEQUENCE: 291
gttctttcgc tgtgaggttg                                               20

<210> SEQ ID NO 292
<211> LENGTH: 20
<212> TYPE: DNA
<213> ORGANISM: Homo sapiens

<400> SEQUENCE: 292
aacagagttc tttcgctgtg                                               20
```

<210> SEQ ID NO 293
<211> LENGTH: 20
<212> TYPE: DNA
<213> ORGANISM: Homo sapiens

<400> SEQUENCE: 293
gcccctaagt ctgcgtcgca                                             20

<210> SEQ ID NO 294
<211> LENGTH: 20
<212> TYPE: DNA
<213> ORGANISM: Homo sapiens

<400> SEQUENCE: 294
tcaccatgcg acgcagactt                                             20

<210> SEQ ID NO 295
<211> LENGTH: 20
<212> TYPE: DNA
<213> ORGANISM: Homo sapiens

<400> SEQUENCE: 295
caccatgcga cgcagactta                                             20

<210> SEQ ID NO 296
<211> LENGTH: 20
<212> TYPE: DNA
<213> ORGANISM: Homo sapiens

<400> SEQUENCE: 296
accatgcgac gcagacttag                                             20

<210> SEQ ID NO 297
<211> LENGTH: 20
<212> TYPE: DNA
<213> ORGANISM: Homo sapiens

<400> SEQUENCE: 297
aaggatttcc aattttcttc                                             20

<210> SEQ ID NO 298
<211> LENGTH: 20
<212> TYPE: DNA
<213> ORGANISM: Homo sapiens

<400> SEQUENCE: 298
cttaggggcc agaagaaaat                                             20

<210> SEQ ID NO 299
<211> LENGTH: 20
<212> TYPE: DNA
<213> ORGANISM: Homo sapiens

<400> SEQUENCE: 299
ttcctgtgtt gatgaagtaa                                             20

<210> SEQ ID NO 300
<211> LENGTH: 20
<212> TYPE: DNA
<213> ORGANISM: Homo sapiens

<400> SEQUENCE: 300

```
atcctttact tcatcaacac                                           20

<210> SEQ ID NO 301
<211> LENGTH: 30
<212> TYPE: DNA
<213> ORGANISM: Homo sapiens

<400> SEQUENCE: 301
cagcgagtac agccccgcca tggccggctg                                30

<210> SEQ ID NO 302
<211> LENGTH: 30
<212> TYPE: DNA
<213> ORGANISM: Homo sapiens

<400> SEQUENCE: 302
gggatcccgg ccagccggcc atggcggggc                                30

<210> SEQ ID NO 303
<211> LENGTH: 30
<212> TYPE: DNA
<213> ORGANISM: Homo sapiens

<400> SEQUENCE: 303
ggatcccggc cagccggcca tggcggggct                                30

<210> SEQ ID NO 304
<211> LENGTH: 30
<212> TYPE: DNA
<213> ORGANISM: Homo sapiens

<400> SEQUENCE: 304
gatcccggcc agccggccat ggcggggctg                                30

<210> SEQ ID NO 305
<211> LENGTH: 30
<212> TYPE: DNA
<213> ORGANISM: Homo sapiens

<400> SEQUENCE: 305
ctcccagcga gtacagcccc gccatggccg                                30

<210> SEQ ID NO 306
<211> LENGTH: 30
<212> TYPE: DNA
<213> ORGANISM: Homo sapiens

<400> SEQUENCE: 306
cggccatggc ggggctgtac tcgctgggag                                30

<210> SEQ ID NO 307
<211> LENGTH: 30
<212> TYPE: DNA
<213> ORGANISM: Homo sapiens

<400> SEQUENCE: 307
ggccatggcg gggctgtact cgctgggagt                                30

<210> SEQ ID NO 308
<211> LENGTH: 30
<212> TYPE: DNA
<213> ORGANISM: Homo sapiens

<400> SEQUENCE: 308
```
tgggagtgag cgtcttctcc gaccagggcg                                            30

<210> SEQ ID NO 309
<211> LENGTH: 30
<212> TYPE: DNA
<213> ORGANISM: Homo sapiens

<400> SEQUENCE: 309
gggagtgagc gtcttctccg accagggcgg                                            30

<210> SEQ ID NO 310
<211> LENGTH: 30
<212> TYPE: DNA
<213> ORGANISM: Homo sapiens

<400> SEQUENCE: 310
ccatgtactt cctcccgccc tggtcggaga                                            30

<210> SEQ ID NO 311
<211> LENGTH: 30
<212> TYPE: DNA
<213> ORGANISM: Homo sapiens

<400> SEQUENCE: 311
agtgagcgtc ttctccgacc agggcgggag                                            30

<210> SEQ ID NO 312
<211> LENGTH: 30
<212> TYPE: DNA
<213> ORGANISM: Homo sapiens

<400> SEQUENCE: 312
gtgagcgtct tctccgacca gggcgggagg                                            30

<210> SEQ ID NO 313
<211> LENGTH: 30
<212> TYPE: DNA
<213> ORGANISM: Homo sapiens

<400> SEQUENCE: 313
tcctccatgt acttcctccc gccctggtcg                                            30

<210> SEQ ID NO 314
<211> LENGTH: 30
<212> TYPE: DNA
<213> ORGANISM: Homo sapiens

<400> SEQUENCE: 314
agcgtcttct ccgaccaggg cgggaggaag                                            30

<210> SEQ ID NO 315
<211> LENGTH: 30
<212> TYPE: DNA
<213> ORGANISM: Homo sapiens

<400> SEQUENCE: 315
ccgaccaggg cgggaggaag tacatggagg                                            30

<210> SEQ ID NO 316
<211> LENGTH: 30
<212> TYPE: DNA
<213> ORGANISM: Homo sapiens

```
<400> SEQUENCE: 316
accagggcgg gaggaagtac atggaggacg                                  30

<210> SEQ ID NO 317
<211> LENGTH: 30
<212> TYPE: DNA
<213> ORGANISM: Homo sapiens

<400> SEQUENCE: 317
tggaggacgt tactcaaatc gttgtggagc                                  30

<210> SEQ ID NO 318
<211> LENGTH: 30
<212> TYPE: DNA
<213> ORGANISM: Homo sapiens

<400> SEQUENCE: 318
gggcttttct tcagccgtcg gttcgggctc                                  30

<210> SEQ ID NO 319
<211> LENGTH: 30
<212> TYPE: DNA
<213> ORGANISM: Homo sapiens

<400> SEQUENCE: 319
aaatcgttgt ggagcccgaa ccgacggctg                                  30

<210> SEQ ID NO 320
<211> LENGTH: 30
<212> TYPE: DNA
<213> ORGANISM: Homo sapiens

<400> SEQUENCE: 320
agggcttttc ttcagccgtc ggttcgggct                                  30

<210> SEQ ID NO 321
<211> LENGTH: 30
<212> TYPE: DNA
<213> ORGANISM: Homo sapiens

<400> SEQUENCE: 321
cggcgagggc ttttcttcag ccgtcggttc                                  30

<210> SEQ ID NO 322
<211> LENGTH: 30
<212> TYPE: DNA
<213> ORGANISM: Homo sapiens

<400> SEQUENCE: 322
acggctgaag aaaagccctc gccgcggcgg                                  30

<210> SEQ ID NO 323
<211> LENGTH: 30
<212> TYPE: DNA
<213> ORGANISM: Homo sapiens

<400> SEQUENCE: 323
ctgagacagc gaccgccgcg gcgagggctt                                  30

<210> SEQ ID NO 324
<211> LENGTH: 30
<212> TYPE: DNA
<213> ORGANISM: Homo sapiens
```

<400> SEQUENCE: 324
gctgagacag cgaccgccgc ggcgagggct                                    30

<210> SEQ ID NO 325
<211> LENGTH: 30
<212> TYPE: DNA
<213> ORGANISM: Homo sapiens

<400> SEQUENCE: 325
gctgaagaaa agccctcgcc gcggcggtcg                                    30

<210> SEQ ID NO 326
<211> LENGTH: 30
<212> TYPE: DNA
<213> ORGANISM: Homo sapiens

<400> SEQUENCE: 326
caacggctga gacagcgacc gccgcggcga                                    30

<210> SEQ ID NO 327
<211> LENGTH: 30
<212> TYPE: DNA
<213> ORGANISM: Homo sapiens

<400> SEQUENCE: 327
ggccggcgac ggccgcggag gcaacggctg                                    30

<210> SEQ ID NO 328
<211> LENGTH: 30
<212> TYPE: DNA
<213> ORGANISM: Homo sapiens

<400> SEQUENCE: 328
tcgctgtctc agccgttgcc tccgcggccg                                    30

<210> SEQ ID NO 329
<211> LENGTH: 30
<212> TYPE: DNA
<213> ORGANISM: Homo sapiens

<400> SEQUENCE: 329
aagggcggcc ggcgacggcc gcggaggcaa                                    30

<210> SEQ ID NO 330
<211> LENGTH: 30
<212> TYPE: DNA
<213> ORGANISM: Homo sapiens

<400> SEQUENCE: 330
gggaagggcg gccggcgacg gccgcggagg                                    30

<210> SEQ ID NO 331
<211> LENGTH: 30
<212> TYPE: DNA
<213> ORGANISM: Homo sapiens

<400> SEQUENCE: 331
agccgttgcc tccgcggccg tcgccggccg                                    30

<210> SEQ ID NO 332
<211> LENGTH: 30
<212> TYPE: DNA

```
<213> ORGANISM: Homo sapiens

<400> SEQUENCE: 332
gccgccggga agggcggccg gcgacggccg                                    30

<210> SEQ ID NO 333
<211> LENGTH: 30
<212> TYPE: DNA
<213> ORGANISM: Homo sapiens

<400> SEQUENCE: 333
gacttcgccg ccgggaaggg cggccggcga                                    30

<210> SEQ ID NO 334
<211> LENGTH: 30
<212> TYPE: DNA
<213> ORGANISM: Homo sapiens

<400> SEQUENCE: 334
ccgagacttc gccgccggga agggcggccg                                    30

<210> SEQ ID NO 335
<211> LENGTH: 30
<212> TYPE: DNA
<213> ORGANISM: Homo sapiens

<400> SEQUENCE: 335
gcggccgtcg ccggccgccc ttcccggcgg                                    30

<210> SEQ ID NO 336
<211> LENGTH: 30
<212> TYPE: DNA
<213> ORGANISM: Homo sapiens

<400> SEQUENCE: 336
tccccgagac ttcgccgccg ggaagggcgg                                    30

<210> SEQ ID NO 337
<211> LENGTH: 30
<212> TYPE: DNA
<213> ORGANISM: Homo sapiens

<400> SEQUENCE: 337
ttccccgaga cttcgccgcc gggaagggcg                                    30

<210> SEQ ID NO 338
<211> LENGTH: 30
<212> TYPE: DNA
<213> ORGANISM: Homo sapiens

<400> SEQUENCE: 338
gccgtcgccg gccgcccttc ccggcggcga                                    30

<210> SEQ ID NO 339
<211> LENGTH: 30
<212> TYPE: DNA
<213> ORGANISM: Homo sapiens

<400> SEQUENCE: 339
gcctttcccc gagacttcgc cgccgggaag                                    30

<210> SEQ ID NO 340
<211> LENGTH: 30
```

```
<212> TYPE: DNA
<213> ORGANISM: Homo sapiens

<400> SEQUENCE: 340
ggcctttccc cgagacttcg ccgccgggaa                              30

<210> SEQ ID NO 341
<211> LENGTH: 30
<212> TYPE: DNA
<213> ORGANISM: Homo sapiens

<400> SEQUENCE: 341
ccgcccttcc cggcggcgaa gtctcgggga                              30

<210> SEQ ID NO 342
<211> LENGTH: 30
<212> TYPE: DNA
<213> ORGANISM: Homo sapiens

<400> SEQUENCE: 342
cgcccttccc ggcggcgaag tctcggggaa                              30

<210> SEQ ID NO 343
<211> LENGTH: 30
<212> TYPE: DNA
<213> ORGANISM: Homo sapiens

<400> SEQUENCE: 343
gcccttcccg gcggcgaagt ctcggggaaa                              30

<210> SEQ ID NO 344
<211> LENGTH: 30
<212> TYPE: DNA
<213> ORGANISM: Homo sapiens

<400> SEQUENCE: 344
tcccggcggc gaagtctcgg ggaaaggccc                              30

<210> SEQ ID NO 345
<211> LENGTH: 30
<212> TYPE: DNA
<213> ORGANISM: Homo sapiens

<400> SEQUENCE: 345
gcgaagtctc ggggaaaggc ccagcggtgg                              30

<210> SEQ ID NO 346
<211> LENGTH: 30
<212> TYPE: DNA
<213> ORGANISM: Homo sapiens

<400> SEQUENCE: 346
aagtctcggg gaaaggccca gcggtggcag                              30

<210> SEQ ID NO 347
<211> LENGTH: 30
<212> TYPE: DNA
<213> ORGANISM: Homo sapiens

<400> SEQUENCE: 347
cgagcctctc gggctgccac cgctgggcct                              30

<210> SEQ ID NO 348
```

```
<211> LENGTH: 30
<212> TYPE: DNA
<213> ORGANISM: Homo sapiens

<400> SEQUENCE: 348
gcgagcctct cgggctgcca ccgctgggcc                                    30

<210> SEQ ID NO 349
<211> LENGTH: 30
<212> TYPE: DNA
<213> ORGANISM: Homo sapiens

<400> SEQUENCE: 349
aaggcccagc ggtggcagcc cgagaggctc                                    30

<210> SEQ ID NO 350
<211> LENGTH: 30
<212> TYPE: DNA
<213> ORGANISM: Homo sapiens

<400> SEQUENCE: 350
ccgggagagg gtcgcgagcc tctcgggctg                                    30

<210> SEQ ID NO 351
<211> LENGTH: 30
<212> TYPE: DNA
<213> ORGANISM: Homo sapiens

<400> SEQUENCE: 351
tccgggagag ggtcgcgagc ctctcgggct                                    30

<210> SEQ ID NO 352
<211> LENGTH: 30
<212> TYPE: DNA
<213> ORGANISM: Homo sapiens

<400> SEQUENCE: 352
cccgagaggc tcgcgaccct ctcccggacg                                    30

<210> SEQ ID NO 353
<211> LENGTH: 30
<212> TYPE: DNA
<213> ORGANISM: Homo sapiens

<400> SEQUENCE: 353
ggcgaggccc cggcgtccgg gagagggtcg                                    30

<210> SEQ ID NO 354
<211> LENGTH: 30
<212> TYPE: DNA
<213> ORGANISM: Homo sapiens

<400> SEQUENCE: 354
cggcgaggcc ccggcgtccg ggagagggtc                                    30

<210> SEQ ID NO 355
<211> LENGTH: 30
<212> TYPE: DNA
<213> ORGANISM: Homo sapiens

<400> SEQUENCE: 355
ggctcgcgac cctctcccgg acgccggggc                                    30
```

```
<210> SEQ ID NO 356
<211> LENGTH: 30
<212> TYPE: DNA
<213> ORGANISM: Homo sapiens

<400> SEQUENCE: 356
ggtgccggcg aggccccggc gtccgggaga                             30

<210> SEQ ID NO 357
<211> LENGTH: 30
<212> TYPE: DNA
<213> ORGANISM: Homo sapiens

<400> SEQUENCE: 357
gctcgcgacc ctctcccgga cgccggggcc                             30

<210> SEQ ID NO 358
<211> LENGTH: 30
<212> TYPE: DNA
<213> ORGANISM: Homo sapiens

<400> SEQUENCE: 358
aggtgccggc gaggccccgg cgtccgggag                             30

<210> SEQ ID NO 359
<211> LENGTH: 30
<212> TYPE: DNA
<213> ORGANISM: Homo sapiens

<400> SEQUENCE: 359
ctcgcgaccc tctcccggac gccggggcct                             30

<210> SEQ ID NO 360
<211> LENGTH: 30
<212> TYPE: DNA
<213> ORGANISM: Homo sapiens

<400> SEQUENCE: 360
agcggctagg tgccggcgag gccccggcgt                             30

<210> SEQ ID NO 361
<211> LENGTH: 30
<212> TYPE: DNA
<213> ORGANISM: Homo sapiens

<400> SEQUENCE: 361
ctctcccgga cgccggggcc tcgccggcac                             30

<210> SEQ ID NO 362
<211> LENGTH: 30
<212> TYPE: DNA
<213> ORGANISM: Homo sapiens

<400> SEQUENCE: 362
ggcagcagcg gctaggtgcc ggcgaggccc                             30

<210> SEQ ID NO 363
<211> LENGTH: 30
<212> TYPE: DNA
<213> ORGANISM: Homo sapiens

<400> SEQUENCE: 363
gcggcggcag cagcggctag gtgccggcga                             30
```

<210> SEQ ID NO 364
<211> LENGTH: 30
<212> TYPE: DNA
<213> ORGANISM: Homo sapiens

<400> SEQUENCE: 364
ggaacggcgg cggcagcagc ggctaggtgc                               30

<210> SEQ ID NO 365
<211> LENGTH: 30
<212> TYPE: DNA
<213> ORGANISM: Homo sapiens

<400> SEQUENCE: 365
acggaggaac ggcggcggca gcagcggcta                               30

<210> SEQ ID NO 366
<211> LENGTH: 30
<212> TYPE: DNA
<213> ORGANISM: Homo sapiens

<400> SEQUENCE: 366
aaaaaggcca cggaggaacg gcggcggcag                               30

<210> SEQ ID NO 367
<211> LENGTH: 30
<212> TYPE: DNA
<213> ORGANISM: Homo sapiens

<400> SEQUENCE: 367
gcgaaaaagg ccacggagga acggcggcgg                               30

<210> SEQ ID NO 368
<211> LENGTH: 30
<212> TYPE: DNA
<213> ORGANISM: Homo sapiens

<400> SEQUENCE: 368
acggcgaaaa aggccacgga ggaacggcgg                               30

<210> SEQ ID NO 369
<211> LENGTH: 30
<212> TYPE: DNA
<213> ORGANISM: Homo sapiens

<400> SEQUENCE: 369
gctgctgccg ccgccgttcc tccgtggcct                               30

<210> SEQ ID NO 370
<211> LENGTH: 30
<212> TYPE: DNA
<213> ORGANISM: Homo sapiens

<400> SEQUENCE: 370
cgcacacggc gaaaaaggcc acggaggaac                               30

<210> SEQ ID NO 371
<211> LENGTH: 30
<212> TYPE: DNA
<213> ORGANISM: Homo sapiens

<400> SEQUENCE: 371
cgtcgcacac ggcgaaaaag gccacggagg                               30

<210> SEQ ID NO 372
<211> LENGTH: 30
<212> TYPE: DNA
<213> ORGANISM: Homo sapiens

<400> SEQUENCE: 372
cgtgcccgtc gcacacggcg aaaaaggcca                                    30

<210> SEQ ID NO 373
<211> LENGTH: 30
<212> TYPE: DNA
<213> ORGANISM: Homo sapiens

<400> SEQUENCE: 373
cccgcccgcc gtgcccgtcg cacacggcga                                    30

<210> SEQ ID NO 374
<211> LENGTH: 30
<212> TYPE: DNA
<213> ORGANISM: Homo sapiens

<400> SEQUENCE: 374
cgtggccttt ttcgccgtgt gcgacgggca                                    30

<210> SEQ ID NO 375
<211> LENGTH: 30
<212> TYPE: DNA
<213> ORGANISM: Homo sapiens

<400> SEQUENCE: 375
gtggcctttt tcgccgtgtg cgacgggcac                                    30

<210> SEQ ID NO 376
<211> LENGTH: 30
<212> TYPE: DNA
<213> ORGANISM: Homo sapiens

<400> SEQUENCE: 376 cttttcgcc gtgtgcgacg ggcacggcgg                                     30

<210> SEQ ID NO 377
<211> LENGTH: 30
<212> TYPE: DNA
<213> ORGANISM: Homo sapiens

<400> SEQUENCE: 377
tttcgccgtg tgcgacgggc acggcgggcg                                    30

<210> SEQ ID NO 378
<211> LENGTH: 30
<212> TYPE: DNA
<213> ORGANISM: Homo sapiens

<400> SEQUENCE: 378
ttcgccgtgt gcgacgggca cggcgggcgg                                    30

<210> SEQ ID NO 379
<211> LENGTH: 30
<212> TYPE: DNA
<213> ORGANISM: Homo sapiens

<400> SEQUENCE: 379
gccgtgtgcg acgggcacgg cgggcgggag 30

<210> SEQ ID NO 380
<211> LENGTH: 30
<212> TYPE: DNA
<213> ORGANISM: Homo sapiens

<400> SEQUENCE: 380
ccgtgtgcga cgggcacggc gggcgggagg 30

<210> SEQ ID NO 381
<211> LENGTH: 30
<212> TYPE: DNA
<213> ORGANISM: Homo sapiens

<400> SEQUENCE: 381
tgtgcgacgg gcacggcggg cgggaggcgg 30

<210> SEQ ID NO 382
<211> LENGTH: 30
<212> TYPE: DNA
<213> ORGANISM: Homo sapiens

<400> SEQUENCE: 382
gcgacgggca cggcgggcgg gaggcggcac 30

<210> SEQ ID NO 383
<211> LENGTH: 30
<212> TYPE: DNA
<213> ORGANISM: Homo sapiens

<400> SEQUENCE: 383
gggcgggagg cggcacagtt tgcccgggag 30

<210> SEQ ID NO 384
<211> LENGTH: 30
<212> TYPE: DNA
<213> ORGANISM: Homo sapiens

<400> SEQUENCE: 384
ggcgggaggc ggcacagttt gcccgggagc 30

<210> SEQ ID NO 385
<211> LENGTH: 30
<212> TYPE: DNA
<213> ORGANISM: Homo sapiens

<400> SEQUENCE: 385
tgatgaaacc ccacaagtgc tcccgggcaa 30

<210> SEQ ID NO 386
<211> LENGTH: 30
<212> TYPE: DNA
<213> ORGANISM: Homo sapiens

<400> SEQUENCE: 386
ttgatgaaac cccacaagtg ctcccgggca 30

<210> SEQ ID NO 387
<211> LENGTH: 30
<212> TYPE: DNA
<213> ORGANISM: Homo sapiens

<400> SEQUENCE: 387

```
gcacagtttg cccgggagca cttgtggggt                                              30
```

<210> SEQ ID NO 388
<211> LENGTH: 30
<212> TYPE: DNA
<213> ORGANISM: Homo sapiens

<400> SEQUENCE: 388

```
cacagtttgc ccgggagcac ttgtggggtt                                              30
```

<210> SEQ ID NO 389
<211> LENGTH: 30
<212> TYPE: DNA
<213> ORGANISM: Homo sapiens

<400> SEQUENCE: 389

```
acagtttgcc cgggagcact tgtggggttt                                              30
```

<210> SEQ ID NO 390
<211> LENGTH: 30
<212> TYPE: DNA
<213> ORGANISM: Homo sapiens

<400> SEQUENCE: 390

```
tgtggggttt catcaagaag cagaagggtt                                              30
```

<210> SEQ ID NO 391
<211> LENGTH: 30
<212> TYPE: DNA
<213> ORGANISM: Homo sapiens

<400> SEQUENCE: 391

```
gtggggtttc atcaagaagc agaagggttt                                              30
```

<210> SEQ ID NO 392
<211> LENGTH: 30
<212> TYPE: DNA
<213> ORGANISM: Homo sapiens

<400> SEQUENCE: 392

```
cgcaaacctt agccggctcg gacgaggtga                                              30
```

<210> SEQ ID NO 393
<211> LENGTH: 30
<212> TYPE: DNA
<213> ORGANISM: Homo sapiens

<400> SEQUENCE: 393

```
agaagggttt cacctcgtcc gagccggcta                                              30
```

<210> SEQ ID NO 394
<211> LENGTH: 30
<212> TYPE: DNA
<213> ORGANISM: Homo sapiens

<400> SEQUENCE: 394

```
tggcagcgca aaccttagcc ggctcggacg                                              30
```

<210> SEQ ID NO 395
<211> LENGTH: 30
<212> TYPE: DNA
<213> ORGANISM: Homo sapiens

```
<400> SEQUENCE: 395
gtttcacctc gtccgagccg gctaaggttt                                    30

<210> SEQ ID NO 396
<211> LENGTH: 30
<212> TYPE: DNA
<213> ORGANISM: Homo sapiens

<400> SEQUENCE: 396
gcggatggca gcgcaaacct tagccggctc                                    30

<210> SEQ ID NO 397
<211> LENGTH: 30
<212> TYPE: DNA
<213> ORGANISM: Homo sapiens

<400> SEQUENCE: 397
gacaagcgag aaagcctttg cggatggcag                                    30

<210> SEQ ID NO 398
<211> LENGTH: 30
<212> TYPE: DNA
<213> ORGANISM: Homo sapiens

<400> SEQUENCE: 398
taaggtttgc gctgccatcc gcaaaggctt                                    30

<210> SEQ ID NO 399
<211> LENGTH: 30
<212> TYPE: DNA
<213> ORGANISM: Homo sapiens

<400> SEQUENCE: 399
aggtgacaag cgagaaagcc tttgcggatg                                    30

<210> SEQ ID NO 400
<211> LENGTH: 30
<212> TYPE: DNA
<213> ORGANISM: Homo sapiens

<400> SEQUENCE: 400
ttacccagtt tcttccacat ggcaaggtga                                    30

<210> SEQ ID NO 401
<211> LENGTH: 30
<212> TYPE: DNA
<213> ORGANISM: Homo sapiens

<400> SEQUENCE: 401
tttctcgctt gtcaccttgc catgtggaag                                    30

<210> SEQ ID NO 402
<211> LENGTH: 30
<212> TYPE: DNA
<213> ORGANISM: Homo sapiens

<400> SEQUENCE: 402
ggaacttacc cagtttcttc cacatggcaa                                    30

<210> SEQ ID NO 403
<211> LENGTH: 30
<212> TYPE: DNA
<213> ORGANISM: Homo sapiens
```

```
<400> SEQUENCE: 403
gtcaccttgc catgtggaag aaactgggta                              30

<210> SEQ ID NO 404
<211> LENGTH: 30
<212> TYPE: DNA
<213> ORGANISM: Homo sapiens

<400> SEQUENCE: 404
tcaccttgcc atgtggaaga aactgggtaa                              30

<210> SEQ ID NO 405
<211> LENGTH: 30
<212> TYPE: DNA
<213> ORGANISM: Homo sapiens

<400> SEQUENCE: 405
attttatttc ttattacagc ggaatggcca                              30

<210> SEQ ID NO 406
<211> LENGTH: 30
<212> TYPE: DNA
<213> ORGANISM: Homo sapiens

<400> SEQUENCE: 406
gctaggaaga cccgtcatag tctttggcca                              30

<210> SEQ ID NO 407
<211> LENGTH: 30
<212> TYPE: DNA
<213> ORGANISM: Homo sapiens

<400> SEQUENCE: 407
cagcggaatg gccaaagact atgacgggtc                              30

<210> SEQ ID NO 408
<211> LENGTH: 30
<212> TYPE: DNA
<213> ORGANISM: Homo sapiens

<400> SEQUENCE: 408
agcggaatgg ccaaagacta tgacgggtct                              30

<210> SEQ ID NO 409
<211> LENGTH: 30
<212> TYPE: DNA
<213> ORGANISM: Homo sapiens

<400> SEQUENCE: 409
actggcagtt gtccctgatg tgctaggaag                              30

<210> SEQ ID NO 410
<211> LENGTH: 30
<212> TYPE: DNA
<213> ORGANISM: Homo sapiens

<400> SEQUENCE: 410
tatgacgggt cttcctagca catcagggac                              30

<210> SEQ ID NO 411
<211> LENGTH: 30
<212> TYPE: DNA
```

<213> ORGANISM: Homo sapiens

<400> SEQUENCE: 411
atgacgggtc ttcctagcac atcagggaca                                    30

<210> SEQ ID NO 412
<211> LENGTH: 30
<212> TYPE: DNA
<213> ORGANISM: Homo sapiens

<400> SEQUENCE: 412
gcacatcagg gacaactgcc agtgtggtca                                    30

<210> SEQ ID NO 413
<211> LENGTH: 30
<212> TYPE: DNA
<213> ORGANISM: Homo sapiens

<400> SEQUENCE: 413
tcatgccccg aatgatgacc acactggcag                                    30

<210> SEQ ID NO 414
<211> LENGTH: 30
<212> TYPE: DNA
<213> ORGANISM: Homo sapiens

<400> SEQUENCE: 414
acaactgcca gtgtggtcat cattcggggc                                    30

<210> SEQ ID NO 415
<211> LENGTH: 30
<212> TYPE: DNA
<213> ORGANISM: Homo sapiens

<400> SEQUENCE: 415
caactgccag tgtggtcatc attcggggca                                    30

<210> SEQ ID NO 416
<211> LENGTH: 30
<212> TYPE: DNA
<213> ORGANISM: Homo sapiens

<400> SEQUENCE: 416
aactgccagt gtggtcatca ttcggggcat                                    30

<210> SEQ ID NO 417
<211> LENGTH: 30
<212> TYPE: DNA
<213> ORGANISM: Homo sapiens

<400> SEQUENCE: 417
catgaagatg tatgtagctc acgtaggtga                                    30

<210> SEQ ID NO 418
<211> LENGTH: 30
<212> TYPE: DNA
<213> ORGANISM: Homo sapiens

<400> SEQUENCE: 418
gtatgtagct cacgtaggtg actcaggggt                                    30

<210> SEQ ID NO 419
<211> LENGTH: 30

```
<212> TYPE: DNA
<213> ORGANISM: Homo sapiens

<400> SEQUENCE: 419
tatgtagctc acgtaggtga ctcaggggtg                                           30

<210> SEQ ID NO 420
<211> LENGTH: 30
<212> TYPE: DNA
<213> ORGANISM: Homo sapiens

<400> SEQUENCE: 420
atgtagctca cgtaggtgac tcaggggtgg                                           30

<210> SEQ ID NO 421
<211> LENGTH: 30
<212> TYPE: DNA
<213> ORGANISM: Homo sapiens

<400> SEQUENCE: 421
tagctcacgt aggtgactca ggggtggttc                                           30

<210> SEQ ID NO 422
<211> LENGTH: 30
<212> TYPE: DNA
<213> ORGANISM: Homo sapiens

<400> SEQUENCE: 422
cgtaggtgac tcaggggtgg ttcttggaat                                           30

<210> SEQ ID NO 423
<211> LENGTH: 30
<212> TYPE: DNA
<213> ORGANISM: Homo sapiens

<400> SEQUENCE: 423
actcaggggt ggttcttgga attcaggatg                                           30

<210> SEQ ID NO 424
<211> LENGTH: 30
<212> TYPE: DNA
<213> ORGANISM: Homo sapiens

<400> SEQUENCE: 424
ttcttggaat tcaggatgac ccgaaggatg                                           30

<210> SEQ ID NO 425
<211> LENGTH: 30
<212> TYPE: DNA
<213> ORGANISM: Homo sapiens

<400> SEQUENCE: 425
acagctctga caaagtcatc cttcgggtca                                           30

<210> SEQ ID NO 426
<211> LENGTH: 30
<212> TYPE: DNA
<213> ORGANISM: Homo sapiens

<400> SEQUENCE: 426
cacagctctg acaaagtcat ccttcgggtc                                           30

<210> SEQ ID NO 427
```

```
<211> LENGTH: 30
<212> TYPE: DNA
<213> ORGANISM: Homo sapiens

<400> SEQUENCE: 427
cgaaggatga ctttgtcaga gctgtggagg                                              30

<210> SEQ ID NO 428
<211> LENGTH: 30
<212> TYPE: DNA
<213> ORGANISM: Homo sapiens

<400> SEQUENCE: 428
aggatgactt tgtcagagct gtggaggtga                                              30

<210> SEQ ID NO 429
<211> LENGTH: 30
<212> TYPE: DNA
<213> ORGANISM: Homo sapiens

<400> SEQUENCE: 429
ttgtcagagc tgtggaggtg acacaggacc                                              30

<210> SEQ ID NO 430
<211> LENGTH: 30
<212> TYPE: DNA
<213> ORGANISM: Homo sapiens

<400> SEQUENCE: 430
ctttccttgg gaagttctgg cttatggtcc                                              30

<210> SEQ ID NO 431
<211> LENGTH: 30
<212> TYPE: DNA
<213> ORGANISM: Homo sapiens

<400> SEQUENCE: 431
tcgttctctt tccttgggaa gttctggctt                                              30

<210> SEQ ID NO 432
<211> LENGTH: 30
<212> TYPE: DNA
<213> ORGANISM: Homo sapiens

<400> SEQUENCE: 432
aggaccataa gccagaactt cccaaggaaa                                              30

<210> SEQ ID NO 433
<211> LENGTH: 30
<212> TYPE: DNA
<213> ORGANISM: Homo sapiens

<400> SEQUENCE: 433
tccttcgatt cgttctcttt ccttgggaag                                              30

<210> SEQ ID NO 434
<211> LENGTH: 30
<212> TYPE: DNA
<213> ORGANISM: Homo sapiens

<400> SEQUENCE: 434
gtccttcgat tcgttctctt tccttgggaa                                              30
```

```
<210> SEQ ID NO 435
<211> LENGTH: 30
<212> TYPE: DNA
<213> ORGANISM: Homo sapiens

<400> SEQUENCE: 435
tcccaaggaa agagaacgaa tcgaaggact                              30

<210> SEQ ID NO 436
<211> LENGTH: 30
<212> TYPE: DNA
<213> ORGANISM: Homo sapiens

<400> SEQUENCE: 436
ggaaagagaa cgaatcgaag gacttggtgg                              30

<210> SEQ ID NO 437
<211> LENGTH: 30
<212> TYPE: DNA
<213> ORGANISM: Homo sapiens

<400> SEQUENCE: 437
aagagaacga atcgaaggac ttggtgggag                              30

<210> SEQ ID NO 438
<211> LENGTH: 30
<212> TYPE: DNA
<213> ORGANISM: Homo sapiens

<400> SEQUENCE: 438
agagaacgaa tcgaaggact tggtgggagg                              30

<210> SEQ ID NO 439
<211> LENGTH: 30
<212> TYPE: DNA
<213> ORGANISM: Homo sapiens

<400> SEQUENCE: 439
gaacgaatcg aaggacttgg tgggaggtaa                              30

<210> SEQ ID NO 440
<211> LENGTH: 30
<212> TYPE: DNA
<213> ORGANISM: Homo sapiens

<400> SEQUENCE: 440 tattttagt gtaatgaaca agtctggggt                               30

<210> SEQ ID NO 441
<211> LENGTH: 30
<212> TYPE: DNA
<213> ORGANISM: Homo sapiens

<400> SEQUENCE: 441 attttagtg taatgaacaa gtctggggtg                               30

<210> SEQ ID NO 442
<211> LENGTH: 30
<212> TYPE: DNA
<213> ORGANISM: Homo sapiens

<400> SEQUENCE: 442
tttttagtgt aatgaacaag tctggggtga                              30
```

```
<210> SEQ ID NO 443
<211> LENGTH: 30
<212> TYPE: DNA
<213> ORGANISM: Homo sapiens

<400> SEQUENCE: 443
aagtctgggg tgaatcgtgt agtttggaaa                                       30

<210> SEQ ID NO 444
<211> LENGTH: 30
<212> TYPE: DNA
<213> ORGANISM: Homo sapiens

<400> SEQUENCE: 444
aacaggtcca ttgtgagtga gtcgaggtcg                                       30

<210> SEQ ID NO 445
<211> LENGTH: 30
<212> TYPE: DNA
<213> ORGANISM: Homo sapiens

<400> SEQUENCE: 445
gaaacgacct cgactcactc acaatggacc                                       30

<210> SEQ ID NO 446
<211> LENGTH: 30
<212> TYPE: DNA
<213> ORGANISM: Homo sapiens

<400> SEQUENCE: 446
gtcaataact gtgctccttc taacaggtcc                                       30

<210> SEQ ID NO 447
<211> LENGTH: 30
<212> TYPE: DNA
<213> ORGANISM: Homo sapiens

<400> SEQUENCE: 447
ctcactcaca atggacctgt tagaaggagc                                       30

<210> SEQ ID NO 448
<211> LENGTH: 30
<212> TYPE: DNA
<213> ORGANISM: Homo sapiens

<400> SEQUENCE: 448
cttgctactg ccagaaaagg aatctggtca                                       30

<210> SEQ ID NO 449
<211> LENGTH: 30
<212> TYPE: DNA
<213> ORGANISM: Homo sapiens

<400> SEQUENCE: 449
cagttattga ccagattcct tttctggcag                                       30

<210> SEQ ID NO 450
<211> LENGTH: 30
<212> TYPE: DNA
<213> ORGANISM: Homo sapiens

<400> SEQUENCE: 450
aagtgctctt gctactgcca gaaaaggaat                                       30
```

```
<210> SEQ ID NO 451
<211> LENGTH: 30
<212> TYPE: DNA
<213> ORGANISM: Homo sapiens

<400> SEQUENCE: 451
ttttctggca gtagcaagag cacttggtaa                                    30

<210> SEQ ID NO 452
<211> LENGTH: 30
<212> TYPE: DNA
<213> ORGANISM: Homo sapiens

<400> SEQUENCE: 452
aatcatagct ccacaaatca cctgggggaa                                    30

<210> SEQ ID NO 453
<211> LENGTH: 30
<212> TYPE: DNA
<213> ORGANISM: Homo sapiens

<400> SEQUENCE: 453
aaatcatagc tccacaaatc acctggggga                                    30

<210> SEQ ID NO 454
<211> LENGTH: 30
<212> TYPE: DNA
<213> ORGANISM: Homo sapiens

<400> SEQUENCE: 454
gaaatcatag ctccacaaat cacctggggg                                    30

<210> SEQ ID NO 455
<211> LENGTH: 30
<212> TYPE: DNA
<213> ORGANISM: Homo sapiens

<400> SEQUENCE: 455
tgctcccttc ccccaggtga tttgtggagc                                    30

<210> SEQ ID NO 456
<211> LENGTH: 30
<212> TYPE: DNA
<213> ORGANISM: Homo sapiens

<400> SEQUENCE: 456
tttgtggagc tatgatttct tcagtggtga                                    30

<210> SEQ ID NO 457
<211> LENGTH: 30
<212> TYPE: DNA
<213> ORGANISM: Homo sapiens

<400> SEQUENCE: 457
atgatttctt cagtggtgaa tttgtggtgt                                    30

<210> SEQ ID NO 458
<211> LENGTH: 30
<212> TYPE: DNA
<213> ORGANISM: Homo sapiens

<400> SEQUENCE: 458
```
agtgtggaca cttgtgtctg gttcaggtga                               30

<210> SEQ ID NO 459
<211> LENGTH: 30
<212> TYPE: DNA
<213> ORGANISM: Homo sapiens

<400> SEQUENCE: 459
gtcaagagtg tggacacttg tgtctggttc                               30

<210> SEQ ID NO 460
<211> LENGTH: 30
<212> TYPE: DNA
<213> ORGANISM: Homo sapiens

<400> SEQUENCE: 460
ttgtgcttct gagggtcaag agtgtggaca                               30

<210> SEQ ID NO 461
<211> LENGTH: 30
<212> TYPE: DNA
<213> ORGANISM: Homo sapiens

<400> SEQUENCE: 461
aatataatat acttgtgctt ctgagggtca                               30

<210> SEQ ID NO 462
<211> LENGTH: 30
<212> TYPE: DNA
<213> ORGANISM: Homo sapiens

<400> SEQUENCE: 462
caatataata tacttgtgct tctgagggtc                               30

<210> SEQ ID NO 463
<211> LENGTH: 30
<212> TYPE: DNA
<213> ORGANISM: Homo sapiens

<400> SEQUENCE: 463
ctcagaagca caagtatatt atattgggga                               30

<210> SEQ ID NO 464
<211> LENGTH: 30
<212> TYPE: DNA
<213> ORGANISM: Homo sapiens

<400> SEQUENCE: 464
tcagaagcac aagtatatta tattggggag                               30

<210> SEQ ID NO 465
<211> LENGTH: 30
<212> TYPE: DNA
<213> ORGANISM: Homo sapiens

<400> SEQUENCE: 465
cagaagcaca agtatattat attggggagt                               30

<210> SEQ ID NO 466
<211> LENGTH: 30
<212> TYPE: DNA
<213> ORGANISM: Homo sapiens

<400> SEQUENCE: 466

```
caagtatatt atattgggga gtgatggact                                30

<210> SEQ ID NO 467
<211> LENGTH: 30
<212> TYPE: DNA
<213> ORGANISM: Homo sapiens

<400> SEQUENCE: 467
attatattgg ggagtgatgg actttggaat                                30

<210> SEQ ID NO 468
<211> LENGTH: 30
<212> TYPE: DNA
<213> ORGANISM: Homo sapiens

<400> SEQUENCE: 468
gcacattgag atggcatctt gtggtggaat                                30

<210> SEQ ID NO 469
<211> LENGTH: 30
<212> TYPE: DNA
<213> ORGANISM: Homo sapiens

<400> SEQUENCE: 469
ctggcacatt gagatggcat cttgtggtgg                                30

<210> SEQ ID NO 470
<211> LENGTH: 30
<212> TYPE: DNA
<213> ORGANISM: Homo sapiens

<400> SEQUENCE: 470
cctcttggtc ctggcacatt gagatggcat                                30

<210> SEQ ID NO 471
<211> LENGTH: 30
<212> TYPE: DNA
<213> ORGANISM: Homo sapiens

<400> SEQUENCE: 471
cacaagatgc catctcaatg tgccaggacc                                30

<210> SEQ ID NO 472
<211> LENGTH: 30
<212> TYPE: DNA
<213> ORGANISM: Homo sapiens

<400> SEQUENCE: 472
aggtattttt tctcctcttg gtcctggcac                                30

<210> SEQ ID NO 473
<211> LENGTH: 30
<212> TYPE: DNA
<213> ORGANISM: Homo sapiens

<400> SEQUENCE: 473
ccatctcaat gtgccaggac caagaggaga                                30

<210> SEQ ID NO 474
<211> LENGTH: 30
<212> TYPE: DNA
<213> ORGANISM: Homo sapiens
```

<400> SEQUENCE: 474
accatcaggt attttttctc ctcttggtcc                                    30

<210> SEQ ID NO 475
<211> LENGTH: 30
<212> TYPE: DNA
<213> ORGANISM: Homo sapiens

<400> SEQUENCE: 475
accaagagga gaaaaaatac ctgatggtga                                    30

<210> SEQ ID NO 476
<211> LENGTH: 30
<212> TYPE: DNA
<213> ORGANISM: Homo sapiens

<400> SEQUENCE: 476
gttcttttga atacaggtg agcatggaca                                     30

<210> SEQ ID NO 477
<211> LENGTH: 30
<212> TYPE: DNA
<213> ORGANISM: Homo sapiens

<400> SEQUENCE: 477
ccaatgctcg attcacaagc attttggcac                                    30

<210> SEQ ID NO 478
<211> LENGTH: 30
<212> TYPE: DNA
<213> ORGANISM: Homo sapiens

<400> SEQUENCE: 478
ccaaaatgct tgtgaatcga gcattgggcc                                    30

<210> SEQ ID NO 479
<211> LENGTH: 30
<212> TYPE: DNA
<213> ORGANISM: Homo sapiens

<400> SEQUENCE: 479
caaaatgctt gtgaatcgag cattgggccg                                    30

<210> SEQ ID NO 480
<211> LENGTH: 30
<212> TYPE: DNA
<213> ORGANISM: Homo sapiens

<400> SEQUENCE: 480
cttgtgaatc gagcattggg ccgctggagg                                    30

<210> SEQ ID NO 481
<211> LENGTH: 30
<212> TYPE: DNA
<213> ORGANISM: Homo sapiens

<400> SEQUENCE: 481
gtgaatcgag cattgggccg ctggaggcag                                    30

<210> SEQ ID NO 482
<211> LENGTH: 30
<212> TYPE: DNA
<213> ORGANISM: Homo sapiens

```
<400> SEQUENCE: 482
gctcggagca tacgctgcct ccagcggccc                                    30

<210> SEQ ID NO 483
<211> LENGTH: 30
<212> TYPE: DNA
<213> ORGANISM: Homo sapiens

<400> SEQUENCE: 483
actatggcac tagtgttatc tgctcggagc                                    30

<210> SEQ ID NO 484
<211> LENGTH: 30
<212> TYPE: DNA
<213> ORGANISM: Homo sapiens

<400> SEQUENCE: 484
cttctggaga gatgcagatt actatggcac                                    30

<210> SEQ ID NO 485
<211> LENGTH: 30
<212> TYPE: DNA
<213> ORGANISM: Homo sapiens

<400> SEQUENCE: 485
tagtaatctg catctctcca gaagtggaca                                    30

<210> SEQ ID NO 486
<211> LENGTH: 30
<212> TYPE: DNA
<213> ORGANISM: Homo sapiens

<400> SEQUENCE: 486
aaagtttccc tgattgtcca cttctggaga                                    30

<210> SEQ ID NO 487
<211> LENGTH: 30
<212> TYPE: DNA
<213> ORGANISM: Homo sapiens

<400> SEQUENCE: 487
gcatctctcc agaagtggac aatcagggaa                                    30

<210> SEQ ID NO 488
<211> LENGTH: 30
<212> TYPE: DNA
<213> ORGANISM: Homo sapiens

<400> SEQUENCE: 488
catctctcca gaagtggaca atcagggaaa                                    30

<210> SEQ ID NO 489
<211> LENGTH: 30
<212> TYPE: DNA
<213> ORGANISM: Homo sapiens

<400> SEQUENCE: 489
ggttcaggta taactcatct tcattggtaa                                    30

<210> SEQ ID NO 490
<211> LENGTH: 30
<212> TYPE: DNA
```

<213> ORGANISM: Homo sapiens

<400> SEQUENCE: 490
taggaagggc tgtcagtcag gttcaggtat                                30

<210> SEQ ID NO 491
<211> LENGTH: 30
<212> TYPE: DNA
<213> ORGANISM: Homo sapiens

<400> SEQUENCE: 491
ctattatagg aagggctgtc agtcaggttc                                30

<210> SEQ ID NO 492
<211> LENGTH: 30
<212> TYPE: DNA
<213> ORGANISM: Homo sapiens

<400> SEQUENCE: 492
caggtttctt gactattata ggaagggctg                                30

<210> SEQ ID NO 493
<211> LENGTH: 30
<212> TYPE: DNA
<213> ORGANISM: Homo sapiens

<400> SEQUENCE: 493
acaggtttct tgactattat aggaagggct                                30

<210> SEQ ID NO 494
<211> LENGTH: 30
<212> TYPE: DNA
<213> ORGANISM: Homo sapiens

<400> SEQUENCE: 494
tcacacaggt ttcttgacta ttataggaag                                30

<210> SEQ ID NO 495
<211> LENGTH: 30
<212> TYPE: DNA
<213> ORGANISM: Homo sapiens

<400> SEQUENCE: 495
aacatgggga aggagtcatc acacaggttt                                30

<210> SEQ ID NO 496
<211> LENGTH: 30
<212> TYPE: DNA
<213> ORGANISM: Homo sapiens

<400> SEQUENCE: 496
gactggtggt gtagaacatg gggaaggagt                                30

<210> SEQ ID NO 497
<211> LENGTH: 30
<212> TYPE: DNA
<213> ORGANISM: Homo sapiens

<400> SEQUENCE: 497
ccttgactgg tggtgtagaa catggggaag                                30

<210> SEQ ID NO 498
<211> LENGTH: 30

<212> TYPE: DNA
<213> ORGANISM: Homo sapiens

<400> SEQUENCE: 498
accttgactg gtggtgtaga acatgggaa                                30

<210> SEQ ID NO 499
<211> LENGTH: 30
<212> TYPE: DNA
<213> ORGANISM: Homo sapiens

<400> SEQUENCE: 499
taccttgact ggtggtgtag aacatgggga                                30

<210> SEQ ID NO 500
<211> LENGTH: 30
<212> TYPE: DNA
<213> ORGANISM: Homo sapiens

<400> SEQUENCE: 500
tatggaacta tataccttga ctggtggtgt                                30

<210> SEQ ID NO 501
<211> LENGTH: 30
<212> TYPE: DNA
<213> ORGANISM: Homo sapiens

<400> SEQUENCE: 501
ccccatgttc tacaccacca gtcaaggtat                                30

<210> SEQ ID NO 502
<211> LENGTH: 30
<212> TYPE: DNA
<213> ORGANISM: Homo sapiens

<400> SEQUENCE: 502
aactatggaa ctatataccT tgactggtgg                                30

<210> SEQ ID NO 503
<211> LENGTH: 30
<212> TYPE: DNA
<213> ORGANISM: Homo sapiens

<400> SEQUENCE: 503
tttaccttct tattttcag tcactggagg                                30

<210> SEQ ID NO 504
<211> LENGTH: 30
<212> TYPE: DNA
<213> ORGANISM: Homo sapiens

<400> SEQUENCE: 504
accttcttat ttttcagtca ctggaggagg                                30

<210> SEQ ID NO 505
<211> LENGTH: 30
<212> TYPE: DNA
<213> ORGANISM: Homo sapiens

<400> SEQUENCE: 505
ttcttatttt tcagtcactg gaggaggatc                                30

<210> SEQ ID NO 506

```
<211> LENGTH: 30
<212> TYPE: DNA
<213> ORGANISM: Homo sapiens

<400> SEQUENCE: 506
tttcagtcac tggaggagga tccatggcca                                    30

<210> SEQ ID NO 507
<211> LENGTH: 30
<212> TYPE: DNA
<213> ORGANISM: Homo sapiens

<400> SEQUENCE: 507
tcactggagg aggatccatg gccaagggtg                                    30

<210> SEQ ID NO 508
<211> LENGTH: 30
<212> TYPE: DNA
<213> ORGANISM: Homo sapiens

<400> SEQUENCE: 508
gtccttagaa ttcacccttg gccatggatc                                    30

<210> SEQ ID NO 509
<211> LENGTH: 30
<212> TYPE: DNA
<213> ORGANISM: Homo sapiens

<400> SEQUENCE: 509
cactggagga ggatccatgg ccaagggtga                                    30

<210> SEQ ID NO 510
<211> LENGTH: 30
<212> TYPE: DNA
<213> ORGANISM: Homo sapiens

<400> SEQUENCE: 510
tatatggtcc ttagaattca cccttggcca                                    30

<210> SEQ ID NO 511
<211> LENGTH: 30
<212> TYPE: DNA
<213> ORGANISM: Homo sapiens

<400> SEQUENCE: 511
atccatggcc aagggtgaat tctaaggacc                                    30

<210> SEQ ID NO 512
<211> LENGTH: 30
<212> TYPE: DNA
<213> ORGANISM: Homo sapiens

<400> SEQUENCE: 512
ttgctacgaa ccagggcagg tatatggtcc                                    30

<210> SEQ ID NO 513
<211> LENGTH: 30
<212> TYPE: DNA
<213> ORGANISM: Homo sapiens

<400> SEQUENCE: 513
attctaagga ccatatacct gccctggttc                                    30
```

```
<210> SEQ ID NO 514
<211> LENGTH: 30
<212> TYPE: DNA
<213> ORGANISM: Homo sapiens

<400> SEQUENCE: 514
gaaggcattg ctacgaacca gggcaggtat                                    30

<210> SEQ ID NO 515
<211> LENGTH: 30
<212> TYPE: DNA
<213> ORGANISM: Homo sapiens

<400> SEQUENCE: 515
ctgagaaggc attgctacga accagggcag                                    30

<210> SEQ ID NO 516
<211> LENGTH: 30
<212> TYPE: DNA
<213> ORGANISM: Homo sapiens

<400> SEQUENCE: 516
tctgagaagg cattgctacg aaccagggca                                    30

<210> SEQ ID NO 517
<211> LENGTH: 30
<212> TYPE: DNA
<213> ORGANISM: Homo sapiens

<400> SEQUENCE: 517
aaacctctaa aaaattctct gagaaggcat                                    30

<210> SEQ ID NO 518
<211> LENGTH: 30
<212> TYPE: DNA
<213> ORGANISM: Homo sapiens

<400> SEQUENCE: 518
atgccttctc agagaatttt ttagaggttt                                    30

<210> SEQ ID NO 519
<211> LENGTH: 30
<212> TYPE: DNA
<213> ORGANISM: Homo sapiens

<400> SEQUENCE: 519
tgagatagct cgagagaatg tccaaggtgt                                    30

<210> SEQ ID NO 520
<211> LENGTH: 30
<212> TYPE: DNA
<213> ORGANISM: Homo sapiens

<400> SEQUENCE: 520
tcttttgagg gtatgactac accttggaca                                    30

<210> SEQ ID NO 521
<211> LENGTH: 30
<212> TYPE: DNA
<213> ORGANISM: Homo sapiens

<400> SEQUENCE: 521
ttcaagtggt tctggatctt ttgagggtat                                    30
```

```
<210> SEQ ID NO 522
<211> LENGTH: 30
<212> TYPE: DNA
<213> ORGANISM: Homo sapiens

<400> SEQUENCE: 522
cttcaagtgg ttctggatct tttgagggta                                    30

<210> SEQ ID NO 523
<211> LENGTH: 30
<212> TYPE: DNA
<213> ORGANISM: Homo sapiens

<400> SEQUENCE: 523
agcgcaattt tcttcaagtg gttctggatc                                    30

<210> SEQ ID NO 524
<211> LENGTH: 30
<212> TYPE: DNA
<213> ORGANISM: Homo sapiens

<400> SEQUENCE: 524
ggctttagcg caattttctt caagtggttc                                    30

<210> SEQ ID NO 525
<211> LENGTH: 30
<212> TYPE: DNA
<213> ORGANISM: Homo sapiens

<400> SEQUENCE: 525
aagaatcatg tatccttaaa gtcagggctt                                    30

<210> SEQ ID NO 526
<211> LENGTH: 30
<212> TYPE: DNA
<213> ORGANISM: Homo sapiens

<400> SEQUENCE: 526
aaagaatcat gtatccttaa agtcagggct                                    30

<210> SEQ ID NO 527
<211> LENGTH: 30
<212> TYPE: DNA
<213> ORGANISM: Homo sapiens

<400> SEQUENCE: 527
aattgcgcta aagccctgac tttaaggata                                    30

<210> SEQ ID NO 528
<211> LENGTH: 30
<212> TYPE: DNA
<213> ORGANISM: Homo sapiens

<400> SEQUENCE: 528
ttagtaggca caaggccaat tggaaggcta                                    30

<210> SEQ ID NO 529
<211> LENGTH: 30
<212> TYPE: DNA
<213> ORGANISM: Homo sapiens

<400> SEQUENCE: 529
ttctttgaat aatagccttc caattggcct                                    30
```

<210> SEQ ID NO 530
<211> LENGTH: 30
<212> TYPE: DNA
<213> ORGANISM: Homo sapiens

<400> SEQUENCE: 530
tgaattagta ggcacaaggc caattggaag            30

<210> SEQ ID NO 531
<211> LENGTH: 30
<212> TYPE: DNA
<213> ORGANISM: Homo sapiens

<400> SEQUENCE: 531
gtgtttgttg aattagtagg cacaaggcca            30

<210> SEQ ID NO 532
<211> LENGTH: 30
<212> TYPE: DNA
<213> ORGANISM: Homo sapiens

<400> SEQUENCE: 532
catgacagtg tttgttgaat tagtaggcac            30

<210> SEQ ID NO 533
<211> LENGTH: 30
<212> TYPE: DNA
<213> ORGANISM: Homo sapiens

<400> SEQUENCE: 533
ctactaattc aacaaacact gtcatggacc            30

<210> SEQ ID NO 534
<211> LENGTH: 30
<212> TYPE: DNA
<213> ORGANISM: Homo sapiens

<400> SEQUENCE: 534
ggagttgaca tcttcaaatt tttttggtcc            30

<210> SEQ ID NO 535
<211> LENGTH: 30
<212> TYPE: DNA
<213> ORGANISM: Homo sapiens

<400> SEQUENCE: 535
aaaaaatttg aagatgtcaa ctcctggcca            30

<210> SEQ ID NO 536
<211> LENGTH: 30
<212> TYPE: DNA
<213> ORGANISM: Homo sapiens

<400> SEQUENCE: 536
aatttcttgg gctttcattt ggccaggagt            30

<210> SEQ ID NO 537
<211> LENGTH: 30
<212> TYPE: DNA
<213> ORGANISM: Homo sapiens

<400> SEQUENCE: 537
ctttcaattt cttgggcttt catttggcca                              30

<210> SEQ ID NO 538
<211> LENGTH: 30
<212> TYPE: DNA
<213> ORGANISM: Homo sapiens

<400> SEQUENCE: 538
ttggaggggt tctttcaatt tcttgggctt                              30

<210> SEQ ID NO 539
<211> LENGTH: 30
<212> TYPE: DNA
<213> ORGANISM: Homo sapiens

<400> SEQUENCE: 539
gttggagggg ttctttcaat ttcttgggct                              30

<210> SEQ ID NO 540
<211> LENGTH: 30
<212> TYPE: DNA
<213> ORGANISM: Homo sapiens

<400> SEQUENCE: 540
atgtcctttt aaagtttgtt ggaggggttc                              30

<210> SEQ ID NO 541
<211> LENGTH: 30
<212> TYPE: DNA
<213> ORGANISM: Homo sapiens

<400> SEQUENCE: 541
aatgtccttt taaagtttgt tggaggggtt                              30

<210> SEQ ID NO 542
<211> LENGTH: 30
<212> TYPE: DNA
<213> ORGANISM: Homo sapiens

<400> SEQUENCE: 542
taatgtcctt ttaaagtttg ttggaggggt                              30

<210> SEQ ID NO 543
<211> LENGTH: 30
<212> TYPE: DNA
<213> ORGANISM: Homo sapiens

<400> SEQUENCE: 543
ttctaatgtc cttttaaagt ttgttggagg                              30

<210> SEQ ID NO 544
<211> LENGTH: 30
<212> TYPE: DNA
<213> ORGANISM: Homo sapiens

<400> SEQUENCE: 544
agaacccctc caacaaactt taaaaggaca                              30

<210> SEQ ID NO 545
<211> LENGTH: 30
<212> TYPE: DNA
<213> ORGANISM: Homo sapiens

<400> SEQUENCE: 545
aaggacatta gaagagtcca attctggccc                                30

<210> SEQ ID NO 546
<211> LENGTH: 30
<212> TYPE: DNA
<213> ORGANISM: Homo sapiens

<400> SEQUENCE: 546
gcttcttcat caggggcca gaattggact                                 30

<210> SEQ ID NO 547
<211> LENGTH: 30
<212> TYPE: DNA
<213> ORGANISM: Homo sapiens

<400> SEQUENCE: 547
tttcgtctat gcttcttcat caggggcca                                 30

<210> SEQ ID NO 548
<211> LENGTH: 30
<212> TYPE: DNA
<213> ORGANISM: Homo sapiens

<400> SEQUENCE: 548
atttcgtcta tgcttcttca tcaggggcc                                 30

<210> SEQ ID NO 549
<211> LENGTH: 30
<212> TYPE: DNA
<213> ORGANISM: Homo sapiens

<400> SEQUENCE: 549
catttcgtct atgcttcttc atcaggggc                                 30

<210> SEQ ID NO 550
<211> LENGTH: 30
<212> TYPE: DNA
<213> ORGANISM: Homo sapiens

<400> SEQUENCE: 550
ccatttcgtc tatgcttctt catcagggg                                 30

<210> SEQ ID NO 551
<211> LENGTH: 30
<212> TYPE: DNA
<213> ORGANISM: Homo sapiens

<400> SEQUENCE: 551
cctgatgaag aagcatagac gaaatggctt                                30

<210> SEQ ID NO 552
<211> LENGTH: 30
<212> TYPE: DNA
<213> ORGANISM: Homo sapiens

<400> SEQUENCE: 552
acgaaatggc ttaagtcgaa gtagtggtgc                                30

<210> SEQ ID NO 553
<211> LENGTH: 30
<212> TYPE: DNA
<213> ORGANISM: Homo sapiens

<400> SEQUENCE: 553
ctgtgaggtt gtggggagac ttgcaggctg                30

<210> SEQ ID NO 554
<211> LENGTH: 30
<212> TYPE: DNA
<213> ORGANISM: Homo sapiens

<400> SEQUENCE: 554
gagttctttc gctgtgaggt tgtggggaga                30

<210> SEQ ID NO 555
<211> LENGTH: 30
<212> TYPE: DNA
<213> ORGANISM: Homo sapiens

<400> SEQUENCE: 555
agagttcttt cgctgtgagg ttgtggggag                30

<210> SEQ ID NO 556
<211> LENGTH: 30
<212> TYPE: DNA
<213> ORGANISM: Homo sapiens

<400> SEQUENCE: 556
cagagttctt tcgctgtgag gttgtgggga                30

<210> SEQ ID NO 557
<211> LENGTH: 30
<212> TYPE: DNA
<213> ORGANISM: Homo sapiens

<400> SEQUENCE: 557
gtttaacaga gttctttcgc tgtgaggttg                30

<210> SEQ ID NO 558
<211> LENGTH: 30
<212> TYPE: DNA
<213> ORGANISM: Homo sapiens

<400> SEQUENCE: 558
tctggcccct aagtctgcgt cgcatggtga                30

<210> SEQ ID NO 559
<211> LENGTH: 30
<212> TYPE: DNA
<213> ORGANISM: Homo sapiens

<400> SEQUENCE: 559
aaactcacca tgcgacgcag acttaggggc                30

<210> SEQ ID NO 560
<211> LENGTH: 30
<212> TYPE: DNA
<213> ORGANISM: Homo sapiens

<400> SEQUENCE: 560
aactcaccat gcgacgcaga cttaggggcc                30

<210> SEQ ID NO 561
<211> LENGTH: 30
<212> TYPE: DNA
<213> ORGANISM: Homo sapiens

```
<400> SEQUENCE: 561
actcaccatg cgacgcagac ttaggggcca                                   30

<210> SEQ ID NO 562
<211> LENGTH: 30
<212> TYPE: DNA
<213> ORGANISM: Homo sapiens

<400> SEQUENCE: 562
agtaaaggat ttccaatttt cttctggccc                                   30

<210> SEQ ID NO 563
<211> LENGTH: 30
<212> TYPE: DNA
<213> ORGANISM: Homo sapiens

<400> SEQUENCE: 563
cagacttagg ggccagaaga aaattggaaa                                   30

<210> SEQ ID NO 564
<211> LENGTH: 30
<212> TYPE: DNA
<213> ORGANISM: Homo sapiens

<400> SEQUENCE: 564
agttttcctg tgttgatgaa gtaaaggatt                                   30

<210> SEQ ID NO 565
<211> LENGTH: 30
<212> TYPE: DNA
<213> ORGANISM: Homo sapiens

<400> SEQUENCE: 565
ggaaatcctt tacttcatca acacaggaaa                                   30
```

COMPOSITIONS AND METHODS FOR TREATING CHEMOTHERAPY RESISTANT CANCER

CROSS-REFERENCE TO RELATED APPLICATIONS

This application is a divisional of U.S. patent application Ser. No. 16/083,687, filed Sep. 10, 2018, now U.S. Pat. No. 11,304,938, issued Apr. 19, 2022, which is the U.S. National Stage Application, pursuant to 35 U.S.C. § 371, of International PCT Application No. PCT/US2017/021830, filed Mar. 10, 2017, designating the United States and published in English, which claims priority to and benefit of U.S. Provisional Application No. 62/306,952, filed Mar. 11, 2016, the disclosure of each of which is incorporated herein by reference in its entirety.

STATEMENT OF RIGHTS TO INVENTIONS MADE UNDER FEDERALLY SPONSORED RESEARCH

This invention was made with government support under Grant No. P01 CA066996 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 29, 2020, is named 167741_010402_US_SL.txt and is 102,996 bytes in size.

BACKGROUND OF THE INVENTION

Cancer remains a global health problem. A common treatment for patients with cancer is chemotherapy. However, patients receiving chemotherapy often develop resistance to the chemotherapy. New, improved methods of treating cancer in patients, particularly patients who have developed resistance to chemotherapy, are urgently needed.

SUMMARY OF THE INVENTION

As described below, the present invention features compositions and methods that are useful for treating a cancer in a subject, particularly a subject that is resistant to chemotherapy and/or has mutations in Protein phosphatase 1D (PPM1D). The present invention also features compositions and methods that are useful for treating clonal hematopoiesis (e.g., clonal hematopoiesis of indeterminate potential (CHIP)) in a subject, particularly a subject that has mutations in PPM1D.

In one aspect, the invention provides a pharmaceutical composition containing an effective amount of an agent that inhibits the expression or activity of a PPM1D polynucleotide or polypeptide, in a pharmaceutically acceptable carrier. In various embodiments, the agent that inhibits the expression or activity of PPM1D polynucleotide or polypeptide is a small molecule PPM1D inhibitor or an inhibitory polynucleotide that reduces PPM1D expression.

In some embodiments, the pharmaceutical composition further contains a chemotherapeutic agent. In some other embodiments, the chemotherapeutic agent is a DNA damaging agent. In still other embodiments, the chemotherapeutic agent is Cytarabine, Doxorubicin, Cyclophosphamide, or Cisplatin. In some embodiments, the small molecule PPM1D inhibitor is GSK2830371, CCT007093, or an analog thereof.

In some embodiments, the small molecule PPM1D inhibitor inhibits activity of a PPM1D polypeptide comprising a truncation mutation and/or a gain-of-function mutation.

In another aspect, the invention provides a method of increasing sensitivity or reversing resistance of a cancer cell to a chemotherapeutic agent. The method contains the step of contacting the cell with an effective amount of a PPM1D inhibitor, an agent that inhibits the expression or activity of PPM1D polypeptide or polynucleotide, thereby increasing sensitivity of the cell the chemotherapeutic agent.

In yet another aspect, the invention provides a method of inhibiting proliferation of a cancer cell, the method containing the step of contacting the cell with an effective amount of a PPM1D inhibitor and contacting the cell with an effective amount of a chemotherapeutic agent, thereby inhibiting proliferation of the cell.

In another aspect, the invention provides a method of treating or preventing clonal hematopoiesis of indeterminate potential (CHIP) or a therapy-related myeloid neoplasm in a subject, the method involving administering a PPM1D inhibitor to a subject identified as having or having a propensity to develop CHIP or a therapy-related myeloid neoplasm.

In still another aspect, the invention provides a method of increasing sensitivity or reversing resistance to a chemotherapeutic agent in a subject having a cancer. The method contains the step of administering to the subject an effective amount of a PPM1D inhibitor, thereby increasing sensitivity or reversing resistance to the chemotherapeutic agent in the subject having a cancer.

In another aspect, the invention provides a method of treating a cancer in a subject. The method contains the step of administering to the subject an effective amount of a PPM1D inhibitor and administering to the subject an effective amount of a chemotherapeutic agent, thereby treating the cancer in the subject.

In another aspect, the invention provides a method of treating a cancer in a pre-identified subject, the method containing the step of administering to the subject an effective amount of a PPM1D inhibitor and an effective amount of a chemotherapeutic agent, where the subject is pre-identified as having a mutation in a PPM1D polynucleotide or polypeptide relative to a reference in a biological sample obtained from the subject.

In yet another aspect, the invention provides a method of treating clonal hematopoiesis of indeterminate potential in a pre-identified subject, the method containing the step of administering to the subject an effective amount of a PPM1D inhibitor, where the subject is pre-identified as having a mutation in a PPM1D polynucleotide or polypeptide relative to a reference in a biological sample obtained from the subject.

In various embodiments of any one of the aspects delineated herein, the subject is resistant to a chemotherapeutic agent. In some embodiments, the cell or the subject contains a mutation in a PPM1D polynucleotide or polypeptide. In some other embodiments, the mutation is a truncation mutation and/or a gain-of-function mutation.

In some embodiments, the cell is in vivo or in vitro. In some other embodiments, the agent that inhibits the expression or activity of PPM1D polypeptide or polynucleotide is one or more of small molecule PPM1D inhibitors GSK2830371 CCT007093, and analogs thereof. In some embodiments, the chemotherapeutic agent is any one of DNA damaging agents Cytarabine, Doxorubicin, Cyclophosphamide, and Cisplatin. In still other embodiments, the small molecule PPM1D inhibitor inhibits activity of a PPM1D polypeptide comprising a truncation mutation and/or a gain-of-function mutation.

In various embodiments of any one of the aspects delineated herein, the subject is human or murine. In various embodiments, the cell is a blood cell. In some embodiments, the cancer is a hematologic cancer. In some embodiments, the cancer is a therapy-related myeloid neoplasm. In still other embodiments, the biological sample is a blood, bone marrow, or tumor sample. In various embodiments of any one of the aspects delineated herein, the treatment selectively targets cells comprising a PPM1D mutation. In some embodiments, the propensity to develop CHIP is associated with chemotherapy.

In one aspect, the invention provides a kit containing a capture reagent specifically binding a PPM1D polynucleotide or polypeptide and an agent that inhibits the expression or activity of a PPM1D polynucleotide or polypeptide.

In another aspect, the invention provides a kit containing a capture reagent specifically binding a PPM1D polynucleotide or polypeptide and at least one agent selected from the group consisting of an agent that inhibits the expression or activity of a PPM1D polynucleotide or polypeptide and a chemotherapeutic agent. In some embodiments, the agent that inhibits the expression or activity of a PPM1D polynucleotide or polypeptide is one or more of PPM1D small molecule inhibitor such as GSK2830371, CCT007093, and analogs thereof. In some other embodiments, the chemotherapeutic agent is any one of DNA damaging agents Cytarabine, Doxorubicin, Cyclophosphamide and Cisplatin. In some embodiments, the capture reagent is a probe or primer.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person of ordinary skill in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, a 25% change, a 40% change, and a 50% or greater change in expression levels.

By "analog" is meant a molecule that is not identical, but has analogous functional or structural features. For example, an analog of an agent of the invention (e.g., GSK2830371, CCT007093) retains the biological activity of the corresponding agent, while having certain chemical modifications that enhance the analog's function relative to the corresponding agent. Such modifications could increase the analog's protease resistance, membrane permeability, or half-life, without altering, for example, ligand binding.

"Biological sample" as used herein means a biological material isolated from a subject, including any tissue, cell, fluid, or other material obtained or derived from the subject. In some embodiments, the subject is human. The biological sample may contain any biological material suitable for detecting the desired analytes, and may comprise cellular and/or non-cellular material obtained from the subject. Biological samples include tissue samples (e.g., cell samples, biopsy samples). Biological samples also include bodily fluids, including, but not limited to, blood, blood serum, plasma, saliva, and urine. In particular embodiments, the biological sample is blood. In some embodiments, the biological sample is a blood, bone marrow, or tumor sample.

By "chemotherapeutic agent" is meant an agent having anti-neoplastic activity. In some embodiments, the chemotherapeutic agent is a DNA damaging agent. In certain embodiments, the chemotherapeutic agent is Cytarabine, Doxorubicin, Cyclophosphamide, or Cisplatin.

In some embodiments, the chemotherapeutic agent contains platinum. Examples of such an agent include, without limitation, cisplatin, carboplatin, and oxaliplatin. In some other embodiments, the chemotherapeutic agent is an anthracycline. Examples of anthracyclines include, without limitation, doxorubicin, daunorubicin, and idarubicin. In still other embodiments, the chemotherapeutic agent is an alkylating agent. Examples of alkylating agents include, without limitation, cyclophosphamide, melphalan, chlorambucil, and busulfan. In some embodiments, the chemotherapeutic agent is an antimetabolite. Exemplary antimetabolites include, without limitation, cytarabine, 5-fluorouracil, methotrexate, azathioprine, 6-mercaptopurine, 6-thioguanine, and fludarabine.

By "clonal hematopoiesis of indeterminate potential (CHIP)" is meant a clonal somatic mutation in the bone marrow or blood, that may increase the risk of a hematological malignancy. In various embodiments, clonal hematopoiesis of indeterminate potential does not display diagnostic criteria for a hematologic malignancy. In various embodiments, there is an absence of definitive morphological evidence of a hematological neoplasm. In certain embodiments, the somatic mutation associated with hematological neoplasia is in one or more of PPM1D, TP53, DNMT3A, TET2, JAK2, SF3B1, ASXL1, CBL, GNB1, BCOR, U2AF1, CREBBP, CUX1, SRSF2, MLL2, SETD2, SETDB1, GNAS, BCORL1). In some embodiments, progression to overt neoplasia is approximately 0.5-1%.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "CCT007093" or "CAS 1087-07-6" is meant a small molecule inhibitor having the following structure:

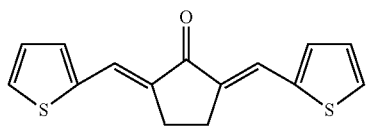 [SMILES: O=C1/C(=C/c2cccs2)CC/C1=C\c1cccs1]

In some embodiments, CCT007093 is a small molecule PPM1D inhibitor.

By "Cisplatin" is meant a chemotherapeutic agent having the following structure:

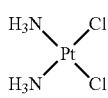

In some embodiments, Cisplatin inhibits DNA replication by reacting with DNA to form intra- and interstrand crosslinks.

By "Cytarabine" is meant a chemotherapeutic agent having the following structure:

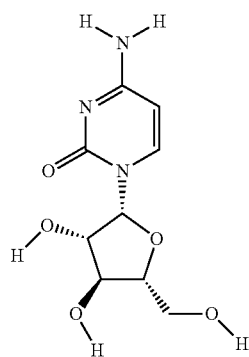 [SMILES: Nc1ccn([C@@H]2O[C@H](CO)[C@@H](O)[C@@H]2O)c(=O)n1]

In some embodiments, Cytarabine inhibits synthesis of DNA.

By "Cyclophosphamide" is meant a chemotherapeutic agent having the following structure:

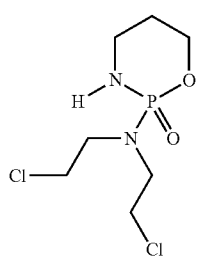 [SMILES: O=P1(N(CCCl)CCCl)NCCCO1]

In some embodiments, Cyclophosphamide adds an alkyl group to DNA and inhibits DNA replication by forming intra- and interstrand DNA crosslinks.

"Detect" refers to identifying the presence, absence or amount of the analyte to be detected. In some embodiments, a PPM1D polypeptide or polynucleotide comprising a mutation is detected. In some embodiments, the mutation is a truncation mutation. In some embodiments, the mutation is a frameshift mutation that results in expression of a truncated PPM1D polypeptide relative to a wild-type PPM1D polypeptide.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include cancer. In some embodiments, the cancer is a blood cancer. In some other embodiments, the blood cancer is acute myeloid leukemia.

By "DNA damaging agent" is meant any agent that alters the structure of DNA and/or inhibits DNA replication or DNA synthesis in a cell or in vitro. In some embodiments, the DNA damaging agent is Cytarabine, Doxorubicin, Cyclophosphamide, or Cisplatin.

By "Doxorubicin" is meant a chemotherapeutic agent having the following structure:

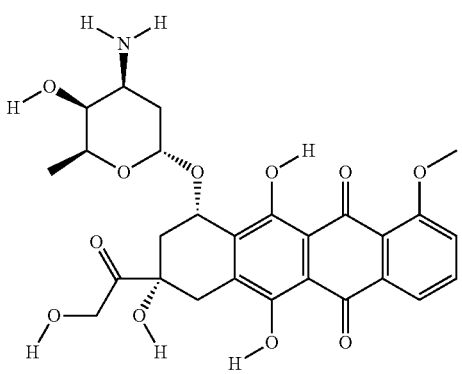 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]

In some embodiments, Doxorubicin inhibits DNA replication.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "GSK2830371" is meant a small molecule inhibitor having the following structure:

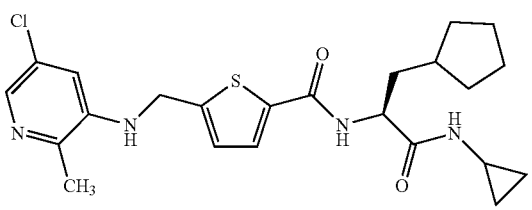 [SMILES: Cc1ncc(Cl)cc1NCc1ccc(C(=O)N[C@@H](CC2CCCC2)C(=O)NC2CC2)s1]

In some embodiments, GSK2830371 is a small molecule PPM1D inhibitor.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibitory nucleic acid" or "inhibitory polynucleotide" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. The preparation can be at least 75%, at least 90%, and at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "mutation" is meant a change in a polypeptide or polynucleotide sequence relative to a reference sequence. In some embodiments, the reference sequence is a wild-type sequence. Exemplary mutations include point mutations, missense mutations, amino acid substitutions, and frameshift mutations. As used herein, a "truncation mutation" is a mutation that results in expression of a polypeptide having a decreased number of amino acid residues relative to the wild-type polypeptide. A "loss-of-function mutation" is a mutation that decreases or abolishes an activity or function of a polypeptide. A "gain-of-function mutation" is a mutation that enhances or increases an activity or function of a polypeptide. In some embodiments, the PPM1D mutation is a truncation mutation. In some embodiments, the PPM1D truncation mutation is a gain-of-function mutation.

As used herein, "obtaining" as in "obtaining an agent" includes synthesizing, purchasing, or otherwise acquiring the agent.

By "Protein phosphatase 1D (PPM1D) polypeptide" is meant a polypeptide or fragment thereof having at least about 85% amino acid identity to NCBI Accession No. NP_003611.1 and having phosphatase activity. The sequence at NCBI Accession No. NP_003611.1 is shown below:

```
                                                            (SEQ ID NO: 1)
  1 maglyslgvs vfsdqggrky medvtqivve peptaeekps prrslsqplp prpspaalpg 61 gevsgkgpav aareardplp dagaspapsr ccrrrssvaf favcdghggr eaaqfarehl 121 wgfikkqkgf tssepakvca airkgflach lamwkklaew pktmtglpst sgttasvvii 181 rgmkmyvahv gdsgvvlgiq ddpkddfvra vevtqdhkpe ipkererieg lggsvmnksg 241 vnrvvwkrpr lthngpvrrs tvidqipfla varalgdlws ydffsgefvv spepdtsvht 301 ldpqkhkyii lgsdglwnmi ppqdaismcq dqeekkylmg ehgqscakml vnralgrwrq
```

-continued

```
361 rmlradntsa ivicispevd nqgnftnede lylnltdsps ynsqetcvmt pspcstppvk 421 sleedpwprv nskdhipalv rsnafsenfl evsaeiaren vqgvvipskd pepleencak 481 altlrihdsl nnslpiglvp tnstntvmdq knlkmstpgq mkaqeiertp ptnfkrtlee 541 snsgplmkkh rrnglsrssg aqpaslptts qrknsvkltm rrrlrgqkki gnpllhqhrk 601 tvcvc
```

By "Protein phosphatase 1D (PPM1D) polynucleotide" is meant a polynucleotide encoding a PPM1D polypeptide. An exemplary PPM1D polynucleotide sequence is provided at NCBI Accession No. NM_003620.3. The sequence is provided below:

(SEQ ID NO: 2)
```
   1 ggggaagcgc agtgcgcagg cgcaactgcc tggctctgct cgctccggcg ctccggccca 61 gctctcgcgg acaagtccag acatcgcgcg ccccccttc tccgggtccg cccctcccc 121 cttctcggcg tcgtcgaaga taaacaatag ttggccggcg agcgcctagt gtgtctccg 181 ccgccggatt cggcgggctg cgtgggaccg gcgggatccc ggccagccgg ccatggcggg 241 gctgtactcg ctgggagtga gcgtcttctc cgaccagggc gggaggaagt acatggagga 301 cgttactcaa atcgttgtgg agcccgaacc gacggctgaa gaaaagccct cgccgcggcg 361 gtcgctgtct cagccgttgc ctccgcggcc gtcgccggcc gccctcccg gcggcgaagt 421 ctcggggaaa ggcccagcgg tggcagcccg agaggctcgc gaccctctcc cggacgccgg 481 ggcctcgccg gcacctagcc gctgctgccg ccgccgttcc tccgtggcct ttttcgccgt 541 gtgcgacggg cacggcgggc gggaggcggc acagtttgcc cgggagcact tgtggggttt 601 catcaagaag cagaagggtt tcacctcgtc cgagccggct aaggtttgcg ctgccatccg 661 caaaggcttt ctcgcttgtc accttgccat gtggaagaaa ctggcggaat ggccaaagac 721 tatgacgggt cttcctagca catcaggac aactgccagt gtggtcatca ttcggggcat 781 gaagatgtat gtagctcacg taggtgactc aggggtggtt cttggaattc aggatgaccc 841 gaaggatgac tttgtcagag ctgtggaggt gacacaggac cataagccag aacttcccaa 901 ggaaagagaa cgaatcgaag gacttggtgg gagtgtaatg aacaagtctg gggtgaatcg 961 tgtagtttgg aaacgacctc gactcactca caatggacct gttagaagga gcacagttat 1021 tgaccagatt cctttctgg cagtagcaag agcacttggt gatttgtgga gctatgattt 1081 cttcagtggt gaatttgtgg tgtcacctga accagacaca agtgtccaca ctcttgaccc 1141 tcagaagcac aagtatatta tattggggag tgatggactt tggaatatga ttccaccaca 1201 agatgccatc tcaatgtgcc aggaccaaga ggagaaaaaa tacctgatgg gtgagcatgg 1261 acaatcttgt gccaaaatgc ttgtgaatcg agcattgggc cgctggaggc agcgtatgct 1321 ccgagcagat aacactagtg ccatagtaat ctgcatctct ccagaagtgg acaatcaggg 1381 aaactttacc aatgaagatg agttatacct gaacctgact gacagccctt cctataatag 1441 tcaagaaacc tgtgtgatga ctccttcccc atgttctaca ccaccagtca agtcactgga 1501 ggaggatcca tggccaaggg tgaattctaa ggaccatata cctgccctgg ttcgtagcaa 1561 tgccttctca gagaattttt tagaggtttc agctgagata gctcgagaga atgtccaagg 1621 tgtagtcata ccctcaaaag atccagaacc acttgaagaa aattgcgcta aagccctgac 1681 tttaaggata catgattctt tgaataatag ccttccaatt ggccttgtgc ctactaattc 1741 aacaaacact gtcatggacc aaaaaaattt gaagatgtca actcctggcc aaatgaaagc 1801 ccaagaaatt gaaagaaccc ctccaacaaa ctttaaaagg acattagaag agtccaattc
```

-continued

```
1861 tggcccctg atgaagaagc atagacgaaa tggcttaagt cgaagtagtg gtgctcagcc
1921 tgcaagtctc cccacaacct cacagcgaaa gaactctgtt aaactcacca tgcgacgcag
1981 acttaggggc cagaagaaaa ttggaaatcc tttacttcat caacacagga aaactgtttg
2041 tgtttgctga aatgcatctg ggaaatgagg ttttccaaa ettaggatat aagagggctt
2101 tttaaatttg gtgccgatgt tgaactttt ttaaggggag aaaattaaaa gaaatataca
2161 gtttgactt ttggaattca gcagttttat cctggccttg tacttgcttg tattgtaaat
2221 gtggattttg tagatgttag ggtataagtt gctgtaaaat ttgtgtaaat ttgtatccac
2281 acaaattcag tctctgaata cacagtattc agagtctctg atacacgta attgtgacaa
2341 tagggctaaa tgtttaaaga aatcaaaaga atctattaga ttttagaaaa acatttaaac
2401 tttttaaaat acttattaaa aaatttgtat aagccacttg tcttgaaaac tgtgcaactt
2461 tttaaagtaa attattaagc agactggaaa agtgatgtat tttcatagtg acctgtgttt
2521 cacttaatgt tcttagagc caagtgtctt taaacatta ttttttattt ctgatttcat
2581 aattcagaac taaattttc atagaagtgt tgagccatgc tacagttagt cttgtcccaa
2641 ttaaaatact atgcagtatc tcttacatca gtagcatttt tctaaaacct tagtcatcag
2701 atatgcttac taaatcttca gcatagaagg aagtgtgttt gcctaaaaca atctaaaaca
2761 attcccttct ttttcatccc agaccaatgg cattattagg tcttaaagta gttactccct
2821 tctcgtgttt gcttaaaata tgtgaagttt tccttgctat ttcaataaca gatggtgctg
2881 ctaattccca acatttctta aattatttta tatcatacag ttttcattga ttatatgggt
2941 atatattcat ctaataaatc agtgaactgt tcctcatgtt gctgaatttg tagttgttgg
3001 tttattttaa tggtatgtac aagttgagta tcccttatcc aaaatgcttg ggaccagaag
3061 tgtttcagat tttttaaaat tttggaatat ttgctttata ctgagctttt gagtgttccc
3121 aatctgaaat tcaaaatgct ctaatgagca tttcctttga gcatcatgcc tgctctgaaa
3181 aagtttctga ttctggagca ttttggattt tggattttca gattagggat gcttaacctg
3241 gattaacatt ctgttgtgcc atgatcatgc tttacagtga gtgtatttta tttatttatt
3301 atttgtttg tttgtttgag atggagtctc actctgtcat ccaggctaga gtgcagtggc
3361 gtgatctcgg ctgactgcaa cctctgcctc ccgggttcaa gtgattctcc tgcctcaatc
3421 tctctcccca gaagctggga ttacaggtgt gtgccaccac acccggctaa tttttttttt
3481 ttttttgag atggagtcta gctctgtcat ccaggctgga gtgcagtggt gtgatctcgg
3541 ctccctgcaa cctctgcctt ctgggttcct gcgattctcc tgcctcagcc tcctgagtag
3601 ctgagattac aggcacgcgc cactgtgccc agccaatttt tgtattttta gtagagatgg
3661 ggtttcacat gtcagtcatg ctggtcttga tctcctgacc tcgtgatcca cccgcctcga
3721 cctcccaaag tactgggatt acaggcgtga gccaccgcat ccggcctgag ttttatgctt
3781 tcaatgtatt tcttacattt cagttcaagt gattttcatg tctcagcctc ctgagtagct
3841 ggaactacag gtgcgtgcca ccatgcctgg ctaagttttg tattttagt agagatgggt
3901 tttcatcatg ttggccaaga tggtcttgat ctcttgacct catgatccac cagcctaggc
3961 ctcccaaagt gctgggatta caggtgtgag ccaccgtgcc cagccaacta tgccattatt
4021 taaccatgtc cacacattct ggttattttc aatatttgc agaagataat tcttgatcgg
4081 tgtgtcttat gccacaagga ttaaaatatg tattcattgc tacaaaacaa tatctcgaaa
4141 tttagcagtt taaacaaca aatattatct ccagttctg agcctcagaa atctgagagt
4201 ggtttagctg ggtgatagtc tcgtggtttt ggtcaagcta ccaaccaggg ctacaatctt
```

```
-continued
4261 tcgaaggtgt cattggggct agaagatctg cttcccgcaa gactcacagc tgttggcagg 4321 agacctcagt ttgttgccac atgttcccct ccagagggcc tctcacaaca tggcagttat 4381 ttgtcoccag agcaagcaac accggagggc aaggaagaag ccatgatgtt ttttgtaacc 4441 tagcctctga aagtgtcata ccaattctgt attttgttgg tcacacagac caagtcaact 4501 acaacgtggg agactcctac acaaggcatg aattctagga ggtgggcatt tttaagtgtc 4561 atctggaagg aggctgtcac aacctggaag ttaaaagcat tgatattctg aaatacagcg 4621 tgtataacat tgttttagta gggtgtgcaa tagttatgtt ttggtaatag cattaatgaa 4681 caatgttatt ttcatcttcc agacatctgg aagattgctc tagtggagta aaacatctta 4741 atgtattttg tccctaaata aactatctca ctaacaaaaa aaaaaaaaa
```

By "PPM1D inhibitor" is meant an agent that reduces or eliminates a biological function or activity of a PPM1D polypeptide. Exemplary biological activities or functions of a PPM1D polypeptide include serine/threonine phosphatase activity, dephosphorylation of p53 and Chk1, and negative regulation of cell stress response. Examples of a PPM1D inhibitor include, without limitation, GSK2830371 and CCT007093. In particular embodiments, the PPM1D inhibitor is GSK2830371 or CCT007093. Other PPM1D inhibitors are described in, for example, Belova, Demidov et al, Cancer Biology & Therapy 2005, October; 4(10):1154-8, and Yagi, Sakaguchi et al, Bioorganic & Medicinal Chemistry Letters 2012 Jan. 1; 22(1):729-32.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. In some embodiments, the reference sequence is a wild-type PPM1D polynucleotide or polypeptide sequence. For polypeptides, the length of the reference polypeptide sequence will generally be at least about 16 amino acids, at least about 20 amino acids, or at least about 25 amino acids. The length of the reference polypeptide sequence can be about 35 amino acids, about 50 amino acids, or about 100 amino acids. For nucleic acids, the length of the reference nucleic acid sequence will generally be at least about 50 nucleotides, at least about 60 nucleotides, or at least about 75 nucleotides. The length of the reference nucleic acid sequence can be about 100 nucleotides, about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the invention, but which does not substantially recognize and bind other molecules in a sample, for example, a biological sample, which naturally includes a polypeptide of the invention. In some embodiments, a capture reagent specifically binds a PPM1D polypeptide or polynucleotide. In some embodiments, the capture reagent that specifically binds a PPM1D polypeptide or polynucleotide is an antibody, a primer, or a probe.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, or at least about 50% formamide. Stringent temperature conditions will ordinarily include temperatures of at least about 30° C., at least about 37° C., and at least about 42° C. Varying additional parameters, such as hybridization time, the concentration of detergent, e.g., sodium dodecyl sulfate (SDS), and the inclusion or exclusion of carrier DNA, are well known to those of ordinary skill in the art. Various levels of stringency are accomplished by combining these various conditions as needed. In one embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide, and 100 µg/ml denatured salmon sperm DNA (ssDNA). In yet another embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those of ordinary skill in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will be less than about 30 mM NaCl and 3 mM trisodium citrate, or less than about 15 mM NaCl and 1.5 mM trisodium citrate. Stringent temperature conditions for the wash steps will ordinarily include a temperature of at least about 25° C., at least about 42° C., and at least about 68° C. In one embodiment, wash steps will occur at 25° C. in 30 mM NaCl, 3 mM trisodium citrate, and 0.1% SDS. In another embodiment, wash steps will occur at 42° C. in 15 mM NaCl, 1.5 mM trisodium citrate, and 0.1% SDS. In yet another embodiment, wash steps will occur at 68° C. in 15 mM NaCl, 1.5 mM trisodium citrate, and 0.1% SDS. Additional variations on these conditions will be readily apparent to those of ordinary skill in the art. Hybridization techniques are well known to those of ordinary skill in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence is at least 60%, at least 80%, at least 85%, at least 90%, at least 95% or even at least 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, mouse, rat, or feline. In some embodiments, the subject is a human.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A depicts a CRISPR-Cas9 system with an sgRNA targeting the last exon of hPPM1D, which was used to induce mutations in exon six of PPM1D. FIG. 1B provides immunoblots showing that mutations in the last exon of PPM1D result in truncation of the protein in subcloned and pooled Molm13 cells. FIG. 1C is a plot showing that mutations in PPM1D resulted in a resistance to treatment with Cytarabine. FIG. 1D is a plot showing that PPM1D mutant cells had a competitive advantage under the selective pressure of chemotherapy (Cytarabine) treatment. FIG. 1E is a plot showing that PPM1D mutations led to chemotherapy resistance. PPM1D mutant cells had a competitive advantage under the selective pressure of Cyclophosphamide treatment.

FIG. 2A is a map of the PPM1D gene showing the location of frame-shift and nonsense mutations in PPM1D identified in the blood cells of a cohort of 29,562 persons. FIG. 2B provides immunoblots of whole cell lysates from Molm13 control cells (control), PPM1D-mutant pooled clones and PPM1D frame-shift (fs) mutant single cell clones probed with anti-PPM1D and anti-Actin. FIG. 2C is a plot depicting viability assays in Molm13 PPM1D-mutant or control single cells clones that were treated with increasing concentrations of cytarabine for 72 hours. FIG. 2D is a plot depicting viability assays in Molm13 PPM1D-mutant or control single cells clones that were treated with increasing concentrations of cyclophosphamide for 72 hours. FIG. 2E is a plot depicting viability assays in Molm13 PPM1D-mutant or control single cells clones that were treated with increasing concentrations of cisplatin for 72 hours. FIG. 2F is a plot depicting flow cytometric readout of competition experiment with 5% pooled Molm13 PPM1D-mutant cells and 95% pooled Molm13 control cells exposed to 100 nM Cytarabine or vehicle for 24 days. FIG. 2G is a plot depicting flow cytometric readout of competition experiment with 5% pooled Molm13 PPM1D-mutant cells and 95% pooled Molm13 control cells exposed to 350 nM Cyclophosphamide or vehicle for 24 days. FIG. 2H is a plot depicting flow cytometric readout of competition experiment with 5% pooled Molm13 PPM1D-mutant cells and 95% pooled Molm13 control cells exposed to 1 µM Cisplatin or vehicle for 24 days. FIG. 2I is a plot depicting flow cytometric analysis of peripheral blood leukocytes in mice exposed to several rounds of cytarabine or vehicle treatment. PPM1D and control sgRNAs were identified through their fluorophores.

FIG. 3A is a plot depicting Next Generation Sequencing readout of cells collected on day 4 and 16 of in vitro competition experiment in which 5% pooled Molm13 PPM1D-mutant cells and 95% Molm13 control cells were mixed and exposed to 100 nM Cytarabine or vehicle. FIG. 3B is a plot depicting Next Generation Sequencing readout of cells collected on day 4 and 16 of in vitro competition experiment in which 5% pooled Molm13 PPM1D-mutant cells and 95% Molm13 control cells were mixed and exposed to 350 nM Cyclophosphamide or vehicle. FIG. 3C is a plot depicting Next Generation Sequencing readout of cells collected on day 4 and 16 of in vitro competition experiment in which 5% pooled Molm13 PPM1D-mutant cells and 95% Molm13 control cells were mixed and exposed to 1 µM Cisplatin or vehicle.

FIG. 4A is a graph showing that PPM1D mutant cKIT positive cells had increased serial replating potential in vitro. FIG. 4B provides an in vivo experimental schema. cKIT positive cells from a Cas9$^{+/-}$VavCre$^+$ mouse were infected with sgRNAs targeting mPPM1D or non-coding region of the genome (control). Eight hours after lentiviral transduction, cKIT positive cells were mixed in 1 to 10 or 1 to 1 ratio of PPM1D mutant to control cells and transplanted into irradiated syngeneic recipients. FIG. 4C is a plot showing that the percentage of PPM1D mutant cells increased >2.5 fold over two weeks in vivo while the percentage of control cells remained stable.

FIG. 6A is a plot showing flow cytometric analysis of peripheral blood lymphocytes in mice exposed to several rounds of cytarabine or vehicle treatment. PPM1D and control sgRNAs were identified through their fluorophores. FIG. 6B is a plot showing flow cytometric analysis of monocytes in mice exposed to several rounds of cytarabine or vehicle treatment. PPM1D and control sgRNAs were identified through their fluorophores. FIG. 6C is a plot showing flow cytometric analysis of granulocytes in mice exposed to several rounds of cytarabine or vehicle treatment. PPM1D and control sgRNAs were identified through their fluorophores. FIG. 6D is a plot showing change in the ratio of PPM1D sgRNAs to total sgRNAs (PPM1D plus control sgRNAs) after three rounds of treatment with cytarabine compared to pre-treatment, assessed by flow cytometric analysis of the sgRNA fluorophores in peripheral blood leukocytes. FIG. 6E is a plot showing change in the ratio of PPM1D sgRNAs to total sgRNAs (PPM1D plus control sgRNAs) after three rounds of treatment with cytarabine compared to pre-treatment, assessed by flow cytometric analysis of the sgRNA fluorophores in lymphocytes. FIG. 6F is a plot showing change in the ratio of PPM1D sgRNAs to total sgRNAs (PPM1D plus control sgRNAs) after three rounds of treatment with cytarabine compared to pre-treatment, assessed by flow cytometric analysis of the sgRNA fluorophores in monocytes. FIG. 6G is a plot showing change in the ratio of PPM1D sgRNAs to total sgRNAs (PPM1D plus control sgRNAs) after three rounds of treatment with cytarabine compared to pre-treatment, assessed by flow cytometric analysis of the sgRNA fluorophores in granulocytes. FIG. 6H is a plot of the ratio of PPM1D indels to total indels (control plus PPM1D) as identified through Next Generation Sequencing in cKit$^+$ cells pre-transplant and post three rounds of cytarabine or vehicle treatment.

FIG. 7A is a plot depicting Log-fold enrichment of sgRNAs targeting PPM1D (black dots) as assessed through Next Generation Sequencing of integrated sgRNAs in Molm13 cells exposed to cytarabine treatment versus vehicle treatment at 12 days. FIG. 7B is a plot depicting Log-fold enrichment of sgRNAs targeting PPM1D (black dots) as assessed through Next Generation Sequencing of integrated sgRNAs in Molm13 cells exposed to cytarabine treatment versus vehicle treatment at 20 days. FIG. 7C is a plot depicting Log-fold enrichment of sgRNAs targeting PPM1D (black dots) as assessed through Next Generation Sequencing of integrated sgRNAs in Molm13 cells exposed to cytarabine treatment versus vehicle treatment at 24 days. The line represents the locally weighted scatterplot smoothing (LOESS).

FIG. 8A is a plot showing Log-fold enrichment of sgRNAs (black dots) in Molm13 cells exposed to cytarabine treatment versus vehicle treatment, 12 day time-point. The line represents the locally weighted scatterplot smoothing (LOESS) of 0.1. Overlaid are frame-shift and non-sense mutations (black bars) identified in the blood cells of 29,562 persons as described in FIG. 2A. FIG. 8B is a vector map of the degradation reporter vector, with different PPM1D cDNA constructs inserted. FIG. 8C is a graph showing EGFP/mCherry ratio for Molm13 cells with overexpression of wild type PPM1D, truncated PPM1D or the C-terminal end of PPM1D. FIG. 8D is a graph showing EGFP/mCherry ratio for Molm13 p53$^{-/-}$ cells with overexpression of wild type PPM1D, truncated PPM1D or the C-terminal end of PPM1D. FIG. 8E is a graph showing EGFP/mCherry ratio in Molm13 cells before and after exposure to MG132 (10 µM, 6 hours), normalized to pre-treatment values. FIG. 8F is a plot showing cell viability analysis in Molm13 control cells (control), Molm13 PPM1D truncating mutant cells (PPM1D mutant) and Molm13 cells with overexpression of wild-type PPM1D (WT overexpression). Cells were exposed to increasing concentrations of cytarabine for 72 hours. For all experiments the following apply: *=p<0.05, =p<0.01, *=p<0.001, ****=p<0.0001

FIG. 9A provides immunoblots showing that PPM1D mutant cells had decreased phosphorylation of p53 and Chk1 in response to treatment with Cytarabine. Whole cell lysates of Molm13 PPM1D-mutant and Molm13 control single cell clones exposed to 400 nM cytarabine for 4 hours were probed with anti-p53 Ser15 and anti-Chk1 Ser345. FIG. 9B is a graph showing percent Annexin V positive cells in cells treated with Cytarabine or vehicle. Molm13 PPM1D-mutant and control single cell clones exposed to 400 nM cytarabine or vehicle treatment for 24 hours were analyzed by Annexin V staining and flow cytometric analysis. FIG. 9C is a graph depicting percent viable cells from Molm13 PPM1D-mutant and control single cell clones after 24 hours of exposure to 100 nM cytarabine, as analyzed by BrdU staining and flow cytometric analysis. FIG. 9D is a heatmap of phosphosites that belong to the KEGG P53 pathway and were significantly regulated with an FDR<0.1 in either Molm13 PPM1D mutant/wild-type at baseline (Mut/wt) or after 4 hour treatment with 400 nM cytarabine (AraC). FIG. 9E is a chart depicting the consensus sequence of PPM1D based on substrate analysis of 43 substrate candidates of PPM1D. FIG. 9F depicts 43 potential PPM1D substrate sites on pSer/Thr residues on 25 proteins. Phosphosites were significantly down-regulated in either Mut/wt of AraC treated or untreated samples (FDR<0.05) and unregulated for PPM1Di/ctrl (FDR<0.05). Only localized sites were considered. Figure discloses SEQ ID NOS 4-20 and 20-31, respectively, in order of appearance. FIG. 9G depicts a schema illustrating the components of the DNA-damage response pathway that are targeted by PPM1D in leukemia cells, based on the results from the phosphoproteomics analysis. Phospho-targets of PPM1D identified by mass spectrometry (FDR<0.1) are shown in bold. Predicted PPM1D target sites that were based on the identified consensus sequence with a glutamine at +1 and >2 acidic residues (p=3.595e-13, Fisher's exact test) are shown in italics.

FIG. 10A provides immunoblots showing that PPM1D inhibition increased the phosphorylation of p53 during Cytarabine treatment. Whole cell lysate of Molm13 PPM1D-mutant singe cell clones 1 hour pretreated with the indicated concentrations of GSK2830371 and exposed to 400 nM cytarabine or vehicle were probed for p53 Ser15 and Actin as a loading control. FIG. 10B is a heatmap of phosphosites belonging to the KEGG P53 pathway that are significantly regulated (FDR<0.1). Molm13 PPM1D mutant/wild-type after 4 hour treatment with 400 nM cytarabine (AraC) (Mut/wt) or Molm13 PPM1D-mutant cells treated with 400 nM AraC+1 µM PPM1D inhibitor GSK2830371/Molm13 PPM1D mut cells treated with 400 nM AraC (Mut AraC+iPPM1D/Mut AraC) for 4 hours. FIG. 10C is a plot showing that the sensitivity of PPM1D mutant cells to Cytarabine increased when combined with PPM1D inhibition. Viability analysis of Molm13 PPM1D-mutant cells pre-treated for 1 hour with 3 µM GSK2830371 or vehicle, and Molm13 control single cell clones, exposed to increasing doses of 72-hour cytarabine treatment. FIG. 10D is a plot showing that PPM1D inhibition reversed the competitive advantage of PPM1D mutant cells during treatment with Cytarabine. Competition experiment with Molm13 PPM1D-mutant pooled cells and control pooled cells mixed in resp. a 1:9 ratio and exposed to 100 nM cytarabine, 100 nM cytarabine plus 100 nM GSK2830371 or vehicle treatment. FIG. 10E is a plot showing that PPM1D mutant cells had an increased sensitivity to PPM1D inhibition with compound GSK2830371. 72 hour cell viability analysis in Molm13 PPM1D-mutant and control single cell clones after exposure to increasing doses of GSK2830371. FIG. 10F is a graph showing percent Annexin V positive cells in cells treated with PPM1D inhibitor or vehicle. Annexin V staining and flow cytometric analysis of Molm13 PPM1D-mutant and control single cell clones exposed to 3 µM of GSK2830371. *=p<0.05, =p<0.01, *=p<0.001

FIG. 11A is a plot showing that PPM1D mutant cells had an increased sensitivity to PPM1D inhibition with compound GSK2830371. FIG. 11B is a plot showing PPM1D mutant cells were sensitive to PPM1D inhibition with compound CCT007093. PPM1D mutant cells had an increased sensitivity to treatment with the PPM1D inhibitor CCT007093 in comparison to wild-type (wt) control cells.

FIG. 12 is a table of showing generation of PPM1D sgRNA sequences for the saturation mutagenesis CRISPR screen. Figure discloses sgRNA Target Sequences as SEQ ID NOs: 36-300, respectively, in order of appearance. Figure discloses Target Context Sequences as SEQ ID NOs: 301-565, respectively, in order of appearance.

DETAILED DESCRIPTION OF THE INVENTION

Figure 1A:
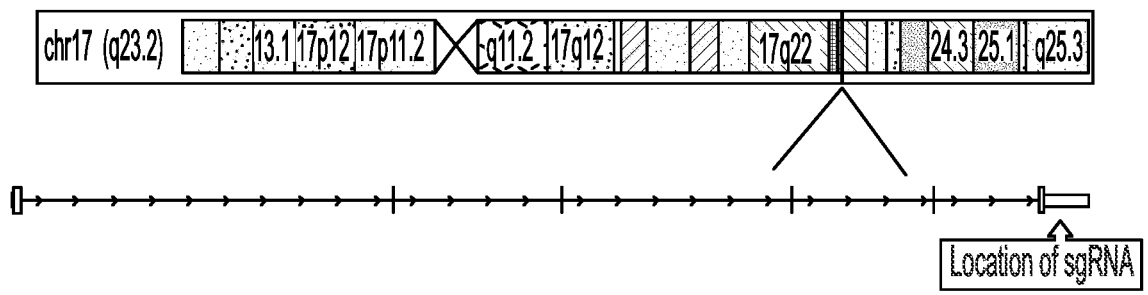
FIGS. 1A-1E show that PPM1D mutations lead to chemotherapy resistance.

The invention features compositions and methods that are useful for treating a cancer in a subject, particularly a subject that is resistant to chemotherapy and/or has mutations in PPM1D. The invention also features compositions and methods that are useful for treating clonal hematopoiesis of indeterminate potential (CHIP) in a subject, particularly a subject that has mutations in PPM1D. The invention is based, at least in part, on the discovery that PPM1D truncating mutations caused clonal dominance and chemotherapy resistance, which could be reversed by PPM1D inhibition.

Results described herein demonstrate that truncating PPM1D mutations, which can be found in the blood of individuals with hematologic cancers, as well as in individuals with a pre-malignant state for hematologic cancers, and are causally associated with resistance to chemotherapy in both normal and malignant hematopoietic cells. Importantly, this finding allows for the reversal of clonal dominance and chemotherapy resistance caused by these mutations through the use of PPM1D inhibitors.

PPM1D mutations have been identified in the blood of individuals, particularly after exposure to chemotherapy. It was not known whether PPM1D mutations were causally related to blood cell chemotherapy resistance. Results described herein demonstrate a causal association, and also demonstrates that a therapy targeting PPM1D specifically can be used to treat malignant and non-malignant cells bearing PPM1D mutations with PPM1D inhibitor to reverse the chemotherapy resistance and suppress the neoplastic clone.

Described herein is a finding that truncating, gain of function PPM1D mutations cause clonal dominance and chemotherapy resistance specifically in hematopoietic cells. While amplification of PPM1D has been described in some solid tumors, and PPM1D mutations have been described to occur in the blood of cancer patients, no direct evidence for blood cell clonal dominance due to chemotherapy resistance to be caused by these truncating PPM1D mutations has been provided.

PPM1D inhibitors have been described to be effective in solid tumor cell lines and in vivo models that have overexpression of PPM1D, but they have not before been used in cell lines or in vivo models with truncating PPM1D mutations, nor have they been tested in hematologic cells. In addition, no studies have provided evidence for reversal of chemotherapy resistance and clonal dominance caused by PPM1D mutations in blood cells using PPM1D inhibitors.

In some aspects, the invention features a method of treating a cancer in a pre-identified subject, where the subject is pre-identified as having a mutation in a PPM1D polynucleotide or polypeptide relative to a reference. In some embodiments, the cancer is a hematologic cancer. Identification of patients with hematologic cancers who have PPM1D mutations should be selected for treatment with a PPM1D inhibitor. The inclusion of patients for this treatment (or studies) will be based on the presence of truncating PPM1D mutations as identified by DNA sequencing of blood, bone marrow, or tumor sample.

Further, methods described herein can be used as an intervention to prevent the development of future secondary hematologic malignancies and/or therapy-related hematological malignancy in those currently being treated for cancer or those who have been treated for cancer (and have a PPM1D clone). A significant proportion of individuals being treated for cancer later develop a secondary hematologic malignancy. This invention discloses a method to identify a group at high-risk of developing a secondary hematologic malignancy (i.e., the presence of a pre-existing PPM1D mutation), and of treating that group with a PPM1D inhibitor in combination with chemotherapy for their cancer to lower the risk of secondary malignancy. By "in combination" is meant before, during, or after chemotherapy.

In other aspects, the invention provides a method of increasing sensitivity or reversing resistance of a cancer cell to a chemotherapeutic agent. The methods described herein are useful for reversal or prevention of chemotherapy resistance caused by PPM1D mutations in patients with clonal hematopoiesis of indeterminate potential (CHIP). CHIP is defined as the presence of an expanded clonal hematopoietic population due to a somatic mutation in a hematopoietic stem cell. CHIP progresses to a frank malignancy at a rate of approximately 1% per year. Methods provided by the invention identify individuals with CHIP due to PPM1D mutations that can benefit from a PPM1D targeted therapy to prevent future malignancy.

In still other aspects, the invention provides targeted treatment of malignancies that have PPM1D mutations. In some aspects, the targeted treatment is an agent that inhibits the expression or activity of a PPM1D polynucleotide or polypeptide. In some embodiments, the agent is a small molecule PPM1D inhibitor. The treatment can be administered to patients with solid tumors or hematological malignancies that carry truncating PPM1D mutations, such as gliomas, myelodysplastic syndrome, or acute myeloid leukemia. The PPM1D inhibitor treatment can be combined with chemotherapy treatment, or given (neo)adjuvantly. The addition of a PPM1D inhibitor to the treatment protocol of patients with PPM1D mutations specifically targets PPM1D mutant clones, which confer chemotherapy resistance. In some embodiments, the treatment is administered to a patient with solid tumors and hematological malignancies. In some other embodiments, the treatment is administered to a patient having a truncating PPM1D mutation. In some embodiments, the treatment is administered to a patient with a solid tumor, a hematological malignancy and/or clonal hematopoiesis of indeterminate potential (CHIP).

PPM1D Mutations and Clonal Dominance

PPM1D (WIP1) is a known oncogene that has been associated with a poor prognosis in patients with solid tumors (Yang, H. et al., *Tumor Biol* 36, 2179-2184 (2014); PENG, T. S. et al., *Exp Ther Medicine* 8, 430-434 (2014); Lu, X. et al., *Cancer Metastasis Rev.* 27, 123-35 (2008)). While overexpression and amplification of PPM1D are relatively common, mutations in PPM1D have only recently been described. In a seminal study by Ruark et al, PPM1D mutations were found to be strongly associated with breast and ovarian cancer (Ruark, E. et al., *Nature* 493, 406-10 (2013)). The mutations all clustered in the last exon of PPM1D, leading to a truncation of the protein. Intriguingly, the mutations were found in the lymphocyte DNA, but not the tumor DNA of these patients. Since then, several others groups have reported the presence of truncating PPM1D mutations in the blood, but not tumor tissue of patients with breast, ovarian and lung cancer (Zajkowicz, A. et al., Br. *J. Cancer* 112, 1114-20 (2015); Akbari, M. R. et al., *J. Natl. Cancer Inst.* 106, djt323 (2014)).

In addition to being found in the blood of cancer patients, somatic truncating PPM1D mutations were recently identified in hematopoietic cells of aging adults (Genovese, G. et al., *N. Engl. J. Med.* 371, 2477-87 (2014)). Again, the mutations were found to cluster in the last exon of the gene, leading to truncation of the protein. While PPM1D was among the most commonly mutated genes in clonal hematopoiesis, it has in contrast to other CHIP mutations, not been associated with hematological malignancies until recently (Lindsley et al., *N. Engl. J. Med.* 376, 536-547 (2017)). PPM1D truncating mutations have been detected in myelodysplastic syndrome (MDS) and these mutations are strongly enriched in therapy related MDS (Lindsley et al., *N. Engl. J. Med.* 376, 536-547 (2017)).

Truncating mutations of PPM1D have been shown to cause gain of function of PPM1D, which is a member of the PP2C family of Ser/Thr protein phosphatases (Kleiblova, P. et al., *J. Cell Biol.* 201, 511-21 (2013); Jaiswal, S. et al., *N. Engl. J. Med.* 371, 2488-98 (2014); Xie, M. et al., *Nat. Med.* 20, 1472-8 (2014)). As its original name indicates, Wild-type p53 Induced Phosphatase 1 (Wip1) is induced by p53 and is best known for its role as a negative regulator of the stress response. Targets of PPM1D include p53, Chk1/Chk2, ATM and ATR.

The presence of PPM1D mutations in clonal hematopoiesis implies a clonal dominance phenotype for PPM1D mutant cells. What is more, the finding of PPM1D mutations in the blood of cancer patients, who are likely to have experienced genotoxic stress due to chemotherapy treatment, combined with the function of PPM1D as a negative regulator of p53, indicates that PPM1D mutant cells can selectively expand during genotoxic stress.

The results presented here provide evidence for clonal dominance and chemotherapy resistance caused by truncating, gain of function PPM1D mutations. Without being bound by theory, it is believed that this leads to preferential expansion of PPM1D mutant cells during genotoxic stress. While gain of function driver mutations in cancer are rare, mutations in PPM1D were the most common new mutations identified in clonal hematopoiesis. In addition, truncating PPM1D mutations were recently shown to occur in 6% of patients with high-risk myelodysplastic syndromes (MDS) and to be enriched in therapy-related myelodysplastic syndromes (t-MDS), where they occur in 15% of cases (Lindsley et al., *N. Engl. J. Med.* 376, 536-547 (2017)). While no studies have reported on the presence of PPM1D mutations in acute myeloid leukemia (AML), it is believed that future studies will identify these mutations in a subset of patients with secondary or therapy related AML.

The finding that PPM1D mutations are gain of function is of great clinical relevance, as gain of function mutations are more amenable to pharmacological intervention. Indeed, our results demonstrate reversal of PPM1D induced clonal dominance through PPM1D inhibition. In addition, results herein demonstrate that chemotherapy resistance caused by PPM1D mutations can be overturned by the addition of low-dose or high dose PPM1D inhibitors to chemotherapy treatment. The fact that these results were obtained using two mechanistically different PPM1D inhibitors, diminishes the chances of the results being due to a specific compound.

While the use of PPM1D inhibitors on solid tumor cell lines with amplification of PPM1D has been reported in the past, no studies have employed PPM1D inhibitors for truncating, gain-of-function PPM1D mutations (Gilmartin, A. G. et al., Nat. Chem. Biol. 10, 181-7 (2014); Rayter S et al., Oncogene. 27, 1036-1044 (2008)). In addition, the use of PPM1D inhibition in hematological malignancies has not before been shown. Finally, reversal of chemotherapy resistance and clonal dominance by PPM1D inhibition is a new and clinically relevant finding.

Lastly, in view of the strong biological relationship between PPM1D and p53, pharmacological intervention of PPM1D may provide a route to modulation of p53. Considering the central role of p53 in many tumors, and the difficulties of targeting this oncogene, modulation of p53 through PPM1D may open the door to effective treatments for a multitude of malignancies.

Methods of Treatment

Results herein demonstrate reversal of chemotherapy resistance by PPM1D inhibition, which is a new and clinically relevant finding. Thus, the present invention provides methods of treating a cancer, particularly chemotherapy-resistant cancer or cancer associated with a PPM1D mutation, and/or disorders or symptoms thereof, which comprise administering a therapeutically effective amount of a pharmaceutical composition comprising an agent that inhibits the expression or activity of a PPM1D polynucleotide or polypeptide herein (e.g., a PPM1D inhibitor or an inhibitory polynucleotide that reduces PPM1D expression) to a subject (e.g., a mammal such as a human). Thus, one embodiment is a method of treating a subject suffering from or susceptible to a cancer, particularly chemotherapy-resistant cancer or cancer associated with a PPM1D mutation, or disorder or symptom thereof. The method includes the step of administering to the mammal a therapeutic amount of an amount of an agent herein sufficient to treat the disease or disorder or symptom thereof, under conditions such that the disease or disorder is treated.

The methods herein include administering to the subject (including a subject identified as in need of such treatment) an effective amount of an agent described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the agents herein, such as an agent that inhibits the expression or activity of a PPM1D polynucleotide or polypeptide herein, to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, PPM1D mutation, family history, and the like). The agents herein may be also used in the treatment of any other disorders in which a PPM1D mutation may be implicated.

Pharmaceutical Compositions

The present invention features compositions useful for treating or preventing a cancer, chemotherapy-resistant cancer, a cancer associated with a PPM1D mutation, clonal hematopoiesis of indeterminate potential (CHIP), or clonal hematopoiesis associated with a PPM1D mutation in a subject. In some embodiments, the composition comprises one or more of a therapeutic agent as described herein (e.g., an agent that inhibits the expression or activity of a PPM1D polynucleotide or polypeptide, a chemotherapeutic agent, or any combination thereof). In some embodiments, the therapeutic agent is a small molecule PPM1D inhibitor. In some other embodiments, the therapeutic agent is an inhibitory polynucleotide that inhibits expression of PPM1D. In some embodiments, the therapeutic agent is a chemotherapeutic agent. In some embodiments, the composition further comprises a vehicle for intracellular delivery of a polypeptide or polynucleotide (e.g., a liposome).

The administration of a composition comprising a therapeutic agent herein for the treatment or prevention of a cancer, particularly chemotherapy resistant and/or PPM1D mutation associated cancer or treating clonal hematopoiesis of indeterminate potential (CHIP)), particularly associated with a PPM1D mutation, may be by any suitable means that results in a concentration of the therapeutic that, combined with other components, is effective in ameliorating, reducing, or stabilizing a cancer or clonal hematopoiesis of indeterminate potential in a subject. In some embodiments, the cancer is a blood cancer, such as acute myeloid leukemia. The composition may be administered systemically, for example, formulated in a pharmaceutically-acceptable buffer such as physiological saline. Preferable routes of administration include, for example, subcutaneous, intravenous, intraperitoneally, intramuscular, or intradermal injections that provide continuous, sustained levels of the agent in the patient. The amount of the therapeutic agent to be administered varies depending upon the manner of administration, the age and body weight of the patient, and with the clinical symptoms of the cancer. Generally, amounts will be in the range of those used for other agents used in the treatment of cancers, although in certain instances lower amounts will be needed because of the increased specificity of the agent. A composition is administered at a dosage that decreases effects or symptoms of cancer as determined by a method known to one of ordinary skill in the art.

The therapeutic agent (e.g., an agent that inhibits the expression or activity of a PPM1D polynucleotide or polypeptide, a chemotherapeutic agent, or any combination thereof) may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active agent substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with an organ, such as the liver; (v) formulations that allow for convenient dosing, such that doses are administered, for example, once every one or two weeks; and (vi) formulations that target a cancer using carriers or chemical derivatives to deliver the therapeutic agent to a particular cell type (e.g., liver cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the agent in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those of ordinary skill in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a cancer, the composition may include suitable parenterally acceptable carriers and/or excipients. The active therapeutic agent(s) (e.g., an agent that inhibits the expression or activity of a PPM1D polynucleotide or polypeptide, a chemotherapeutic agent, or any combination thereof, as described herein) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

In some embodiments, the composition comprising the active therapeutic (e.g., an agent that inhibits the expression or activity of a PPM1D polynucleotide or polypeptide, a chemotherapeutic agent, or any combination thereof), is formulated for intravenous delivery. As indicated above, the pharmaceutical compositions according to the invention may be in the form suitable for sterile injection. To prepare such a composition, the suitable therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the agents is only sparingly or slightly soluble in water, a dissolution enhancing or solubilizing agent can be added, or the solvent may include 10-60% w/w of propylene glycol or the like.

Polynucleotide Therapy

Another therapeutic approach for treating or preventing a cancer, particularly a chemotherapy resistant and/or PPM1D mutation associated cancer, or clonal hematopoiesis of indeterminate potential (CHIP), particularly associated with a PPM1D mutation, is polynucleotide therapy using an inhibitory polynucleotide that reduces PPM1D expression. In some aspects, the invention provides a therapeutic composition comprising an inhibitory polynucleotide that reduces PPM1D expression (e.g., siRNA).

Provided herein are inhibitory polynucleotides that reduce PPM1D expression. Delivery or expression of such polynucleotides in a cell, such as a cell in a subject having a chemotherapy resistant cancer associated with PPM1D mutation, is expected to increase sensitivity to chemotherapy in the subject. Such inhibitory polynucleotides can be delivered to cells of a subject having a cancer (in particular, subjects having a chemotherapy resistant and/or PPM1D mutation associated cancer) or clonal hematopoiesis of indeterminate potential (in particular, CHIP associated with a PPM1D mutation). The inhibitory polynucleotides must be delivered to or expressed in the cells of a subject such that expression levels of PPM1D in the cells are effectively reduced.

Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding an inhibitory polynucleotide that reduces PPM1D expression, can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). In some embodiments, a viral vector is used to administer an inhibitory polynucleotide that reduces PPM1D expression systemically.

Non-viral approaches can also be employed for the introduction of the therapeutic to a cell of a patient requiring treatment of a cancer (particularly, a chemotherapy resistant and/or PPM1D mutation associated cancer). For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). In some embodiments, the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of a polynucleotide (e.g., DNA) encoding inhibitory polynucleotides (e.g., siRNA) into the affected tissues of a patient can also be accomplished by transferring a polynucleotide encoding the inhibitory polynucleotide into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Delivery of polynucleotides of the invention may also include or be performed in combination with gene or genome editing methods, such as CRISPR-Cas systems, to introduce polynucleotides encoding inhibitory polynucleotide PPM1D in cells. Gene or genome editing methods such as CRISPR-Cas systems are further described in for example, Sander et al. (2014), Nature Biotechnology 32, 347-355; Hsu et al. (2014), Cell 157(6): 1262-1278.

Stratifying Patient Population and Monitoring Effectiveness of Chemotherapy

The results of studies described herein provide evidence for chemotherapy resistance caused by truncating, gain of function PPM1D mutations. Thus, information on PPM1D status in a subject having cancer may predict clinical response of the cancer to chemotherapeutic agents, particularly DNA damaging agents. Accordingly, in one aspect, the invention provides a method of identifying a subject having a cancer that is resistant or sensitive to a chemotherapeutic agent, particularly a DNA damaging agent. The method includes the step of measuring a level and/or sequence of a PPM1D polynucleotide or polypeptide in a biological sample obtained from the subject. In some embodiments, a subject is identified as having a cancer that is resistant to a chemotherapeutic agent if a mutation in a PPM1D polynucleotide or polypeptide relative to a reference sequence is detected. In some embodiments, a subject is identified as having a cancer that is sensitive to a chemotherapeutic agent if a mutation in a PPM1D polynucleotide or polypeptide relative to a reference sequence is not detected. In some embodiments, the chemotherapeutic agent is a DNA damaging agent. In some embodiments, the chemotherapeutic agent is Cytarabine, Doxorubicin, Cyclophosphamide, or Cisplatin.

Diagnostic analysis of PPM1D status should be performed in cancer patients who are receiving, have received, or are expected to receive chemotherapy, particularly cancer patients who are receiving chemotherapy and have developed resistance to chemotherapy. A subject identified as sensitive to chemotherapeutic agent can be administered a chemotherapeutic agent. Over time, many patients treated with a chemotherapeutic agent acquire resistance to the therapeutic effects of the chemotherapeutic agent. The early identification of resistance to chemotherapy in a cancer patient can be important to patient survival because it allows for the selection of alternative therapies. Subjects identified as having a cancer resistant to a chemotherapeutic agent are identified as in need of alternative treatment. In some embodiments, a subject identified as in need of alternative treatment is administered an alternative therapy to chemotherapy or is recommended to receive an alternative therapy. In certain embodiments, the alternative therapy includes an agent that inhibits expression or activity of PPM1D polypeptide or polynucleotide. In some embodiments, the alternative therapy is a combination of an agent that inhibits expression or activity of PPM1D polypeptide or polynucleotide and a chemotherapeutic agent. In particular embodiments, the agent that inhibits expression or activity of PPM1D polypeptide or polynucleotide is a PPM1D inhibitor. In some embodiments, the PPM1D inhibitor is GSK2830371, CCT007093, or an analog thereof.

Methods of monitoring the sensitivity or resistance to a chemotherapeutic agent are useful in managing subject treatment. The results presented here provide evidence for clonal dominance and chemotherapy resistance caused by truncating, gain of function PPM1D mutations. Without being bound by theory, it is believed that this leads to preferential expansion of PPM1D mutant cells during genotoxic stress. Accordingly, monitoring the fraction of a cell population that harbors PPM1D mutations can be used to monitor a patient's resistance or sensitivity to chemotherapy.

Thus, in some embodiments, alterations in a polynucleotide or polypeptide of PPM1D (e.g., sequence, level, biological activity) are analyzed before and again after subject management or treatment. In these cases, the methods are used to monitor the status of sensitivity to a chemotherapeutic agent. The level, biological activity, or sequence of a polypeptide or polynucleotide of PPM1D may be assayed before treatment, during treatment, or following the conclusion of a treatment regimen. In some embodiments, multiple assays (e.g., 2, 3, 4, 5) are made at one or more of those times to assay resistance to a chemotherapeutic agent.

In one embodiment, the method includes the step of determining a level and/or sequence of a diagnostic marker (e.g., PPM1D polynucleotide or polypeptide) or diagnostic measurement (e.g., screen, assay) in a subject suffering from or susceptible to cancer or a disorder or symptoms thereof, in which the subject has been administered a therapeutic amount of an agent herein (e.g., a PPM1D inhibitor and/or a chemotherapeutic agent) sufficient to treat the disease or symptoms thereof. The level of PPM1D polypeptide or polynucleotide determined in the method can be compared to known levels or sequence of PPM1D polypeptide or polynucleotide in either healthy normal controls or in other afflicted patients to establish the subject's disease status. In some embodiments, the level of PPM1D polynucleotide or polypeptide containing a mutation ("mutant PPM1D") in a biological sample obtained from the subject relative to a reference is determined. The reference can be the level of wild-type PPM1D polynucleotide or polypeptide in the biological sample. In some embodiments, a second level of mutant PPM1D polypeptide or polynucleotide in the subject is determined at a time point later than the determination of the first level, and the two levels are compared to monitor the course of disease or the efficacy of the therapy. In certain embodiments, a pre-treatment level of mutant PPM1D polypeptide or polynucleotide in the subject is determined prior to beginning treatment according to this invention; this pre-treatment level of mutant PPM1D polypeptide or polynucleotide can then be compared to the level of mutant PPM1D polypeptide or polynucleotide in the subject after the treatment commences, to determine the efficacy of the treatment.

Alterations in polynucleotides or polypeptides of PPM1D (e.g., sequence, level, biological activity) are detected in a biological sample obtained from a patient that has or has a propensity to develop a cancer. Biological samples include tissue samples (e.g., cell samples, biopsy samples). Biological samples that are used to evaluate the herein disclosed markers include without limitation tumor cells, blood, serum, plasma, urine. In one embodiment, the biological sample is blood.

While the examples provided herein describe specific methods of detecting levels of polynucleotides or polypeptides of PPM1D, those of ordinary skill in the art appreciate that the invention is not limited to such methods. The biomarkers of this invention can be detected or quantified by any suitable method. For example, methods include, but are not limited to real-time PCR, Southern blot, PCR, mass spectroscopy, and/or antibody binding. Methods for detecting a mutation of the invention include immunoassay, direct sequencing, and probe hybridization to a polynucleotide encoding the mutant polypeptide.

Combination Therapies

Also provided herein are methods of increasing sensitivity to a chemotherapeutic agent, particularly a DNA damage agent, in a subject having a cancer (in particular, a chemotherapy resistant and/or PPM1D mutation associated cancer). The findings herein indicate that a combination of a chemotherapeutic agent and an agent that inhibits expression or activity of PPM1D polypeptide or polynucleotide would benefit patients with PPM1D mutations (particularly, a PPM1D truncation mutation that is a gain-of-function mutation).

Thus, in some embodiments, a therapeutic composition comprising a chemotherapeutic agent may be administered to a subject having a cancer, in combination with a composition comprising an agent that inhibits expression or activity of PPM1D polypeptide or polynucleotide. In particular embodiments, the subject is identified as resistant to a chemotherapeutic agent. In certain embodiments, the subject is identified as having a PPM1D mutation. An agent that inhibits expression or activity of PPM1D polypeptide or polynucleotide (e.g., an inhibitory polynucleotide that reduces PPM1D expression or a small molecule PPM1D inhibitor) is administered to a subject identified as resistant to a chemotherapeutic agent. In some embodiments, the chemotherapeutic agent is a DNA damaging agent. In some embodiments, the chemotherapeutic agent is Cytarabine, Doxorubicin, Cyclophosphamide, or Cisplatin. In some embodiments, the small molecule PPM1D inhibitor is GSK2830371, CCT007093, or an analog thereof.

Kits

The invention provides kits for treating or preventing a cancer or clonal hematopoiesis of indeterminate potential (CHIP) in a subject and/or identifying resistance or sensitivity to a chemotherapeutic agent in a subject having a cancer. A kit of the invention provides a capture reagent (e.g., a primer or hybridization probe specifically binding to a PPM1D polynucleotide) for measuring relative expression level or a sequence of a marker (e.g., PPM1D).

In one embodiment, the kit includes a diagnostic composition comprising a capture reagent detecting a PPM1D polynucleotide or polypeptide. In one embodiment, the capture reagent detecting a polynucleotide of PPM1D is a primer or hybridization probe that specifically binds to a PPM1D polynucleotide.

The kits may further comprise a therapeutic composition comprising a chemotherapeutic agent. In some embodiments, the chemotherapeutic agent is a DNA damaging agent. In some embodiments, the chemotherapeutic agent is Cytarabine, Doxorubicin, Cyclophosphamide, or Cisplatin.

The kits may also further comprise a therapeutic composition comprising an agent that inhibits expression or activity of a PPM1D polypeptide or polynucleotide. In some embodiments, the agent that inhibits expression or activity of a PPM1D polypeptide or polynucleotide is an inhibitory polynucleotide that reduces PPM1D expression. In particular embodiments, the agent that inhibits expression or activity of a PPM1D polypeptide or polynucleotide is a small molecule PPM1D inhibitor. In some embodiments, the PPM1D inhibitor is GSK2830371, CCT007093, or an analog thereof.

In some embodiments, the kit comprises a sterile container which contains a therapeutic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, the kit further comprises instructions for administering the therapeutic combinations of the invention. In particular embodiments, the instructions include at least one of the following: description of the therapeutic agent; dosage schedule and administration for enhancing anti-tumor activity; precautions; warnings; indications; counter-indications; over dosage information; adverse reactions; animal pharmacology; clinical studies; and/or references.

The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of those of ordinary skill in the art. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Truncating Mutations of PPM1D Lead to Chemotherapy Resistance

Figure 1B:
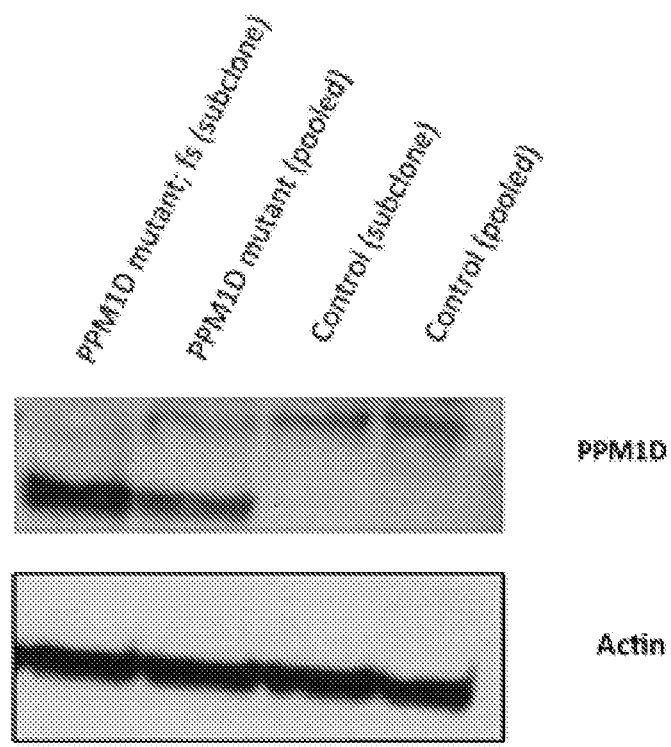
Figure 1C:
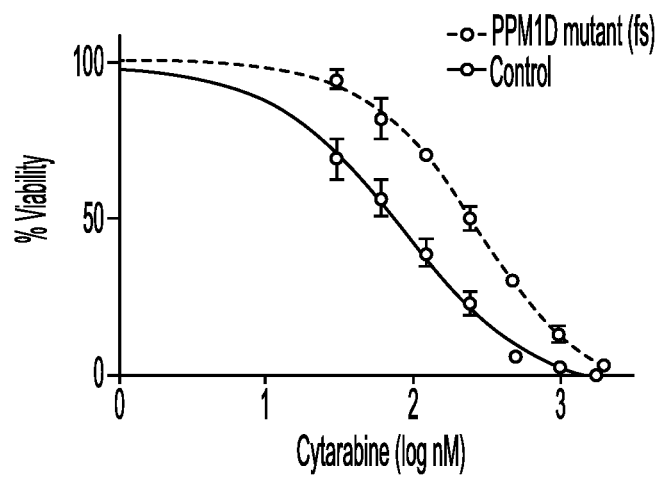

To study the role of PPM1D mutations in chemotherapy resistance, mutations in PPM1D were induced using the CRISPR-Cas9 system. The sgRNA is located in the last exon of the gene (FIG. 1A), similar to where truncating mutations in patients occur (Ruark, E. et al. Nature 493, 406-10 (2013); Zajkowicz, A. et al. Br. J. Cancer 112, 1114-20 (2015); Akbari, M. R. et al. J. Natl. Cancer Inst. 106, djt323 (2014); Genovese, G. et al. N. Engl. J. Med. 371, 2477-87 (2014); Xie, M. et al. Nat. Med. 20, 1472-8 (2014). Molm13 cells were transduced with a CRISPR-Cas9 lentivirus targeting hPPM1D, or a non-targeting guide. The presence of mutations was confirmed by Next Generation Sequencing. Frameshift mutations of PPM1D led to truncation and overexpression of the protein in subcloned and pooled Molm13 cells (FIG. 1B). Using sequence verified PPM1D mutant (fs) and empty vector control Molm13 cells, the effects of mutant and wild type PPM1D in the response to DNA damaging chemotherapy were analyzed. The therapies included Cytarabine, Doxorubicin, Cyclophosphamide and Cisplatin. Cell viability analysis in the presence of increasing drug concentrations demonstrated an increased resistance to Cytarabine in PPM1D mutant cells compared to empty vector controls. (FIG. 1C).

Figure 1D:
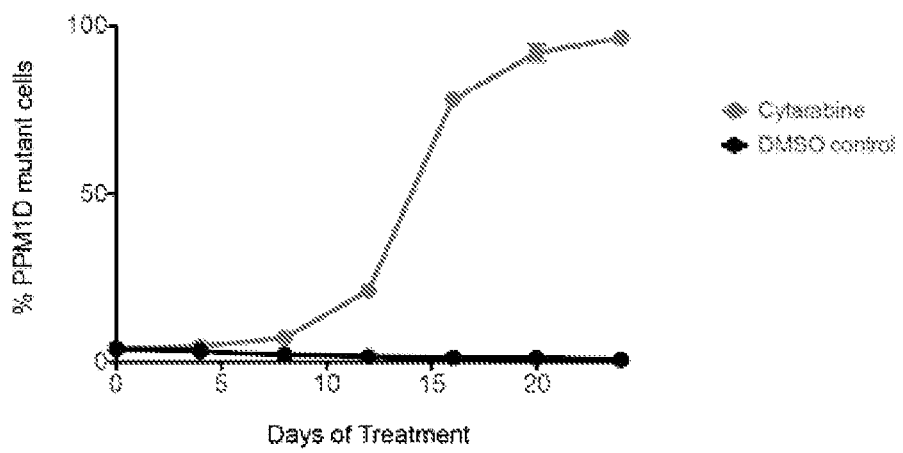
Figure 1E:
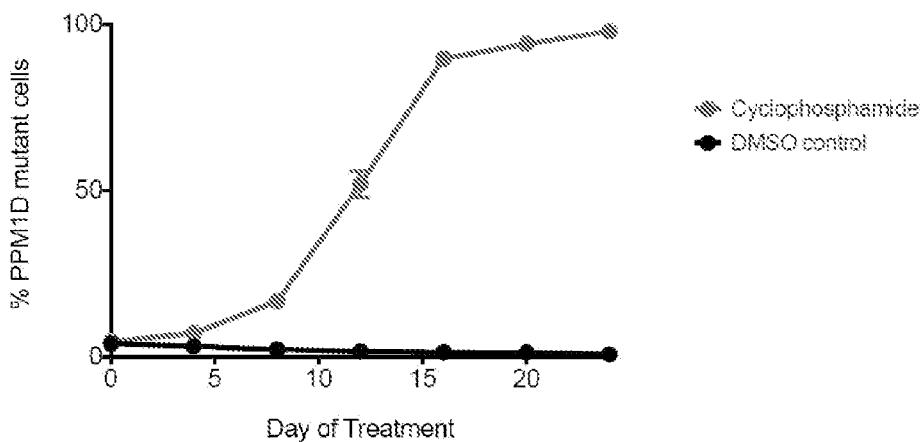

Whether PPM1D mutations conferred a competitive advantage during chemotherapy treatment was tested. In order to simulate a PPM1D mutant, subclonal environment similar to that seen in clonal hematopoiesis, a competition experiment in which pooled PPM1D mutant Molm13 cells were mixed with Molm13 control cells in a 1:99 ratio was performed. The mixed populations were treated with DNA damaging therapies, including Cytarabine and Cyclophosphamide, or DMSO every four days. Chemotherapy treatment induced a significant competitive advantage of PPM1D mutant cells, leading to an over 100-fold increase in the number of PPM1D mutant cells during treatment. Within 25 days of treatment, the mixed population was entirely taken over by PPM1D mutant cells (FIGS. 1D and 1E). As expected, exposure to DMSO did not select for PPM1D mutant cells.

The PPM1D gene has recently been found to be commonly somatically mutated in therapy-related myeloid neoplasms (t-MNs), clonal hematopoiesis of indeterminate potential (CHIP), and in the blood of patients with ovarian cancer, breast cancer and lung cancer (Jaiswal, S. et al. N. Engl. J. Med. 371, 2488-98 (2014); Genovese, G. et al. N. Engl. J. Med. 371, 2477-87 (2014); Xie, M. et al. Nat. Med. 20, 1472-8 (2014); Ruark, E. et al. Nature 493, 406-10 (2013); Zajkowicz, A. et al. Br. J. Cancer 112, 1114-20 (2015); Akbari, M. R. et al. J. Natl. Cancer Inst. 106, djt323 (2014); Pharoah, P. D. et al. J. Natl. Cancer Inst. 108, (2016); Swisher, E. M. et al. JAMA Oncol (2016); Gibson, C. J. et al. J. Clin. Oncol. JCO2016716712 (2017)). Mutations in PPM1D and TP53 are more highly associated with prior exposure to chemotherapy than any other mutations in myelodysplastic syndrome (MDS) (Lindsley, R. C. et al. N. Engl. J. Med. 376, 536-547 (2017)). PPM1D encodes a serine-threonine phosphatase that is transcriptionally unregulated in a p53-dependent manner in response to DNA damage (Gibson, C. J. et al. J. Clin. Oncol. JCO2016716712 (2017)). PPM1D in turn negatively regulates p53 and several members of the DNA damage response pathway (also termed "DDR") (Lu, X. et al. Cell Cycle 4, 4060-4064 (2005); Fujimoto, H. et al. Cell Death Differ. 13, 1170-80 (2006); Takekawa, M. et al. EMBO J. 19, 6517-26 (2000)), and hence has been proposed to be a primary homeostatic regulator of the DNA damage response pathway, facilitating return to steady state after the cells have repaired damaged DNA (Lu, X. et al. Cell Cycle 4, 4060-4064 (2005); Lu, X. et al. Cancer Metastasis Rev. 27, 123-35 (2008)).

Figure 2A:
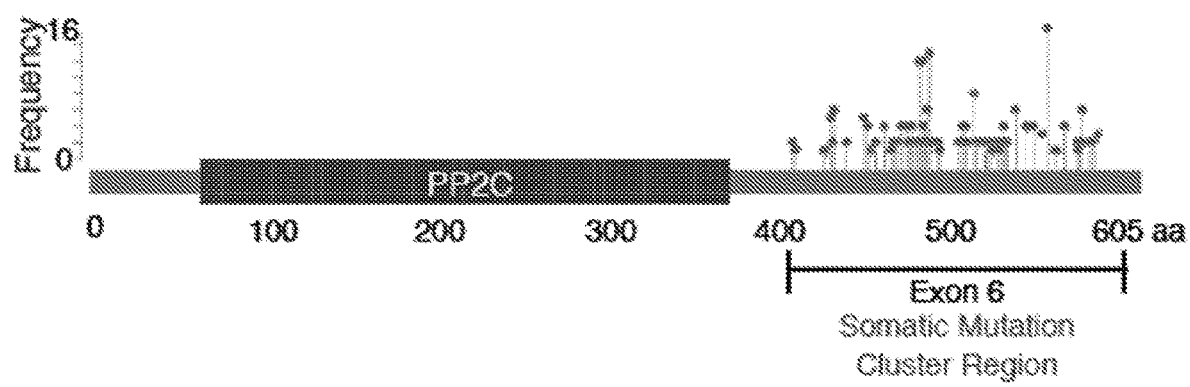
FIGS. 2A-2I show that truncating PPM1D mutations confer chemotherapy resistance.

PPM1D gene in exome sequencing data from the peripheral blood of 29,562 individuals (Jaiswal, S. et al. N. Engl. J. Med. 371, 2488-98 (2014); Genovese, G. et al. N. Engl. J. Med. 371, 2477-87 (2014)) was analyzed to define the spectrum of genetic lesions and found localization of somatic frame-shift and nonsense mutations exclusively in exon 6, which would produce a protein truncated downstream of amino acid 400 (FIG. 2A). These PPM1D mutations match those observed in therapy-related myeloid neoplasms and in the blood of cancer patients who have received chemotherapy (Ruark, E. et al. Nature 493, 406-10 (2013); Zajkowicz, A. et al. Br. J. Cancer 112, 1114-20 (2015); Akbari, M. R. et al. J. Natl. Cancer Inst. 106, djt323 (2014); Swisher, E. M. et al. JAMA Oncol (2016)).

Figure 2B:
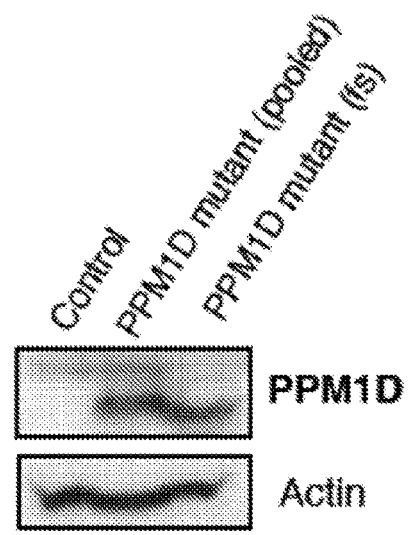
Figure 2C:
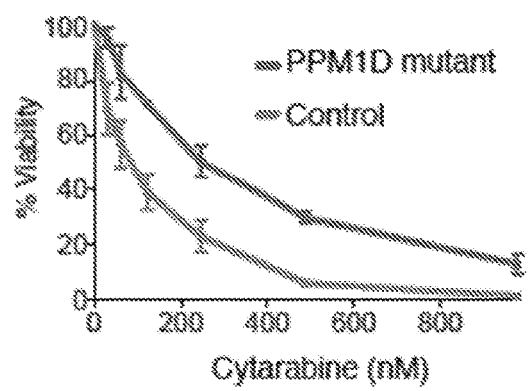
Figure 2D:
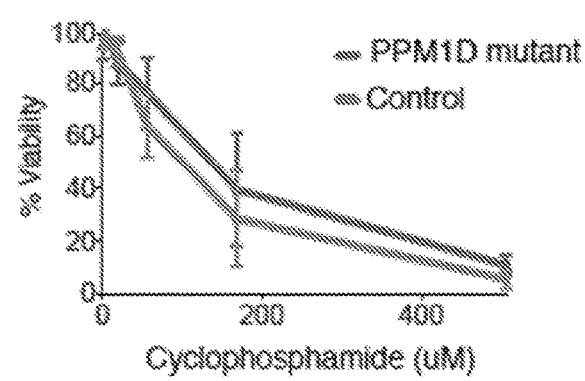
Figure 2E:
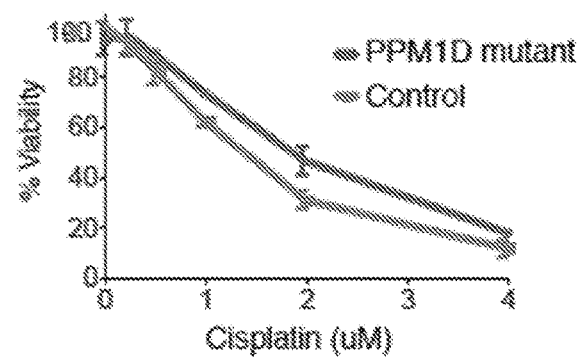
Figure 2F:
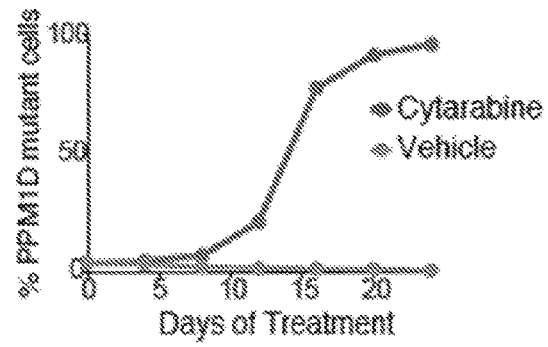
Figure 2G:
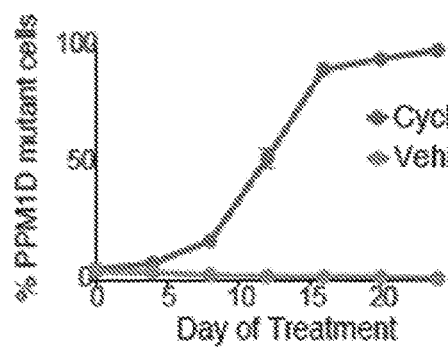
Figure 2H:
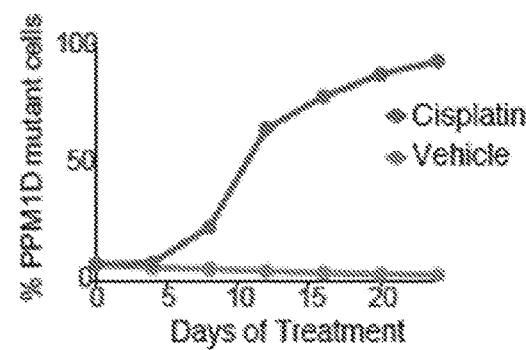
Figure 2I:
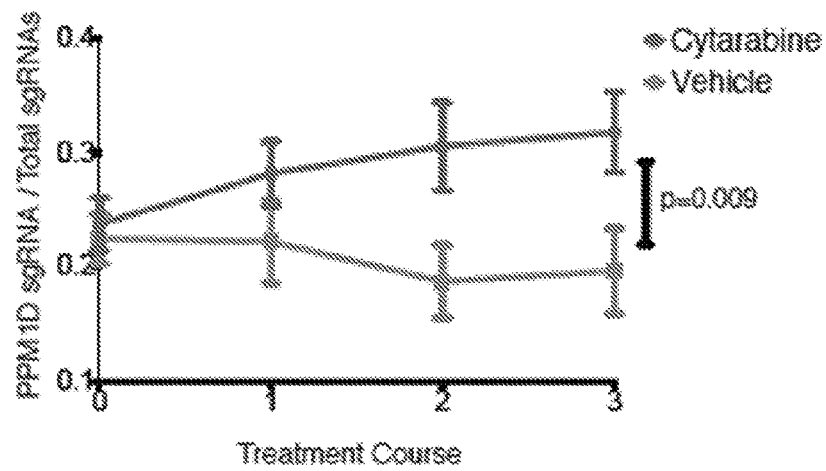
Figure 3A:
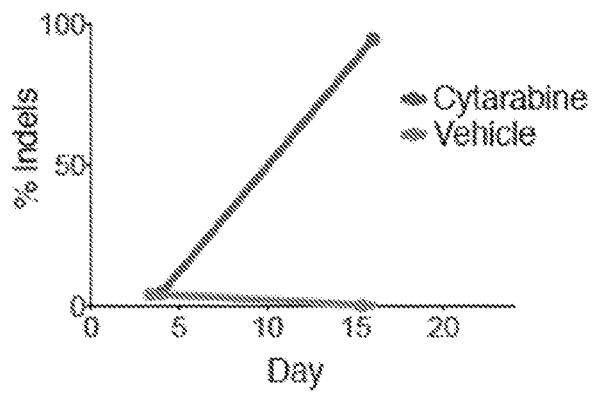
FIGS. 3A-3C show the sequencing read-out of an in vitro competition experiment.
Figure 3B:
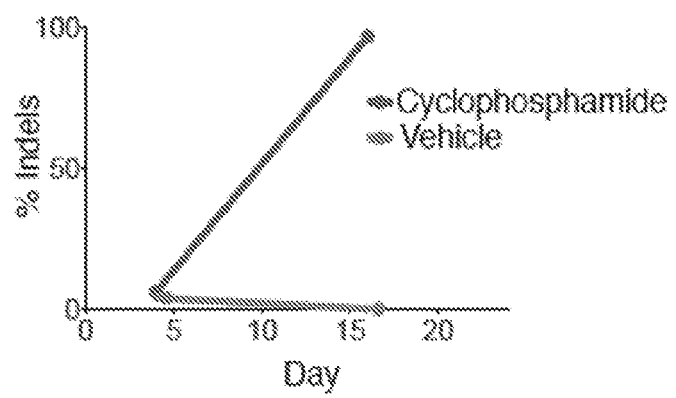
Figure 3C:
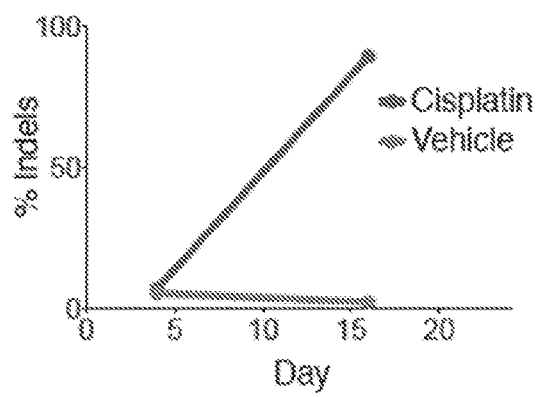

To study the sensitivity of PPM1D truncating mutations to chemotherapy exposure, frame-shift mutations were introduced in the PPM1D gene in Molm13 AML cells, which are TP53 wild-type, using CRISPR-Cas9. Exon 6 frame-shift mutations caused truncation and overexpression of PPM1D (FIG. 2B). PPM1D-mutant cells, compared to control cells expressing a non-targeting sgRNA, had increased viability at 72 hours in the presence of cytotoxic chemotherapeutic agents commonly used in the treatment of hematologic malignancies and solid tumors, such as cytarabine, cyclophosphamide, and cisplatin (FIGS. 2C-2E). To examine whether PPM1D-mutant cells have a competitive advantage relative to control cells over a longer time period, a competition experiment was performed. PPM1D-mutant Molm13 cells were mixed with control cells in a 1:25 ratio and exposed to chemotherapy or vehicle. Following exposure to chemotherapeutic agents, the PPM1D-mutant cells gained a competitive advantage, comprising more than 95% of cells within 24 days (FIGS. 2F-2H). When cells were cultured in the presence of vehicle instead of chemotherapy, PPM1D-mutant cells did not have a competitive advantage (FIGS. 2E-2G; 3A-3C). These findings demonstrate that PPM1D truncating mutations conferred chemotherapy resistance, leading to a competitive advantage of PPM1D-mutant leukemia cells under the selective pressure of chemotherapy.

Example 2: Truncation of PPM1D LED to Clonal Dominance

Figure 4A:
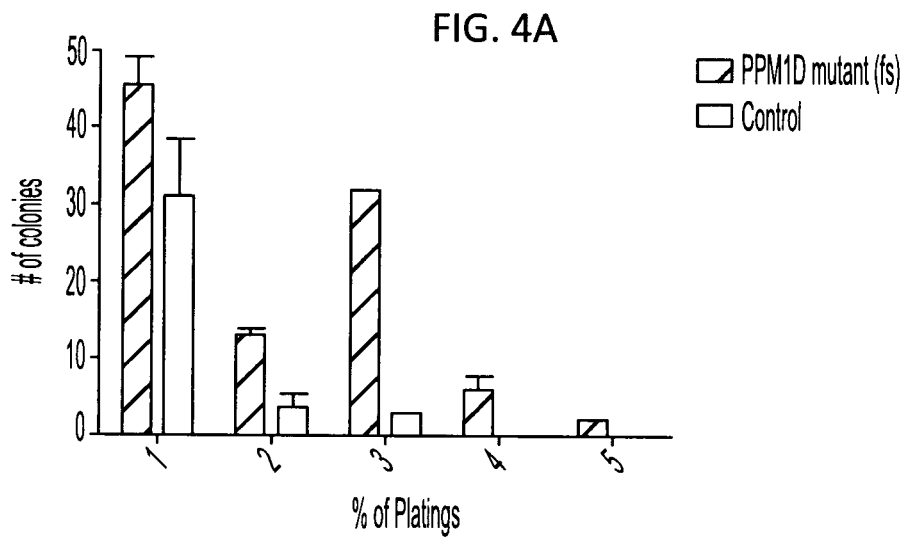
FIGS. 4A-4C show that PPM1D mutations led to increased serial replating potential and clonal dominance.

In view of the presence of PPM1D mutations in clonal hematopoiesis, it was hypothesized that PPM1D mutations confer clonal dominance. In order to study this in vitro, a serial replating assay was performed in which murine cKIT positive cells were transduced with a CRISPR-Cas9 targeting mPPM1D or a non-targeting CRISPR-Cas9 control guide. PPM1D mutant cKIT positive cells grew more colonies per replating, and could be replated more often than control cells (FIG. 4A).

Figure 4B:
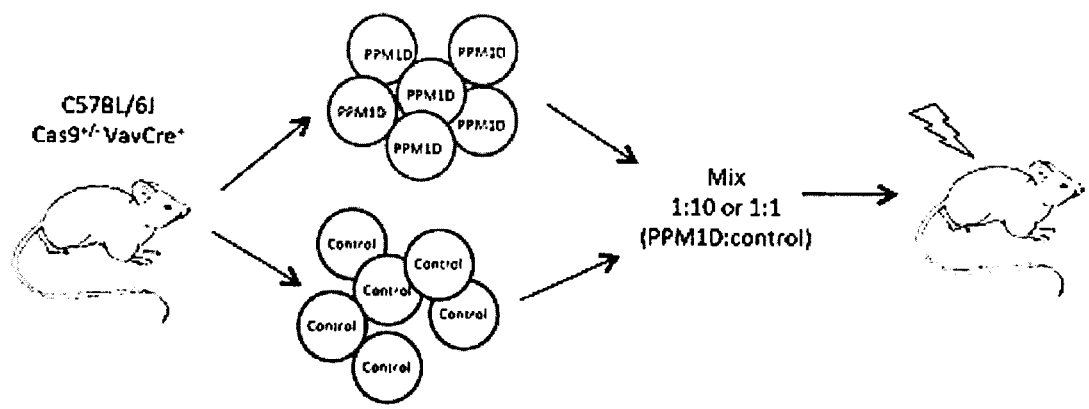
Figure 4C:
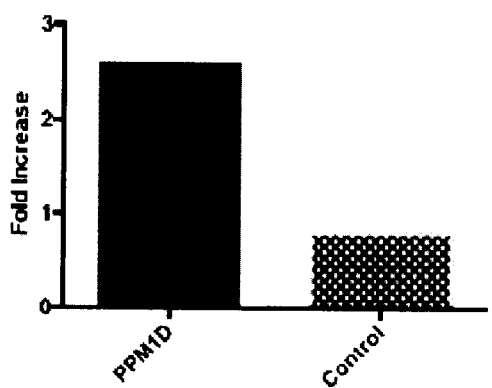

To test directly whether PPM1D mutations lead to clonal dominance, mix bone marrow chimaeras containing both PPM1D mutant and control cells were generated (FIG. 4B). A>2.5 fold increase in the percentage of PPM1D mutant cells over a two-week period was observed, while the percentage of control cells remained stable (FIG. 4C).

Figure 5:
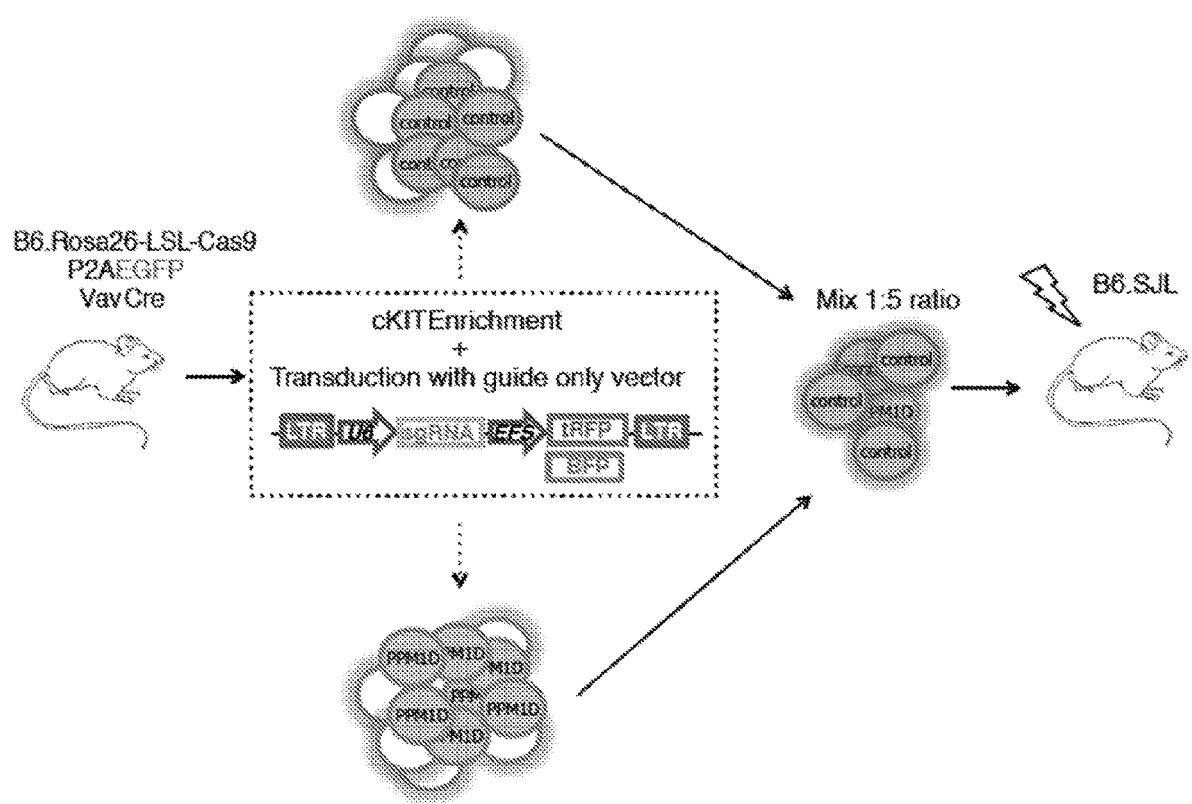
FIG. 5 provides an experimental schema of an in vivo competition experiment. Bone marrow chimaeras were generated by transplanting Mx-Cre Cas9 cKit$^+$Cas9 cells transduced with a BFP-tagged sgRNA targeting exon 6 of PPM1D or a tRFP-tagged control sgRNA into lethally-irradiated syngeneic recipients in a 1:5 ratio.

Whether PPM1D mutations confer resistance to chemotherapy in vivo was examined. In another experiment, bone marrow chimeras were generated using Mx-Cre Cas9 c-Kit+ cells that were transduced with a BFP-tagged sgRNA targeting exon 6 of PPM1D or a tRFP-tagged control sgRNA and transplanted into lethally-irradiated syngeneic recipients in a 1:5 ratio (FIG. 5). Mice were treated with cytarabine or vehicle after hematopoietic reconstitution. A significant, selective increase of PPM1D-mutant cells in the peripheral blood was observed after cytarabine treatment (FIG. 2F; 6A-6G). Without being bound by theory, this indicated that PPM1D-mutant cells had a competitive advantage over control cells in vivo after exposure to genotoxic stress.

Figure 6A:
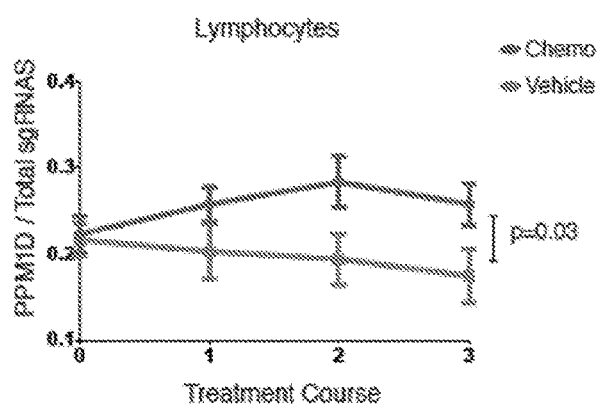
FIGS. 6A-6H show that PPM1D-mutant peripheral blood and bone marrow cells undergo expansion after cytarabine exposure in vivo.
Figure 6B:
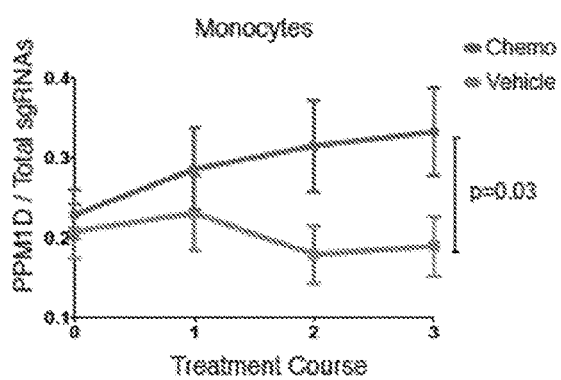
Figure 6C:
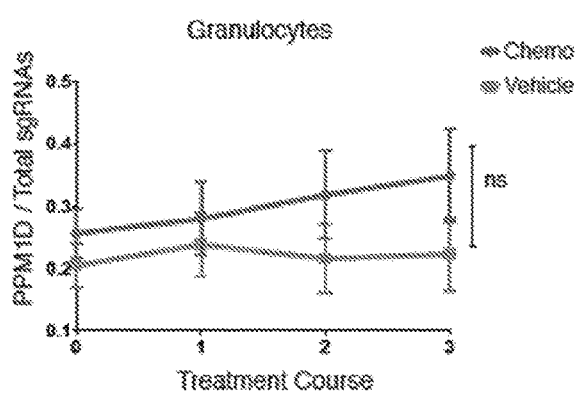
Figure 6D:
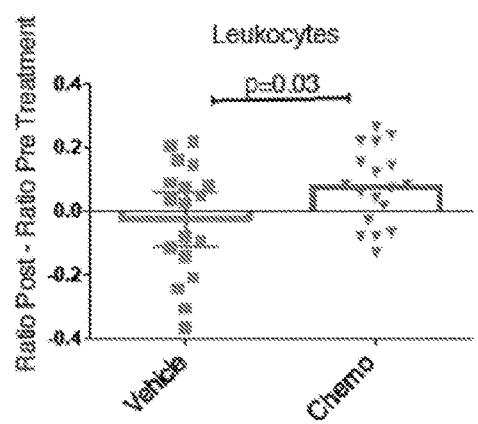
Figure 6E:
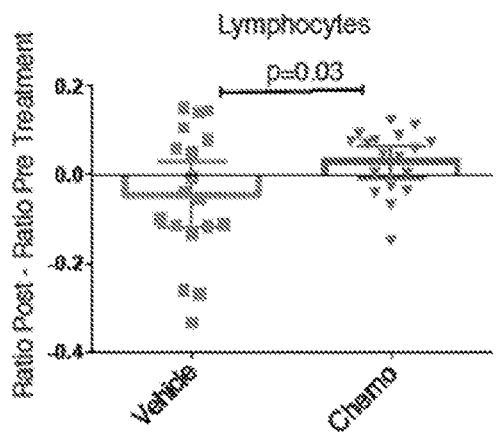
Figure 6F:
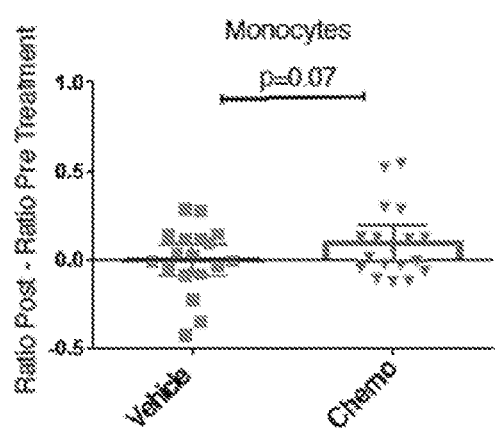
Figure 6G:
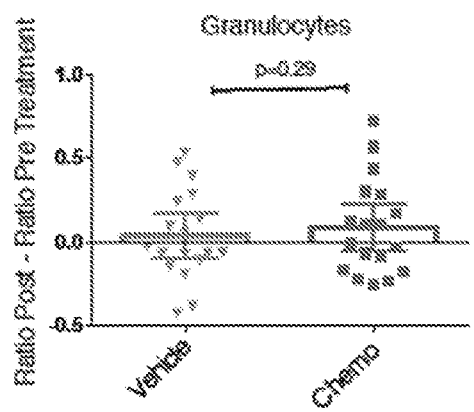
Figure 6H:
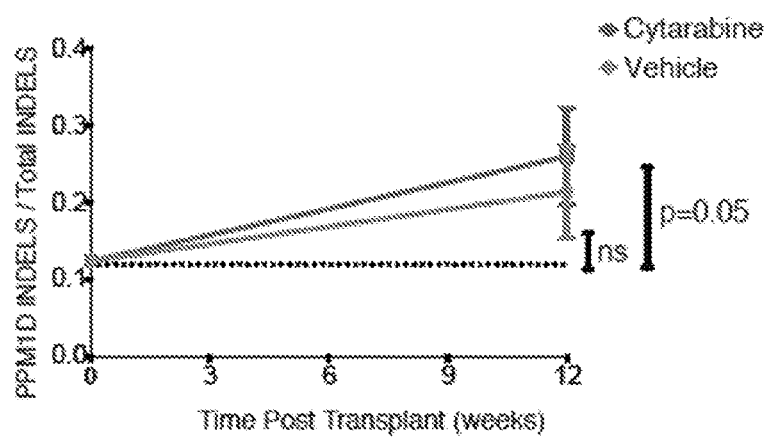
Figure 7A:
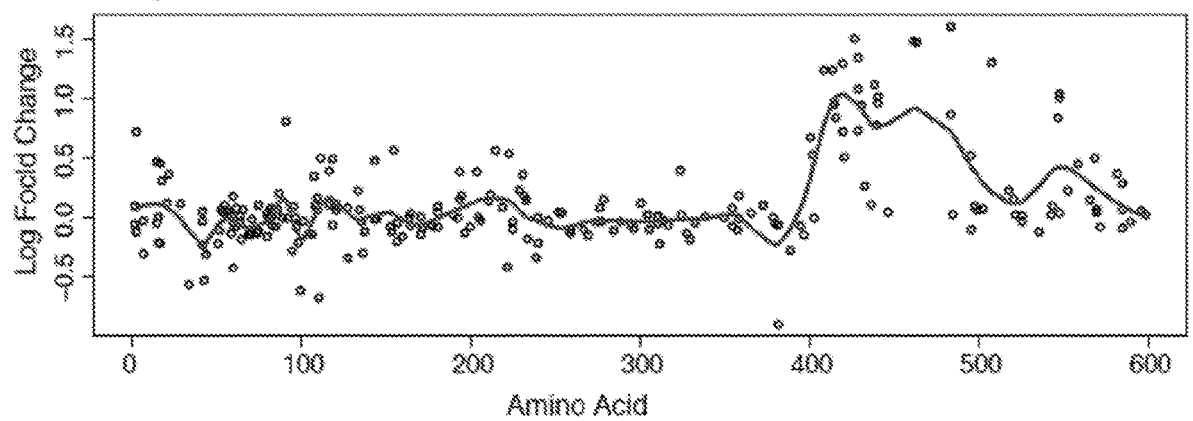
FIGS. 7A-7C shows a time course of Log-fold enrichment of sgRNAs targeting PPM1D. |
Figure 7B:
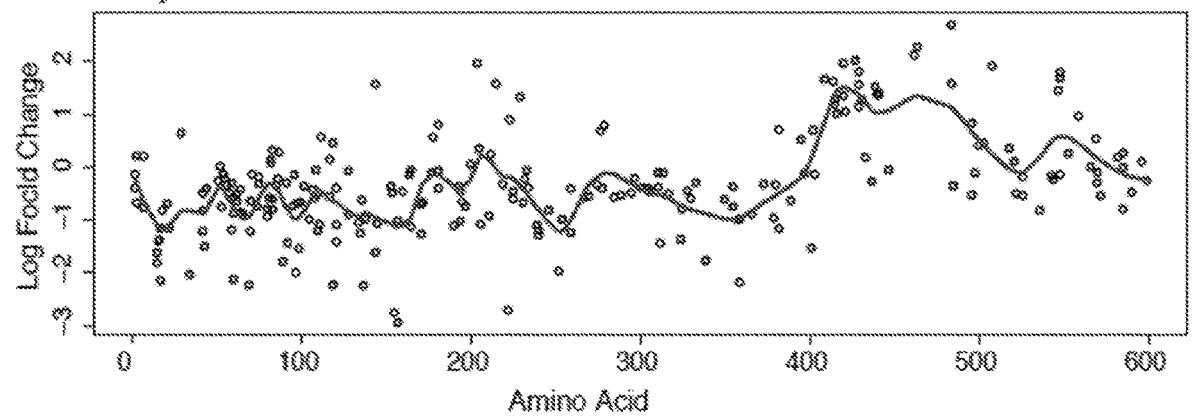
Figure 7C:
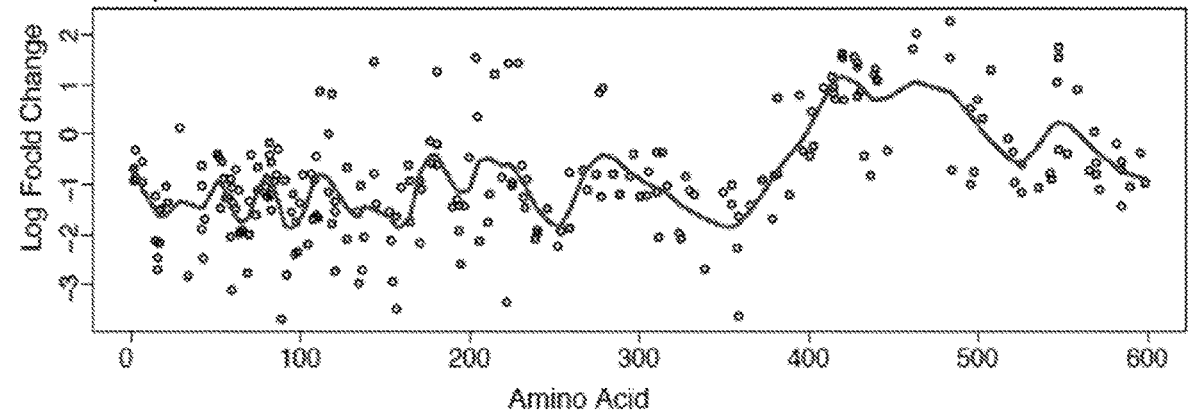

PPM1D-mutant hematopoietic stem and progenitor cells in the bone marrow were also increased at 12 weeks following 3 rounds of cytarabine (FIG. 6H).

Example 3: Chemotherapy Exposure Selects for Specific Mutations in PPM1D

Figure 8A:
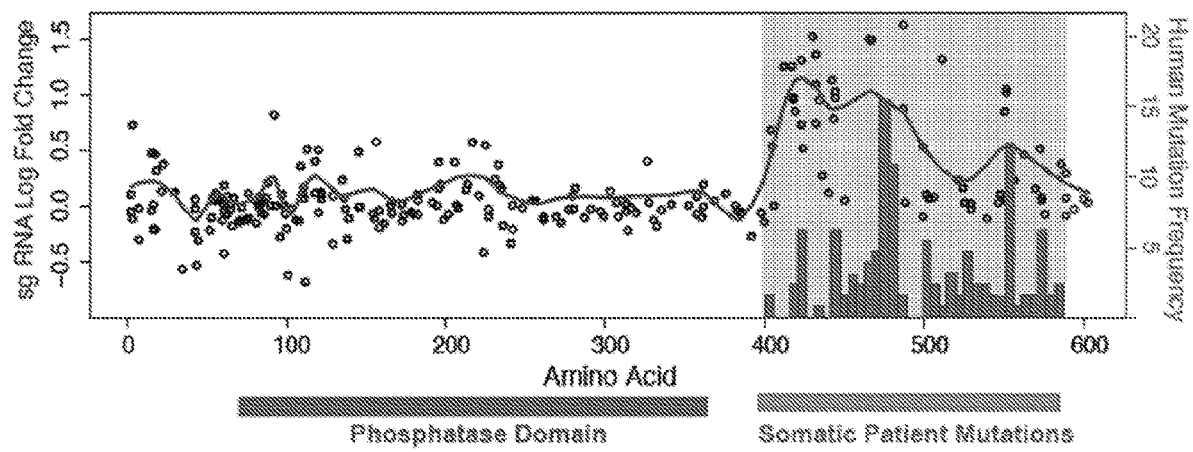
FIGS. 8A-8F show that truncating PPM1D mutations led to decreased degradation of PPM1D.

Whether chemotherapy exposure selects for specific mutations in PPM1D was investigated. A saturation mutagenesis CRISPR screen was performed in which cells were infected with a CRISPR library of 265 sgRNAs tiling all exons of PPM1D (FIG. 12), at a multiplicity of infection of 1000 so that cells would receive zero or one sgRNA per cell. Cells were treated for 24 days with cytarabine or vehicle, and the representation of sgRNAs in the two groups was determined by sequencing the integrated sgRNAs. A selective enrichment of sgRNAs targeting amino acids 400-585 (exon 6) of PPM1D was observed in cells treated with chemotherapy compared to vehicle. Without being bound by theory, this indicated that these sgRNAs introduce PPM1D mutations that confer resistance to chemotherapy (FIGS. 7A-7C, FIG. 12). This region tightly overlaps with the region of PPM1D mutations identified in individuals with clonal hematopoiesis of indeterminate potential (CHIP) (FIG. 8A). In contrast, sgRNAs targeting the last 20 amino acids of exon 6 did not have a selective advantage during chemotherapy treatment and no human CHIP or t-MN mutations have been identified to occur in this region. These studies demonstrated that the non-random localization of somatic PPM1D mutations in patients with therapy-related malignancies corresponded to the CRISPR-generated mutations that cause chemotherapy resistance.

Figure 8B:
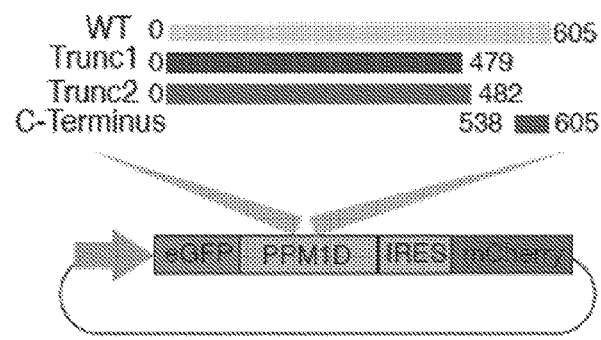

Because PPM1D exon 6 mutations led to increased protein expression, and previous studies have indicated that PPM1D may be targeted to the proteasome (Kleiblova, P. et al. J. Cell Biol. 201, 511-21 (2013)), it was hypothesized that the C-terminal domain of PPM1D contains a sequence that mediates degradation of PPM1D. A reporter vector was generated in which wild-type PPM1D cDNA (wt), PPM1D truncation mutants, or the last 80 amino-acids (C-terminal region) were cloned in frame with GFP, so the level of expression of the PPM1D sequences could be monitored by GFP expression (FIG. 8B, Table 1).

TABLE 1

Reporter Vector Sequences

| Construct | Sequence |
| --- | --- |
| WT (SEQ ID NO: 32) | ATGGCGGGGCTGTACTCGCTGGGAGTGAGCGTCTTCTCCGACCA GGGCGGGAGGAAGTACATGGAGGACGTTACTCAAATCGTTGTGG AGCCCGAACCGACGGCTGAAGAAAAGCCCTCGCCGCGGCGGTC GCTGTCTCAGCCGTTGCCTCCGCGGCCGTCGCCGGCCGCCCTTC CCGGCCGCGAAGTCTCGGGGAAAGGCCCAGCGGTGGCAGCCCG AGAGGCTCGCGACCCTCTCCCGGACGCCGGGGCCTCGCCGGCA CCTAGCCGCTGCTGCCGCCGCCGTTCCTCCGTGGCCTTTTTCGCC GTGTGCGACGGGCACGGCGGGCGGGAGGCGGCCACAGTTTGCCC GGGAGCACTTGTGGGGTTTCATCAAGAAGCAGAAGGGTTTCACCT CGTCCGAGCCGGCTAAGGTTTGCGCTGCCATCCGCAAAGGCTTTC TCGCTTGTCACCTTGCCATGTGGAAGAAACTGGCGGAATGGCCAA AGACTATGACGGGTCTTCCTAGCACATCAGGGACAACTGCCAGTG TGGTCATCATTCGGGGCATGAAGATGTATGTAGCTCACGTAGGTG ACTCAGGGGTGGTTCTTGGAATTCAGGATGACCCGAAGGATGACT TTGTCAGAGCTGTGGAGGTGACACAGGACCATAAGCCAGAACTT CCCAAGGAAAGAGAACGAATCGAAGGACTTGGTGGGAGTGTAAT GAACAAGTCTGGGGTGAATCGTGTAGTTTGGAAACGACCTCGAC TCACTCACAATGGACCTGTTAGAAGGAGCACAGTTATTGACCAGA TTCCTTTTCTGGCAGTAGCAAGAGCACTTGGTGATTTGTGGAGCT ATGATTTCTTCAGTGGTGAATTTGTGGTGTCACCTGAACCAGACAC AAGTGTCCACACTCTTGACCCTCAGAAGCACAAGTATATTATATTG GGGAGTGATGGACTTTGGAATATGATTCCACCACAAGATGCCATC |

TABLE 1-continued

Reporter Vector Sequences

| Construct | Sequence |
|---|---|
| | TCAATGTGCCAGGACCAAGAGGAGAAAAAATACCTGATGGGTGAG |
| | CATGGACAATCTTGTGCCAAAATGCTTGTGAATCGAGCATTGGGC |
| | CGCTGGAGGCAGCGTATGCTCCGAGCAGATAACACTAGTGCCAT |
| | AGTAATCTGCATCTCTCCAGAAGTGGACAATCAGGGAAACTTTAC |
| | CAATGAAGATGAGTTATACCTGAACCTGACTGACAGCCCTTCCTA |
| | TAATAGTCAAGAAACCTGTGTGATGACTCCTTCCCCATGTTCTACA |
| | CCACCAGTCAAGTCACTGGAGGAGGATCCATGGCCAAGGGTGAA |
| | TTCTAAGGACCATATACCTGCCCTGGTTCGTAGCAATGCCTTCTCA |
| | GAGAATTTTTTAGAGGTTTCAGCTGAGATAGCTCGAGAGAATGTCC |
| | AAGGTGTAGTCATACCCTCAAAAGATCCAGAACCACTTGAAGAAAA |
| | TTGCGCTAAAGCCCTGACTTTAAGGATACATGATTCTTTGAATAATA |
| | GCCTTCCAATTGGCCTTGTGCCTACTAATTCAACAAACACTGTCAT |
| | GGACCAAAAAAATTTGAAGATGTCAACTCCTGGCCAAATGAAAGCC |
| | CAAGAAATTGAAAGAACCCCTCCAACAAACTTTAAAAGGACATTAG |
| | AAGAGTCCAATTCTGGCCCCCTGATGAAGAAGCATAGACGAAATG |
| | GCTTAAGTCGAAGTAGTGGTGCTCAGCCTGCAAGTCTCCCCACAA |
| | CCTCACAGCGAAAGAACTCTGTTAAACTCACCATGCGACGCAGAC |
| | TTAGGGGCCAGAAGAAAATTGGAAATCCTTTACTTCATCAACACAG |
| | GAAAACTGTTTGTGTTTGCTGA |
| Trunc (SEQ ID NO: 33) | ATGGCGGGGCTGTACTCGCTGGGAGTGAGCGTCTTCTCCGACCA |
| | GGGCGGGAGGAAGTACATGGAGGACGTTACTCAAATCGTTGTGG |
| | AGCCCGAACCGACGGCTGAAGAAAAGCCCTCGCCGCGGCGGTC |
| | GCTGTCTCAGCCGTTGCCTCCGCGGCCGTCGCCGGCCGCCCTTC |
| | CCGGCGGCGAAGTCTCGGGGAAAGGCCCAGCGGTGGCAGCCCG |
| | AGAGGCTCGCGACCCTCTCCCGGACGCCGGGGCCTCGCCGGCA |
| | CCTAGCCGCTGCTGCCGCCGCCGTTCCTCCGTGGCCTTTTTCGCC |
| | GTGTGCGACGGGCACGGCGGGCGGGAGGCGGCACAGTTTGCCC |
| | GGGAGCACTTGTGGGGTTTCATCAAGAAGCAGAAGGGTTTCACCT |
| | CGTCCGAGCCGGCTAAGGTTTGCGCTGCCATCCGCAAAGGCTTTC |
| | TCGCTTGTCACCTTGCCATGTGGAAGAAACTGGCGGAATGGCCAA |
| | AGACTATGACGGGTCTTCCTAGCACATCAGGGACAACTGCCAGTG |
| | TGGTCATCATTCGGGGCATGAAGATGTATGTAGCTCACGTAGGTG |
| | ACTCAGGGGTGGTTCTTGGAATTCAGGATGACCCGAAGGATGACT |
| | TTGTCAGAGCTGTGGAGGTGACACAGGACCATAAGCCAGAACTTC |
| | CCAAGGAAAGAGAACGAATCGAAGGACTTGGTGGGAGTGTAATGA |
| | ACAAGTCTGGGGTGAATCGTGTAGTTTGGAAACGACCTCGACTCA |
| | CTCACAATGGACCTGTTAGAAGGAGCACAGTTATTGACCAGATTCC |
| | TTTTCTGGCAGTAGCAAGAGCACTTGGTGATTTGTGGAGCTATGAT |
| | TTCTTCAGTGGTGAATTTGTGGTGTCACCTGAACCAGACACAAGTG |
| | TCCACACTCTTGACCCTCAGAAGCACAAGTATATTATATTGGGGAG |
| | TGATGGACTTTGGAATATGATTCCACCACAAGATGCCATCTCAATG |
| | TGCCAGGACCAAGAGGAGAAAAAATACCTGATGGGTGAGCATGGA |
| | CAATCTTGTGCCAAAATGCTTGTGAATCGAGCATTGGGCCGCTGGA |
| | GGCAGCGTATGCTCCGAGCAGATAACACTAGTGCCATAGTAATCTG |
| | CATCTCTCCAGAAGTGGACAATCAGGGAAACTTTACCAATGAAGAT |
| | GAGTTATACCTGAACCTGACTGACAGCCCTTCCTATAATAGTCAAG |
| | AAACCTGTGTGATGACTCCTTCCCCATGTTCTACACCACCAGTCAA |
| | GTCACTGGAGGAGGATCCATGGCCAAGGGTGAATTCTAAGGACCA |
| | TATACCTGCCCTGGTTCGTAGCAATGCCTTCTCAGAGAATTTTTTAG |
| | AGGTTTCAGCTGAGATAGCTCGAGAGAATGTCCAAGGTGTAGTCAT |
| | ACCCTCAAAAGATCCAGAACCACTTGAAGAAAATTGCTAA |
| Trunc2 (SEQ ID NO: 34) | ATGGCGGGGCTGTACTCGCTGGGAGTGAGCGTCTTCTCCGACCAG |
| | GGCGGGAGGAAGTACATGGAGGACGTTACTCAAATCGTTGTGGAG |
| | CCCGAACCGACGGCTGAAGAAAAGCCCTCGCCGCGGCGGTCGCT |
| | GTCTCAGCCGTTGCCTCCGCGGCCGTCGCCGGCCGCCCTTCCCG |
| | GCGGCGAAGTCTCGGGGAAAGGCCCAGCGGTGGCAGCCCGAGAG |
| | GCTCGCGACCCTCTCCCGGACGCCGGGGCCTCGCCGGCACCTAG |
| | CCGCTGCTGCCGCCGCCGTTCCTCCGTGGCCTTTTTCGCCGTGTG |
| | CGACGGGCACGGCGGGCGGGAGGCGGCACAGTTTGCCCGGGAGC |
| | ACTTGTGGGGTTTCATCAAGAAGCAGAAGGGTTTCACCTCGTCCG |
| | AGCCGGCTAAGGTTTGCGCTGCCATCCGCAAAGGCTTTCTCGCTT |
| | GTCACCTTGCCATGTGGAAGAAACTGGCGGAATGGCCAAAGACTA |
| | TGACGGGTCTTCCTAGCACATCAGGGACAACTGCCAGTGTGGTCA |
| | TCATTCGGGGCATGAAGATGTATGTAGCTCACGTAGGTGACTCAG |
| | GGGTGGTTCTTGGAATTCAGGATGACCCGAAGGATGACTTTGTCA |
| | GAGCTGTGGAGGTGACACAGGACCATAAGCCAGAACTTCCCAAGG |
| | AAAGAGAACGAATCGAAGGACTTGGTGGGAGTGTAATGACAAGTC |
| | TGGGGTGAATCGTGTAGTTTGGAAACGACCTCGACTCACTCACAAT |
| | GGACCTGTTAGAAGGAGCACAGTTATTGACCAGATTCCTTTTCTGG |
| | CAGTAGCAAGAGCACTTGGTGATTTGTGGAGCTATGATTTCTTCAG |
| | TGGTGAATTTGTGGTGTCACCTGAACCAGACACAAGTGTCCACACT |
| | CTTGACCCTCAGAAGCACAAGTATATTATATTGGGGAGTGATGGAC |
| | TTTGGAATATGATTCCACCACAAGATGCCATCTCAATGTGCCAGGA |
| | CCAAGAGGAGAAAAAATACCTGATGGGTGAGCATGGACAATCTTGT |

TABLE 1-continued

Reporter Vector Sequences

| Construct | Sequence |
|---|---|
| | GCCAAAATGCTTGTGAATCGAGCATTGGGCCGCTGGAGGCAGCGT<br>ATGCTCCGAGCAGATAACACTAGTGCCATAGTAATCTGCATCTCTC<br>CAGAAGTGGACAATCAGGGAAACTTTACCAATGAAGATGAGTTATA<br>CCTGAACCTGACTGACAGCCCTTCCTATAATAGTCAAGAAACCTGT<br>GTGATGACTCCTTCCCCATGTTCTACACCACCAGTCAAGTCACTGG<br>AGGAGGATCCATGGCCAAGGGTGAATTCTAAGGACCATATACCTG<br>CCCTGGTTCGTAGCAATGCCTTCTCAGAGAATTTTTTAGAGGTTTC<br>AGCTGAGATAGCTCGAGAGAATGTCCAAGGTGTAGTCATACCCTCA<br>AAAGATCCAGAACCACTTGAATGA |
| C-terminal<br>(SEQ ID NO: 35) | CGAAATGGCTTAAGTCGAAGTAGTGGTGCTCAGCCTGCAAGTCTCC<br>CCACAACCTCACAGCGAAAGAACTCTGTTAAACTCACCATGCGACG<br>CAGACTTAGGGGCCAGAAGAAAATTGGAAATCCTTTACTTCATCAAC<br>ACAGGAAAACTGTTTGTGTTTGCTGA |

Figure 8C:
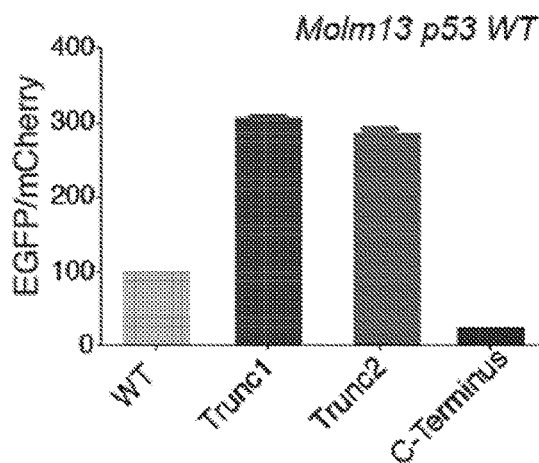
Figure 8D:
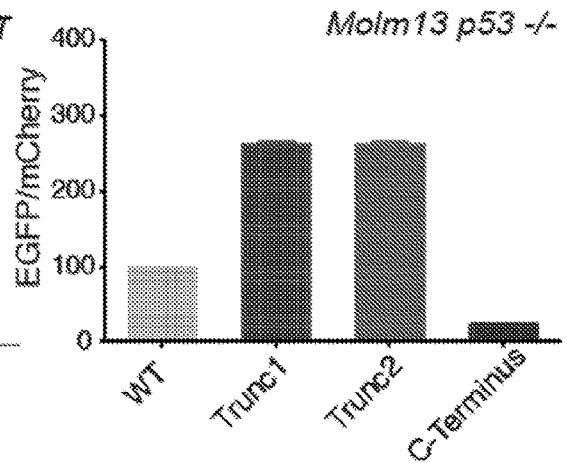
Figure 8E:
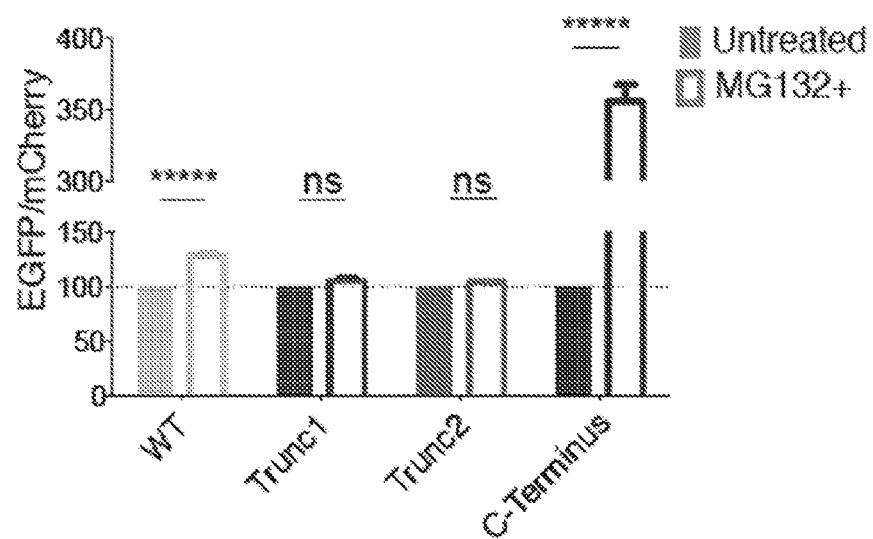

The fluorescence level of mCherry, which is expressed following an IRES sequence, provided an internal control for vector expression in each cell. Using this system, it was found that the PPM1D truncation mutations increased the GFP/mCherry ratio, indicating a relative decrease in degradation of truncated PPM1D (FIG. 8C), consistent with Western blots of the truncated protein (FIG. 2B). In contrast, the GFP/mCherry ratio in cells expressing the C-terminal region of PPM1D was decreased, indicating the presence of a degradation signal in this region (FIG. 8C). The GFP/mCherry ratios did not differ between Molm13 p53 wild type and Molm13 p53$^{-/-}$ cells (FIG. 8D). Without being bound by theory this demonstrated that, while PPM1D gene expression is regulated by p53, the degradation of PPM1D is p53-independent. Treatment with the proteasome-inhibitor MG132 led to decreased degradation of wild-type and C-terminal PPM1D, but not of the truncating mutants (FIG. 8E). These data demonstrate that the C-terminal domain of PPM1D contains a degradation signal that is deleted by PPM1D exon 6 truncation mutations, leading to decreased proteosomal degradation and consequent overexpression of PPM1D.

Figure 8F:
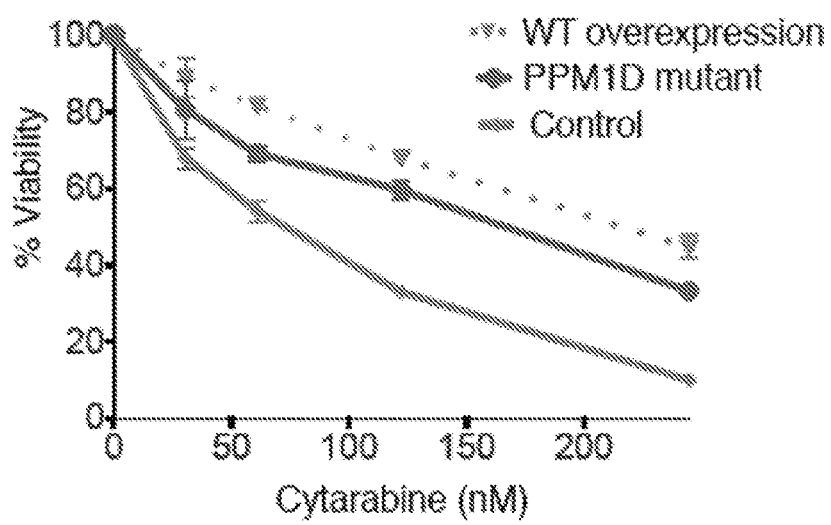

Whether overexpression of PPM1D is sufficient to induce chemotherapy resistance, or whether a novel function of the truncated protein is required for this phenotype was examined. Full length PPM1D was over-expressed in Molm13 cells and these cells were exposed to cytarabine. A similar degree of chemotherapy resistance was observed in PPM1D-mutant cells and cells with overexpression of wild type PPM1D (FIG. 8F). Thus, PPM1D overexpression, as occurs due to C-terminal deletions, was sufficient to induce chemotherapy resistance.

Figure 9A:
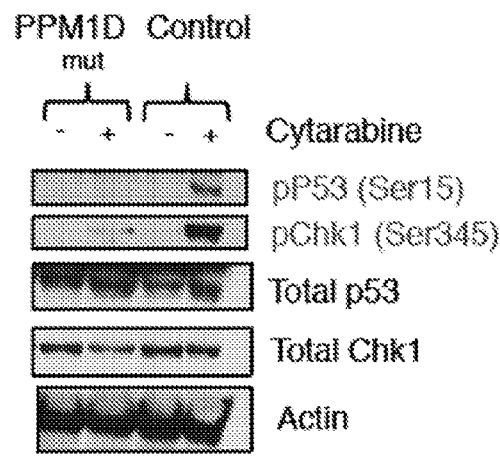
FIGS. 9A-9G show that truncating PPM1D mutations abrogated the DNA damage response.
Figure 9B:
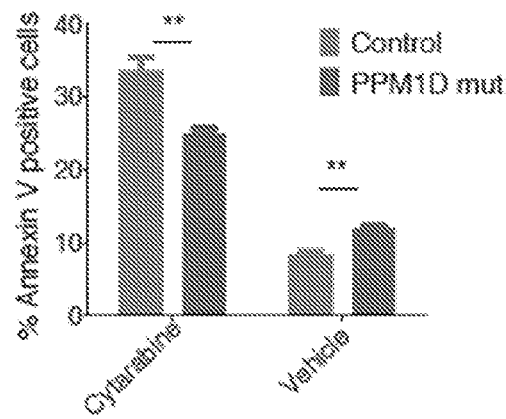
Figure 9C:
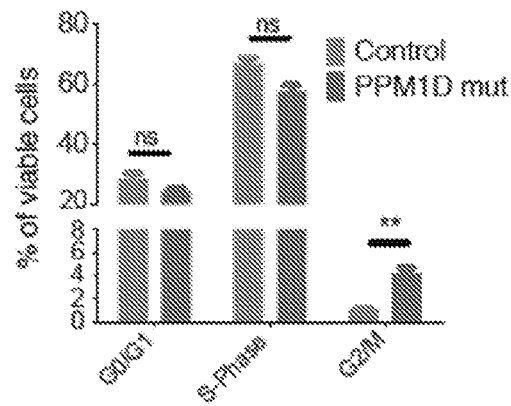

Example 4: Mutations in PPM1D Abrogate the DNA Damage Response to Genotoxic Therapy PPM1D directly regulates TP53 and other components of the DNA damage response pathway through its protein phosphatase activity (Fiscella et al. Proc. Natl. Acad. Sci. U.S.A. 94, 6048-53 (1997); Lu, X. et al. Cell Cycle 4, 4060-4064 (2005); Fujimoto, H. et al. Cell Death Differ. 13, 1170-80 (2006); Takekawa, M. et al. EMBO J. 19, 6517-26 (2000); Lu, X. et al. Cancer Metastasis Rev. 27, 123-35 (2008); Lu, X. et al. Genes Dev. 19, 1162-74 (2005)). Whether PPM1D mutations abrogate the p53-dependent DNA damage response pathway in leukemia cells was examined. The genotoxic effects of chemotherapy elicit a strong DNA damage response (DDR), which among others includes the phosphorylation of Chk1 and p53. PPM1D is best known for its role as a negative regulator of this response, leading to dephosphorylation of these targets. In view of the gain of function induced by truncating PPM1D mutations, the effects of truncating PPM1D mutations on the response to chemotherapy treatment were studied. Molm13 PPM1D mutant and wild type control cells were exposed to Cytarabine treatment. Cytarabine induced phosphorylation of known PPM1D targets (Lu, X. et al. Genes Dev. 19, 1162-74 (2005)), p53 Ser15 and Chk1 Ser345, in control leukemia cells, but this response was abrogated in PPM1D-mutant cells (FIG. 9A). Moreover, PPM1D mutation decreased apoptosis as assessed by Annexin V staining (FIG. 9B) and increased progression to G2/M phase compared to control cells following exposure to chemotherapy (FIG. 9C).

Figure 9D:
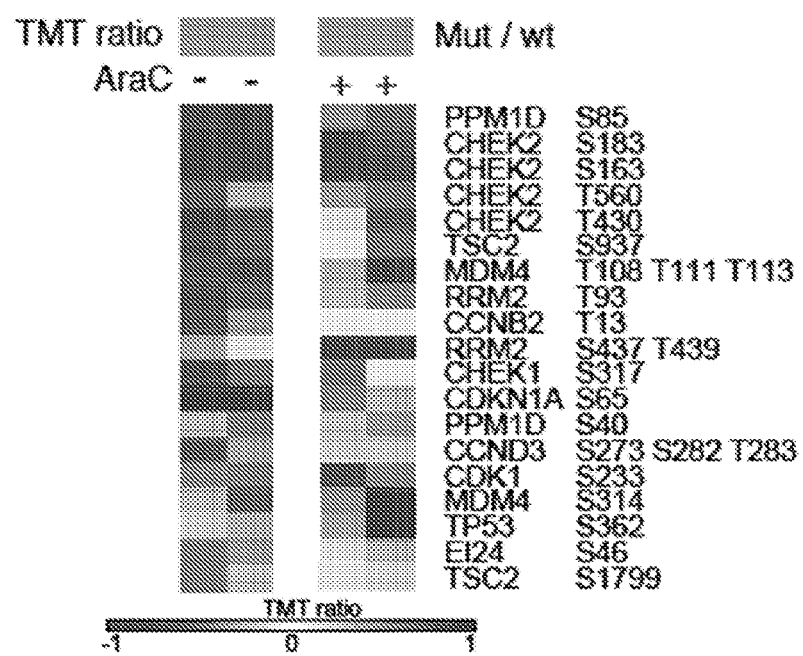
Figure 9E:
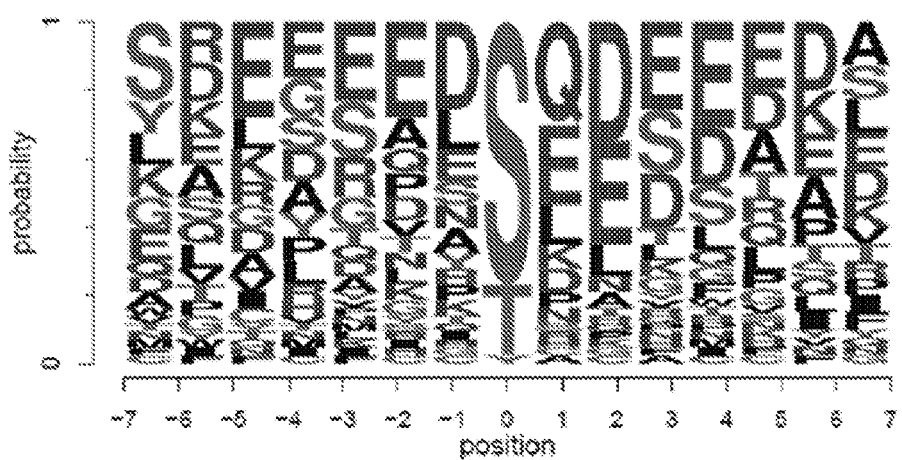
Figure 9F:
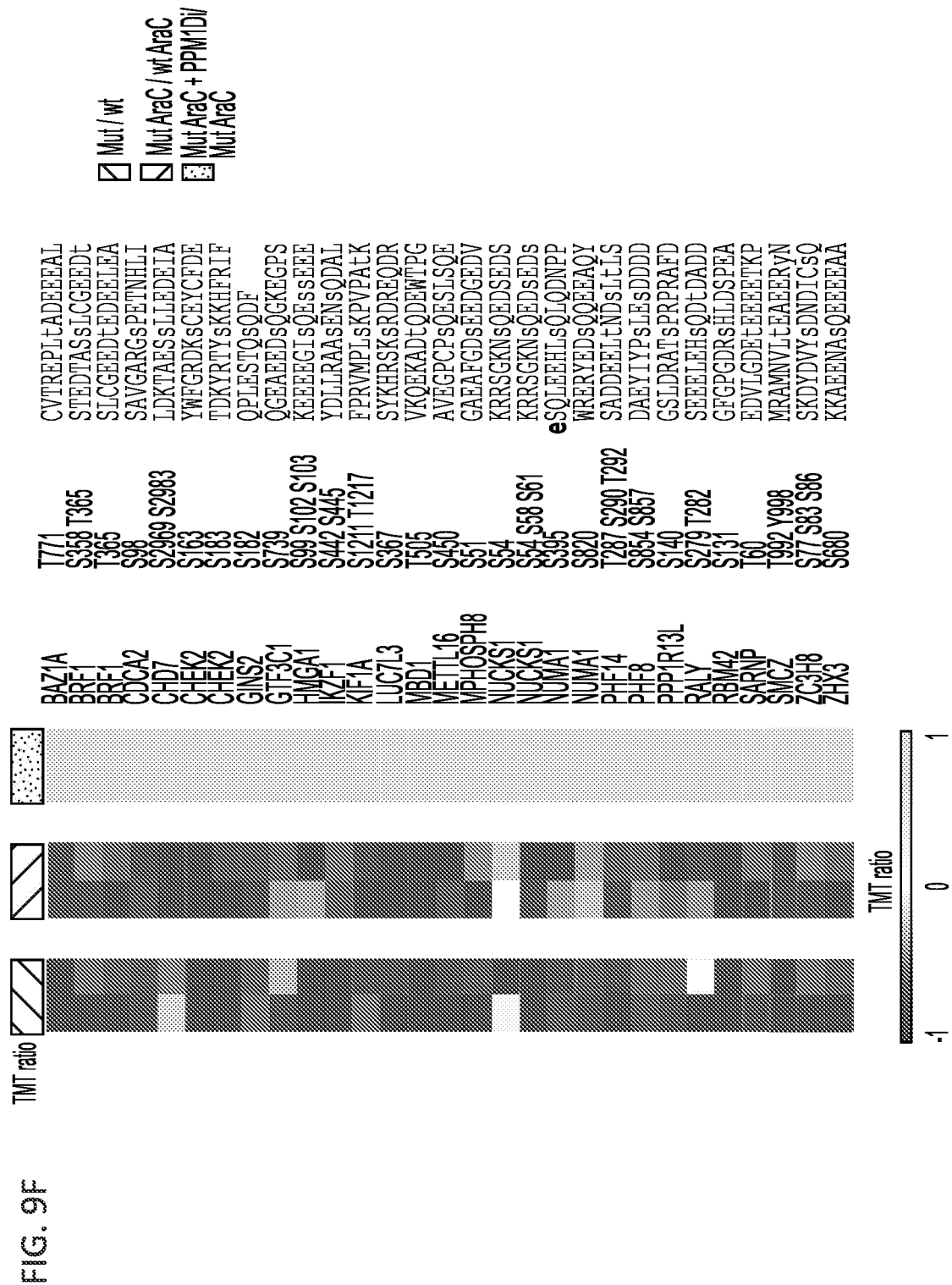
Figure 9G:
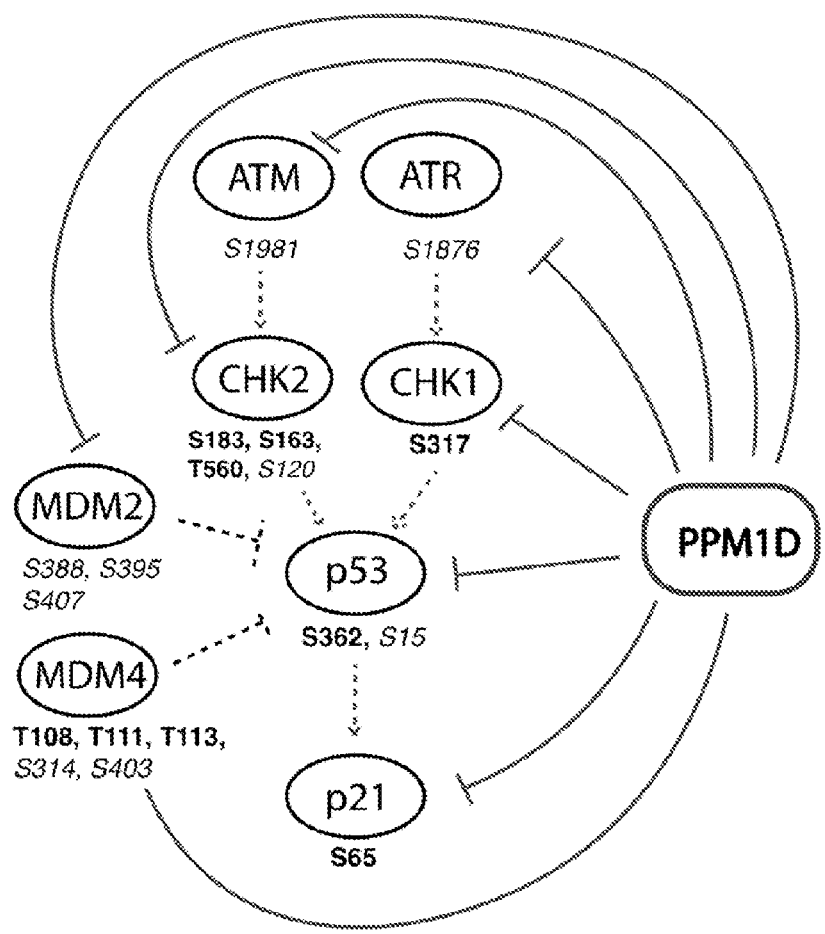

To explore the spectrum of PPM1D targets in hematopoietic cells, a quantitative phosphoproteomic analysis was performed in PPM1D wild-type and mutant cells at baseline and in response to chemotherapy. Altered phosphorylation of many components of the full DNA damage response pathway was observed in PPM1D-mutant leukemia cells (FIG. 9D), including differential phosphorylation of TP53, PPM1D, CHEK1, CHEK2 and MDM4 (Lu, X. et al. Cancer Metastasis Rev. 27, 123-35 (2008); Lu, X. et al. Genes Dev. 19, 1162-74 (2005); Zhang, X. et al. Cancer Res. 69, 7960-8 (2009)). In addition, CDKN1A (p21) was identified as a new DNA damage response target of PPM1D. Based on the peptides with altered phosphorylation in PPM1D-mutant cells, a consensus sequence was identified for the serine-threonine phosphatase activity of PPM1D (FIGS. 9E and 9F). Because many phosphorylation sites are not located on peptides that are detected by mass spectrometry, the consensus sequence was used to predict additional PPM1D targets. Known PPM1D targets, including TP53, CHEK1, CHEK2, ATM, ATR and MDM2, bear the consensus target sequence. In addition, new phosphorylation sites were identified in components of the DNA damage response pathway that are predicted targets of PPM1D based on the consensus sequence. Without being bound by theory, these data demonstrate the central role of PPM1D in the DNA damage pathway (FIG. 9G), and demonstrate the full extent to which PPM1D mutation in leukemia cells alter this pathway.

Because C-terminal PPM1D mutations lead to increased protein expression, it was tested whether inhibition of PPM1D could reverse the aberrant phosphorylation pattern observed in PPM1D-mutant cells. An allosteric PPM1D inhibitor, GKS2830371, has previously been shown to be highly selective for the PPM1D phosphatase (Gilmartin, A.

Figure 10A:
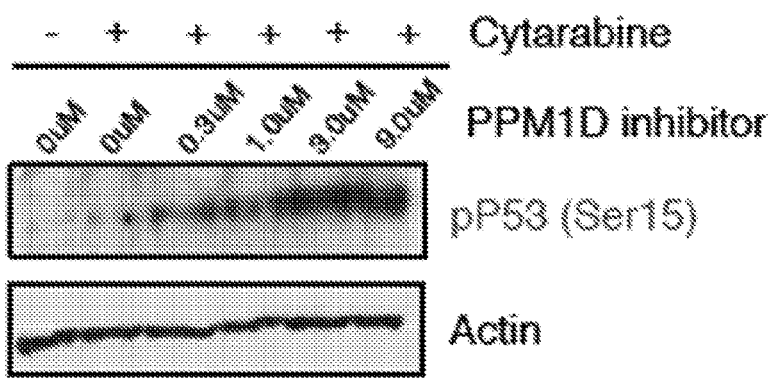
FIGS. 10A-10F show that PPM1D inhibition with GSK2830371 reversed the aberrant PPM1D mutant phosphorylation pattern, reverses chemotherapy resistance, and selectively targets PPM1D-mutant cells.
Figure 10B:
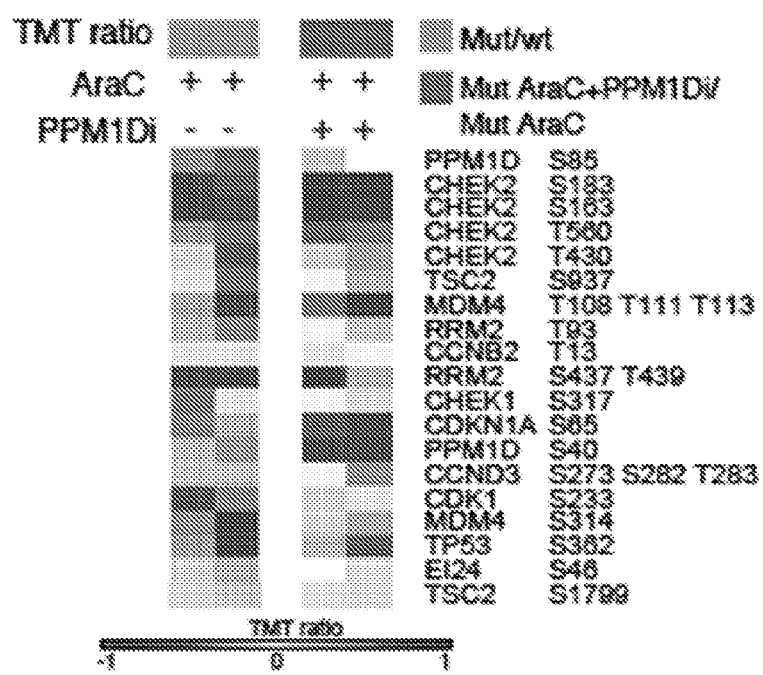

G. et al. *Nat. Chem. Biol.* 10, 181-7 (2014)). Treatment with GKS2830371 increased p53 Ser15 phosphorylation, an established PPM1D target, in Molm13 PPM1D-mutant cells following cytarabine treatment (FIG. 10A). Using phosphoproteomic analysis, it was found that the addition of low-dose GSK2830371 to cytarabine treatment led to a complete reversal of the aberrant phosphorylation pattern observed in PPM1D-mutant cells in response to chemotherapy (FIG. 10B).

Figure 10C:
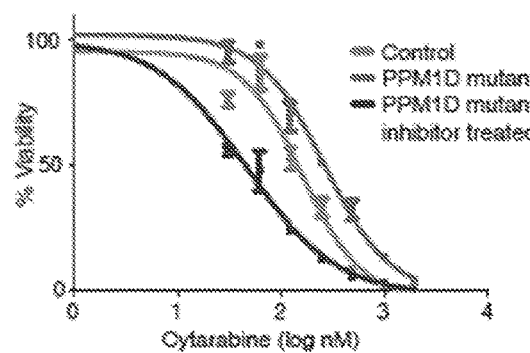
Figure 10D:
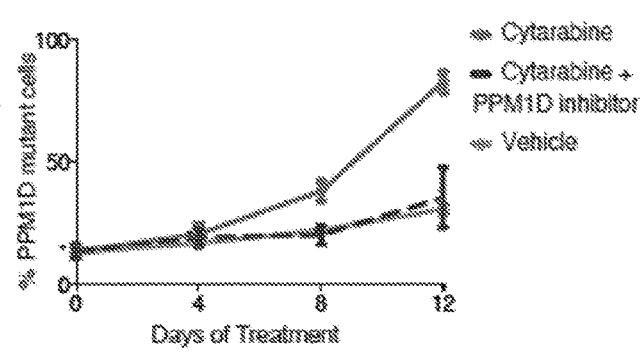
Figure 10E:
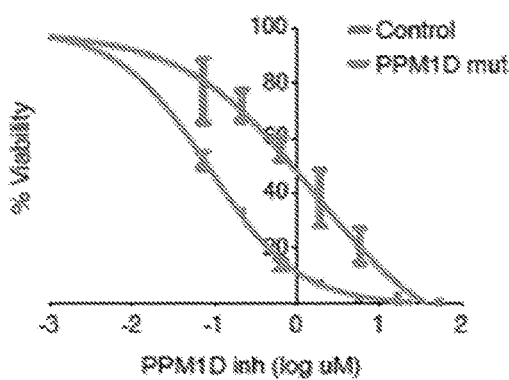
Figure 10F:
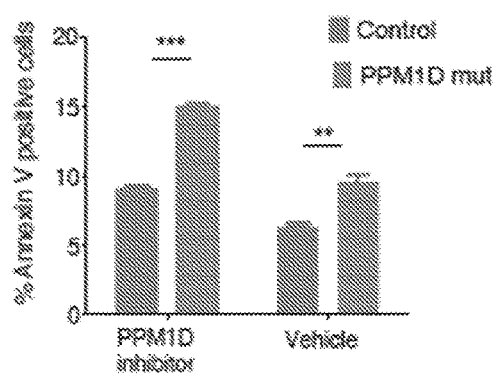

Whether treatment with GSK2830371 could reverse the chemotherapy resistance induced by PPM1D mutation was examined. Combined treatment with cytarabine and GSK2830371 increased the sensitivity of Molm13 PPM1D-mutant cells to cytarabine (FIG. 10C). In addition, the competitive advantage of Molm13 PPM1D-mutant cells in cytarabine-exposed cells could be reversed through the addition of GSK2830371 treatment (FIG. 10D). Moreover, it was found that Molm13 PPM1D-mutant cells had an increased sensitivity to single agent PPM1D inhibitor treatment when compared to control cells, as assessed by cell viability analysis (FIG. 10E) and Annexin V staining (FIG. 10F). These data indicate that PPM1D inhibition can re-sensitize PPM1D-mutant cells to chemotherapy treatment, and is beneficial for the targeted elimination of PPM1D-mutant cells.

Figure 11A:
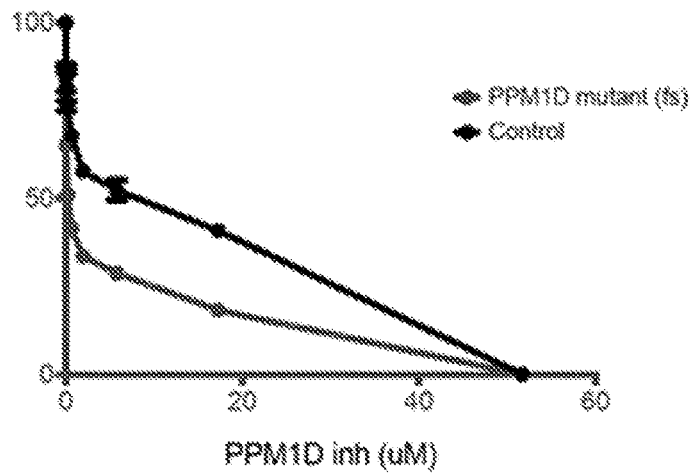
FIGS. 11A and 11B show that PPM1D inhibition reversed chemotherapy resistance.
Figure 11B:
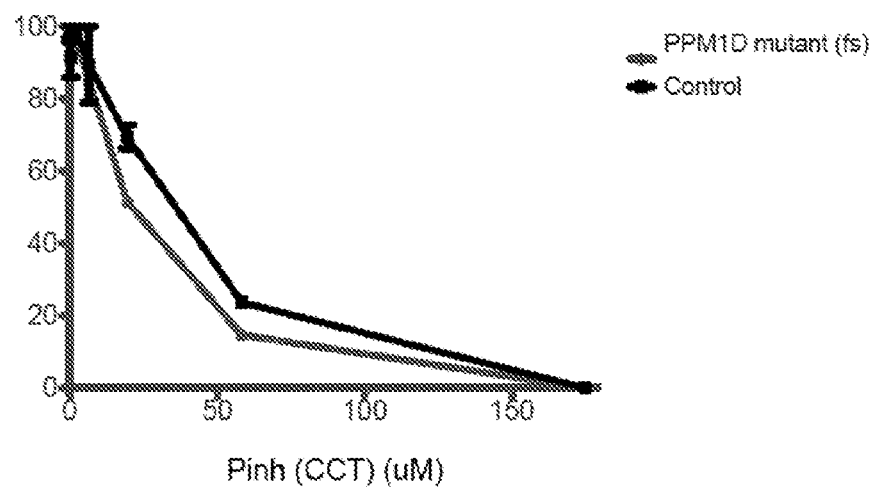

Truncating mutations of PPM1D lead to gain of function of the protein, resulting in resistance to DNA damaging therapy. It was therefore determined whether inhibition of the protein could sensitize PPM1D mutant cells to chemotherapy treatment. To test the response of PPM1D mutant and wild type cells to PPM1D inhibition, the cells were exposed to increasing drug concentrations of two commercially available PPM1D inhibitors (GSK2830371 and CCT007093), that work through different mechanisms (Gilmartin, A. G. et al. *Nat. Chem. Biol.* 10, 181-7 (2014); Rayter S et al. *Oncogene.* 27, 1036-1044 (2008)). As shown by a 72-hour cell viability assay, PPM1D mutant cells have an increased sensitivity to PPM1D inhibition with either compound in comparison to wild type control cells (FIGS. 11A and 11B). The addition of a PPM1D inhibitor sensitized PPM1D mutant cells to treatment with Cytarabine in a dose dependent manner In line with these results, treatment with the PPM1D inhibitor caused a dose dependent upregulation of phospo p53 (Ser15), thereby reversing the abrogated DDR response characteristic of PPM1D mutant cells (FIG. 10D).

Collectively, these results demonstrate that PPM1D mutations confer a competitive advantage to hematopoietic cells undergoing genotoxic stress through an extensive abrogation of the DNA damage response pathway. These findings provide evidence for a model in which HSPCs carrying PPM1D mutations selectively expand during chemotherapy treatment, providing the initiating mutation in a large proportion of therapy-related myeloid neoplasms. This model is consistent with reports of PPM1D mutations in the peripheral blood of cancer patients having received chemotherapy, and with the enrichment of PPM1D and TP53 mutations in therapy-related MDS (Lindsley, R. C. et al. N. Engl. J. Med. 376, 536-547 (2017)). TP53 mutations have also been found to expand during chemotherapy treatment and to be associated with therapy-related myeloid neoplasms (Wong, T. et al. Nature 518, 552-555 (2015)). However, while TP53 mutations are characterized by a complex karyotype, PPM1D mutations are not, demonstrating that the biology and clinical phenotype associated with PPM1D mutations is distinct from p53 inactivation (Lindsley, R. C. et al. N. Engl. J. Med. 376, 536-547 (2017)). The phosphoproteomic data described herein support this rationale, as PPM1D mutations were found to inhibit the full DNA damage response pathway rather than merely inhibiting p53.

In addition to providing a model for the selective advantage of PPM1D-mutant HSPCs in the presence of chemotherapy, it was demonstrated that PPM1D mutations cause a gain-of-function through increased PPM1D protein expression that is responsive to targeted treatment with a PPM1D inhibitor, highlighting several potential therapeutic opportunities. Chemotherapy treatment can result in the development of therapy-related myeloid neoplasms (also termed "t-MNs"), which are characterized by chemotherapy resistance and a poor prognosis (Morton, L. M. et al. Blood 121, 2996-3004 (2013); Malmgren, J., et al. Leukemia Res 47, 178-184 (2016); Candelaria, M. and Dueñas-Gonzalez, A. Expert Opin Drug Saf 14, 655-65 (2015)). Recent studies have demonstrated that truncating mutations of the protein phosphatase $Mg2^+/Mn2^+1D$ (PPM1D) were detected in the blood of healthy people (Jaiswal, S. et al. N. Engl. J. Med. 371, 2488-98 (2014); Genovese, G. et al. N. Engl. J. Med. 371, 2477-87 (2014); Xie, M. et al. Nat. Med. 20, 1472-8 (2014)), as well as in up to 25% of solid tumor cancer patients exposed to chemotherapy (Ruark, E. et al. Nature 493, 406-10 (2013); Zajkowicz, A. et al. Br. J. Cancer 112, 1114-20 (2015); Akbari, M. R. et al. J. Natl. Cancer Inst. 106, djt323 (2014); Pharoah, P. D. et al. J. Natl. Cancer Inst. 108, (2016); Swisher, E. M. et al. JAMA Oncol (2016)). Additionally, PPM1D mutations were recently found to occur in myelodysplastic syndromes (MDS) and to be enriched in therapy-related MDS, where they are present in 15% of cases (Lindsley, R. C. et al. N. Engl. J. Med. 376, 536-547 (2017)).

As described herein, truncating PPM1D mutations conferred chemotherapy resistance through an abrogation of the DNA damage response. This leads to a competitive advantage of PPM1D-mutant cells and induces selective outgrowth of PPM1D-mutant hematopoietic stem and progenitor cells (HSPCs) during chemotherapy exposure in vivo. Through quantitative phosphoproteomic analysis, a consensus target sequence for PPM1D was identified. It was demonstrated that PPM1D targets the full DNA damage response pathway in hematopoietic cells, and that truncating PPM1D mutations cause a gain-of-function through loss of a C-terminal degradation signal. Treatment with an allosteric PPM1D inhibitor, GSK2830371 (Gilmartin, A. G. et al. Nat. Chem. Biol. 10, 181-7 (2014)), reverses the chemotherapy resistance phenotype and selectively kills PPM1D-mutant cells. In addition to providing an explanation for the high frequency of PPM1D mutations in chemotherapy treated patients and therapy-related myeloid neoplasms, these findings have the potential to open up a new therapeutic avenue for the targeted treatment of chemotherapy resistant, PPM1D-mutant therapy-related myeloid neoplasms which are known to have a poor prognosis. PPM1D inhibitor therapy could be employed to prevent the emergence of PPM1D-mutant CHIP clones. Similarly, PPM1D inhibitor treatment might be used to inhibit chemotherapy-induced outgrowth of PPM1D-mutant hematopoietic stem cells, potentially decreasing the likelihood of future development of therapy-related myeloid neoplasms (t-MNs). Finally, PPM1D inhibition may be used as a therapy for t-MN, highly lethal diseases that are resistant to chemotherapy and in great need of new treatment options. Thus, these data provide a rationale for preventative cancer care, through which t-MN development can be prevented by adjuvant depletion of PPM1D-mutant cells.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of treating or preventing clonal hematopoiesis of indeterminate potential (CHIP) or a chemotherapy-resistant hematologic or blood cancer or malignancy in a subject, the method comprising:
   administering a protein phosphatase 1D (PPM1D) inhibitor to a subject identified as having, or having a propensity to develop, CHIP or a chemotherapy-resistant hematologic or blood cancer or malignancy; wherein the subject is identified as having, or having the propensity to develop, CHIP or a chemotherapy-related hematologic or blood cancer or malignancy by detection of a truncating and/or a gain-of-function mutation in the PPM1D polynucleotide or polypeptide in a hematopoietic or blood cell or stem cell of the subject, wherein the PPM1D mutation causes clonal dominance and resistance to chemotherapy or a chemotherapeutic agent; and
   treating or preventing CHIP or a chemotherapy-related hematologic or blood cancer or malignancy in the subject following administration of the PPM1D inhibitor by selectively targeting PPM1D-mutant cells and reversing clonal dominance and resistance to chemotherapy or a chemotherapeutic agent.

2. The method of claim 1, wherein the cell is in a subject having hematologic or blood cancer.

3. The method of claim 1, wherein the cell is in a subject having a hematologic or blood malignancy.

4. The method of claim 1, wherein the cell is a blood cell.

5. The method of claim 1, wherein the cancer is a chemotherapy-related myeloid neoplasm.

6. The method of claim 1, wherein the biological sample is a blood, bone marrow, or tumor sample.

7. The method of claim 1, wherein the PPM1D inhibitor is selected from the group consisting of GSK2830371, CCT007093, and analogs thereof.

8. The method of claim 1, wherein the chemotherapeutic agent is a DNA damaging agent selected from the group consisting of Cytarabine, Doxorubicin, Cyclophosphamide, and Cisplatin.

9. The method of claim 1, wherein the PPM1D inhibitor inhibits the activity of a PPM1D polypeptide comprising the truncation mutation and/or a gain-of-function mutation.

10. A method of treating clonal hematopoiesis of indeterminate potential (CHIP) in a pre-identified subject, the method comprising administering to the subject an effective amount of a protein phosphatase 1D (PPM1D) inhibitor, wherein the subject is pre-identified as having a truncation mutation and/or a gain-of-function mutation in a PPM1D polynucleotide or polypeptide relative to a reference in a biological sample obtained from the subject; and
   treating CHIP and preventing emergence of PPM1D-mutant CHIP clones in the subject by reversing clonal dominance and chemotherapy resistance of the PPM1D-mutant CHIP clones following administration of the PPM1D inhibitor.

11. The method of claim 10, wherein said treatment selectively targets a cell comprising the mutation in the PPM1D polynucleotide or polypeptide.

12. The method of claim 11, wherein the cell is in a subject having a cancer.

13. The method of claim 12, wherein the cancer is a hematologic cancer or a chemotherapy-related myeloid neoplasm.

14. The method of claim 10, wherein the biological sample is a blood, bone marrow, or tumor sample.

15. The method of claim 10, wherein the PPM1D inhibitor is selected from the group consisting of GSK2830371, CCT007093, and analogs thereof.

16. The method of claim 10, wherein the PPM1D inhibitor inhibits the activity of a PPM1D polypeptide comprising a truncation mutation and/or a gain-of-function mutation.

17. The method of claim 10, wherein the subject is pre-identified as having a PPM1D truncation mutation and/or a gain-of-function mutation and/or a cancer that is resistant to a chemotherapeutic agent by
measuring a level and/or sequence of a mutant PPM1D polynucleotide or polypeptide in a biological sample obtained from the subject relative to the level of a PPM1D polynucleotide or polypeptide in a normal, healthy, or wild-type reference sample; and/or
detecting in a biological sample obtained from the subject a truncation mutation and/or a gain-of-function mutation in a PPM1D polynucleotide or polypeptide relative to a reference sequence.

* * * * *